(12) United States Patent
Palatnik et al.

(10) Patent No.: US 9,890,388 B2
(45) Date of Patent: Feb. 13, 2018

(54) GRF3 MUTANTS, METHODS AND PLANTS

(71) Applicants: Universidad Nacional de Rosario, Rosario (AR); Consejo Nacional de Investigaciones Cientificas y Técnicas (CONICET), Buenos Aires (AR)

(72) Inventors: Javier Palatnik, Rosario (AR); Ramiro Rodriguez, Rosario (AR); Martin Mecchia, Rosario (AR); Juan Manuel Debernardi, Rosario (AR)

(73) Assignees: Universidad Nacional de Rosario, Rosario (AR); Consejo Nacional de Investigaciones Cientificas y Tecnicas, Automous City of Buenos Aires (AR)

( * ) Notice: Subject to any disclaimer, the term of this patent is extended or adjusted under 35 U.S.C. 154(b) by 0 days.

(21) Appl. No.: 14/370,361

(22) PCT Filed: Jan. 4, 2013

(86) PCT No.: PCT/GB2013/050005
§ 371 (c)(1),
(2) Date: Jul. 2, 2014

(87) PCT Pub. No.: WO2013/102762
PCT Pub. Date: Jul. 11, 2013

(65) Prior Publication Data
US 2015/0033413 A1    Jan. 29, 2015

(30) Foreign Application Priority Data
Jan. 4, 2012   (GB) .................................. 1200075.8

(51) Int. Cl.
*A01H 5/00* (2006.01)
*C12N 15/82* (2006.01)
*C07K 14/415* (2006.01)

(52) U.S. Cl.
CPC ........ *C12N 15/8261* (2013.01); *C07K 14/415* (2013.01); *C12N 15/8202* (2013.01); *C12N 15/8218* (2013.01); *C12N 15/8266* (2013.01); *C12N 15/8273* (2013.01)

(58) Field of Classification Search
None
See application file for complete search history.

(56) References Cited

FOREIGN PATENT DOCUMENTS

| EP | 0120516 A2 | 10/1984 |
|---|---|---|
| EP | 0449375 A2 | 10/1991 |
| WO | WO-2012/149316 A2 | 11/2012 |

OTHER PUBLICATIONS

Rodriguez et al. (Control of cell proliferation in *Arabidopsis thaliana* by microRNA miR396, Development (Cambridge), vol. 137, No. 1, Jan. 2010 (Jan. 2010), pp. 103-112).

Wang et al., ("miR396-targeted AtGRF transcription factors are required for coordination of cell division and differentiation during leaf development in *Arabidopsis*", J Expt. Bot., vol. 62, No. 2, Oct. 29, 2010 (Oct. 29, 2010), pp. 761-773).*
Jeong et al. (The ATGRPF family of putative transcription factors involved in leaf and cotyledon growth in *Arabidopsis*; The Plant Journal, Blackwell Scientific Publications, Oxford, GB, vol. 36, No. 1, Oct. 1, 2003, pp. 94-104).*
Rodriguez et al. (Development, 137:103-112, Published 2010).*
Wang et al. (Journal Expt. Bot., 62:761-773, Published Oct. 29, 2010).*
Chinese Office Action issued in counterpart Chinese Application No. 201380004805.7 dated Aug. 24, 2015 with English translation (17 pages).
"Bioinformatics", Chapter 18 IN: Ausubel et al. (eds.), Short Protocols in Molecular Biology, 4th ed., Wiley (1999).
"Homology Searching" pp. 7-58-7-60 IN: Ausubel et al. (eds.), Short Protocols in Molecular Biology, 4th edition, Wiley (1999).
Altschul et al., Basic local alignment search tool, J. Mol. Biol., 215(3):403-10 (1990).
An et al., Binary vectors, Plant Mol. Biol. Manual, A3:1-19 (1988).
An et al., New cloning vehicles for transformation of higher plants, EMBO J., 4(2):277-84 (1985).
An et al., Transformation of Tobacco, Tomato, Potato, and *Arabidopsis thaliana* Using a Binary Ti Vector System, Plant Physiol., 81(1):301-5 (1986).
Aukerman et al., Regulation of flowering time and floral organ identity by a MicroRNA and its APETALA2-like target genes, Plant Cell, 15(11):2730-41 (2003).
Axtell et al., Antiquity of microRNAs and their targets in land plants, Plant Cell, 17(6):1658-73 (2005).
Baker et al., The early extra petals1 mutant uncovers a role for microRNA miR164c in regulating petal number in *Arabidopsis*, Curr. Biol., 15(4):303-15 (2005).
Baker, Chlorophyll fluorescence: a probe of photosynthesis in vivo, Annu. Rev. Plant Biol., 59:89-113 (2008).
Bartel et al., Micromanagers of gene expression: the potentially widespread influence of metazoan microRNAs, Nat. Rev. Genet., 5(5):396-400 (2004).
Busov et al., Genes for control of plant stature and form, New Phytologist, 177:589-607 (2008).
Butcher et al., "The role of tissue culture in the study of crown-gall tumorigenesis", pp. 202-208, IN: Ingram et al., Tissue Culture Methods for Plant Pathologists (1980).
Cartolano et al., A conserved microRNA module exerts homeotic control over Petunia hybrida and Antirrhinum majus floral organ identity, Nat. Genet., 39(7):901-5 (2007).
Caruthers et al., New chemical methods for synthesizing polynucleotides, Nucleic Acids Symp. Ser., 7:215-23 (1980).

(Continued)

*Primary Examiner* — Vinod Kumar
(74) *Attorney, Agent, or Firm* — Crowell & Moring LLP

(57) ABSTRACT

The present disclosure provides a novel modified gene, rGRF3, or an ortholog thereof, which is shown to be decoupled from control by miR396, particularly in the presence of over-expression of at least one GIF gene, such as GIF1, AtGIF 2, AtGIF 3, Os11g40100, Os12g31350, Os03g52320 or combinations thereof. When present in a plant, the rGRF3 results in a phenotype of increased productivity (e.g. increased yield, increased biomass, increased stress resistance, increased seed production, increased seed yield, increased root growth, increased root elongation speed, delayed leaf senescence or increased drought tolerance and combinations thereof).

10 Claims, 108 Drawing Sheets

(56) References Cited

OTHER PUBLICATIONS

Chen et al., Real-time quantification of microRNAs by stem-loop RT-PCR, Nucleic Acids Res., 33(20):e179 (2005).
Chen, A microRNA as a translational repressor of APETALA2 in *Arabidopsis* flower development, Science, 303(5666):2022-5 (2004).
Choi et al., Whole genome analysis of the OsGRF gene family encoding plant-specific putative transcription activators in rice (*Oryza sativa* L.), Plant Cell Physiol., 45(7):897-904 (2004).
Christou, Genetic engineering of crop legumes and cereals: current status and recent advances, Agro-Food-Industry Hi-Tech, pp. 17-27 (Mar./Apr. 1994).
Chuck et al., The heterochronic maize mutant Corngrass1 results from overexpression of a tandem microRNA, Nat. Genet., 39(4):544-9 (2007).
Colbert et al., High-throughput screening for induced point mutations, Plant Physiol., 126(2):480-4 (2001).
Czechowski et al., Genome-wide identification and testing of superior reference genes for transcript normalization in *Arabidopsis*, Plant Physiol., 139(1):5-17 (2005).
De Veylder et al., Functional analysis of cyclin-dependent kinase inhibitors of *Arabidopsis*, Plant Cell, 13(7):1653-68 (2001).
Devereux et al., A comprehensive set of sequence analysis programs for the VAX, Nucleic Acids Res., 12(1 Pt. 1):387-95 (1984).
Dinneny et al., The role of JAGGED in shaping lateral organs, Development, 131(5):1101-10 (2004).
Donnelly et al., Cell cycling and cell enlargement in developing leaves of *Arabidopsis*, Dev. Biol., 215(2):407-19 (1999).
Efroni et al., A protracted and dynamic maturation schedule underlies *Arabidopsis* leaf development, Plant Cell, 20(9):2293-306 (2008).
Felsenstein, "Mathematics vs. Evolution" book review of "Mathematical Evolutionary Theory" by March W. Feldman, Science, pp. 941-942 (Nov. 17, 1989).
Ferjani et al., Analysis of leaf development in fugu mutants of *Arabidopsis* reveals three compensation modes that modulate cell expansion in determinate organs, Plant Physiol., 144(2):988-99 (2007).
Fraley et al., Genetic transformation in higher plants, CRC Crit Rev. Plant Sci., 4(1):1-46 (1986).
Frame et al., Production of fertile transgenic maize plants by silicon carbide whisker-mediated transofmration, The Plant J., 6(6):941-8 (1994).
Fujikura et al., Coordination of cell proliferation and cell expansion mediated by ribosome-related processes in the leaves of *Arabidopsis thaliana*, Plant J., 59(3):499-508 (2009).
Gamborg et al., Nutrient requirements of suspension cultures of soybean root cells, Exp. Cell Res., 50(1):151-8 (1968).
Gaudin et al., The expression of D-cyclin genes defines distinct developmental zones in snapdragon apical meristems and is locally regulated by the Cycloidea gene, Plant Physiol., 122(4):1137-48 (2000).
Gonzalez et al., David and Goliath: what can the tiny weed *Arabidopsis* teach us to improve biomass production in crops?, Curr. Opin. Plant Biol. 12:157-64 (2009).
Gonzalez et al., Increased Leaf Size: Different Means to an End, Plant Physiol., 153:1261-79 (Jul. 2010).
Ha et al., The Blade-On-Petiole 1 gene controls leaf pattern formation through the modulation of meristematic activity in *Arabidopsis*, Development, 130(1):161-72 (2003).
Haga et al., R1R2R3-Myb proteins positively regulate cytokinesis through activation of KNOLLE transcription in *Arabidopsis thaliana*, Development, 134(6):1101-10 (2007).
Hellens et al., pGreen: a versatile and flexible binary Ti vector for Agrobacterium-mediated plant transformation, Plant Mol. Biol., 42(6):819-32 (2000).
Higgins et al., CLUSTAL: a package for performing multiple sequence alignment on a microcomputer, Gene, 73(1):237-44 (1988).

Horiguchi et al., Coordination of cell proliferation and cell expansion in the control of leaf size in *Arabidopsis thaliana*, J. Plant Res., 119(1):37-42 (2006).
Horiguchi et al., The transcription factor AtGRF5 and the transcription coactivator AN3 regulate cell proliferation in leaf primordia of *Arabidopsis thaliana*, The Plant J., 43:68-78 (2005).
Horn et al., Synthesis of oligonucleotides on cellulose. Part II: Design and synthetic strategy to the synthesis of 22 oligodeoxynucleotides coding for gastric inhibitory polypeptide (GIP), Nucleic Acids Symp. Ser., 7:225-32 (1980).
Hornstein et al., Canalization of development by microRNAs, Nat. Genet., 38 Suppl:S20-4 (2006).
International Search Report and Written Opinion for corresponding International Application No. PCT/GB2013/050005, dated Mar. 13, 2013.
International Preliminary Report on Patentability for corresponding International Application No. PCT/GB2013/050005, dated Jul. 18, 2014.
Inze et al., Cell cycle regulation in plant development, Annu. Rev. Genet., 40:77-105 (2006).
Irizarry et al., Summaries of Affymetrix GeneChip probe level data, Nucleic Acids Res., 31(4):e15 (2003).
Jarvis et al., An *Arabidopsis* mutant defective in the plastid general protein import apparatus, Science, 282(5386):100-3 (1998).
Jones-Rhoades et al., Computational identification of plant microRNAs and their targets, including a stress-induced miRNA, Mol. Cell, 14(6):787-99 (2004).
Kim et al., A transcriptional coactivator, AtGIF1, is involved in regulating leaf growth and morphology in *Arabidopsis*, Proc. Natl. Acad. Sci. USA, 101(36):13374-9 (2004).
Kim et al., Growth-regulating factor4 of *Arabidopsis thaliana* is requierd for development of leaves, cotyledons, and shoot apical meristem, J. Plant Biol., 49(6):463-8 (2006).
Kim et al., The AtGRF family of putative transcription factors is involved in leaf and cotyledon growth in *Arabidopsis*, Plant J., 36(1):94-104 (2003).
Koyama et al., TCP transcription factors control the morphology of shoot lateral organs via negative regulation of the expression of boundary-specific genes in *Arabidopsis*, Plant Cell, 19(2):473-84 (2007).
Krizek, Ectopic expression of AINTEGUMENTA in *Arabidopsis* plants results in increased growth of floral organs, Dev. Genet., 25(3):224-36 (1999).
Lee et al., The *Arabidopsis* GRF-Interacting Factor gene family performs an overlapping function in determining organ size as well as multiple developmental properties, Plant Physiol., 151(2):655-68 (2009).
Lemon et al., A high performance test of differential gene expression for oligonucleotide, Genome Biol., 4(10):R67 (2003).
Li et al., The developmental dynamics of the maize leaf transcriptome, Nat. Genet., 42(12):1060-7 (2010).
Liu et al., Ectopic expression of miR396 suppresses GRF target gene expression and alters leaf growth in *Arabidopsis*, Physiol. Plant, 136(2):223-36 (2009).
Livingstone et al., Protein sequence alignments: a strategy for the hierarchical analysis of residue conservation, Comput. Appl. Biosci., 9(6):745-56 (1993).
Lukowitz et al., Cytokinesis in the *Arabidopsis* embryo involves the syntaxin-related KNOLLE gene product, Cell, 84(1):61-71 (1996).
Masuda et al., ABAP1 is a novel plant Armadillo BTB protein involved in DNA replication and transcription, EMBO J., 28(20):2746-56 (2008).
Menges et al., Global analysis of the core cell cycle regulators of *Arabidopsis* identifies novel genes, reveals multiple and highly specific profiles of expression and provides a coherent model for plant cell cycle control, Plant J., 41(4):546-66 (2005).
Meyer et al., The use of African cassava mosaic virus as a vector system for plants, Gene, 110(2):213-7 (1992).
Mizukami et al., Plant organ size control: AINTEGUMENTA regulates growth and cell numbers during organogenesis, Proc. Natl. Acad. Sci. USA, 97(2):942-7 (2000).
Moloney et al., High efficiency transformation of *Brassica napus* using Agrobacterium vectors, Plant Cell Rep., 8(4):238-42 (1989).

(56) References Cited

OTHER PUBLICATIONS

Moretti et al., The M-Coffee web server: a meta-method for computing multiple sequence alignments by combining alternative alignment methods, Nucleic Acids Res., 35(Web Server Issue): W645-8 (2007).
Murashige et al., A revised medium for rapid growth and bio assays with tobacco tissue cultures, Physiologia Plantarum, 15:473-97 (1962).
Nath et al., Genetic control of surface curvature, Science, 299(5611):1404-7 (2003).
Nikovics et al., The balance between the MIR164A and CUC2 genes controls leaf margin serration in *Arabidopsis*, Plant Cell, 18(11):2929-45 (2006).
Ohno et al., The *Arabidopsis* JAGGED gene encodes a zinc finger protein that promotes leaf tissue development, Development, 131(5):1111-22 (2004).
Ori et al., Regulation of LANCEOLATE by miR319 is required for compound-leaf development in tomato, Nat. Genet., 39(6):787-91 (2007).
Page, TreeView: an application to display phylogenetic trees on personal computers, Comput. Appl. Biosci., 12(4):357-8 (1996).
Palatnik et al., Control of leaf morphogenesis by microRNAs, Nature, 425(6955):257-63 (2003).
Palatnik et al., Sequence and expression differences underlie functional specialization of *Arabidopsis* microRNAs miR159 and miR319, Dev. Cell, 13(1):115-25 (2007).
Piazza et al., Evolution of leaf developmental mechanisms, New Phytol., 167(3):693-710 (2005).
Potrykus, Gene Transfer to Plants: Assessment of Published Approaches and Results, pp. 205-225 IN: Briggs et al. (eds.), Annual Review of Plant Physiology and Plant Molecular Biology, Annual Reviews Inc., vol. 42 (1991).
Rice et al., EMBOSS: the European Molecular Biology Open Software Suite, Trends Genet., 16(6):276-7 (2000).
Rodriguez et al., Control of cell proliferation in *Arabidopsis thaliana* by microRNA miR396, Development, 137(1):103-12 (2010).
Sambrook et al., Molecular Cloning: A Laboratory Manual, Third Edition, Cold Spring Harbour Press (2001).
Schmid et al., A gene expression map of *Arabidopsis thaliana* development, Nat. Genet., 37(5):501-6 (2005).
Schommer et al., Control of jasmonate biosynthesis and senescence by miR319 targets, PLoS Biol., 6(9):e230 (2008).
Schwab et al., Specific effects of microRNAs on the plant transcriptome, Dev. Cell, 8(4):517-27 (2005).
Sparrow et al., The use of phenotypic markers to identify *Brassica oleracea* genotypes for routine high-throughput Agrobacterium-mediated transformation, Plant Cell Rep., 23(1-2):64-70 (2004).
Stryer, Biochemistry, Third Edition, New York: W.H. Freeman and Company (1988).
Subramanian et al., Gene set enrichment analysis: a knowledge-based approach for interpreting genome-wide expression profiles, Proc. Natl. Acad. Sci. USA, 102(43):15545-50 (2005).
Subramanian et al., GSEA-P: a desktop application for Gene Set Enrichment Analysis, Bioinformatics, 23(23):3251-3 (2007).
Tatusova et al., BLAST 2 Sequences, a new tool for comparing protein and nucleotide sequences, FEMS Microbiol. Lett., 174(2):247-50 (1999).
Tatusova et al., Erratum to "BLAST 2 Sequences, a new tool for comparing protein and nucleotide sequences", FEMS Microbiol. Lett., 177:187-8 (1999).
Taylor, The classification of amino acid conservation, J. Theor. Biol., 119(2):205-18 (1986).
Taylor, Tropical Plant Database entry for Papaya, downloaded from the Internet at: <http://www.rain-tree.com/papaya.htm> (Nov. 29, 2011).
Tsukaya, Leaf shape: genetic controls and environmental factors, Int. J. Dev. Biol., 49(5-6):547-55 (2005).
Tsukaya, Mechanism of leaf-shape determination, Annu. Rev. Plant Biol., 57:477-96 (2006).
van der Knaap et al., A novel Gibberellin-induced gene from rice and its potential regulatory role in stem growth, Plant Physiol., 122:695-704 (Mar. 2000).
Wang et al., Dual effects of miR156-targeted SPL genes and CYP78A5/KLUH on plastochron length and organ size in *Arabidopsis thaliana*, Plant Cell, 20(5):1231-43 (2008).
Wang et al., miR396-targeted AtGRF transcription factors are required for coordination of cell division and differentiation during leaf development in *Arabidopsis*, J. Exp. Bot., 62(2):761-73 (2011).
White, PEAPOD regulates lamina size and curvature in *Arabidopsis*, Proc. Natl. Acad. Sci. USA, 103(35):13238-43 (2006).
Winter et al., An "Electronic Fluorescent Pictograph" browser for exploring and analyzing large-scale biological data sets, PLoS One, 2(8):e718 (2007).
Wu et al., Temporal regulation of shoot development in *Arabidopsis thaliana* by miR156 and its target SPL3, Development, 133(18):3539-47 (2006).
Yang et al., *Arabidopsis* MiR396 Mediates the Development of Leaves and Flowers in Trangenic Tobacco, J. Plant Biol., 52:475-81 (2009).
Zhang et al., Isolation and characterization of genes encoding GRF transcription factors and GIF transcriptional coactivators in Maize (*Zea mays* L.), Plant Sci., 175:809-17 (2008).
Zhang et al., PlantTFDB 2.0: update and improvement of the comprehensive plant transcription factor database, Nucleic Acids Res., 39(Database Issue):D1114-7 (2011).

\* cited by examiner

FIGURE 16
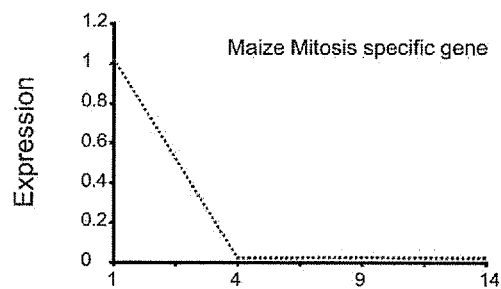
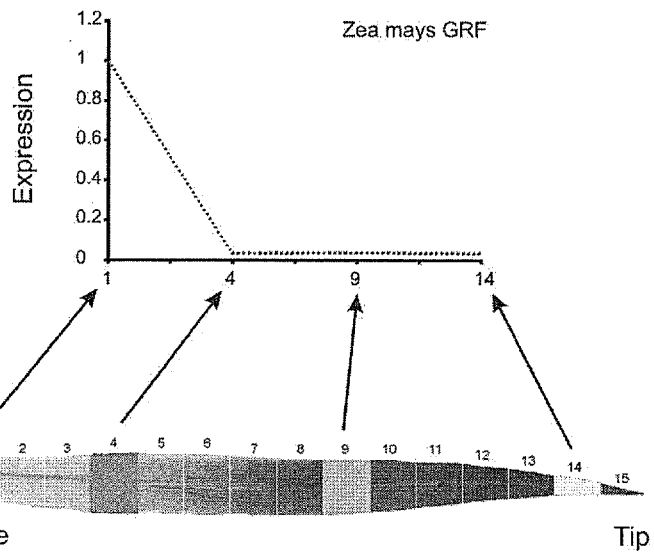
Base　　　　　　　　　　　　　Tip

FIGURE 17
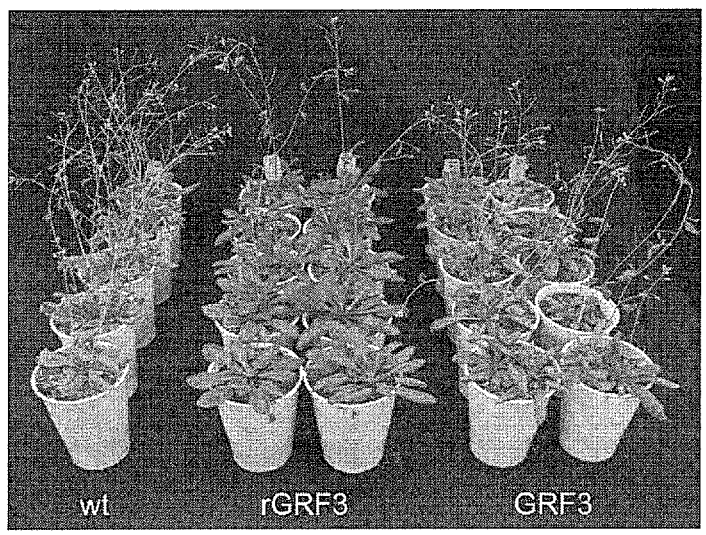
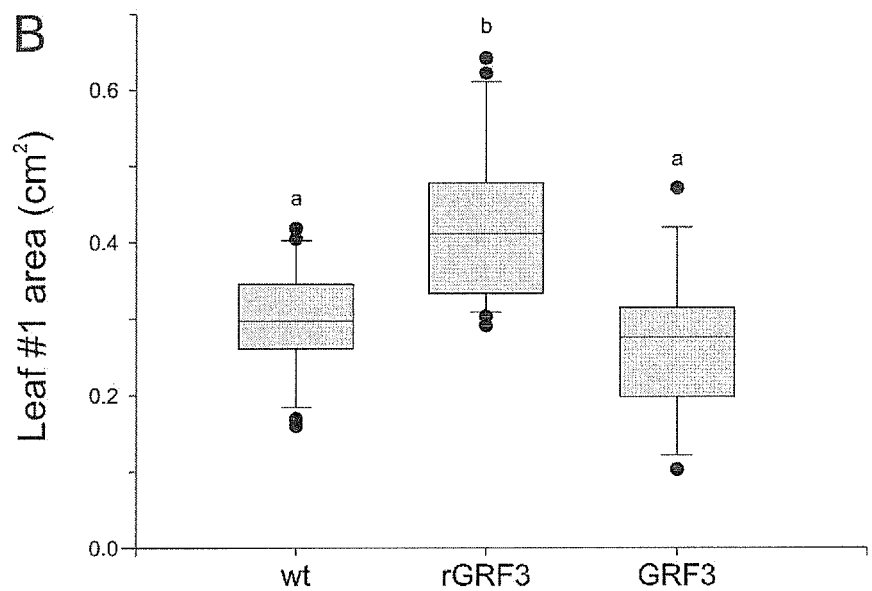

FIG. 21A

>AtGRF1 SEQ ID N°: 40

ATGGATCTTGGAGTTCGTGTTTCTGGTCATGAAACCGTTTCTTCTCCGGGTCAAA
CTGAACTCGGATCTGGTTTCAGTAACAAGCAAGAAAGATCCGGTTTCGATGGTG
AAGATTGCTGGAGAAGTTCAAAGCTCTCACGAACATCAACTGATGGATTCTCTTC
TTCCCCTGCCTCTGCTAAAACGCTGTCGTTTCATCAAGGCATCCCTTTACTGAGA
TCTACCACTATTAATGATCCTCGTAAAGGACAAGAACACATGCTTAGCTTCTCTT
CTGCTTCAGGCAAATCAGATGTCTCACCTTATCTTCAGTACTGTAGAAACTCAGG
ATATGGTTTAGGAGGAATGATGAACACAAGCAACATGCATGGAAACTTGTTGAC
AGGAGTAAAAGGACCTTTTTCATTGACTCAGTGGGCAGAGCTAGAGCAACAGGC
GTTGATCTATAAGTATATCACAGCCAATGTCCCTGTTCCATCTAGTTTACTTCTCT
CTCTCAAGAAATCTTTTTTCCCTTATGGTTCCTTGCCTCCTAATTCTTTTGGATGG
GGCTCTTTTCATCTGGGCTTTTCCGGTGGTAACATGGATCCCGAGCCAGGGAG
ATGTCGCCGGACAGATGGAAAGAAA<u>TGGCGGTGC</u>TCGAGGGACGCTGTTCCCG
ATCAAAAGTACTGTAACGACATATTAACAGAGGCCGCCAT<u>CGTTCAAGAAAGC</u>
<u>CTGTGGAA</u>GGCCAAAATGGCCACAATACTAATGCTGCCGCCGCTGCTTCTGCT
GCTGCCGCTTCTACCGCTGCTGCTGTGTCCAAAGCGGCAGCGGGGACTTCAGC
TGTTGCGATGCGTGGATCAGATAATAACAATAGCCTTGCCGCTGCTGTTGGAAC
ACAACATCATACCAATAATCAATCTACAGATTCTTTGGCTAACAGAGTTCAAAATT
CTCGAGGGGCTTCGGTTTTTCCTGCCACGATGAACTTACAGTCGAAGGAAACTC
ATCCGAAACAAAGCAATAATCCCTTTGAATTCGGACTCATCTCTTCTGATTCGTT
ACTTAATCCGTCGCATAAACAAGCCTCGTATGCAACCTCTTCCAAAGGCTTTGG
ATCGTATCTTGACTTCGGCAACCAAGCCAAGCACGCGGGGAATCACAACAATGT
CGATTCTTGGCCCGAAGAGCTGAAATCGGATTGGACTCAGCTCTCAATGTCAAT
CCCTATGGCTCCATCTTCCCCTGTTCAAGATAAACTTGCACTCTCACCTTTAAGG
TTATCGCGTGAGTTTGACCCCGCGATCCACATGGGATTAGGCGTCAACACCGA
GTTTCTTGACCCCGGGAAAAAGACGAATAACTGGATACCAATCTCCTGGGGTAA
TAACAACTCCATGGGAGGTCCACTCGGCGAGGTACTAAACAGCACGACCAATA
GTCCCAAGTTTGGTTCCTCTCCAACAGGCGTCTTGCAAAAGTCGACATTTGGTT
CTCTTTCTAACAGCAGCTCGGCAAGCAGCACCATCATTGGCGATAACAACAATA
AGAACGGTGATGGAAAAGATCCGCTTGGCCCGACCACGCTGATGAATACTTCT
GCTACTGCTCCTTCTCTGTGA

FIG. 21B

>At*GRF2* SEQ ID N°: 87

ATGGATATTGGTGTTCATGTTCTTGGGTCGGTTACTAGTAATGAAAATGAGTCAC
TTGGTCTAAAAGAGCTTATAGGAACTAAACAAGATAGATCCGGATTCATCGGTG
AGGATTGCTTGCAACGAAGCTTGAAGCTAGCAAGAACGACAACTAGAGCGGAA
GAAGAAGAAAACTTGTCTTCTTCTGTTGCAGCTGCTTATTGCAAAACGATGTCGT
TTCACCAAGGCATTCCTCTCATGAGATCTGCTTCTCCTCTTTCCTCTGATTCTCG
CCGTCAAGAACAAATGCTTAGCTTCTCAGATAAACCAGACGCTCTTGATTTCAGT
AAATATGTCGGTTTGGATAATAGCAGTAATAACAAGAACTCTCTCTCGCCGTTTC
TTCACCAGATTCCTCCACCTTCTTACTTTAGAAGCTCAGGAGGATATGGTTCTGG
TGGAATGATGATGAACATGAGCATGCAAGGGAACTTCACAGGTGTTAAAGGACC
TTTTACATTGACTCAATGGGCTGAGTTAGAGCAACAGGCGTTGATCTATAAGTAC
ATCACAGCCAATGTCCCTGTTCCTTCTAGTTTGCTCATCTCTATCAAGAAGTCTT
TTTATCCTTACGGATCTTTGCCTCCTAGTTCCTTCGGATGGGGAACTTTCCATCT
CGGTTTCGCAGGCGGTAACATGGACCCTGAGCCAGGGAGATGCCGCAGAACA
GATGGGAAGAAA<u>TGGCGGTGC</u>TCAAGAGACGCCGTTCCTGATCAGAAATACTG
TGAAAGACACATCAACAGAGGCCGTCAT<u>CGTTCAAGAAAGCCTGTGGAA</u>GTCC
AATCTGGCCAAAACCAAACCGCCGCTGCTGCATCCAAAGCGGTTACTACACCAC
AACAGCCTGTTGTCGCTGGTAATACTAACAGAAGCAATGCCCGTGCATCAAGCA
ACCGCAGCCTCGCCATTGGAAGTCAATATATCAATCCTTCTACAGAATCTTTACC
TAACAACAGAGGAGTTTCGATATATCCTTCCACCGTCAACTTACAACCCAAGGAA
TCTCCGGTTATTCATCAGAAACACAGAAACAACAACAACCCTTTTGAGTTTGGAC
ACATATCCTCTGATTCGTTACTCAACCCGAATACCGCAAAGACCTATGGATCATC
GTTCTTGGATTTCAGCAGCAACCAAGAGAAGCATTCAGGGAATCACAATCACAA
TTCTTGGCCTGAAGAGCTGACATCAGATTGGACACAGCTCTCAATGTCAATTCC
AATAGCATCATCATCCCCTTCCTCCACACACAACAACAACAATGCTCAAGAAAAA
ACAACACTCTCGCCTCTCAGGCTATCCCGCGAGCTTGACCTATCGATCCAAACC
GATGAAACAACAATCGAGCCTACTGTGAAAAAGGTGAATACTTGGATACCAATC
TCATGGGGAAACTCCTTAGGAGGTCCTCTAGGTGAAGTACTAAACAGTACAACG
AATAGTCCAACATTTGGATCTTCTCCTACAGGGGTTTTGCAAAAGTCCACATTTT
GTTCACTCTCTAACAACAGCTCCGTGAGCAGCCCCATTGCAGAGAACAACAGAC
ACAATGGCGATTACTTTCATTACACAACCTGA

FIG. 21C

\>At*GRF3* SEQ ID N°: 2

ATGGATTTGCAACTGAAACAATGGAGAAGCCAGCAGCAGCAACAACATCAGACA
GAGTCAGAAGAACAACCTTCTGCAGCTAAGATACCAAAACATGTCTTTGACCAG
ATTCATTCTCACACTGCAACTTCTACTGCTCTTCCTCTCTTTACCCCTGAGCCTA
CTTCTTCTAAACTCTCCTCTTTGTCTCCTGATTCTTCCTCCAGGTTCCCCAAGAT
GGGGAGCTTCTTTAGCTGGGCACAGTGGCAAGAACTTGAACTACAAGCTCTGAT
CTACAGGTACATGTTGGCTGGTGCTGCTGTTCCTCAGGAGCTCCTTTTACCAAT
CAAGAAAAGCCTTCTCCATCTATCTCCTTCCTACTTTCTTCACCATCCTCTTCAAC
ACCTACCTCATTACCAACCTGCTTGGTATTTGGGAAGGGCAGCGATGGATCCTG
AGCCAGGCAGATGCAGGAGAACGGATGGTAAGAAG<u>TGGAGATGTT</u>CAAGAGAC
GTCTTCGCTGGCCACAAGTATTGCGAGCGCCACATGCACCGTGGCCGCAAC<u>CG</u>
<u>TTCAAGAAAGCCTGTGGAA</u>ACTCCAACCACCGTCAATGCAACTGCCACGTCCA
TGGCTTCATCAGTAGCAGCCGCAGCCACCACTACAACAGCAACAACAACATCTA
CGTTTGCTTTTGGTGGTGGTGGTGGTAGTGAGGAAGTGGTTGGTCAAGGAGGA
TCTTTCTTCTTCTCTGGCTCTTCTAACTCTTCATCTGAACTTCTCCACCTTAGTCA
AAGTTGTTCGGAGATGAAGCAAGAAAGCAACAACATGAACAACAAGAGGCCATA
CGAGTCCCACATCGGATTCAGTAACAACAGATCAGATGGAGGACACATCCTGAG
GCCCTTCTTTGACGATTGGCCTCGTTCTTCGCTCCAAGAAGCTGACAATAGTTC
AAGCCCCATGAGCTCAGCCACTTGTCTCTCCATCTCCATGCCCGGGAACTCTTC
CTCAGACGTCTCTCTGAAGCTGTCCACAGGCAACGAAGAGGGAGCCCGGAGCA
ACAACAATGGGAGAGATCAGCAAAACATGAGCTGGTGGAGCGGTGGAGGTTCC
AACCACCATCATCACAACATGGGCGGACCATTGGCCGAAGCCCTGAGATCTTCT
TCCTCATCTTCCCCAACCAGTGTTCTCCATCAGCTTGGTGTCTCGACACAAGCC
TTTCATTGA

FIG. 21D

>AtGRF4 SEQ ID N°: 19

ATGGACTTGCAACTGAAACAATGGAGAAGTCAGCAGCAGAATGAGTCAGAAGAA
CAAGGCTCTGCTGCAACTAAGATATCAAACTTTTTCTTTGATCAGATTCAGTCCC
AAACTGCTACTTCTGCTGCTGCGGCTCCTCTTCCTCTCTTTGTCCCTGAACCCA
CTTCTTCCTCTTCTTTCTCTTGCTTCTCTCCTGACTCTTCTAATTCTTCTTCTTCTT
CCAGGTTCCTCAAGATGGGAAACTTCTTCAGCTGGGCACAGTGGCAAGAACTTG
AGCTACAAGCACTGATCTATAGATACATGTTGGCTGGTGCTTCTGTTCCTCAAGA
GCTTCTCTTACCTATTAAGAAAAGTCTCCTCCATCAATCTCCTATGCATTTCCTTC
ACCATCCTCTTCAACATAGTTTTCCTCATCACCAACCTTCTTGGTATTGGGGAAG
AGGAGCAATGGATCCTGAGCCAGGGAGGTGTAAGAGAACTGACGGCAAGAAA<u>T
GGAGATGT</u>TCAAGGGATGTTGTAGCGGGCCACAAGTATTGTGACCGCCACATT
CACCGTGGAAGAAAC<u>CGTTCAAGAAAGCCTGTGGAA</u>ACCGCCACAACCACCAT
CACAACGACAGCCACAACAACCGCATCTTCTTTTGTCTTAGGTGAGGAGCTTGG
TCATGGACCAAACAACAACCACTTCTTCTCCTCTGGTTCATCTCAACCTCTCCAC
CTTAGTCATCAACAAAGTTGTTCTTCAGAGATGAAACAAGAAAGCAACAACAACA
AGAGGCCATATGAAGCTAACAGTGGATTCAGCAATGGAAGATCAGACGATGGTC
ACATCTTGAGGCATTTCTTTGACGATTGGCCACGATCATCAGACTCTACCTCCA
GTCCAATGAGCTCATCCACTTGTCATCTTTCAATCTCCATGCCCGGTAACAACAC
GTCCTCAGATGTTTCTCTAAAACTTTCCACAGGCAATGAAGAAGAAGAAGAGAA
CATGAGAAATAACAACAATGAGAGGGAGCAAATGAATTGGTGGAGCAATGGAG
GGAATCACCACAACAATATGGGAGGACCATTAGCTGAGGCTTTGAGGTCAGCTT
CTTCGACGTCAAGTGTTCTTCATCAGATGGGAATCTCTACTCAAGTTTTTCATTA
A

FIG. 21E

>AtGRF5 SEQ ID N°: 41

ATGATGAGTCTAAGTGGAAGTAGCGGGAGAACAATAGGAAGGCCTCCATTTACA
CCAACACAATGGGAAGAACTGGAACATCAAGCCCTAATCTACAAGTACATGGTC
TCTGGTGTTCCTGTCCCACCTGAGCTCATCTTCTCCATTAGAAGAAGCTTGGAC
ACTTCCTTGGTCTCTAGACTCCTTCCTCACCAATCCCTTGGATGGGGGTGTTAC
CAGATGGGATTTGGGAGAAAACCAGATCCAGAGCCAGGAAGATGCAGAAGAAC
AGATGGTAAGAAA<u>TGGAGATGC</u>TCAAGAGAAGCTTACCCAGATTCGAAGTACTG
TGAAAAACACATGCACAGAGGAAGAAAC<u>CGTGCCAGAAATCTCTTGAT</u>CAGAA
TCAGACAACAACAACTCCTTTAACATCACCATCTCTCTCATTCACCAACAACAAC
AACCCAAGTCCCACCTTGTCTTCTTCTTCTTCCTCTAATTCCTCTTCTACTACTTA
TTCTGCTTCTTCTTCTTCAATGGATGCCTACAGTAACAGTAATAGGTTTGGGCTT
GGTGGAAGTAGTAGTAACACTAGAGGTTATTTCAACAGCCATTCTCTTGATTATC
CTTATCCTTCTACTTCACCCAAACAACAACAACAAACTCTTCATCATGCTTCCGC
TTTGTCACTTCATCAAAATACTAATTCTACTTCTCAGTTCAATGTCTTAGCCTCTG
CTACTGACCACAAAGACTTCAGGTACTTTCAAGGGATTGGGGAGAGAGTTGGAG
GAGTTGGGGAGAGAACGTTCTTTCCAGAAGCATCTAGAAGCTTTCAAGATTCTC
CATACCATCATCACCAACAACCGTTAGCAACAGTGATGAATGATCCGTACCACC
ACTGTAGTACTGATCATAATAAGATTGATCATCATCACACATACTCATCCTCATCA
TCATCTCAACATCTTCATCATGATCATGATCATAGACAGCAACAGTGTTTTGTTTT
GGGCGCCGACATGTTCAACAAACCTACAAGAAGTGTCCTTGCAAACTCATCAAG
ACAAGATCAAAATCAAGAAGAAGATGAGAAAGATTCATCAGAGTCGTCCAAGAA
GTCTCTACATCACTTCTTTGGTGAGGACTGGGCACAGAACAAGAACAGTTCAGA
TTCTTGGCTTGACCTTTCTTCCCACTCAAGACTCGACACTGGTAGCTAA

FIG. 21F

>AtGRF6 SEQ ID N°: 42

ATGGCTACAAGGATTCCATTCACAGAATCACAATGGGAAGAACTTGAAAACCAA
GCTCTTGTGTTCAAGTACTTAGCTGCAAATATGCCTGTTCCACCTCATCTTCTCT
TCCTCATCAAAAGACCCTTTCTCTTCTCTTCTTCTTCTTCTTCATCTTCTTCTTCAA
GCTTCTTCTCTCCCACTCTTTCTCCACACTTTGGGTGGAATGTGTATGAGATGG
GAATGGGAAGAAAGATAGATGCAGAGCCAGGAAGATGTAGAAGAACTGATGGC
AAGAAA<ins>TGGAGATGC</ins>TCTAAAGAAGCTTACCCTGACTCTAAGTACTGTGAGAGA
CATATGCATAGAGGCAAGAACCGTTCTTCCTCAAGAAAGCCTCCTCCTACTCAA
TTCACTCCAAATCTCTTTCTCGACTCTTCTTCCAGAAGAAGAAGAAGTGGATACA
TGGATGATTTCTTCTCCATAGAACCTTCCGGGTCAATCAAAAGCTGCTCTGGCT
CAGCAATGGAAGATAATGATGATGGCTCATGTAGAGGCATCAACAACGAGGAGA
AGCAGCCGGATCGACATTGCTTCATCCTTGGTACTGACTTGAGGACACGTGAGA
GGCCATTGATGTTAGAGGAGAAGCTGAAACAAAGAGATCATGATAATGAAGAAG
AGCAAGGAAGCAAGAGGTTTTATAGGTTTCTTGATGAATGGCCTTCTT

FIG. 21G

>AtGRF7 SEQ ID N°: 43

ATGGACTTTCTCAAAGTTTCAGACAAGACAACAATTCCATATAGAAGTGATTCTT
TGTTTAGTTTGAATCAGCAACAATACAAAGAGTCTTCTTTTGGATTCAGAGACAT
GGAGATTCATCCGCATCCTACTCCATATGCAGGAAATGGACTTTTGGGTTGTTAT
TACTATTACCCTTTCACAAACGCACAATTGAAGGAGCTTGAGAGACAAGCAATG
ATCTACAAGTACATGATCGCATCTATTCCTGTTCCTTTCGATCTACTTGTTTCTTC
ACCATCCTCTGCCTCTCCTTGTAACAATAAAAACATCGCCGGAGATTTAGAGCC
GGGAAGATGCCGGAGAACAGACGGAAAGAAATGGAGATGCGCGAAAGAAGTC
GTCTCTAATCACAAATACTGTGAGAAACACTTACACAGAGGTCGTCCT**CGTTCA
AGAAAGCATGTGGAA**CCTCCTTATTCTCGCCCTAACAACAATGGTGGTTCTGTG
AAAAACAGAGATCTCAAAAAGCTTCCTCAAAAGTTATCTAGTAGTTCCATCAAAG
ACAAAACACTTGAGCCAATGGAGGTTTCATCATCAATCTCAAACTATAGAGACTC
CAGAGGAAGTGAGAAATTTACTGTATTGGCAACAACAGAGCAAGAGAACAAGTA
TCTGAATTTCATAGATGTATGGTCCGATGGAGTAAGATCATCTGAAAAACAGAGT
ACAACTTCAACACCTGTTTCTTCTTCCAATGGCAATCTCTCTCTTTACTCGCTTGA
TCTCTCAATGGGAGGAAACAACTTAATGGGCCAAGACGAAATGGGCCTGATACA
AATGGGCTTAGGTGTAATCGGGTCGGGTAGTGAGGATCATCACGGGTATGGTC
CTTATGGTGTGACTTCTTCACTAGAGGAGATGTCAAGCTGGCTTGCTCCGATGT
CTACCACACCTGGTGGACCATTAGCGGAGATACTGAGGCCGAGTACGAATTTG
GCGATCTCTGGTGATATCGAATCGTATAGCTTGATGGAGACTCCCACTCCAAGC
TCGTCCCCGTCTAGAGTGATGAAGAAGATGACTAGTTCAGTGTCCGACGAAAGC
AGCCAGGTTTAG

FIG. 21H

>AtGRF8 SEQ ID N°: 44

ATGAGGATGCTTCTTGGGATTCCTTACGTAGACAAGTCGGTTCTTTCCAACTCTG
TTCTTGAGAGAGGCAAGCAGGATAAAAGCAAACTATTGTTAGTCGACAAATGCC
ATTATGAGCTTGATGTTGAAGAACGCAAGGAAGATTTTGTTGGTGGGTTTGGATT
TGGTGTTGTAGAAAATTCGCATAAAGACGTTATGGTGCTACCTCATCATCACTAT
TATCCATCATATTCATCACCTTCCTCTTCTTCTTTGTGTTACTGTTCTGCTGGTGT
TAGCGATCCCATGTTCTCTGTTTCTAGCAATCAGGCTTACACTTCTTCACAGT
GGTATGTTCACACCCGCCGGTTCTGGTTCTGCTGCTGTGACTGTAGCAGATCCT
TTTTTCTCCTTGAGCTCTTCAGGGGAAATGAGAAGAAGTATGAACGAAGATGCT
GGTGCAGCTTTCAGCGAAGCTCAATGGCATGAGCTTGAGAGGCAGAGGAATAT
ATACAAGTACATGATGGCTTCTGTTCCTGTTCCTCCAGAGCTTCTCACACCCTTT
CCCAAGAACCACCAATCAAACACTAACCCGGATGTGGATACATATAGGAGTGGA
ATGTTTAGTATTTATGCTGATTACAAGAATCTGCCGTTGTCTATGTGGATGACAG
TAACTGTGGCAGTGGCGACAGGAGGCTCATTGCAGCTGGGGATTGCTTCAAGC
GCAAGCAATAACACGGCTGATCTGGAGCCATGGAGGTGCAAGAGAACAGATGG
GAAGAAA<u>TGGAGGTGC</u>TCTAGAAACGTGATTCCTGATCAGAAATACTGTGAGAG
ACACACACACAAGAGCCGTCCTCGTTCAAGAAAGCATGTGGAATCATCTCACC
AATCATCTCACCACAATGACATTCGTACGGCTAAGAATGATACTAGCCAGCTTGT
GAGAACTTATCCTCAGTTTTACGGACAACCTATAAGCCAGATCCCTGTGCTTTCT
ACTCTTCCGTCTGCCTCCTCTCCATATGATCACCACAGAGGACTGAGGTGGTTT
ACGAAAGAAGATGATGCCATTGGAACCTTAAACCCGGAGACTCAAGAAGCTGTC
CAGCTGAAAGTTGGATCAAGCAGAGAGCTCAAACGGGGATTCGATTATGATCTG
AATTTCAGGCAGAAAGAGCCAATAGTAGACCAGAGCTTTGGAGCATTGCAGGGT
CTATTAAGTCTAAACCAGACACCACAACATAACCAAGAAACAAGACAGTTTGTTG
TAGAAGGAAAGCAAGATGAAGCGATGGGAAGCTCTCTGACACTCTCAATGGCT
GGAGGAGGCATGGAGGAAACAGAGGGAACAAACCAGCATCAGTGGGTTAGCC
ATGAAGGTCCATCATGGCTCTATTCAACAACACCAGGTGGACCATTGGCTGAAG
CACTGTGTCTCGGTGTCTCCAACAACCCAAGTTCTAGTACTACTACTAGTAGCT
GCAGCAGAAGCTCAAGCTAA

FIG. 21I

>AtGRF9 SEQ ID N°: 45

ATGCAGAGCCCTAAAATGGAGCAGGAGGAGGTTGAGGAGGAGAGGATGAGGA
ATAAGTGGCCGTGGATGAAGGCGGCGCAGTTAATGGAGTTTCGGATGCAAGCT
TTGGTGTATAGATACATAGAGGCTGGTCTCCGTGTGCCTCATCATCTCGTGGTG
CCTATTTGGAACAGTCTTGCTCTCTCTTCTTCCTCCAATTACAACTATCACTCTTC
TTCTCTGTTGAGTAACAAGGGAGTAACCCATATCGACACGTTGGAAACTGAACC
AACTAGGTGCAGGAGAACAGATGGGAAGAAA<u>TGGCGCTGT</u>AGCAACACGGTCC
TTCTATTCGAGAAGTACTGTGAACGGCACATGCATAGAGGTCGTAAA**<u>CGTTCAA
GAAAGCTTGTGGAA</u>**TCTTCTTCTGAGGTTGCTTCATCATCAACCAAATACGACA
ACACTTATGGTTTGGATAGGTATAACGAGAGTCAGAGTCATCTTCATGGGACAA
TCTCGGGTTCTAGTAATGCGCAGGTAGTTACCATTGCTTCACTGCCTAGTGCCA
GATCCTGTGAAAATGTCATTCGTCCGTCTTTAGTGATCTCTGAATTCACAAACAA
AAGTGTGAGTCACGGCAGAAGAACATGGAGATGAGTTATGATGACTTTATTAA
TGAAAAGAGGCGAGTATGTGTGTTGGAGTTGTTCCTCTTCAAGGTGATGAGAG
CAAACCTTCGGTTCAAAAGTTCTTCCCTGAGGTATCTGATAAATGCTTAGAAGCT
GCAAAATTCTCAAGCAACAGGAAGAATGATATAATTGCAAGAAGCAGAGAATGG
AAGAATATGAATGTTAATGGTGGTTTGTTTCATGGTATCCACTTTTCTCCAGACA
CTGTTCTTCAAGAACGTGGTTGTTTTCGTTTACAAGGAGTTGAAACAGACAATGA
ACCAGGAAGGTGCCGAAGAACAGATGGGAAGAAG<u>TGGAGATGC</u>AGCAAAGATG
TTTTGTCTGGTCAGAAGTACTGCGATAAGCACATGCATAGAGGTATGAAGAAGA
AGCATCCAGTTGATACTACTAACTCACATGAGAATGCCGGGTTTAGCCCGTTAA
CCGTGGAAACAGCTGTTAGATCGGTTGTGCCTTGCAAAGATGGAGATGACCAG
AAGCATTCTGTTTCAGTCATGGGAATTACACTGCCCCGAGTTTCTGATGAGAAG
AGCACTAGCAGTTGCAGTACCGACACTACCATTACTGACACAGCTTTAAGGGGT
GAAGACGACGATGAGGAGTACTTGTCTTTGTTTTCACCAGGTGTTTAG

FIG. 22A

>AtGRF1 SEQ ID N°: 46

MDLGVRVSGHETVSSPGQTELGSGFSNKQERSGFDGEDCWRSSKLSRTSTDGFS
SSPASAKTLSFHQGIPLLRSTTINDPRKGQEHMLSFSSASGKSDVSPYLQYCRNSG
YGLGGMMNTSNMHGNLLTGVKGPFSLTQWAELEQQALIYKYITANVPVPSSLLLSL
KKSFFPYGSLPPNSFGWGSFHLGFSGGNMDPEPGRCRRTDGKK<u>WRC</u>SRDAVPD
QKYCERHINRGRHRSRKPVEGQNGHNTNAAAAASAAAASTAAAVSKAAAGTSAVA
MRGSDNNNSLAAAVGTQHHTNNQSTDSLANRVQNSRGASVFPATMNLQSKETHP
KQSNNPFEFGLISSDSLLNPSHKQASYATSSKGFGSYLDFGNQAKHAGNHNNVDS
WPEELKSDWTQLSMSIPMAPSSPVQDKLALSPLRLSREFDPAIHMGLGVNTEFLDP
GKKTNNWIPISWGNNNSMGGPLGEVLNSTTNSPKFGSSPTGVLQKSTFGSLSNSS
SASSTIIGDNNNKNGDGKDPLGPTTLMNTSATAPSL

FIG. 22B

>At*GRF2* SEQ ID N°: 47

MDIGVHVLGSVTSNENESLGLKELIGTKQDRSGFIGEDCLQRSLKLARTTTRAEEEE
NLSSSVAAAYCKTMSFHQGIPLMRSASPLSSDSRRQEQMLSFSDKPDALDFSKYV
GLDNSSNNKNSLSPFLHQIPPPSYFRSSGGYGSGGMMMNMSMQGNFTGVKGPFT
LTQWAELEQQALIYKYITANVPVPSSLLISIKKSFYPYGSLPPSSFGWGTFHLGFAGG
NMDPEPGRCRRTDGKK<u>WRC</u>SRDAVPDQKYCERHINRGRHRSRKPVEVQSGQNQ
TAAAASKAVTTPQQPVVAGNTNRSNARASSNRSLAIGSQYINPSTESLPNNRGVSIY
PSTVNLQPKESPVIHQKHRNNNNPFEFGHISSDSLLNPNTAKTYGSSFLDFSSNQEK
HSGNHNHNSWPEELTSDWTQLSMSIPIASSSPSSTHNNNNAQEKTTLSPLRLSREL
DLSIQTDETTIEPTVKKVNTWIPISWGNSLGGPLGEVLNSTTNSPTFGSSPTGVLQK
STFCSLSNNSSVSSPIAENNRHNGDYFHYTT

FIG. 22C

>At*GRF3* SEQ ID N°: 20

MDLQLKQWRSQQQQQHQTESEEQPSAAKIPKHVFDQIHSHTATSTALPLFTPEPTS
SKLSSLSPDSSSRFPKMGSFFSWAQWQELELQALIYRYMLAGAAVPQELLLPIKKSL
LHLSPSYFLHHPLQHLPHYQPAWYLGRAAMDPEPGRCRRTDGKK<u>WRC</u>SRDVFAG
HKYCERHMHRGRNRSRKPVETPTTVNATATSMASSVAAAATTTTATTTSTFAFGG
GGGSEEVVGQGGSFFFSGSSNSSSELLHLSQSCSEMKQESNNMNNKRPYESHIG
FSNNRSDGGHILRP<u>FFD</u>DWPRSSLQEADNSSSPMSSATCLSISMPGNSSSDVSLKL
STGNEEGARSNNNGRDQQNMSWWSGGGSNHHHHNMGGPLAEALRSSSSSSPT
SVLHQLGVSTQAFH

FIG. 22D

>AtGRF4 SEQ ID N°: 21

MDLQLKQWRSQQQNESEEQGSAATKISNFFFDQIQSQTATSAAAAPLPLFVPEPTS
SSSFSCFSPDSSNSSSSSRFLKMGNFFSWAQWQELELQALIYRYMLAGASVPQEL
LLPIKKSLLHQSPMHFLHHPLQHSFPHHQPSWYWGRGAMDPEPGRCKRTDGKK<u>W</u>
<u>RC</u>SRDVVAGHKYCDRHIHRGRNRSRKPVETATTTITTTATTTASSFVLGEELGHGP
NNNHFFSSGSSQPLHLSHQQSCSSEMKQESNNNKRPYEANSGFSNGRSDDGHIL
RH<u>FFD</u>DWPRSSDSTSSPMSSSTCHLSISMPGNNTSSDVSLKLSTGNEEEEENMRN
NNNEREQMNWWSNGGNHHNNMGGPLAEALRSASSTSSVLHQMGISTQVFH

FIG. 22E

>AtGRF5 SEQ ID N°: 48

MMSLSGSSGRTIGRPPFTPTQWEELEHQALIYKYMVSGVPVPPELIFSIRRSLDTSL
VSRLLPHQSLGWGCYQMGFGRKPDPEPGRCRRTDGKK<u>WRC</u>SREAYPDSKYCEK
HMHRGRNRARKSLDQNQTTTTPLTSPSLSFTNNNNPSPTLSSSSSSNSSSTTYSAS
SSSMDAYSNSNRFGLGGSSSNTRGYFNSHSLDYPYPSTSPKQQQQTLHHASALSL
HQNTNSTSQFNVLASATDHKDFRYFQGIGERVGGVGERTFFPEASRSFQDSPYHH
HQQPLATVMNDPYHHCSTDHNKIDHHHTYSSSSSSQHLHHDHDHRQQQCFVLGA
DMFNKPTRSVLANSSRQDQNQEEDEKDSSESSKKSLHHFFGEDWAQNKNSSDSW
LDLSSHSRLDTGS

FIG. 22F

>AtGRF6 SEQ ID N°: 49

MATRIPFTESQWEELENQALVFKYLAANMPVPPHLLFLIKRPFLFSSSSSSSSSSFF
SPTLSPHFGWNVYEMGMGRKIDAEPGRCRRTDGKKWRCSKEAYPDSKYCERHM
HRGKNRSSSRKPPPTQFTPNLFLDSSSRRRRSGYMDDFFSIEPSGSIKSCSGSAME
DNDDGSCRGINNEEKQPDRHCFILGTDLRTRERPLMLEEKLKQRDHDNEEEQGSK
RFYRFLDEWPSSKSSVSTSLFI

FIG. 22G

>AtGRF7 SEQ ID N°: 50

MDFLKVSDKTTIPYRSDSLFSLNQQQYKESSFGFRDMEIHPHPTPYAGNGLLGCYY
YYPFTNAQLKELERQAMIYKYMIASIPVPFDLLVSSPSSASPCNNKNIAGDLEPGRC
RRTDGKKWRCAKEVVSNHKYCEKHLHRGRPRSRKHVEPPYSRPNNNGGSVKNR
DLKKLPQKLSSSSIKDKTLEPMEVSSSISNYRDSRGSEKFTVLATTEQENKYLNFIDV
WSDGVRSSEKQSTTSTPVSSSNGNLSLYSLDLSMGGNNLMGQDEMGLIQMGLGVI
GSGSEDHHGYGPYGVTSSLEEMSSWLAPMSTTPGGPLAEILRPSTNLAISGDIESY
SLMETPTPSSSPSRVMKKMTSSVSDESSQV

FIG. 22H

>AtGRF8 SEQ ID N°: 51

MRMLLGIPYVDKSVLSNSVLERGKQDKSKLLLVDKCHYELDVEERKEDFVGGFGFG
VVENSHKDVMVLPHHHYYPSYSSPSSSSLCYCSAGVSDPMFSVSSNQAYTSSHSG
MFTPAGSGSAAVTVADPFFSLSSSGEMRRSMNEDAGAAFSEAQWHELERQRNIYK
YMMASVPVPPELLTPFPKNHQSNTNPDVDTYRSGMFSIYADYKNLPLSMWMTVTV
AVATGGSLQLGIASSASNNTADLEPWRCKRTDGKKWRCSRNVIPDQKYCERHTHK
SRPRSRKHVESSHQSSHHNDIRTAKNDTSQLVRTYPQFYGQPISQIPVLSTLPSASS
PYDHHRGLRWFTKEDDAIGTLNPETQEAVQLKVGSSRELKRGFDYDLNFRQKEPIV
DQSFGALQGLLSLNQTPQHNQETRQFVVEGKQDEAMGSSLTLSMAGGGMEETEG
TNQHQWVSHEGPSWLYSTTPGGPLAEALCLGVSNNPSSSTTTSSCSRSSS

FIG. 22I

>AtGRF9 SEQ ID N°: 52

MQSPKMEQEEVEEERMRNKWPWMKAAQLMEFRMQALVYRYIEAGLRVPHHLVVP
IWNSLALSSSSNYNYHSSSLLSNKGVTHIDTLETEPTRCRRTDGKK<u>WRC</u>SNTVLLFE
KYCERHMHRGRKRSRKLVESSSEVASSSTKYDNTYGLDRYNESQSHLHGTISGSS
NAQVVTIASLPSARSCENVIRPSLVISEFTNKSVSHGRKNMEMSYDDFINEKEASMC
VGVVPLQGDESKPSVQKFFPEVSDKCLEAAKFSSNRKNDIIARSREWKNMNVNGG
LFHGIHFSPDTVLQERGCFRLQGVETDNEPGRCRRTDGKKWRCSKDVLSGQKYC
DKHMHRGMKKKHPVDTTNSHENAGFSPLTVETAVRSVVPCKDGDDQKHSVSVMG
ITLPRVSDEKSTSSCSTDTTITDTALRGEDDDEEYLSLFSPGV

FIG. 23A

\>OsGRF1 SEQ ID N°: 3

ATGATGATGATGAGCGGTCGCCCGAGCGGCGGCGCCGGCGGAGGTCGGTACC
CGTTCACGGCGTCGCAGTGGCAGGAGCTGGAGCACCAGGCGCTCATCTACAA
GTACATGGCGTCCGGGACTCCCATCCCCTCCGACCTCATCCTCCCCCTCCGCC
GCAGCTTCCTCCTCGACTCCGCCCTCGCCACCTCCCCTTCCCTCGCCTTCCCTC
CCCAACCTTCACTGGGGTGGGGTTGCTTTGGCATGGGGTTTGGGCGGAAGGC
GGAGGACCCGGAGCCAGGGCGATGCCGGCGTACGGACGGCAAGAAGTGGCG
GTGCTCCAAGGAGGCGTACCCGGACTCCAAGTACTGCGAGAAGCACATGCACC
GTGGCAAGAACCGTTCAAGAAAGCCTGTGGAAATGTCCTTGGCCACGCCGCC
GCCGCCGTCCTCCTCCGCCACCTCCGCCGCGTCGAACACCTCCGCCGGCGTC
GCCCCCACCACCACCACCACCTCCTCCCCGGCGCCCTCCTACAGCCGCCCGG
CGCCGCACGACGCGGCGCCGTACCAGGCGCTCTACGGCGGGCCCTACGCCG
CGGCCACCGCGCGCACCCCGCCGCCGCGGCGTACCACGCGCAGGTGAGCC
CGTTCCACCTCCAGCTCGACACCACCCACCCGCACCCGCCGCCGTCCTACTAC
TCCATGGACCACAAGGAGTACGCGTACGGGCACGCCACCAAGGAGGTGCACG
GCGAGCACGCCTTCTTCTCCGATGGCACCGAGAGGGAGCACCACCACGCCGC
CGCCGGGCACGGCCAGTGGCAGTTCAAGCAGCTCGGCATGGAGCCCAAGCAG
AGCACCACGCCTCTCTTCCCGGGCGCCGGCTACGGCCACACCGCGGCGTCGC
CGTACGCCATTGATCTTTCAAAAGAGGACGACGATGAGAAAGAGAGGCGGCAA
CAGCAGCAGCAGCAGCAGCAGCACTGCTTCCTCCTGGGCGCCGACCTCC
GTCTGGAGAAGCCGGCGGGCCACGACCACGCGGCGGCGGCGCAGAAACCTCT
CCGCCACTTCTTCGACGAGTGGCCGCATGAGAAGAACAGCAAGGGCTCCTGGA
TGGGGCTCGAAGGCGAGACGCAGCTGTCCATGTCCATCCCCATGGCCGCCAAC
GACCTCCCGATCACCACCACCTCCCGCTACCACAATGATGATTAA

FIG. 23B

>OsGRF2 SEQ ID N°: 4

ATGGCGATGCCCTTTGCCTCCCTGTCGCCGGCAGCCGACCACCGGCCCTCCTT
CATCTTCCCCTTCTGCCGCTCCTCCCCTCTCTCCGCGGTCGGGGAGGAGGCGC
AGCAGCACATGATGGGCGCGAGGTGGGCGGCGGCGGTGGCCAGGCCGCCGC
CCTTCACGGCGGCGCAGTACGAGGAGCTGGAGCAGCAGGCGCTCATATACAA
GTACCTCGTCGCCGGCGTGCCCGTCCCGGCGGATCTCCTCCTCCCCATCCGCC
GTGGCCTCGACTCACTCGCCTCGCGCTTCTACCACCACCCTGTCCTTGGATAC
GGTTCCTACTTCGGCAAGAAGCTGGACCCGGAGCCCGGACGGTGCCGGCGTA
CGGACGGCAAGAAGTGGCGGTGCTCCAAGGAGGCCGCGCCGGACTCCAAGTA
CTGTGAGCGACACATGCACCGCGGCCGCAACCGTTCAAGAAAGCCTGTGGAA
GCGCAGCTCGTCGCCCCCCACTCGCAGCCCCCGCCACGGCGCCGGCCGCC
GCCGTCACCTCCACCGCCTTCCAGAACCACTCGCTGTACCCGGCGATTGCTAA
TGGCGGCGGCGCCAACGGAGGCGGTGGTGGTGGCGGTGGCGGCAGCGC
GCCTGGCTCGTTCGCCTTGGGGTCTAATACTCAGCTGCACATGGACAATGCTG
CGTCTTACTCGACTGTTGCTGCTGGTGCCGGAAACAAAGATTTCAGGTATTCTG
CTTATGGAGTGAGACCATTGGCAGATGAGCACAGCCCACTCATCACTGGAGCTA
TGGATACCTCTATTGACAATTCGTGGTGCTTGCTGCCTTCTCAGACCTCCACATT
TTCAGTTTCGAGCTACCCTATGCTTGGAAATCTGAGTGAGCTGGACCAGAACAC
CATCTGCTCGCTGCCGAAGGTGGAGAGGGAGCCATTGTCATTCTTCGGGAGCG
ACTATGTGACCGTCGACTCCGGGAAGCAGGAGAACCAGACGCTGCGCCCCTTT
TTCGACGAGTGGCCAAAGGCAAGGGACTCCTGGCCTGATCTAGCTGATGACAA
CAGCCTTGCCACCTTCTCTGCCACTCAGCTCTCGATCTCCATTCCAATGGCAAC
CTCTGACTTCTCGACCACCAGCTCACGATCACACAACGGTATATACTCCCGATG
A

FIG. 23C

>OsGRF3 SEQ ID N°: 5

ATGGCGATGCCCTTTGCCTCCCTGTCGCCGGCAGCCGACCACCGGCCCTCCTT
CATCTTCCCCTTCTGCCGCTCCTCCCCTCTCTCCGCGGTCGGGGAGGAGGCGC
AGCAGCACATGATGGGCGCGAGGTGGGCGGCGGCGGTGGCCAGGCCGCCGC
CCTTCACGGCGGCGCAGTACGAGGAGCTGGAGCAGCAGGCGCTCATATACAA
GTACCTCGTCGCCGGCGTGCCCGTCCCGGCGGATCTCCTCCTCCCCATCCGCC
GTGGCCTCGACTCACTCGCCTCGCGCTTCTACCACCACCCTGTCCTTGGATAC
GGTTCCTACTTCGGCAAGAAGCTGGACCCGGAGCCCGGACGGTGCCGGCGTA
CGGACGGCAAGAAGTGGCGGTGCTCCAAGGAGGCCGCGCCGGACTCCAAGTA
CTGTGAGCGACACATGCACCGCGGCCGCAACCGTTCAAGAAAGCCTGTGGAA
GCGCAGCTCGTCGCCCCCACTCGCAGCCCCCGCCACGGCGCCGGCCGCC
GCCGTCACCTCCACCGCCTTCCAGAACCACTCGCTGTACCCGGCGATTGCTAA
TGGCGGCGGCGCCAACGGAGGCGGTGGTGGTGGTGGCGGTGGCGGCAGCGC
GCCTGGCTCGTTCGCCTTGGGGTCTAATACTCAGCTGCACATGGACAATGCTG
CGTCTTACTCGACTGTTGCTGCTGGTGCCGGAAACAAAGATTTCAGGTATTCTG
CTTATGGAGTGAGACCATTGGCAGATGAGCACAGCCCACTCATCACTGGAGCTA
TGGATACCTCTATTGACAATTCGTGGTGCTTGCTGCCTTCTCAGACCTCCACATT
TTCAGTTTCGAGCTACCCTATGCTTGGAAATCTGAGTGAGCTGGACCAGAACAC
CATCTGCTCGCTGCCGAAGGTGGAGAGGGAGCCATTGTCATTCTTCGGGAGCG
ACTATGTGACCGTCGACTCCGGGAAGCAGGAGAACCAGACGCTGCGCCCTTT
TTCGACGAGTGGCCAAAGGCAAGGGACTCCTGGCCTGATCTAGCTGATGACAA
CAGCCTTGCCACCTTCTCTGCCACTCAGCTCTCGATCTCCATTCCAATGGCAAC
CTCTGACTTCTCGACCACCAGCTCACGATCACACAACGGTATATACTCCCGATG
A

FIG. 23D

>OsGRF4 SEQ ID N°: 6

ATGGCGATGCCGTATGCCTCCCTGTCTCCGGCGGTGGCCGACCACCGCTCGTC
CCCGGCAGCCGCGACCGCCTCCCTCCTCCCCTTCTGCCGCTCCACCCCGCTCT
CCGCGGGCGGTGGTGGCGTCGCGATGGGGGAGGACGCGCCGATGACCGCGA
GGTGGCCGCCGGCGGCGGCGGCGAGGCTGCCGCCGTTCACCGCGGCGCAGT
ACGAGGAGCTGGAGCAGCAGGCGCTCATATACAAGTACCTGGTGGCAGGCGT
GCCCGTCCCGCCGGATCTCGTGCTCCCCATCCGCCGCGGACTCGACTCCCTC
GCCGCCCGCTTCTACAACCATCCCGCCCTTGGATATGGTCCGTACTTCGGCAA
GAAGCTGGACCCAGAGCCAGGGCGGTGCCGGCGTACGGACGGCAAGAAATGG
CGGTGCTCGAAGGAGGCCGCGCCGGATTCCAAGTACTGCGAGCGCCACATGC
ACCGCGGCCGCAACCGTTCAAGAAAGCCTGTGGAAACGCAGCTGGTCGCCCA
GTCCCAACCGCCCTCATCTGTTGTCGGTTCTGCGGCGGCGCCCCTTGCTGCTG
CCTCCAATGGCAGCAGCTTCCAAAACCACTCTCTTTACCCTGCTATTGCCGGCA
GCAATGGCGGGGGCGGGGGGAGGAACATGCCCAGCTCATTTGGCTCGGCGTT
GGGTTCTCAGCTGCACATGGATAATGCTGCCCCTTATGCAGCTGTTGGTGGTG
GAACAGGCAAAGATCTCAGGTATACTGCTTATGGCACAAGATCTTTGGCGGATG
AGCAGAGTCAACTCATTACTGAAGCTATCAACACATCTATTGAAAATCCATGGCG
GCTGCTGCCATCTCAGAACTCGCCATTTCCCCTTTCAAGCTATTCTCAGCTGGG
GGCACTAAGTGACCTTGGTCAGAACACCCCCAGCTCACTTTCAAAGGTTCAGAG
GCAGCCACTTTCGTTCTTTGGGAACGACTATGCGGCTGTCGATTCTGTGAAGCA
AGAGAACCAGACGCTGCGTCCCTTCTTTGATGAGTGGCCAAAGGGAAGGGATT
CATGGTCAGACCTCGCTGATGAGAATGCTAATCTTTCGTCATTCTCAGGCACCC
AACTGTCGATCTCCATACCAATGGCATCCTCTGACTTCTCGGCGGCCAGTTCTC
GATCAACTAATGGTGACTGA

FIG. 23E

>OsGRF5 SEQ ID N°: 53

ATGCTGAGCTCGTCGCCCTCGGCGGCGGCGCCGGGGATAGGAGGGTACCAGC
CGCAGCGCGGGGCGGCGGTCTTCACGGCGGCGCAGTGGGCGGAGCTGGAGC
AGCAGGCGCTCATTTACAAGTACCTCGTCGCCGGTGTCCCCGTCCCGGGCGAT
CTCCTCCTCCCAATCCGCCCCCACTCCTCCGCCGCCGCCACCTACTCCTTCGC
CAACCCCGCCGCCGCGCCCTTCTACCACCACCACCACCACCCCTCTCTGAGCT
ATTATGCCTACTATGGCAAGAAGCTTGACCCTGAGCCGTGGCGTTGCCGCCGC
ACCGACGGCAAGAAGTGGCGGTGCTCCAAGGAGGCGCACCCCGACTCCAAGT
ACTGCGAGCGCCACATGCACCGTGGCCGCAACCGTTCAAGAAAGCCTGTGGA
ATCCAAGACCGCTGCCCCTGCGCCCCAGTCGCAGCCCCAGCTGTCCAATGTCA
CGACCGCGACTCACGACACCGATGCGCCTCTCCCGTCACTCACTGTGGGTGCT
AAAACCCACGGTCTGTCCCTTGGTGGTGCTGGCTCGTCGCAGTTCCATGTCGA
CGCACCATCGTACGGCAGCAAGTACTCTCTTGGAGCTAAAGCTGATGTGGGTG
AACTGAGCTTCTTCTCAGGAGCATCAGGAAACACCAGGGGCTTCACCATTGATT
CTCCAACAGATAGCTCATGGCATTCACTGCCTTCCAGTGTACCCCATACCCGA
TGTCAAAGCCAAGGGACTCTGGCCTCCTACCAGGTGCCTACTCCTACTCCCACC
TTGAACCTTCACAGGAACTTGGCCAGGTCACCATCGCCTCGCTGTCCCAAGAG
CAGGAGCGCCGCTCTTTTGGTGGTGGAGCGGGGGGGATGCTAGGAAATGTGA
AGCACGAGAACCAGCCGCTGAGGCCTTTCTTCGATGAGTGGCCTGGGAGGCGA
GACTCGTGGTCGGAGATGGATGAGGAGAGGTCCAACCAGACCTCCTTCTCGAC
AACCCAGCTCTCGATCTCCATCCCGATGCCCAGATGTGATTGA

FIG. 23F

>OsGRF6 SEQ ID N°: 54

ATGCAGGGTGCAATGGCCAGGGTGAGGGGTCCCTTCACGCCGTCTCAGTGGAT
CGAGCTGGAGCACCAGGCGCTGATATACAAGTACTTGGCTGCGAATAGCCCTG
TACCACACAGCCTCCTCATCCCCATCAGGAGGAGCCTCACATCGCCCTACTCAC
CTGCCTACTTTGGCTCAAGCACATTGGGATGGGGATCTTTCCAGCTGGGCTACT
CCGGCAGCGCGGATCCGGAGCCCGGCCGGTGCCGCCGGACGGACGGCAAGA
AATGGCGGTGCTCGAGGGATGCGGTCGCCGACCAGAAGTACTGTGAGCGACA
CATGAACCGGGGACGCCACCGTTCAAGAAAGCATGTGGAAGGCCAGCCTGGC
CATGCCGCGAAAGCGATGCCCGCGGCGGTGGCAGCAGCCGCTGCCTCTGCTA
CCCAGCCTAGTGCTCCGGCCGCCCACAGTGGCGGAGCTGTTGCTGGCCTCGC
TATCAACCATCAGCACCAGCAAATGAAGAACTACGCTGCCAACACTGCCAATCC
TTGCTCTCTGCAATATAGCAGGGATCTGGCAAACAAGCATAATGAGAGTGAACA
AGTGCAAGACTCAGACAGTCTCTCGATGCTGACTTCCATTAGCACGAGAAATAC
GGGCAGCCTGTTTCCGTTCTCAAAACAACATAATCCTTTTGAAGTGTCCAACTCA
AGGCCAGATTTTGGCCTAGTATCACCTGATTCACTGATGAGTTCTCCTCATAGCT
CCTTGGAGAACGTCAATTTGCTCACTTCGCAGAGTCTGAATGAACAACAGAGTT
CAGTTTCCCTTCAACACTTTGTGGACTGGCCAAGGACACCTGCACAAGGAGCTC
TCGCATGGCCTGATGCTGAAGACATGCAAGCTCAGAGAAGCCAGCTCTCAATAT
CTGCTCCAATGGCGTCTTCTGACCTGTCATCAGCCTCAACATCTCCCATCCATG
AGAAGCTGATGTTGTCACCACTTAAACTGAGCCGTGAATATAGTCCTATTGGTCT
CGGTTTTGCAGCAAATAGAGATGAGGTTAACCAGGGAGAAGCAAACTGGATGC
CTATGTTCCGTGATTCTTTGATGGGCGGACCATTGGGAGAGGTTTTAACCAAGA
ATAACAACATGGAAGCAAGGAATTGCCTATCGGAGTCTCTGAATCTTTTAAATGA
TGGCTGGGATTCAAGCTCAGGGTTTGATTCATCCCCAGTTGGTGTTCTGCAGAA
GACCACCTTTGGATCAGTATCCAGTAGCACCGGAAGCAGTCCTAGACTGGAGA
ATCATAGTGTTTATGATGGCAACAGTAACCTGCGGGATGATCTCGGTTCAGTTG
TTGTAAATCATCCGAGCATCCGCCTGGTGTGA

FIG. 23G

>OsGRF7 SEQ ID N°: 55

ATGGCAATGGCGACCCCTACGACCAACGGCAGCTTCCTTCTTGGATCAGGGTT
GGATTGTGGAAGCTCAGATGTGGCAAGAATGCAGGGGGTTTTAGCAAGGGTTA
GGGGGCCATTCACACCAACACAATGGATGGAGCTGGAGCACCAGGCTCTGATC
TACAAGCACATTGTGGCGAATGCGCCGGTACCGGCCGGCTTGCTCCTCCCCAT
CAGGAGAAGCCTCCATCCACCAGTGTTCCCACACTTCTCCTCTGGTGGCATTCT
TGGCTCCAGCTCCTTGGGATGGGGGTCATTTCAGCTGGGCTATTCTGGGAGTG
CTGACTCCGAGCCCGGGAGATGCCGTCGAACCGATGGCAAGAAATGGCGGTG
CTCGAGAGACGCAGTTGTCGACCAAAAGTACTGCGAGCGGCACATAAACCGGG
GTCGCCACCGTTCAAGAAAGCATGTGGAAGGCCAATCTAGCCATGCCGCAAAA
GCAACGGTTCCCGCCATAGCACAACCACCCATTGGTGCATCTAATGGCAAATTG
TCAGGCAGCCATGGTGTGTCAAATGAGCTCACGAAAACCTTGGCTACTAACAGG
ATGATGTTGGATAAAGCAAATCTTATTGAACGCTCCCAGGACTACACTAATCAGC
AACACAACATCCTACAGAACAACACAAAAGGTGATAATTGGTCTGAAGAGATGT
CCTCACAAGCAGACTATGCAGTAATCCCTGCTGGCTCTCTCATGAACACACCGC
AATCGGCGAATTTAAATCCAATTCCCCAGCAACAACGCTGTAAGCAGTCACTCTT
TGGCAAAGGGATACAGCATGATGACATTCAGCTGTCGATATCCATTCCCGTGGA
TAACTCCGACTTACCCACTAACTACAACAAGGCTCAAATGGACCATGTAGTAGG
CGGTTCATCGAATGGCGGAAACAACACGCGAGCAAGTTGGATACCGGGCTCCT
GGGAAGCGTCCATAGGTGGACCTCTGGGTGAGTTCTTCACCAACACCAGCAGC
GCATCAGACGACAAAGGCAAAGCCGCCACCCGCCATCTTTGAACCTCTTAGCT
GATGGACATACTACAAGTCCACAGCTGCAATCGCCCACCGGAGTCCTGCAGAT
GACTAGCTTCAGTTCAGTGCCCAGCAGCACTGTTAGTAGTCCTGCAGGCAGCCT
CTGCAATGGCTTGCTCACTTCAGGCCTGGTGAATGCCCAGACTGTCCAAACACT
GTGA

FIG. 23H

>OsGRF8 SEQ ID N°: 56

ATGCTGAGCTCTTGTGGTGGCCATGGCCATGGAAATCCAAGAAGCTTGCAAGAA
GAACACCATGGCAGATGTGGTGAGCAGCAAGGTGGAGGAGGAGGAGGAGGGC
AAGAGCAAGAGCAAGATGGGTTCTTGGTGAGAGAGGCAAGGGCATCCCCACCA
TCTCCATCTTCTTCATCATTTCTTGGATCCACAAGCTCTTCTTGTTCTGGAGGAG
GAGGAGGAGGGCAGATGTTGAGCTTCTCCTCCCCAATGGAACAGCAGGGTTG
GGCTTGAGCTCAGGAGGAAGCATGCAGGGGGTCTTGGCAAGGGTCAGGGGGC
CGTTCACCCCAACACAGTGGATGGAGCTGGAGCACCAGGCACTGATCTACAAG
CACATTGCTGCAAATGTTTCTGTCCCTTCCAGCTTGCTCCTCCCCATCAGGAGA
AGCCTCCATCCATGGGGATGGGGATCATTCCCTCCTGGCTGTGCTGATGTAGA
ACCCAGAAGATGCCGCCGCACAGACGGCAAGAAGTGGCGGTGCTCCAGAGAT
GCTGTTGGGGATCAGAAGTATTGTGAGCGACACATAAACCGTGGTCGCCAT**CG
TTCAAGAAAGCATGTGGAA**GGCCGAAAGGCGACACTCACCATTGCAGAACCAT
CCACGGTTATTGCTGCTGGTGTATCATCTCGCGGCCACACTGTGGCTCGGCAG
AAGCAGGTGAAAGGCTCAGCTGCTACTGTCTCTGATCCTTTCTCGAGACAATCC
AACAGGAAATTTCTGGAGAAACAGAACGTTGTCGACCAATTGTCTCCCATGGAT
TCATTTGATTTCTCATCCACACAATCTTCTCCAAACTATGACAATGTAGCATTGTC
ACCACTGAAGTTGCACCATGATCATGATGAATCTTACATCGGGCATGGAGCAGG
CAGTTCATCAGAAAAGGCAGTATGATGTACGAAAGTCGGTTAACAGTCTCTAA
GGAAACACTTGATGATGGACCTTTAGGTGAAGTTTTCAAAAGAAAGAATTGCCAA
TCAGCTTCTACAGAAATCTTAACTGAAAAATGGACTGAGAACCCCAACTTACATT
GCCCATCTGGAATCCTACAAATGGCTACTAAGTTCAATTCAATTTCCAGCGGCAA
CACAGTAAATAGTGGTGGCACCGCAGTGGAGAATCTTATCACTGATAATGGATA
TCTTACTGCAAGAATGATGAATCCTCATATTGTCCCAACACTTCTCTAA

FIG. 23I

>OsGRF9 SEQ ID N°: 57

ATGTTTGCTGACTTCTCTGCTGCTGCCATGGAGCTTGGAGAGGTGTTGGGCTTG
CAAGGACTCACAGTGCCATCCACCAAGGAGGGTGATCTGAGCCTCATCAAGAG
AGCTGCTGCTGGTAGCTTCACCCAGGCTGCTGCTGCATCATACCCTTCCCCCTT
TCTTGATGAACAGAAGATGCTCAGATTCGCCAAGGCTGCTCACACATTGCCATC
AGGTTTGGATTTTGGGAGGGAAAATGAGCAGAGGTTCTTGTTGTCTAGGACCAA
GAGGCCTTTCACTCCCTCACAGTGGATGGAGCTGGAGCACCAGGCTCTCATTTA
CAAGTATCTCAATGCAAAGGCCCCTATACCTTCCAGCCTGCTCATTTCAATCAGC
AAAAGCTTCAGATCATCAGCTAACAGAATGAGCTGGAGGCCTCTCTATCAAGGC
TTCCCAAATGCAGACTCTGACCCAGAACCTGGAAGATGCCGTCGAACAGATGG
CAAGAAATGGCGGTGTTCAAAGGAGGCCATGGCCGACCACAAGTATTGTGAGA
GGCACATCAACAGAAACCGCCACCGTTCAAGAAAGCCTGTGGAAAACCAAAGT
AGAAAGACTGTGAAAGAGACACCGTGTGCTGGCTCATTGCCATCTTCTGTCGGG
CAGGGCAGCTTCAAGAAGGCAAAAGTTAATGAAATGAAGCCACGCAGTATCAGC
TATTGGACAGATAGTTTGAACAGGACAATGGCGAACAAAGAGAAAGGAAACAAA
GCTGCTGAAGAAAACAATGGCCCACTGCTAAATTTAACGAATCAACAGCCAACA
TTGTCCCTGTTCTCTCAGTTGAAGCAACAGAACAAACCGGAGAAGTTCAATACA
GCAGGAGACAGTGAATCGATTTCTTCAAATACCATGTTGAAGCCTTGGGAGAGC
AGCAACCAGCAGAACAACAAAAGCATTCCTTTCACCAAGATGCATGATCGTGGA
TGCCTTCAGTCAGTCCTTCAGAATTTCAGCTTGCCTAAGGACGAGAAAATGGAG
TTTCAGAAAAGCAAAGATTCCAATGTCATGACAGTTCCATCAACTTTCTATTCCT
CGCCAGAGGACCCACGCGTCAGCTGCCATGCACCTAATATGGCACAAATGCAA
GAGGATAGCATCTCAAGTTCTTGGGAGATGCCTCAAGGTGGACCTCTAGGTGA
GATCTTGACAAACTCCAAAAATCCTGACGATTCAATCATGAAACCAGAAGCAAG
GCCATATGGTTGGTTACTGAACCTCGAGGATCATGCAATGTGA

FIG. 23J

>OsGRF10 SEQ ID N°: 58

ATGGATGAGGAGAAGGAAGCCGACTCGCCGCAGCCACCGTCCAAGCTGCCTC
GCCTCTCCGGCGCTGACCCGAATGCCGGAGTGGTGACCATGGCAGCACCCCC
GCCGCCGGTGGGTCTTGGGCTGGGGCTTGGACTCGGCGGCGACAGCCGCGG
CGAGCGTGACGTGGAAGCGTCGGCGGCGGCGGCGCACAAGGCGACGGCGCT
GACGTTCATGCAGCAGCAGGAGCTGGAGCACCAGGTGCTCATCTACCGCTACT
TCGCCGCGGGCGCGCCCGTGCCGGTGCACCTCGTGCTCCCCATCTGGAAGAG
CGTCGCGTCCTCCTCCTTCGGCCCGCACCGCTTCCCTTCCCTGGCAGTGATGG
GGTTGGGGAACCTGTGCTTCGACTACCGGAGCAGCATGGAGCCGGACCCAGG
GCGGTGCAGGCGCACGGACGGCAAGAAGTGGCGGTGCTCGCGCGACGTGGT
GCCGGGGCACAAGTACTGCGAGCGGCACGTCCACCGCGGACGCGGC**CGTTCA
AGAAAGCCTGTGGAA**GCCTCCGCGGCCGCCACCCCGGCGAACAACGGCGGC
GGCGGTGGCATCGTCTTCTCCCCCACCAGCGTCCTCCTCGCCCACGGCACCGC
GCGCGCCACCTGA

FIG. 23K

>OsGRF11 SEQ ID N°: 59

ATGGCGGCGGAGGGGGAGGCCAAGAAGGACAGCGCCAGCAACCCTCCCGGG
GGAGGAGGCGGCGGAGGTGGAGGGGAGGAGGAGGAGGATAGCAGCCTGGCT
GTCGGGGAGGCGGCGGTCGGGGTGGGCGAGGCTGGTGGAGGAGGAGGAGGA
GGGGAGAAGGCGGATCGAGAGGAGGAGGAGGGGAAGGAGGATGTGGAGGAG
GGCGGCGTGTGTAAGGATCTGGTGCTCGTCGAGGACGCCGTCCCCGTCGAGG
ATCCGGAGGAAGCCGCAGCAACTGCAGCACTTCAGGAAGAAATGAAAGCGCTC
GTTGAATCCGTCCCAGTTGGTGCTGGGGCGGCATTCACCGCGATGCAACTACA
GGAGCTTGAGCAGCAATCTCGTGTCTACCAGTATATGGCTGCCCGTGTGCCTGT
GCCTACTCATCTCGTCTTCCCAATATGGAAGAGTGTTACTGGTGCATCTTCTGAA
GGCGCCCAGAAGTACCCGACATTGATGGGGTTGGCAACACTCTGCTTGGACTT
TGGAAAGAACCCAGAACCAGAACCTGGGAGGTGCCGGCGAACTGATGGAAAGA
AGTGGCGGTGCTGGAGAAATGCAATTGCAAATGAGAAATATTGCGAACGCCATA
TGCACCGTGGCCGCAAGCGTCCTGTACAGCTTGTTGTCGAGGATGACGAGCCT
GATTCTACCTCAGGGTCGAAACCAGCATCTGGCAAGGCCACCGAAGGTGGCAA
GAAGACTGATGACAAGAGCTCAAGTAGCAAGAAGCTTGCAGTGGCAGCACCAG
CTGCTGTGGAGTCTACATGA

FIG. 23L

>OsGRF12 SEQ ID N°: 60

ATGTTGGCCGAGGGAAGGCAAGTCTACTTGCCGCCGCCGCCGTCCAAGCT
TCCTCGTCTCTCCGGCACCGATCCAACCGACGGCGTGGTGACGATGGCAGCGC
CGTCGCCGCTGGTTCTTGGGCTGGGTCTCGGTCTGGGCGGCAGCGGCAGCGA
CAGCAGTGGGAGCGACGCGGAAGCGTCTGCGGCCACCGTGCGGGAGGCGCG
GCCGCCGTCGGCGCTGACGTTCATGCAGCGGCAGGAGCTGGAGCAGCAGGTG
CTCATCTACCGCTACTTCGCCGCCGGCGCGCCTGTGCCGGTTCACCTCGTGCT
GCCCATATGGAAGAGCATCGCCGCCGCCTCCTCGTTCGGCCCGCAAAGCTTTC
CCTCCCTGACGGGCCTGGGGAGCCTGTGCTTCGACTACAGGAGCAGCATGGA
GCCGGAGCCGGGGCGGTGCCGGCGCACGGACGGCAAGAAGTGGCGGTGCTC
GCGCGACGTGGTGCCGGGGCACAAGTATTGCGAGCGGCACGTCCACCGTGGC
CGCGGCCGTTCAAGAAAGCCTATGGAAGCCTCTGCAGCAGTCGCTCCCACATA
TCTCCCGGTCCGGCCGGCACTCCACACCGTCGCCACCCTCGCCACCAGCGCG
CCATCGCTGTCGCACCTCGGTTTCTCCTCCGCCAGCAAAGTGCTCCTCGCCCA
CACCACCACCGGCACCACGCGCGCTACTTGA

FIG. 24A

>OsGRF1 SEQ ID N°: 22

MMMMSGRPSGGAGGGRYPFTASQWQELEHQALIYKYMASGTPIPSDLILPLRRSF
LLDSALATSPSLAFPPQPSLGWGCFGMGFGRKAEDPEPGRCRRTDGKKWRCSKE
AYPDSKYCEKHMHRGKNRSRKPVEMSLATPPPPSSSATSAASNTSAGVAPTTTTT
SSPAPSYSRPAPHDAAPYQALYGGPYAAATARTPAAAAYHAQVSPFHLQLDTTHP
HPPPSYYSMDHKEYAYGHATKEVHGEHAFFSDGTEREHHHAAAGHGQWQFKQLG
MEPKQSTTPLFPGAGYGHTAASPYAIDLSKEDDDEKERRQQQQQQQQQHCFLLG
ADLRLEKPAGHDHAAAAQKPLRHFFDEWPHEKNSKGSWMGLEGETQLSMSIPMA
ANDLPITTTSRYHNDD

FIG. 24B

>Os*GRF2* SEQ ID N°: 23

MMAGGGSGRCLFTATQWQELEHQALIYKYMAAGAPVPPDLLLHLRHRAAAAAAAD
VDTVPSLAFPPHHLGWGCYGAAAAQYGRRVEDPEPGRCRRTDGKKWRCSREAY
GESKYCEKHMHRGKNRSRKPVEMPPPAAAAVYRPSALSISPPPHDADAPSYGAGA
GAPLQLHLDSFHASTSPPPSYHRYAHTSSAPLFPSSAAGYGGGWSLSKEHCLTLG
GAAADLSLDKPADHHHDATSATTEKPLRRFFDEWPRSDDGRTPWDGTQLSISIPTA
AAASPDLAIAGAASRYHSNGDHLRTSE

FIG. 24C

>Os*GRF3* SEQ ID N°: 24

MAMPFASLSPAADHRPSFIFPFCRSSPLSAVGEEAQQHMMGARWAAAVARPPPFT
AAQYEELEQQALIYKYLVAGVPVPADLLLPIRRGLDSLASRFYHHPVLGYGSYFGKK
LDPEPGRCRRTDGKKWRCSKEAAPDSKYCERHMHRGRNRSRKPVEAQLVAPHS
QPPATAPAAAVTSTAFQNHSLYPAIANGGGANGGGGGGGGGSAPGSFALGSNT
QLHMDNAASYSTVAAGAGNKDFRYSAYGVRPLADEHSPLITGAMDTSIDNSWCLLP
SQTSTFSVSSYPMLGNLSELDQNTICSLPKVEREPLSFFGSDYVTVDSGKQENQTL
RPFFDEWPKARDSWPDLADDNSLATFSATQLSISIPMATSDFSTTSSRSHNGIYSR

FIG. 24D

>OsGRF4 SEQ ID N°: 25

MAMPYASLSPAVADHRSSPAAATASLLPFCRSTPLSAGGGGVAMGEDAPMTARW
PPAAAARLPPFTAAQYEELEQQALIYKYLVAGVPVPPDLVLPIRRGLDSLAARFYNH
PALGYGPYFGKKLDPEPGRCRRTDGKKWRCSKEAAPDSKYCERHMHRGRNRSR
KPVETQLVAQSQPPSSVVGSAAAPLAAASNGSSFQNHSLYPAIAGSNGGGGRNM
PSSFGSALGSQLHMDNAAPYAAVGGGTGKDLRYTAYGTRSLADEQSQLITEAINTSI
ENPWRLLPSQNSPFPLSSYSQLGALSDLGQNTPSSLSKVQRQPLSFFGNDYAAVD
SVKQENQTLRP<u>FFD</u>EWPKGRDSWSDLADENANLSSFSGTQLSISIPMASSDFSAAS
SRSTNGD

FIG. 24E

>OsGRF5 SEQ ID N°: 61

MLSSSPSAAAPGIGGYQPQRGAAVFTAAQWAELEQQALIYKYLVAGVPVPGDLLLPI
RPHSSAAATYSFANPAAAPFYHHHHHPSLSYYAYYGKKLDPEPWRCRRTDGKKW
RCSKEAHPDSKYCERHMHRGRNRSRKPVESKTAAPAPQSQPQLSNVTTATHDTD
APLPSLTVGAKTHGLSLGGAGSSQFHVDAPSYGSKYSLGAKADVGELSFFSGASG
NTRGFTIDSPTDSSWHSLPSSVPPYPMSKPRDSGLLPGAYSYSHLEPSQELGQVTI
ASLSQEQERRSFGGGAGGMLGNVKHENQPLRP<u>FFD</u>EWPGRRDSWSEMDEERSN
QTSFSTTQLSISIPMPRCGSPIGPRLP

FIG. 24F

>OsGRF6 SEQ ID N°: 62

MQGAMARVRGPFTPSQWIELEHQALIYKYLAANSPVPHSLLIPIRRSLTSPYSPAYF
GSSTLGWGSFQLGYSGSADPEPGRCRRTDGKKWRCSRDAVADQKYCERHMNRG
RHRSRKHVEGQPGHAAKAMPAAVAAAAASATQPSAPAAHSGGAVAGLAINHQHQ
QMKNYAANTANPCSLQYSRDLANKHNESEQVQDSDSLSMLTSISTRNTGSLFPFSK
QHNPFEVSNSRPDFGLVSPDSLMSSPHSSLENVNLLTSQSLNEQQSSVSLQHFVD
WPRTPAQGALAWPDAEDMQAQRSQLSISAPMASSDLSSASTSPIHEKLMLSPLKLS
REYSPIGLGFAANRDEVNQGEANWMPMFRDSLMGGPLGEVLTKNNNMEARNCLS
ESLNLLNDGWDSSSGFDSSPVGVLQKTTFGSVSSSTGSSPRLENHSVYDGNSNLR
DDLGSVVVNHPSIRLV

FIG. 24G

>OsGRF7 SEQ ID N°: 63

MAMATPTTNGSFLLGSGLDCGSSDVARMQGVLARVRGPFTPTQWMELEHQALIYK
HIVANAPVPAGLLLPIRRSLHPPVFPHFSSGGILGSSSLGWGSFQLGYSGSADSEPG
RCRRTDGKKWRCSRDAVVDQKYCERHINRGRHRSRKHVEGQSSHAAKATVPAIA
QPPIGASNGKLSGSHGVSNELTKTLATNRMMLDKANLIERSQDYTNQQHNILQNNT
KGDNWSEEMSSQADYAVIPAGSLMNTPQSANLNPIPQQQRCKQSLFGKGIQHDDI
QLSISIPVDNSDLPTNYNKAQMDHVVGGSSNGGNNTRASWIPGSWEASIGGPLGEF
FTNTSSASDDKGKSRHPPSLNLLADGHTTSPQLQSPTGVLQMTSFSSVPSSTVSSP
AGSLCNGLLTSGLVNAQTVQTL

FIG. 24H

>OsGRF8 SEQ ID N°: 64

MLSSCGGHGHGNPRSLQEEHHGRCGEQQGGGGGGQEQEQDGFLVREARASP
PSPSSSSFLGSTSSSCSGGGGGGQMLSFSSPNGTAGLGLSSGGSMQGVLARVRG
PFTPTQWMELEHQALIYKHIAANVSVPSSLLLPIRRSLHPWGWGSFPPGCADVEPR
RCRRTDGKKWRCSRDAVGDQKYCERHINRGRHRSRKHVEGRKATLTIAEPSTVIA
AGVSSRGHTVARQKQVKGSAATVSDPFSRQSNRKFLEKQNVVDQLSPMDSFDFS
STQSSPNYDNVALSPLKLHHDHDESYIGHGAGSSSEKGSMMYESRLTVSKETLDD
GPLGEVFKRKNCQSASTEILTEKWTENPNLHCPSGILQMATKFNSISSGNTVNSGG
TAVENLITDNGYLTARMMNPHIVPTLL

FIG. 24I

>OsGRF9 SEQ ID N°: 65

MFADFSAAAMELGEVLGLQGLTVPSTKEGDLSLIKRAAAGSFTQAAAASYPSPFLD
EQKMLRFAKAAHTLPSGLDFGRENEQRFLLSRTKRPFTPSQWMELEHQALIYKYLN
AKAPIPSSLLISISKSFRSSANRMSWRPLYQGFPNADSDPEPGRCRRTDGKKWRCS
KEAMADHKYCERHINRNHRSRKPVENQSRKTVKETPCAGSLPSSVGQGSFKKAK
VNEMKPRSISYWTDSLNRTMANKEKGNKAAEENNGPLLNLTNQQPTLSLFSQLKQ
QNKPEKFNTAGDSESISSNTMLKPWESSNQQNNKSIPFTKMHDRGCLQSVLQNFS
LPKDEKMEFQKSKDSNVMTVPSTFYSSPEDPRVSCHAPNMAQMQEDSISSSWEM
PQGGPLGEILTNSKNPDDSIMKPEARPYGWLLNLEDHAM

FIG. 24J

>OsGRF10 SEQ ID N°: 66

MDEEKEADSPQPPSKLPRLSGADPNAGVVTMAAPPPPVGLGLGLGLGGDSRGER
DVEASAAAAHKATALTFMQQQELEHQVLIYRYFAAGAPVPVHLVLPIWKSVASSSF
GPHRFPSLAVMGLGNLCFDYRSSMEPDPGRCRRTDGKKWRCSRDVVPGHKYCE
RHVHRGRGRSRKPVEASAAATPANNGGGGGIVFSPTSVLLAHGTARAT

FIG. 24K

>OsGRF11 SEQ ID N°: 67

MAAEGEAKKDSASNPPGGGGGGGGGEEEEDSSLAVGEAAVGVGEAGGGGGGG
EKADREEEEGKEDVEEGGVCKDLVLVEDAVPVEDPEEAAATAALQEEMKALVESV
PVGAGAAFTAMQLQELEQQSRVYQYMAARVPVPTHLVFPIWKSVTGASSEGAQKY
PTLMGLATLCLDFGKNPEPEPGRCRRTDGKKWRCWRNAIANEKYCERHMHRGRK
RPVQLVVEDDEPDSTSGSKPASGKATEGGKKTDDKSSSSKKLAVAAPAAVEST

FIG. 24L

>OsGRF12 SEQ ID N°: 68

MLAEGRQVYLPPPPPSKLPRLSGTDPTDGVVTMAAPSPLVLGLGLGLGGSGSDSS
GSDAEASAATVREARPPSALTFMQRQELEQQVLIYRYFAAGAPVPVHLVLPIWKSIA
AASSFGPQSFPSLTGLGSLCFDYRSSMEPEPGRCRRTDGKKWRCSRDVVPGHKY
CERHVHRGRGRSRKPMEASAAVAPTYLPVRPALHTVATLATSAPSLSHLGFSSASK
VLLAHTTTGTTRAT

FIG. 25A

>ZmGRF1 SEQ ID N°: 7 gacaggttgagatggcgatgccgtatgcctctctttccccggcaggcgccgccgaccaccgctcctccacagccacg
gcgtccctcgtccccttctgccgctccaccccgctctccgcgggcggcgggctgggggaggaggacgcccaggcga
gcgcgaggtggccggccgcgaggccggtggtgccgttcacgccggcgcagtaccaggagctggagcagcaggc
gctcatatacaagtacctggtggccggcgtgcccgttccgccggatctcgtggttccaatccgccgcggcctcgactcc
ctcgctacccgcttctacggccaacccacactcgggtacggaccgtacctggggaggaaactggatccggagcccg
gccggtgccggcgaacggacggcaagaagtggcggtgctccaaggaagccgccccggactccaagtactgcga
gcgccacatgcaccgcggccgcaaccgttcaagaaagcctgtggaaacgcagctcgcgcccagtcccaaccg
cccgccgccgcggccgtctccgccgctccgccctggcagccgccgccgccgccgccaccaacggcagcggcttc
cagaaccactctctctacccggccatcgccggcagcactggtggtggaggaggagttggcgggtccggcaatatctc
ctccccgttctcctcgtcgatgggggatcgtctcagctgcacatggacagtgttgccagctactcctacgcagctcttgg
tggtggaactgcaaaggatctcaggtacaacgcttacggaataagatctctggcggacgagcacaaccagctgatc
gcagaagccatcgactcgtcgatagagagccagaggcgcctccccagctcgtcgttcccgctctcgagctacccac
atctcggggcgctgggcgacctgggcggccagaacagcacggtgagctcgctgccgaagatggagaagcagca
gccgccctcgtccttcctagggaacgacaccggggccggcatggccatgggctccgcctccgcgaagcaggaggg
ccagacgctgcggcacttcttcgacgagtggcccaaggcgcgggactcctggccgggcctctccgacgagaccgc
cagcctcgcctcgtccccccggcgacccagctgtcgatgtccatacccatggcgtcctccgacttctccgtggccagc
tcccagtcgcccaacgatgactaatggtgcgtggatcgtcgcgttctggccctttgtctatctcccctccagtcctccaccc
accgcgcagtagtagctgcggaaacagcccatgctcctgtatatttgtcggtcattttccgtgtcagatctgtgtaccaaa
ccaagcggcgg

FIG. 25B

>Zm*GRF2* SEQ ID N°: 69

Ccatctggccatctcccttccctgctccccgaagcagcaagccagcctgcccaccgcagccatcacctccgcc gctctccaccatgaatcccatccaccagcacgacatcgtacccaatccttcgtgactgttgcctccgcgcatctccggg agcaatggaaggaggccgagatgtgttcttaggtgcggcggcaagggcgccgccgccgccgtcttgcccgtttc acggatccgctaccgccacccgctccggtggagcgcagatgctcagcttctcctccaatggcgtagcagggttgggtc tgtgctcaggtgccagcaagatgcagggtgtgttgtcgagggtgaggaggcccttcactccgacgcagtggatggag ctggagcaccaggccctgatctacaagcacttcgctgtgaatgcccctgtgccgtccagcttgctcctccctatcaaaa gaagcctcaatccatggagcagccttggctccagctcattgggatgggcaccatttcgttccggctctgctgatgcaga accaggaagatgccgccgcacagatggcaagaagtggcggtgctctagagatgctgtcggggaccaaaaatactg tgagcgatacataaaacgtggttgccaccgttcaagaaagcatgtggaaggccgaaaggcaacaccgaccact gcagatccaaccatggctgtttctggtggttcattgttgcacagccatgctgttgcttggcagcagcagggcaaaagctc agctgctaatgtgactgatccattctcactagggtccaacaggaatttgctggataagcagaatctaggtgaccagttct ctgtatccacttccatggactcctttgacttctcatcatcacattcttccccaaaccaagccaaagttgcattttcaccggtg gccatgcagcacgaacatgatcagctgtatcttgtgcatggagccggcagctcagcagaaaacgttaacaagtctca ggatggtcagctgctagtctcgagggaaacaattgacgacggacctctgggcgaggtgttcaagggcaagagttgcc agtcagcatccgcagacatcttaactgaccattggacttcgactcgtgacttgcgtcctccaaccggagtcctacaaat gtctagcagcaacacagtgccagcagagaatcacacgagtaacagtagctatctcatggcgaggatggcgaattct cagaccgtcccaacactccactgagtgttcatcaggctggtctttgttgggaccacaaaataactgaagccatgttgatg tcctgagtttgctgatacagtgatactaggttttcagtcgagtcttgtaactcctgttttagagttgttatatgttcacgtcatgtt gcctttcattttcggtttcattcagatgggtgtactaataatttctttccttcttacctgtgaaggatttgagttccaatctgagac gtgggt

FIG. 25C

>ZmGRF3 SEQ ID N°: 8 tagccgtgctccgctcaccttctctcgcgctacagtctcaaggggtagctagccaagctaccaagctcgtcaggaacg
agagaaagaggccggcggtgcgcggggatgatgatgatgagcagcggccgggcgggcggcggggccaccgcg
gggcggtacccgttcacggcgtcgcagtggcaggagctggagcaccaggcgctcatctacaagtgcctggcgtccg
gcaagcccatcccttcctacctcatgccgccgctccgccgcatcctcgactccgccctcgccacgtcgccgtccctcgc
ctacccgccgcaaccctcgctgggctggggctgcttcgggatgggcttcacccggaaggccgacgaggacccgga
gcccgggcggtgccggcgcacggacggcaagaagtggcgctgctccaaggaggcgtaccggactccaagtact
gcgagaagcacatgcaccggggcaagaaccgttcaagaaagcctgtggaaatgtccttggccacgccggcccc
ggcgccggcccccgccgccgccacaaccgccaccgccacctcatccccggcgccgtcctaccaccgcccggccc
acgacgccacgccgtctccgtaccacgcgctgtatgcgaggcggcggcggcggcggcggtagcccttactcggcgtc
ggcacgcccaggagcaaccggaggcggcggcgcgtaccaccacgcgcagcatgtgagcccttccacctccacc
tcgagaccacccacccgcacccgccgccgccctacaactactccgccgaccagagggactacgcgtacgggcac
gcggccgccaaggaggtcggcgagcacgccttcttctcggacggcgcggggcgagcgggtcgaccgccaggccgc
ggcggggcagtggcagttcaggcagctcggggtggagacgaagccgggcccccacgccgctgttccccgtcgccg
ggtacgggcacggcgcggcgtcgccgtacggcgtcgagctgggcaaggacgacgacgagcaggaggagaggc
gccgccagcactgcttcgttcttggagccgacctgcggctggagcggccgtcgtcgggccatggccatggccatggc
catgaccatgacgacgccgccgccgcgcagaagccgctccggcccttcttcgacgagtggccgcaccagaaggg
ggacaaggccgggtcgtggatggggctcgacggcgagacgcagctctccatgtccatccccatggccgctaccgac
ctccccgtcacctcccgcttccgtaacgacgagtgatgccacatcaaacctggcgctggaaactcggaacgtatggtg

FIG. 25D

>ZmGRF4 SEQ ID N°: 70

Tcccttcaccgctgcctcgacccgcgccgaaagataccttcccccccttcctctcgcgccgccgttttggtgcgaccat
ggcggcggagggggaggccaagaacccgtccggcggtggcgaagggggtaaccccccagcaccagcaggcagt
gcaggctgcgccggcggagccgccaatggcacaggggggaagcggtgcaggaggctggagcgcaggcgacgg
gacaagagccggagggggagaaggcgaatcgagatggggagggaagcgcggggagaaggacgacggcg
cgtgcagagatctggttctggttgaggatccggaggtgctcgccgtcgaggacccggaggaagctgcagcaaccgc
agcactccaggaagaaatgaaagcgctcgtggcatccgtccctgacggtgctggggcagcattcacagccatgcag
cttcaggagctagagcagcagtcccgggtttatcagtacatggctgcccgagtacctgtgcctactcacctcgtcttccc
cgtatggaagagtgtaaccggtgcatcctctgaaggcgcccagaagtaccctactttgttgggcttagcaacactctgct
tggacttcgggaagaaccctgaaccagaaccagggaggtgccggcgaacggatggcaaaaaatggcgatgttgg
agaaacactattccaaacgagaagtactgcgaacgccgcatgcatcgcggtcgcaagcgtcctgtacaggtcgtcg
aggaagccgagcctgactctgcttcaggctcaaaatctgctcccggcaaggccaccgaaggcgccaagaaggttg
gcgacaagagcccaggtagcaagaagcttgccgtggcggcggcagctgcagctgctgcgcagtctacgtaattgat
gcagcattttagtagtcgcaggaagagcatggcggcgctggcaactagcgccttcttttcattgcatgtgatctttagctat
aacctcatttagcacactcccagtggtgtccgtgggaggag

FIG. 25E

>ZmGRF5 SEQ ID N°: 9 cagccaggtaaggcaaaagagagagggcggaagcagcggcagagcggagagggagagagaagagcatata
tgggcatggcgatgccctttgcctccccgtctccggcagccgaccaccgcccctcctccctcctcccttctgccgcgcc
gccccctctctccgcggcgggagaggacgccgcgcagcagcacgcgatgagcggcaggtgggccgcgaggccgg
cgctcttcacggcggcgcagtacgaggagctggagcaccaggcgctcatatacaagtacctcgtcgccggcgtgcc
cgtcccgccggacctcctcctcccctgcgccgaggcttcgtcttccaccagccacccgcccttgggtacggcccctac
ttcggcaagaaggtggacccggagcccgggcggtgccggcgtacggacggcaagaagtggcggtgctccaagg
aggccgccccggactccaagtactgcgagcgccacatgcaccgcggccgcaaccgttcaagaaagcctgtgga
agcgcagctcgcgccccccgccgcacgcccagccgccgcagcagcaggccccgcgcccgctgctggcttcc
agaaccactcgctgtacccgtcgatcctcaacggcaacggcggcggcgggttaggtgctggtgctggtggtggcacg
ttcggcctggggcccacctctcagctgcacatggacagtgccgctgcctacgcgactgctgccggtggagggagcaa
atatctcaggtactctgcatacggggtgaaatctctgtcggacgagcacagcacgctcttgtcgggcggcatggatccg
tcgatgatggacaactcgtggcgccttctgccatcccaaaacaacacattccaagccacaagctaccctgtgttcggc
acgctgagtgggctagacgagagcaccatcgcgtcgctgccgaagacccagagggagcccctctctttcttcggga
gcgacttcgtgaccgccgccaagcaggagaaccagacgctgcgcccttttcttcgacgagtggcccaagtcgaggg
actcgtggccggagctgggcgaggacggcagcctcggcttctcggccacccagctctccatctccattcccatggcg
acctccgacttctccaacaccagctccagatcgccgggtggaataccgtcgagatgaacgagtaccgtgcatgtgga
tcccagcgtcttagggttgacgactcttcggtgctggcctcatcgtatcatgctcctaaattttcgaacgatatatgccttatg
taacgctatttctctcattgttacaacacccctttacccgtttggaattgtgttgaagtggatggtctgcgttgctc

FIG. 25F

>ZmGRF6 SEQ ID N°: 10

Gatatatggcgatgcccttttgcctccctgtctccggcagccgaccaccgcccctcctccctcctcccctactgccgcgcc
gcccctctctccgcggtgggagaggacgccgccgcgcaggcgcagcagcagcagcagcagcacgctatgagcg
gcaggtgggcagcgaggccgccggcgctcttcacagcggcgcagtacgaggagctggagcaccaggcgctcata
tacaagtacctcgtcgccggcgtgcccgtcccgccggacctcctcctcccctacgccgaggcttcgtctaccaccaa
cccgcccttgggtacgggccctacttcggcaagaaggtggaccccggagccccggcggtgccggcgtacggacggc
aagaagtggcggtgctccaaggaggccgccccggactccaagtactgcgagcgccacatgcaccgcggccgcaa
c<u>cgttcaagaaagcctgtggaa</u>gcgcagctcgtgccccgccgcacgcccagccgcagcagcaggcccccgc
gcccaccgctggcttccagagccaccccatgtacccatccatcctcgccggcaacggcggcggcggcggcggggt
aggtggcggtgctggcggtggcacgttcggcctgggccccacctctcagctgcgcatggacagtgccgctgcttacgc
gactgctgctgatggagggagcaaagatctcaggtactctgcctacggggtgaagtcactgtcggacgagcacagc
cagctcttgcccggcggcggcggcggcatggacgcgtcaatggacaactcgtggcgcctgttgccgtcccaaaccg
ccgccacgttccaagccacaagctaccctctgttcggcgcgctgagcggtctggacgagagcaccatcgcctcgctg
cccaagacgcagagggagcccctctccttcttcgggagcgacttcgtgaccccgaagcaggagaaccagacgctg
cgccccttcttcgacgagtggcccaagtcgagggactcgtggccggagctgaacgaggacaacagcctcggctcct
cggccacccagctctccacctccatccccatggcgccctccgacttcaacaccagctccagatcgccgaatggaata
ccgtcaagatgaacctgagtaaccatgcggaccccca

FIG. 25G

>ZmGRF7 SEQ ID N°: 11 agcgtgcattgttgagcgagtgcggccaagcaacgcgggctcgaggagatgatgctgagcgggcacggcggcgg
gaggcgcctgttcacggcgtcgcagtggcaggagctcgagcaccaggcgctcatcttcaagtacatggcctcgggc
gcgcccgtgccgcacgacctcgtcctaccgctccgcctcgccaccggcgtcgacaccgcgccctccctcgccttccc
gccccagccttcgccgtcgctggcgtactggggctgctacggcgcgggggcgccgttcgtcggccgcaaggcggcg
gaggacacggagccggggcggtgccggcggacggacggcaagaagtggcggtgctccagggaggcccacgg
cgactccaagtactgcgagaagcacattcaccgcgggaagagccgttcaagaaagcctgtggaagtgacctcct
cccccgccgccggcgccgctgcggcgtaccgaccgtccgcgatctccaccatctcgccgccccgcgcggccgacg
cgccgccgccgagcctcgcctacccgcagcagcatctcctccacggcgcctcctcctccgcagcagcccgcgcccc
cgctggcgctctccagctccacctcgacgcgagcctgcacgcggcggcggcgtcgccatcgccgccgccgtcctac
cacaggtacgcccactacacaccgccagcgtcgtcgctcttcccgggcggcggctacggctacgactacgactacg
ggcagtccaaggagctcaggcgacggcacttccacgcgctcggggccgacctgagcctcgacaagccgctgccc
gagcccgacaccggctccgacgagaagcagccctgcggcgtttcttcgacgagtggccgcgggagagcggcga
catggcggcggacgacgcgacgcagctttccatctccatccccgcggcttcgccctccgacctcgctgctacctccgc
ctccgccgccgccgcgcgattccacaacggggagtgatcggtccatctcctagctgcagccctgcaacagcgtggat
tgaccgctgcatttcctggctgcaatgcaagcctgcaacagcgagcagtaagccagtgacgtggatgcatctcgtagc
ggcaaaccctgcttctgcctct

FIG. 25H

>ZmGRF8 SEQ ID N°: 71 ttcggcacgacccaacaatgcacaccaacatccactccctcgtcaggctcctctcccccaaatgagcgctgagttctg
cgctgctgcgggtgtcgtggccatggagctcggggtcggagatgcgctggggctgcagcaaggcatcgcaatcacc
gcgccatcgcccagggacagcgacctgggtcttctcaagcgagcaggcctcacccaggctgcggctgctgccccct
accccctccccttccttgacggggagaagatgctcaggttctccaaggcggctcacacatcgcactcaggcttggatttt
ggaggcccaggtgagcaggctttcctgctgtccaggaccaagatgccatttactccctcgcagtggatggagctgggg
caccaggctctgatatacaagtacctcaatgcaaaggcccccataccttccagcctgctcatttcaatcagcaagagct
tcagatcatccaatagagtgagctggaggcctctgtatcaaggctacacaaatgcagactctgacccagaacctggg
agatgccgacgaacggatggaaagaagtggcggtgctccaaggaagcaatggctgatcacaagtactgtgagcg
gcacatcaacagaaaccgtcaccgttcaagaaagcctgtggaaaatcaacctaagaagaccaccaaggaggt
gcctgctgctgctggctcattaccatgtgctgggccacaaggtagcttgaagaaggcaaaagttaatgactccaagcc
aggcactgtcagctattgggcagatagtttaaacaggacaatgttgagcagagagaaagcaaacaaaccgacgga
agatagctctttgctgcttacttctacgaacagccaacccacctggtccctgctctctcagctgaagcagcaaaacaaa
ccagataagttaggccccacactggaaaatgagtcaaacccagacacaatattgaaagcctggggtggcaaccag
cctagccacaagagcatttcctctacagagcgccatgatgctgaatccctccaatcagtccttcaaaatctcagcctag
cccagaatgagaagatggagtcagaaaaggacaaatattctgattccgtgctagtttcgtcgactttctattctgcaggc
ggtccaagagctacctgccttacacctaacatgacacaggtgaagcaggattgcatatcaagctcttgggagatgcct
caaggtggacctctaggcgaaatcttaacgaactccaagaatagcaaggacttaagcaagtgcaaaccaaggtcat
atggttggttgttgaatcttgaccatgccatgattcctcaatccatgaagagcttgacatagatgtcccatcatgtaggc
aaacaatggtcagaaaaaggttatgaccacattgcttgccccatgcatgcttgctatctacatttgtatttctgttgcgtagc
atttagctagttgaattatcagttcttctggatacggctgt

FIG. 25I

>ZmGRF9 SEQ ID N°: 12 gtaggtcgttcgcaggtaggtaaccgtaacctagctagctcgtcgggatgatgatgatgagcggtcgagcggccacc
gcggggcggtacccgttcacggcgtcgcagtggcaggagctggagcaccaggcgctcatctacaagtgcctggcgt
ccggcaagcccatcccgtcctacctcatgccaccgctccgccgcatcctcgactccgccctcgccacgtcgccgtcgc
tcgccgccttccagccgcaaccctcgctggggtgggggggctgcttcgggatgggcttcagcaggaagcccgccga
cgaggacccggagcccgggcggtgccggcgcacggacggcaagaagtggcgctgctccaaggaggcgtaccc
ggactccaagtactgcgagaagcacatgcaccggggcaagaaccgttcaagaaagcctgtggaaatgtccttgg
ccacgccggcgccgccggcctcctccgctgccaccacctcgacgtccccggcgccgtcctaccaccgcccggccc
ccgccgcgcacgacgccgtgccgtaccacgcgccctacggcgccgcgtaccatcacacgcagacgcaggtgatg
agccccttccacctccacctcgagaccacccacccgcacccgccgccgccgccgccctactactacgcggaccag
agggactacgcctacggcaaggaggtcggcgagcgcgccttcttctccgacggcgcggggagagggaccgcca
gcagcaggccgcggggcagtggcagttcaagcagctcgggacgatggaggcgacgaagccgtgccccacccc
acgccgctgctccccgccgcgggtacggcgtcggtcaggccaaggaagacgaggaggaggaaacgcggcgg
cagcagcagcagcactgcttcgttcttggcgccgacctgcggctggcggagcggccgtcgggggcacatgacgac
gccgcgcagaagccgctccggcatttcttcgacgagtggccgcacgagaaagggagcaaggcggggtggtggatt
gggggactcgacggcgagacgacgcagctctccatgtccatcccgatggcggccgctgccgacctccccgtcacct
cccgctaccgtacgtga

FIG. 25J

>ZmGRF10 SEQ ID N°: 72 agagcgccgtatcacctgtctctccgtccaccgccgtctcgatccgcgccaaagataccttttcccccaccccttcctcgc
gccgccgtttggtgcgaccatgacggcggagggggaggccaagaacccgtcggccggtggcggaggggataac
ccccagcaccagcaggctgcgccggcgccggcgccggcacaggggggaagtggcgcaggaggctgcagtgcag
gggacgggacaagagcaggagcgggacaaggcggatcgagaggtgcagggcggcgcggggggagaaggacg
acggcgcgtgcagagatctggtcctggtcgaggatccggaggtcctcgccgtcgaggatccggaggaagctgcagc
aaccgcagcactccaggaagaaatgaaagcgcttgtggcatcgatccctgatggtgctggagcagcattcacagcc
atgcagcttcaggagctagagcagcagtcccgggtgtaccagtacatggctgcccgagtacctgtgcctactcacctc
gtcttcccggtatggaagagtgtgaccggtgcatcctctgaaggcgcccagaagtaccctactttgatggcttagcaa
cgctctgcttggactttgggaagaacccggaaccagaaccagggaggtgtcggcgaacagatggtaagaaatggc
gatgttggagaaacactatcccaaacgagaaatactgcgaacgtcacatgcatcgtggccgcaagcgtcctgtaca
ggttttcctggaggacgacgagcccgattctgcttcagggtcaaaacccgccgctcctggcaaggctaccgaaggtg
ccaagaaggccgatgacaagagcccaagcagcaagaagcttgcagtggcagcgcctgccgctgtgcagtctacat
agtcaattgcagctttagtagcccgcagaaagagcata

FIG. 25K

>ZmGRF11 SEQ ID N°: 13 gcctctgacaccagcacaaacctggagactactactagtattggagtcccctccacttccacctcccttgccactgaag cgagagctctcggagccgtcgtcctctgtctctcatccttcttcgttgttgagcaaagcgggctcgaggaggagatgatg ctgagcgggcacggcggcgggaggcgcctgttcacggcgtcgcagtggcaggagctggagcaccaggcgctcat cttcaaatacatggcctccggcgcgcccgtgccgcacgacctcgtcctgccgctccgcctcgccaccggcgtcgaca ccgcgccctccctcgccttcccgccccagccttcgccgtcgctggcgtactggggctgctatggcgcgggggcgccgt tcggccgcaaggcggaggacccggagcccgggcggtgccggcggacggacggcaagaagtggcgatgctcca gggaggcccacggagactccaagtactgcgagaagcacatccaccgcgggaagagc<u>cgttcaagaaagcctg</u>

<u>tggaa</u>gtgacctcccccgccgcctaccgcccgtccgcgttctccatctcgccgctcgcgcggccgacgcgccgccg ccgccgccgggcctcggccacccgcagcagcagcatctccgccacggcgctctctctccagcaggccgcgcccac gccgctggcgctctccagctccacctcgactcgagcctgcacgcggcgtcgccgccgccgtcctaccacaggtacgc ccactcccacgctcactacacgccgccgccgccgccgtcgctctacgactacgggcagtccaaggagcttcgggag gcggcggagctcaggcggcggcacttccacgcgctcggggccgacctgagcctcgacaagccgctggccgacgc cggggccgcggagaagcccctgcggcgttttcttcgacgagtggccgcgggagagaggcgacacgaggccgtcgt gggcgggggcggaggacgcgacgcagctctccatctccatccccgcggcttcgccctcctctgaccacgctgcctct gccgccgcgcgatgccacaacgatgggagtgatcggtgcatctcctagctgcaactgcaatgcaagcctgcaaccg cgtggattgttgttgattggtgtagtttcctagctgcaattcaagcctgcaacagcgagcagtgagcagcaaatgcgtgg ggagggcacgcagctcaggctgatgcgcaaaatccgaagcgagtcaagcagcaataggactctaggtctatgattt gatcttcctttgtagcagtacgttaccaaaatgttagctcgttgttgttcggtgtgacattttcgttcaggttgctcc

FIG. 25L

>ZmGRF12 SEQ ID N°: 73

Cgcatccgttctctatcgaaagggaggaggaggagcgcgcgggagtgggctgggggcccaccgatgctgagctc
ggcgtcctcggccggggcggccatggggatgggcggcgggtaccaacaccagccgctgccactgccgcagcgcg
gggcggcggccgcggtcttcaccgccgcgcagtgggcggagctggagcagcaggcgctcatctacaagtaccta
tggccggcgtccccgtcccgcccgatctcctccgccccgccccccacgccgccgccttctccttcgccagccccgccg
cgtcgcccttctaccatcaccaccaccaccacccgtccctgagttactacgcctactacgggaagaagctggacccg
gagccgtggcggtgccgccgcaccgacggcaagaagtggcggtgctccaaggaggcgcaccccgactccaagt
actgcgagcgccacatgcaccgtggccgcaaccgttcaagaaagcctgtggaatccaagaccgcctcctcgccg
ccccagctgtccaccgtcgtcaccaccaccaccacccgggaggccgccgccgcgacgcccctcgagtccctcgcg
ggggcggggggtaaggctcacggcctgtccctcggcggcggggctggctcgtcgcacctcagcgtcgacgcttcga
acactcactttcgctatggcagcaagtaccctcttggagctaaatccgatgctggcgagctgagcttcttctcaggagca
ccagggaactccaggggcttcaccattgattctccagcagataactcttggcactccctgccatccaacgtgcccccgt
ttacactgtccaagggcagagattctggcctcctgcctggagcgccaccagtcgtcgttcagcagcagcggggccgg
cgctggtgggttgctggggagcgtgaagcaggagaaccagccgctgaggcccttcttcgacgagtggcctgggacg
cgggactcgtggtcggagatggacgacgcgaggtccagtaggacctccttctcgacgacccagctctccatctccatt
ccgatgcccagatgtgattgagaacgaagctcg

FIG. 25M

>ZmGRF13 SEQ ID N°: 74 cctcccgtcagcctcttcttctcccccctgatgagcgctgagttctgtgctgccgccgctggtgctgtggccatggagctcg
gagtcggggatgtgatggggctgcagcaaggcatcgccgccgccaccgggccatcgtccggagacagcgacctg
ggtcttctcaagcgagcaggcctcgcccaggcagccacctcctacccctcccctttcctcgaccaacagaagatgctc
aggttctccaaggcggcggcggctcacacgtcgccctcaggcctagatttcggaggaggcccaagcgagcaggctt
tcctgctgtccaggaccaagcggccgttcaccccgtcgcagtggatggagctggagcaccaggctctcatatacaag
tatctcaatgccaaggcccccatccttccagcctgctcgtttccatcagcaagagcttcaggtcatccaacagagtga
gctggaggcctctttaccaaggctacgcaaacgcagactccgacccagaacctgggaggtgccggcggacagac
ggaaagaagtggcggtgctctaaggaggcgatgcctgatcacaagtactgcgagcgccacatcaataggaaccgc
caccgttcaagaaagcctgtggaaaaccaacctagaaagaccagcaaggaggtgcctaccgctgctgctggctc
gttgccgtgtgccgggccacaaggtagcttgaagaaggcaaaagttaatgactccaagccaggcactggcagctatt
ggacagatagcttaaacaggacaatgctgagcagggagaaggcaaacaaaccgacggaagacgagtctttgctg
cttagttctacgaagaacagccagcccaccttgtccctgctcactcaactgaagcagcagaacaaaccagataagtt
aggtcccacaccggaaaatgagccgaactcggacacaatgttgaaagcctggggtggcagccaccacaagaaca
tttcctccacacagcgccatgacgctgaatccctccaatcagtcctccaaaatttcagcctagcccagaatgacaggtt
ggagtcagaaaagaacagatattctgattccgtgctagtctcatcggctttctattctgcagacggtccacaaactacct
gccttacacctaacatgacacaagtgcagcaggactgcatatcaagctcctgggagatgcctcaaggtggacctcta
ggcgagatcttaacgaactccaagattagtgaggactcaagcaagtgtggatctaggtcatatggttggctattgaatct
tgaccatgcaccatgattcctc

FIG. 25N

>ZmGRF14 SEQ ID N°: 14

Gccaccaagagccctccaacacacacctgacctccccttcccccctctctccgccgcccgttccccgcgcctccgcc
cgtacgtcccgttcccggtcggccggccggtccaaagggaggggaggaggaggggcgcgggagtcggggcccg
caccgatgctgagctcggcatcctcggccgcgggggcggccatggggatgggcggcggcgggtacgcgcaccag
cccccgccacagcgcgcggtcttcaccgccgcgcagtgggcggagctggagcagcaggcgctcatctacaagtac
ctcatggccggcgtccccgtcccgcccgacctcctcctccccgtccgccccggccccgccgccgccttctccttcgccg
gccccgccgccgcgtcgcccttctaccaccaacaccacccgtccctgagctactacgcctactacggcaagaagctg
gacccggagccgtggcggtgccgccgcaccgacggcaagaagtggcggtgctccaaggaggcgcaccccgact
ccaagtactgcgagcgccacatgcaccgtggccgcaaccgttcaagaaagcctgtggaatccaagaccgcctcg
tcgtcgtcgcccgcgcacccgtcgccgccccagctgtccaccgtcaccaccaccgcgcctctcgagccccttgcagc
ggcggggggcaaggtccacggcctgtccctcggcggcggcgctgctggctcgtcgcacctcggcgtcgatgcttcga
atgctcactatcgttatggtagcaacaggtaccctctcggagctaaaccggacggcggcgagttgagcttcttctcagg
agcgtcatcggggaacaactcgaggggtggcttcaccatcgactctccatcagataacaactcgtggcactccgccct
ggcgtccagcgtgcccccgttcacgctgtcgacgaagagcggggactccggcctcctgcccggcgcctacgcctcct
actcccagtcccactcccacatggagccgccgcgggagctcgggcaggtcaccatcgcctcgctggcgcaggagc
aggagcgccagcagccgttcagtggtgggatgctcgggaacgtgaagcaggagaaccagaaccagccgctgcg
gcccttcttcgacgagtggcccgggacgcgggcggactcgtggccgccggagatggacggcgcgccgcgggccg
gcaggacctccttctcctcctccaccacccagctctccatctccatcccgatgcccagatgtgagctgcatctcagaaa
ccagaactcttaattctgttcgctgcccgaatcatgcttgaccgaaacttgttttctgcaggcgactgacgaggaaccgtc
gatcgggcggccactagacggtggacgctcacgctcactagtgcgctgtcgcctggagtggagatcga

FIG. 26A

>ZmGRF1 SEQ ID N°: 26

MAMPYASLSPAGAADHRSSTATASLVPFCRSTPLSAGGGLGEEDAQASARWPAAR
PVVPFTPAQYQELEQQALIYKYLVAGVPVPPDLVVPIRRGLDSLATRFYGQPTLGYG
PYLGRKLDPEPGRCRRTDGKKWRCSKEAAPDSKYCERHMHRGRNRSRKPVETQL
APQSQPPAAAAVSAAPPLAAAAAAATNGSGFQNHSLYPAIAGSTGGGGGVGGSGN
ISSPFSSSMGGSSQLHMDSVASYSYAALGGGTAKDLRYNAYGIRSLADEHNQLIAE
AIDSSIESQRRLPSSSFPLSSYPHLGALGDLGGQNSTVSSLPKMEKQQPPSSFLGN
DTGAGMAMGSASAKQEGQTLRHFFDEWPKARDSWPGLSDETASLASSPPATQLS
MSIPMASSDFSVASSQSPNDD

FIG. 26B

>Zm*GRF2* SEQ ID N°: 75

MEGGRDVFLGAAARAPPPPPSCPFHGSATATRSGGAQMLSFSSNGVAGLGLCSG
ASKMQGVLSRVRRPFTPTQWMELEHQALIYKHFAVNAPVPSSLLLPIKRSLNPWSS
LGSSSLGWAPFRSGSADAEPGRCRRTDGKKWRCSRDAVGDQKYCERYIKRGCHR
SRKHVEGRKATPTTADPTMAVSGGSLLHSHAVAWQQQGKSSAANVTDPFSLGSN
RNLLDKQNLGDQFSVSTSMDSFDFSSSHSSPNQAKVAFSPVAMQHEHDQLYLVHG
AGSSAENVNKSQDGQLLVSRETIDDGPLGEVFKGKSCQSASADILTDHWTSTRDLR
PPTGVLQMSSSNTVPAENHTSNSSYLMARMANSQTVPTLH

FIG. 26C

>Zm*GRF3* SEQ ID N°: 27

MMMMSSGRAGGGATAGRYPFTASQWQELEHQALIYKCLASGKPIPSYLMPPLRRI
LDSALATSPSLAYPPQPSLGWGCFGMGFTRKADEDPEPGRCRRTDGKKWRCSKE
AYPDSKYCEKHMHRGKNRSRKPVEMSLATPAPAPAPAAATTATATSSPAPSYHRP
AHDATPSPYHALYGGGGGGGGSPYSASARPGATGGGGAYHHAQHVSPFHLHLET
THPHPPPPYNYSADQRDYAYGHAAAKEVGEHAFFSDGAGERVDRQAAAGQWQF
RQLGVETKPGPTPLFPVAGYGHGAASPYGVELGKDDDEQEERRRQHCFVLGADL
RLERPSSGHGHGHGHDHDDAAAAQKPLRPFFDEWPHQKGDKAGSWMGLDGETQ
LSMSIPMAATDLPVTSRFRNDE

FIG. 26D

>ZmGRF4 SEQ ID N°: 76

MAAEGEAKNPSGGGEGGNPQHQQAVQAAPAEPPMAQGEAVQEAGAQATGQEPE
GEKANRDGEGSAGEKDDGACRDLVLVEDPEVLAVEDPEEAAATAALQEEMKALVA
SVPDGAGAAFTAMQLQELEQQSRVYQYMAARVPVPTHLVFPVWKSVTGASSEGA
QKYPTLLGLATLCLDFGKNPEPEPGRCRRTDGKKWRCWRNTIPNEKYCERRMHRF
GRKRPVQVVEEAEPDSASGSKSAPGKATEGAKKVGDKSPGSKKLAVAAAAAAAQ
ST

FIG. 26E

>ZmGRF5 SEQ ID N°: 28

MGMAMPFASPSPAADHRPSSLLPFCRAAPLSAAGEDAAQQHAMSGRWAARPALF
TAAQYEELEHQALIYKYLVAGVPVPPDLLLPLRRGFVFHQPPALGYGPYFGKKVDPE
PGRCRRTDGKKWRCSKEAAPDSKYCERHMHRGRNRSRKPVEAQLAPPPHAQPP
QQQQAPAPAAGFQNHSLYPSILNGNGGGGLGAGAGGGTFGLGPTSQLHMDSAAA
YATAAGGGSKYLRYSAYGVKSLSDEHSTLLSGGMDPSMMDNSWRLLPSQNNTFQ
ATSYPVFGTLSGLDESTIASLPKTQREPLSFFGSDFVTAAKQENQTLRP<u>FFD</u>EWPKS
RDSWPELGEDGSLGFSATQLSISIPMATSDFSNTSSRSPGGIPSR

FIG. 26F

>ZmGRF6 SEQ ID N°: 29

MAMPFASLSPAADHRPSSLLPYCRAAPLSAVGEDAAAQAQQQQQQHAMSGRWAA
RPPALFTAAQYEELEHQALIYKYLVAGVPVPPDLLLPLRRGFVYHQPALGYGPYFGK
KVDPEPGRCRRTDGKKWRCSKEAAPDSKYCERHMHRGRNRSRKPVEAQLVPPP
HAQPQQQAPAPTAGFQSHPMYPSILAGNGGGGGGVGGGAGGGTFGLGPTSQLR
MDSAAAYATAADGGSKDLRYSAYGVKSLSDEHSQLLPGGGGGMDASMDNSWRLL
PSQTAATFQATSYPLFGALSGLDESTIASLPKTQREPLSFFGSDFVTPKQENQTLRP
<u>FFD</u>EWPKSRDSWPELNEDNSLGSSATQLSTSIPMAPSDFNTSSRSPNGIPSR

FIG. 26G

>ZmGRF7 SEQ ID N°: 30

MMLSGHGGGRRLFTASQWQELEHQALIFKYMASGAPVPHDLVLPLRLATGVDTAP
SLAFPPQPSPSLAYWGCYGAGAPFVGRKAAEDTEPGRCRRTDGKKWRCSREAHG
DSKYCEKHIHRGKSRSRKPVEVTSSPAAGAAAAYRPSAISTISPPRAADAPPPSLAY
PQQHLLHGASSSAAARAPAGALQLHLDASLHAAAASPSPPPSYHRYAHYTPPASSL
FPGGGYGYDYDYGQSKELRRRHFHALGADLSLDKPLPEPDTGSDEKQPLRR<u>FFDE</u>
WPRESGDMAADDATQLSISIPAASPSDLAATSASAAAARFHNGE

FIG. 26H

>ZmGRF8 SEQ ID N°: 77

MSAEFCAAAGVVAMELGVGDALGLQQGIAITAPSPRDSDLGLLKRAGLTQAAAAP
YPSPFLDGEKMLRFSKAAHTSHSGLDFGGPGEQAFLLSRTKMPFTPSQWMELGHQ
ALIYKYLNAKAPIPSSLLISISKSFRSSNRVSWRPLYQGYTNADSDPEPGRCRRTDG
KKWRCSKEAMADHKYCERHINRNRHRSRKPVENQPKKTTKEVPAAAGSLPCAGP
QGSLKKAKVNDSKPGTVSYWADSLNRTMLSREKANKPTEDSSLLLTSTNSQPTWS
LLSQLKQQNKPDKLGPTLENESNPDTILKAWGGNQPSHKSISSTERHDAESLQSVL
QNLSLAQNEKMESEKDKYSDSVLVSSTFYSAGGPRATCLTPNMTQVKQDCISSSW
EMPQGGPLGEILTNSKNSKDLSKCKPRSYGWLLNLDHAP

FIG. 26I

>ZmGRF9 SEQ ID N°: 31

MMMMSGRAATAGRYPFTASQWQELEHQALIYKCLASGKPIPSYLMPPLRRILDSAL
ATSPSLAAFQPQPSLGWGGCFGMGFSRKPADEDPEPGRCRRTDGKKWRCSKEA
YPDSKYCEKHMHRGKNRSRKPVEMSLATPAPPASSAATTSTSPAPSYHRPAPAAH
DAVPYHAPYGAAYHHTQTQVMSPFHLHLETTHPHPPPPPYYYADQRDYAYGKEV
GERAFFSDGAGERDRQQQAAGQWQFKQLGTMEATKPCPTPTPLLPAAGYGVGQA
KEDEEEETRRQQQQHCFVLGADLRLAERPSGAHDDAAQKPLRH<u>FFD</u>EWPHEKGS
KAGWWIGGLDGETTQLSMSIPMAAAADLPVTSRYRT

FIG. 26J

>ZmGRF10 SEQ ID N°: 78

MTAEGEAKNPSAGGGGDNPQHQQAAPAPAPAQGEVAQEAAVQGTGQEQERDKA
DREVQGGAGEKDDGACRDLVLVEDPEVLAVEDPEEAAATAALQEEMKALVASIPD
GAGAAFTAMQLQELEQQSRVYQYMAARVPVPTHLVFPVWKSVTGASSEGAQKYP
TLMGLATLCLDFGKNPEPEPGRCRRTDGKKWRCWRNTIPNEKYCERHMHRGRKR
PVQVFLEDDEPDSASGSKPAAPGKATEGAKKADDKSPSSKKLAVAAPAAVQST

FIG. 26K

>ZmGRF11 SEQ ID N°: 32

MMLSGHGGGRRLFTASQWQELEHQALIFKYMASGAPVPHDLVLPLRLATGVDTAP
SLAFPPQPSPSLAYWGCYGAGAPFGRKAEDPEPGRCRRTDGKKWRCSREAHGD
SKYCEKHIHRGKSRSRKPVEVTSPAAYRPSAFSISPPRAADAPPPPPGLGHPQQQH
LRHGALSPAGRAHAAGALQLHLDSSLHAASPPPSYHRYAHSHAHYTPPPPPSLYDY
GQSKELREAAELRRRHFHALGADLSLDKPLADAGAAEKPLRRFFDEWPRERGDTR
PSWAGAEDATQLSISIPAASPSSDHAASAAARCHNDGSDRCIS

FIG. 26L

>ZmGRF12 SEQ ID N°: 79

MLSSASSAGAAMGMGGGYQHQPLPLPQRGAAAAVFTAAQWAELEQQALIYKYLM
AGVPVPPDLLRPAPHAAAFSFASPAASPFYHHHHHHPSLSYYAYYGKKLDPEPWR
CRRTDGKKWRCSKEAHPDSKYCERHMHRGRNRSRKPVESKTASSPPQLSTVVTT
TTTREAAAATPLESLAGAGGKAHGLSLGGGAGSSHLSVDASNTHFRYGSKYPLGA
KSDAGELSFFSGAPGNSRGFTIDSPADNSWHSLPSNVPPFTLSKGRDSGLLPGAPP
VVVQQQRGRRWWVAGEREAGEPAAEALLRRVAWDAGLVVGDGRREVQ

FIG. 26M

>ZmGRF13 SEQ ID N°: 80

MSAEFCAAAAGAVAMELGVGDVMGLQQGIAAATGPSSGDSDLGLLKRAGLAQAAT
SYPSPFLDQQKMLRFSKAAAAHTSPSGLDFGGGPSEQAFLLSRTKRPFTPSQWME
LEHQALIYKYLNAKAPIPSSLLVSISKSFRSSNRVSWRPLYQGYANADSDPEPGRCR
RTDGKKWRCSKEAMPDHKYCERHINRNRHRSRKPVENQPRKTSKEVPTAAAGSL
PCAGPQGSLKKAKVNDSKPGTGSYWTDSLNRTMLSREKANKPTEDESLLLSSTKN
SQPTLSLLTQLKQQNKPDKLGPTPENEPNSDTMLKAWGGSHHKNISSTQRHDAES
LQSVLQNFSLAQNDRLESEKNRYSDSVLVSSAFYSADGPQTTCLTPNMTQVQQDCI
SSSWEMPQGGPLGEILTNSKISEDSSKCGSRSYGWLLNLDHAP

FIG. 26N

>ZmGRF14 SEQ ID N°: 33

MLSSASSAAGAAMGMGGGGYAHQPPPQRAVFTAAQWAELEQQALIYKYLMAGVP
VPPDLLLPVRPGPAAAFSFAGPAAASPFYHQHHPSLSYYAYYGKKLDPEPWRCRR
TDGKKWRCSKEAHPDSKYCERHMHRGRNRSRKPVESKTASSSSPAHPSPPQLST
VTTTAPLEPLAAAGGKVHGLSLGGGAAGSSHLGVDASNAHYRYGSNRYPLGAKPD
GGELSFFSGASSGNNSRGGFTIDSPSDNNSWHSALASSVPPFTLSTKSGDSGLLP
GAYASYSQSHSHMEPPRELGQVTIASLAQEQERQQPFSGGMLGNVKQENQNQPL
RPFFDEWPGTRADSWPPEMDGAPRAGRTSFSSSTTQLSISIPMPRCELHLRNQNS

FIG. 27

>GmGRF *Glycine max*, Glyma03g35010 SEQ ID N°: 16

ATGGACTTCCATCTGAAGCAATGGAGAAACCAGCACGAGTCAGAGGAACAACAT
TCTACAAAGATGCCAAAACTTCTCCCTGAATCCCATCAACAACAACAGCCATCAG
CCTCTGCACTCCCTTTGTTTGTACCTGAACCCAACAGCAGCAAAGTCAGCACCC
TATTATTTCCCAGGATGGGGAGCTACTTCAGCTTGTCTCAGTGGCAGGAGCTTG
AGTTGCAGGCTTTGATATTCAGGTACATGTTGGCTGGTGCTGCTGTTCCTCCTG
AACTCCTTCAACCAATCAAGAAAAGCCTTCTTCATTCTCCACACTATTACCTCCA
TCACCCTCTCCAACATTACCAACCTTCTGCTTGGTATTGGGGTAGAGGAGCGAT
GGATCCGGAGCCAGGGCGGTGCCGGAGAACCGACGGCAAGAAGTGGCGCTGT
TCGAGGGACGTGGTGGCTGGGCAAAAGTACTGTGAGCGCCACATGCACCGTG
GAAGAAACCGTTCAAGAAAGCCTGTGGAACTACCCACACCAACTAGTGCTATTA
ACAATTGTGGTGTAACTGGAGTTGGATCCCTAGGACCAGGTGCTTCATCATCTT
CCATTTGTTCACCACCCTTAGCTTCTGCTTCATTCAAATCTCCTTTTGATCTTCAT
CTTGATGAACGTTCCTCTGGGACCAAGAATGAAGACGAAGATCATGTGGGTGG
GGATGGCAGATCAGGTGGAGGTGGTGGCCATATGCTGAGGCATTTCTTCGATG
ATTGGCCACGATCACTCCAAGACTCTGACAACGTTGAAAACAATGCTGCTGCTG
GCCGTAGCCTCTCTATTTCAATGCCCGGTGCTTCCTCGGATGTGTCATTGAAAT
TGTCCACGGGCTATGGAGAGGACTCGGGCCCAGGAAATGAGAATGTAAGCCTC
GAGCCAGAGCAGCTGCAGTTGAATTGGGCCGGAGGATGGGCCTCGTCTAATCA
AGTGGCTTCGATGGGAGGTCCACTTGCTGAGGCACTCAGATCATCTACTTCAAC
CTCATCTCCCACTAGTGTTTTGCATCGTCACTTGCCTCGTGGATCTGAGACCAG
CTTTATTAGCACCTGA

FIGURE 28

\>MtGRF *Medigaco truncatula* SEQ ID N°: 17

Atggactttcctacgaaacaatggagaaaccaacagcatgagtcagagaaacaacattccacaaagatgccaaa
acttcttcaccctgctcaatctcaatcccaatcccattcccatcaacaatcacctgcacttcctttgtttctacctcaaccca
acaccaaagtcaccaacttgtcagattcagcattaccttccaacaacagatttcccagaataggaatgggaagccattt
cagcttatctcaatggcaagaacttgagttacaagctttgatatttaggtacatgttggttggtgcttctgttcctcctgaactt
cttcaacctatcaagaaaagtcttcttcattcatctccttattttcttcatcattatcaacctacagcattgttgcaaagtgggta
ttggggaagaggagcaatggatccagagccaggtcgttgccggagaacagacggtaaaaagtggcggtgtgcga
gggatgtggtggctggacaaaagtactgtgaaagacacatgcatcgtggtagaaac**cgttcaagaaagcctgtgg
aa**cttcccacaccaactagtaatggcggtggatctttctctgctttgtcttctatttcttcacagcctcttgtcacttcctcattca
aatctccttttgatcttcactttactgaacgctccactgggaccaaaattgaagagaagagcttatgtgaaagcgatgatc
Atgtgggtggggatggaagaccaggtgggcaaatgctaaggcatttctttgacgattggccacgatcactgcaagact
ctgacaatgctgaaaacaatggtgggtcatcctccacatgtctctcaatttcaatgccaggaaataacaacacttcttctt
cttcttcagatgtgtcattgaaattgtccactggctatggagaagaaccatgtccaagaaatgagaatgtgggcctagta
caaactgagcagcaacaacaacaacttcaattgaattggatcggaggatggaattcaggtaatcaagtgtcttcaatg
ggaggaccacttgctgaggcacttagatcatctacttcaacttcttcacctactagtgttttacatcaattgccacgttgttct
ggttctcaaaccagctacattagcacctaa

FIGURE 29

>PtGRF *Populus trichocarpa* SEQ ID N°: 18

ATGGACTTCCATCTGAAGCAATGGAGAAACCAGCATGAGGAGTCAGGGCAACA
ACCCTCTGCAAAGATGCCAAAACTCCTCATGGATCCCCATCAACCACAACAACA
TCCACACTCATCTGGGTCTGCTGCCTTCCCTTTGTTTCTACCCGAGCCCAGCTG
CAAAAATAGTAACCTGTCAGCATTTCCTGATTCAAACACAGCTGCAAACACCAGA
CTTCCTAAGATCATGGGGAATTACTTTAGCCTGGAACAGTGGCAAGAGCTAGAG
CTGCAGGCTTTGATCTACAGATTCATGTTAGCCGGTGCAGCTATTCCTCCGGAG
CTCCTCCAACCAATCAAGAAAACCCTTCTTCATTCTCACCCCCTCCATATTTCC
TCCATCATCCTCTTCAATTACATTGCTCTTATTATCAGCCATCTTGGTATTGGGG
AAGAGCAGCCATGGATCCGGAGCCAGGTCGGTGCCGGAGAACAGATGGGAAG
AAATGGCGGTGCTCCAGAGACGTGGTGGCAGGGCACAAGTATTGCGAGCGCC
ACTTGCACCGTGGCCGCAACCGTTCAAGAAAGCCTGTGGAAAATCCCACACCT
ACAATATCCACTAACATCACTTGCATTGGTATTGGAGAATTGGACCAAACTACCT
TTTCATTGTTTTGTTTTGCTTTAATCTTCTTGCTCACCCTTATTGCAGCTCCAAA
ACTGAAAGCAAGGGCTTAATTGGACCACCACCTCCAAATGAGGTTGGTAACAGG
TCTGATGGCCACATTCTGTGGCATTTTTTTGATGACTGGCCACGATCCGTTGAT
GAATCCGACAATATGAATGCTGGAAGCTCAATGAACTCTTTAACCTGCCTCTCC
GTTTCAATGCCTGGAAACTCACCAGCATCAGATGTGTCATTGAAATTGTCCACTG
GGAATAATATTGCAGAGGAGGAGCCGGAGCCAGTCCCAGCCCCGATCCCTAGA
GGCAATACAAGCAATTGGGCTGCTGCAGGATGGGGCACAAAAATTACAAACCA
GGTGGTGACTTCAATGGGGGGACCTCTTGCTGAGGCGCTGAGGTCCTCCACTA
CCAAACTCATCTCCCACGAATGTTCTGCACCAGTTATGTCGC
CCCACTGTTTCTGA

FIGURE 30

>PpGRF *Prunus persica* SEQ ID N°: 15

ATGGACTTTCACCTCAAGCAATGGAGAAACCAGCAGCATGAGTCAGAGGAACAA
CATTCTGCAAAGATACCAAAACTTCACCTTGAGCCCCATCCACACTCAGAGCCA
TCTGGGTATGCTCTCCCTCTGTTTGTTCCTGAGCCCAACAGCAAAATGATCAGC
ACCCTGTCAGCGTTTTCTGAATCTACACCAGCATCTGCCTCCACCAGATTTCCC
AAAATGGGGAGCTATTTCAGCTTCTCCCAGTTGCAGGAGCTTGAGCTGCAGGCT
TTGATATTCAGGTACATGTTAGCTGGTGCTGCTGTTCCTCCTGAACTTCTTCAGC
CAATCAGGAAAAGCCTTCTCCACTCTCCTCCATATTTTCTCCACCACCCTCTTCA
ACAGTACCCTCATTTTCAGCCTGCTTTGTTGCAATCAGGGTATTGGGGAAGAGC
AGCCATGGATCCAGAGCCAACAAGGTGTAGAAGGACAGATGGCAAGAAATGGA
GGTGTTCTAGAGATGTGGTGGCTGGTCAGAAGTACTGTGAGCGCCATGTGCAC
CGTGGCAGAAACCGTTCAAGAAAGCCTGTGGAAGCCACCACTGCTGCTGCTG
GTGGTGGTGGTGGAGGGACAAGTGATATTGCTACCAACACCACCACCAAGACA
TCATCTAGTGGGGCCCATTTTACTCTTTCTGGGTCATCATCATCCCCTTCAATTG
ATCTGCTTCATCTCAACCAGAGTTCCTCAGAGCCCAAAGCTGAGAATAGGAGCC
TCTTTGAACCCCACAGTGAGGTCTCCGGGAGTGCTAAATCCGACAGCCATGTCT
TGCGGCCTTTTTTTGATGACTGGCCGGGGAAGCTCCAAGAACTGGACAATGCA
CGAACCAATGCTGGCTCAATGAACTCTGCCACCAGCCTCTCCATTTCGATACGG
GGAAATTCCTCCTCGGATGTGTCACTGAAATTGTCTACCGGCAATGGAGTTGAG
ACAGGGCGCCTGGACGGCCATGCTGAGCGCGAGCAGCCACAATTGAATTGGC
CTGCCGGATGGGGAACAAACCAAATGGCTTCCATGGGAGGGCCGCTTGCGGA
GGCCCTTAGGTCCTCCTCCAACTCCAATTCCTCACCAACCAGTGTTCTACATCA
GTTGCCCCGCAGCTCCGCCTCAGAAACTAGCTTTATCAGCACTTGA

FIGURE 31

>MtGRF *Medigaco truncatula* SEQ ID N°: 36

MDFPTKQWRNQQHESEKQHSTKMPKLLHPAQSQSQSHSHQQSPALPLFLPQPNT
KVTNLSDSALPSNNRFPRIGMGSHFSLSQWQELELQALIFRYMLVGASVPPELLQPI
KKSLLHSSPYFLHHYQPTALLQSGYWGRGAMDPEPGRCRRTDGKK<u>WRC</u>ARDVVA
GQKYCERHMHRGRNRSRKPVELPTPTSNGGGSFSALSSISSQPLVTSSFKSPFDL
HFTERSTGTKIEEKSLCESDDHVGGDGRPGGQMLRH<u>FFD</u>DWPRSLQDSDNAENN
GGSSSTCLSISMPGNNNTSSSSSDVSLKLSTGYGEEPCPRNENVGLVQTEQQQQQ
LQLNWIGGWNSGNQVSSMGGPLAEALRSSTSTSSPTSVLHQLPRCSGSQTSYIST

FIGURE 32

>GmGRF *Glycine max*, Glyma03g35010 SEQ ID N°: 35

MDFHLKQWRNQHESEEQHSTKMPKLLPESHQQQQPSASALPLFVPEPNSSKVSTL
LFPRMGSYFSLSQWQELELQALIFRYMLAGAAVPPELLQPIKKSLLHSPHYYLHHPL
QHYQPSAWYWGRGAMDPEPGRCRRTDGKK<u>WRC</u>SRDVVAGQKYCERHMHRGR
NRSRKPVELPTPTSAINNCGVTGVGSLGPGASSSSICSPPLASASFKSPFDLHLDER
SSGTKNEDEDHVGGDGRSGGGGGHMLRH<u>FFD</u>DWPRSLQDSDNVENNAAAGRSL
SISMPGASSDVSLKLSTGYGEDSGPGNENVSLEPEQLQLNWAGGWASSNQVASM
GGPLAEALRSSTSTSSPTSVLHRHLPRGSETSFIST

FIGURE 33

>PtGRF (*Populus trichocarpa*) (SEQ ID No. 37)
MDFHLKQWRNQHEESGQQPSAKMPKLLMDPHQPQQHPHSSGSAAFPLFLPEPSC
KNSNLSAFPDSNTAANTRLPKIMGNYFSLEQWQELELQALIYRFMLAGAAIPPELLQ
PIKKTLLHSHPPPYFLHHPLQLHCSYYQPSWYWGRAAMDPEPGRCRRTDGKKWR
CSRDVVAGHKYCERHLHRGRNRSRKPVENPTPTISTNITCIGIGELDQTTFSLFCFC
FNLLAHPYCSSKTESKGLIGPPPPNEVGNRSDGHILWHFFDDWPRSVDESDNMNA
GSSMNSLTCLSVSMPGNSPASDVSLKLSTGNNIAEEEPEPVPAPIPRGNTSNWAAA
GWGTKITNQVVTSMGGPLAEALRSSTTKLISHECSAPVMSPHCF

FIGURE 34

>PpGRF (*Prunus persica*) (SEQ ID No. 34)
MDFHLKQWRNQQHESEEQHSAKIPKLHLEPHPHSEPSGYALPLFVPEPNSKMISTL
SAFSESTPASASTRFPKMGSYFSFSQLQELELQALIFRYMLAGAAVPPELLQPIRKS
LLHSPPYFLHHPLQQYPHFQPALLQSGYWGRAAMDPEPTRCRRTDGKKWRCSRD
VVAGQKYCERHVHRGRNRSRKPVEATTAAAGGGGGTSDIATNTTTKTSSSGAHF
TLSGSSSSPSIDLLHLNQSSSEPKAENRSLFEPHSEVSGSAKSDSHVLRPFFDDWP
GKLQELDNARTNAGSMNSATSLSISIRGNSSSDVSLKLSTGNGVETGRLDGHAERE
QPQLNWPAGWGTNQMASMGGPLAEALRSSSNSNSSPTSVLHQLPRSSASETSFIS
T

FIGURE 35

>At-rGRF3 (SEQ ID No. 81)
ATGGATTTGCAACTGAAACAATGGAGAAGCCAGCAGCAGCAACAACATCAGACA
GAGTCAGAAGAACAACCTTCTGCAGCTAAGATACCAAAACATGTCTTTGACCAG
ATTCATTCTCACACTGCAACTTCTACTGCTCTTCCTCTCTTTACCCCTGAGCCTA
CTTCTTCTAAACTCTCCTCTTTGTCTCCTGATTCTTCCTCCAGGTTCCCCAAGAT
GGGGAGCTTCTTTAGCTGGGCACAGTGGCAAGAACTTGAACTACAAGCTCTGAT
CTACAGGTACATGTTGGCTGGTGCTGCTGTTCCTCAGGAGCTCCTTTTACCAAT
CAAGAAAAGCCTTCTCCATCTATCTCCTTCCTACTTTCTTCACCATCCTCTTCAAC
ACCTACCTCATTACCAACCTGCTTGGTATTTGGGAAGGGCAGCGATGGATCCTG
AGCCAGGCAGATGCAGGAGAACGGATGGTAAGAAGTGGAGATGTTCAAGAGAC
GTCTTCGCTGGCCACAAGTATTGCGAGCGCCACATGCACCGTGGCCGCAAC<u>CG
TTCtAGAAAaCCaGTaGAg</u>ACTCCAACCACCGTCAATGCAACTGCCACGTCCATG
GCTTCATCAGTAGCAGCCGCAGCCACCACTACAACAGCAACAACAACATCTACG
TTTGCTTTTGGTGGTGGTGGTGGTAGTGAGGAAGTGGTTGGTCAAGGAGGATC
TTTCTTCTTCTCTGGCTCTTCTAACTCTTCATCTGAACTTCTCCACCTTAGTCAAA
GTTGTTCGGAGATGAAGCAAGAAAGCAACAACATGAACAACAAGAGGCCATACG
AGTCCCACATCGGATTCAGTAACAACAGATCAGATGGAGGACACATCCTGAGGC
CCTTCTTTGACGATTGGCCTCGTTCTTCGCTCCAAGAAGCTGACAATAGTTCAA
GCCCCATGAGCTCAGCCACTTGTCTCTCCATCTCCATGCCCGGGAACTCTTCCT
CAGACGTCTCTCTGAAGCTGTCCACAGGCAACGAAGAGGGAGCCCGGAGCAAC
AACAATGGGAGAGATCAGCAAAACATGAGCTGGTGGAGCGGTGGAGGTTCCAA
CCACCATCATCACAACATGGGCGGACCATTGGCCGAAGCCCTGAGATCTTCTTC
CTCATCTTCCCCAACCAGTGTTCTCCATCAGCTTGGTGTCTCGACACAAGCCTTT
CATTGA

FIGURE 36

>rGmGRF Glyma03g35010  SEQ ID N°: 82

ATGGACTTCCATCTGAAGCAATGGAGAAACCAGCACGAGTCAGAGGAACAACAT
TCTACAAAGATGCCAAAACTTCTCCCTGAATCCCATCAACAACAACAGCCATCAG
CCTCTGCACTCCCTTTGTTTGTACCTGAACCCAACAGCAGCAAAGTCAGCACCC
TATTATTTCCCAGGATGGGGAGCTACTTCAGCTTGTCTCAGTGGCAGGAGCTTG
AGTTGCAGGCTTTGATATTCAGGTACATGTTGGCTGGTGCTGCTGTTCCTCCTG
AACTCCTTCAACCAATCAAGAAAAGCCTTCTTCATTCTCCACACTATTACCTCCA
TCACCCTCTCCAACATTACCAACCTTCTGCTTGGTATTGGGGTAGAGGAGCGAT
GGATCCGGAGCCAGGGCGGTGCCGGAGAACCGACGGCAAGAAGTGGCGCTGT
TCGAGGGACGTGGTGGCTGGGCAAAAGTACTGTGAGCGCCACATGCACCGTG
GAAGAAAC<u>CGTTCtAGAAAaCCaGTaGAg</u>CTACCCACACCAACTAGTGCTATTAAC
AATTGTGGTGTAACTGGAGTTGGATCCCTAGGACCAGGTGCTTCATCATCTTCC
ATTTGTTCACCACCCTTAGCTTCTGCTTCATTCAAATCTCCTTTTGATCTTCATCT
TGATGAACGTTCCTCTGGGACCAAGAATGAAGACGAAGATCATGTGGGTGGGG
ATGGCAGATCAGGTGGAGGTGGTGGCCATATGCTGAGGCATTTCTTCGATGATT
GGCCACGATCACTCCAAGACTCTGACAACGTTGAAAACAATGCTGCTGCTGGCC
GTAGCCTCTCTATTTCAATGCCCGGTGCTTCCTCGGATGTGTCATTGAAATTGTC
CACGGGCTATGGAGAGGACTCGGGCCCAGGAAATGAGAATGTAAGCCTCGAGC
CAGAGCAGCTGCAGTTGAATTGGGCCGGAGGATGGGCCTCGTCTAATCAAGTG
GCTTCGATGGGAGGTCCACTTGCTGAGGCACTCAGATCATCTACTTCAACCTCA
TCTCCCACTAGTGTTTTGCATCGTCACTTGCCTCGTGGATCTGAGACCAGCTTTA
TTAGCACCTGA

FIGURE 37

>rOsGRF4.1 SEQ ID N°: 83

ATGCCTCCCTGTCTCCGGCGGTGGCCGACCACCGCTCGTCCCCGGCAGCCGC
GACCGCCTCCCTCCTCCCCTTCTGCCGCTCCACCCCGCTCTCCGCGTAAGCAA
CGCGAACCCGCGGCTACAACCCATTTTCTTGGCTCCAGTGGTGCATGTGACAA
CACGGTGAGACGTTGTGTGTGGGTGGGTGGGTGCAGGGGCGGTGGTGGCGTC
GCGATGGGGGAGGACGCGCCGATGACCGCGAGGTGGCCGCCGGCGGCGGCG
GCGAGGCTGCCGCCGTTCACCGCGGCGCAGTACGAGGAGCTGGAGCAGCAGG
CGCTCATATACAAGTACCTGGTGGCAGGCGTGCCCGTCCCGCCGGATCTCGTG
CTCCCCATCCGCCGCGGACTCGACTCCCTCGCCGCCCGCTTCTACAACCATCC
CGCCCTTGGATATGGTCCGTACTTCGGCAAGAAGCTGGACCCAGAGCCAGGGC
GGTGCCGGCGTACGGACGGCAAGAAATGGCGGTGCTCGAAGGAGGCCGCGCC
GGATTCCAAGTACTGCGAGCGCCACATGCACCGCGGCCGCAAC<u>CGTTCtAGAA
AaCCaGTaGAg</u>ACGCAGCTGGTCGCCCAGTCCCAACCGCCCTCATCTGTTGTCG
GTTCTGCGGCGGCGCCCCTTGCTGCTGCCTCCAATGGCAGCAGCTTCCAAAAC
CACTCTCTTTACCCTGCTATTGCCGGCAGCAATGGCGGGGGCGGGGGGAGGA
ACATGCCCAGCTCATTTGGCTCGGCGTTGGGTTCTCAGCTGCACATGGATAATG
CTGCCCCTTATGCAGCTGTTGGTGGTGGAACAGGCAAAGATCTCAGGTATACTG
CTTATGGCACAAGATCTTTGGCGGATGAGCAGAGTCAACTCATTACTGAAGCTA
TCAACACATCTATTGAAAATCCATGGCGGCTGCTGCCATCTCAGAACTCGCCAT
TTCCCCTTTCAAGCTATTCTCAGCTGGGGCACTAAGTGACCTTGGTCAGAACA
CCCCAGCTCACTTTCAAAGGTTCAGAGGCAGCCACTTTCGTTCTTTGGGAACG
ACTATGCGGCTGTCGATTCTGTGAAGCAAGAGAACCAGACGCTGCGTCCCTTCT
TTGATGAGTGGCCAAAGGGAAGGGATTCATGGTCAGACCTCGCTGATGAGAAT
GCTAATCTTTCGTCATTCTCAGGCACCCAACTGTCGATCTCCATACCAATGGCAT
CCTCTGACTTCTCGGCGGCCAGTTCTCGATCAACTAATGGTGACTGA

FIGURE 38

| GRF# | Identity (%) | Similarity (%) | Gaps (%) |
|---|---|---|---|
| AtGRF1 | 26 | 37 | 35 |
| AtGRF2 | 23 | 33 | 41 |
| AtGRF3 | 100 | 100 | 0 |
| AtGRF4 | 69 | 75 | 14 |
| AtGRF5 | 23 | 30 | 50 |
| AtGRF6 | 21 | 27 | 55 |
| AtGRF7 | 36 | 41 | 41 |
| AtGRF8 | 23 | 33 | 34 |
| AtGRF9 | 19 | 27 | 48 |
| OsGRF1 | 21 | 32 | 49 |
| OsGRF2 | 25 | 34 | 43 |
| OsGRF3 | 26 | 35 | 45 |
| OsGRF4 | 26 | 38 | 39 |
| OsGRF5 | 25 | 32 | 47 |
| OsGRF6 | 24 | 33 | 45 |
| OsGRF7 | 24 | 33 | 40 |
| OsGRF8 | 24 | 32 | 39 |
| OsGRF9 | 26 | 37 | 32 |
| OsGRF10 | 23 | 30 | 54 |
| OsGRF11 | 15 | 21 | 54 |
| OsGRF12 | 20 | 23 | 62 |
| ZmGRF1 | 27 | 37 | 40 |
| ZmGRF2 | 26 | 35 | 33 |
| ZmGRF3 | 21 | 30 | 51 |
| ZmGRF4 | 14 | 20 | 65 |
| ZmGRF5 | 24 | 33 | 41 |
| ZmGRF6 | 23 | 33 | 44 |
| ZmGRF7 | 24 | 31 | 48 |
| ZmGRF8 | 24 | 33 | 31 |
| ZmGRF9 | 20 | 30 | 52 |
| ZmGRF10 | 15 | 23 | 60 |
| ZmGRF11 | 25 | 35 | 40 |
| ZmGRF12 | 28 | 35 | 36 |
| ZmGRF13 | 23 | 34 | 30 |
| ZmGRF14 | 23 | 30 | 51 |
| PpGRF | 54 | 63 | 19 |
| GmGRF | 51 | 60 | 17 |
| MtGRF | 45 | 55 | 26 |
| PtGRF | 51 | 60 | 17 |

FIG. 39A

>JD16 SEQ ID N°: 84

TTGATCCCGAGGGGAACCCTGTGGTTGGCATGCACATACAAATGGACGAACGG
ATAAACCTTTTCACGCCCTTTTAAATATCCGTTATTCTAATAAACGCTCTTTTCTC
TTAGgtttacccgccaatatatcctgtcaAACACTGATAGTTTAAACTGAAGGCGGGAAACGA
CAATCTGATCCAAGCTCAAGCTGCTCTAGCCAATACGCAAACCGCCTCTCCCCG
CGCGTTGGCCGATTCATTAATGCAGCTGGCACGACAGGTTTCCCGACTGGAAA
GCGGGCAGTGAGCGCAACGCAATTAATGTGAGTTAGCTCACTCATTAGGCACC
CCAGGCTTTACACTTTATGCTTCCGGCTCGTATGTTGTGTGGAATTGTGAGCGG
ATAACAATTTCACACAGGAAACAGCTATGACCATGATTAC<u>GAATTCGGTCCCCA</u>
<u>GATTAGCCTTTTCAATTTCAGAAAGAATGCTAACCCACAGATGGTTAGAGAGGCT</u>
<u>TACGCAGCAGGTCTCATCAAGACGATCTACCCGAGCAATAATCTCCAGGAAATC</u>
<u>AAATACCTTCCCAAGAAGGTTAAAGATGCAGTCAAAAGATTCAGGACTAACTGC</u>
<u>ATCAAGAACACAGAGAAAGATATATTTCTCAAGATCAGAAGTACTATTCCAGTAT</u>
<u>GGACGATTCAAGGCTTGCTTCACAAACCAAGGCAAGTAATAGAGATTGGAGTCT</u>
<u>CTAAAAAGGTAGTTCCCACTGAATCAAAGGCCATGGAGTCAAAGATTCAAATAG</u>
<u>AGGACCTAACAGAACTCGCCGTAAAGACTGGCGAACAGTTCATACAGAGTCTCT</u>
<u>TACGACTCAATGACAAGAAGAAAATCTTCGTCAACATGGTGGAGCACGACACAC</u>
<u>TTGTCTACTCCAAAAATATCAAAGATACAGTCTCAGAAGACCAAAGGGCAATTGA</u>
<u>GACTTTTCAACAAGGGTAATATCCGGAAACCTCCTCGGATTCCATTGCCCAGC</u>
<u>TATCTGTCACTTTATTGTGAAGATAGTGGAAAAGGAAGGTGGCTCCTACAAATG</u>
<u>CCATCATTGCGATAAAGGAAAGGCCATCGTTGAAGATGCCTCTGCCGACAGTG</u>
<u>GTCCCAAAGATGGACCCCCACCCACGAGGAGCATCGTGGAAAAGAAGACGTT</u>
<u>CCAACCACGTCTTCAAAGCAAGTGGATTGATGTGATATCTCCACTGACGTAAGG</u>
<u>GATGACGCACAATCCCACTATCCTTCGCAAGACCCTTCCTCTATATAAGGAAGTT</u>
<u>CATTTCATTTGGAGAGAACACGGGGGACGAGCTCGGTACCCGG</u>GGATCCCCG
GACC*ATGCAACAGCACCTGATGCAGATGCAGCCCATGATGGCTGGTTACTAC*
*CCCAGCAATGTTACCTCTGATCATATCCAACAGTACTTGGACGAAAACAAATC*
*GTTGATTCTGAAGATTGTTGAGTCTCAAAACTCTGGAAAGCTTAGCGAATGCG*
*CCGAGAATCAAGCAAGGCTTCAACGCAACCTAATGTACCTAGCTGCAATAGC*
*AGATTCTCAGCCTCAGCCACCAAGTGTGCATAGCCAGTATGGATCTGCTGGTG*
*GTGGGATGATTCAGGGAGAAGGAGGGTCACACTATTTGCAGCAGCAACAAGC*
*GACTCAACAGCAACAGATGACTCAGCAGTCTCTAATGGCGGCTCGATCTTCAA*
*TGTTGTATGCTCAGCAACAGCAGCAGCAGCCTTACGCGACGCTTCAGCA*
*TCAGCAATTGCACCATAGCCAGCTTGGAATGAGCTCGAGCAGCGGAGGAGGA*

FIG. 39B

>JD16 SEQ ID N°: 84 CONTINUED

*GGAAGCAGTGGTCTCCATATCCTTCAGGGAGAGGCTGGTGGGTTTCATGATTT
TGGCCGTGGGAAGCCGGAAATGGGAAGTGGTGGTGGCGGTGAAGGCAGAGG
AGGAAGTTCAGGGGATGGTGGAGAAACCCTTTACTTGAAATCATCAGATGATG
GGAATTGA*AAG<u>GTCGAC</u>TACCCATACGACGTTCCAGACTACGCTTCTTTGGGTG
GTTCTAGCCCAAGCTCAGAGCTCCACCGCGGTGGCGGCCGCATCTTTTACCCA
TACGATGTTCCTGACTATGCGGGCTATCCCTATGACGTCCCGGACTATGCAGGA
TGACTCGACC<u>TGCAGAGCTTTCGTTCGTATCATCGGTTTCGACAACGTTCGTCA
AGTTCAATGCATCAGTTTCATTGCGCACACCAGAATCCTACTGAGTTCGAG
TATTATGGCATTGGGAAACATGTTTTTCTTGTACCATTTGTTGTGCTTGTAATTT
ACTGTGTTTTTATTCGGTTTTCGCTATCGAACTGTGAAATGGAAATGGATGGA
GAAGAGTTAATGAATGATATGGTCCTTTTGTTCATTCTCAAATTAATATTATTTG
TTTTTCTCTTATTTGTTGTGTGTTGAATTTGAAAATATAAGAGATATGCAAACA
TTTTGTTTTGAGTAAAAATGTGTCAAATCGTGGCCTCTAATGACCGAAGTTAAT
ATGAGGAGTAAAACACTTGTAGTTGTACCATTATGCTTATTCACTAGGCAACA
AATATATTTTCAGACCTAGAAAAGCTGCAAATGTTACTGAATACAAGTATGTCC
TCTTGTGTTTTAGACATTTATGAACTTTCCTTTATGTAATTTTCCAGAATCCTTGT
CAGATTCTAATCATTGCTTTATAATTATAGTTATACTCATGGATTTGTAGTTGAG
TATGAAAATATTTTTTAATGCATTTTATGACTTGCCAATTGATTGACAACATGCA
TCAATCG</u>AAGCTTGCATGCCTGCAGGTCCTGCTGAGCCTCGACATGTTGTCGC
AAAATTCGCCCTGGACCCGCCCAACGATTTGTCGTCACTGTCAAGGTTTGACCT
GCACTTCATTTGGGGCCCACATACACCAAAAAAATGCTGCATAATTCTCGGGGC
AGCAAGTCGGTTACCCGGCCGCCGTGCTGGACCGGGTTGAATGGTGCCCGTAA
CTTTCGGTAGAGCGGACGGCCAATACTCAACTTCAAGGAATCTCACCCATGCGC
GCCGGCGGGGAACCGGAGTTCCCTTCAGTGAACGTTATTAGTTCGCCGCTCGG
TGTGTCGTAGATACTAGCCCCTGGGGCCTTTTGAAATTTGAATAAGATTTATGTA
ATCAGTCTTTTAGGTTTGACCGGTTCTGCCGCTTTTTTTAAAATTGGATTTGTAAT
AATAAAACGCAATTGTTTGTTATTGTGGCGCTCTATCATAGATGTCGCTATAAAC
CTATTCAGCACAATATATTGTTTTCATTTTAATATTGTACATATAAGTAGTAGGGT
ACAATCAGTAAATTGAACGGAGAATATTATTCATAAAAATACGATAGTAACGGGT
GATATATTCATTAGAATGAACCGAAACCGGCGGTAAGGATCTGAGCTACACATG
CTCAGGTTTTTTACAACGTGCACAACAGAATTGAAAGCAAATATCATGCGATCAT
AGGCGTCTCGCATATCTCATTAAAGCAGGACTCTAGGATCGATCCCCCGGGTCA

FIG. 39C

>JD16 SEQ ID N°: 84 CONTINUED

TCACATCTCGGTGACGGGCAGGACCGGACGGGGCGGTACCGGCAGGCTGAAG
TCCAGCTGCCAGAAACCCACGTCATGCCAGTTCCCGTGCTTGAAGCCGGCCGC
CCGCAGCATGCCGCGGGGGGCATATCCGAGCGCCTCGTGCATGCGCACGCTC
GGGTCGTTGGGCAGCCCGATGACAGCGACCACGCTCTTGAAGCCCTGTGCCTC
CAGGGACTTCAGCAGGTGGGTGTAGAGCGTGGAGCCCAGTCCCGTCCGCTGG
TGGCGGGGGGAGACGTACACGGTTGACTCGGCCGTCCAGTCGTAGGCGTTGC
GTGCCTTCCAGGGGCCCGCGTAGGCGATGCCGGCGACCTCGCCGTCCACCTC
GGCGACGAGCCAGGGATAGCGCTCCCGCAGACGGACGAGGTCGTCCGTCCAC
TCCTGCGGTTCCTGCGGCTCGGTACGGAAGTTGACCGTGCTTGTCTCGATGTA
GTGGTTGACGATGGTGCAGACCGCCGGCATGTCCGCCTCGGTGGCACGGCGG
ATGTCGGCCGGGCGTCGTTCTGGGCTCATGGTAATTGTAAATAGTAATTGTAAT
GTTGTTGTTGTTTGTTGTTGGTAATTGTTGTAAAAATAGAGCTCTTATACTCG
AGGAATTCgctagagTCGATTTGGTGTATCGAGATTGGTTATGAAATTCAGATGCTA
GTGTAATGTATTGGTAATTTGGGAAGATATAATAGGAAGCAAGGCTATTTATCCA
TTTCTGAAAAGGCGAAATGGCGTCACCGCGAGCGTCACGCGCATTCCGTTCTT
GCTGTAAAGCGTTGTTTGGTACACTTTTGACTAGCGAGGCTTGGCGTGTCAGCG
TATCTATTCAAAAGTCGTTAATGGCTGCGGATCAAGAAAAAGTTGGAATAGAAAC
AGAATACCCGCGAAATTCAGGCCCGGTTGCCATGTCCTACACGCCGAAATAAAC
GACCAAATTAGTAGAAAAATAAAAACTgaCTCgGATACTTACGTCACGTCTTGCG
CACTGATTTGAAAAATCTCAATATAAACAAAGACGGCCACAAGAAAAAACCAAAA
CACCGATATTCATTAATCTTATCTAGTTTCTCAAAAAAATTCATATCTTCCACACG
TGAAAATGCCAATTTCTCAGACCTACCTCGGCTCTGCGAAGGCCCCCGCTGGTA
TCAAAAGTTTTTATTTCATCCGACATGGCGCGACCGACCTCAACGAGAAGGAAA
TTGTCGTGAACGGTGAGAAGCTCTGGGGCGTGCAAGGTTCCGGAACGAACATC
GGTCTCAATGCAAAAGGGGAACGCCAGGCTCTgttggccccTCGAAATTCGGCGTT
AATTCAGTACATTAAAAACGTCCGCAATGTGTTATTAAGTTGTCTAAGCGTCAAT
TTgtttacaccacaatatatcctgccaCCAGCCAGCCAACAGCTCCCCGACCGGCAGCTCG
GCACAAAATCACCACTCGATACAGGCAGCCCATCAGTCCGGGACGGCGTCAGC
GGGAGAGCCGTTGTAAGGCGGCAGACTTTGCTCATGTTACCGATGCTATTCGG
AAGAACGGCAACTAAGCTGCCGGGTTTGAAACACGGATGATCTCGCGGAGGGT
AGCATGTTGATTGTAACGATGACAGAGCGTTGCTGCCTGTGATCAATTCGGGCA
CGAACCCAGTGGACATAAGCCTCGTTCGGTTCGTAAGCTGTAATGCAAGTAGCG
TAACTGCCGTCACGCAACTGGTCCAGAACCTTGACCGAACGCAGCGGTGGTAA

FIG. 39D

>JD16 SEQ ID N°: 84 CONTINUED

CGGCGCAGTGGCGGTTTTCATGGCTTCTTGTTATGACATGTTTTTTGGGGTAC
AGTCTATGCCTCGGGCATCCAAGCAGCAAGCGCGTTACGCCGTGGGTCGATGT
TTGATGTTATGGAGCAGCAACGATGTTACGCAGCAGGGCAGTCGCCCTAAAACA
AAGTTAAACATCATGGGGGAAGCGGTGATCGCCGAAGTATCGACTCAACTATCA
GAGGTAGTTGGCGTCATCGAGCGCCATCTCGAACCGACGTTGCTGGCCGTACA
TTTGTACGGCTCCGCAGTGGATGGCGGCCTGAAGCCACACAGTGATATTGATTT
GCTGGTTACGGTGACCGTAAGGCTTGATGAAACAACGCGGCGAGCTTTGATCA
ACGACCTTTTGGAAACTTCGGCTTCCCCTGGAGAGAGCGAGATTCTCCGCGCT
GTAGAAGTCACCATTGTTGTGCACGACGACATCATTCCGTGGCGTTATCCAGCT
AAGCGCGAACTGCAATTTGGAGAATGGCAGCGCAATGACATTCTTGCAGGTATC
TTCGAGCCAGCCACGATCGACATTGATCTGGCTATCTTGCTGACAAAAGCAAGA
GAACATAGCGTTGCCTTGGTAGGTCCAGCGGCGGAGGAACTCTTTGATCCGGT
TCCTGAACAGGATCTATTTGAGGCGCTAAATGAAACCTTAACGCTATGGAACTC
GCCGCCCGACTGGGCTGGCGATGAGCGAAATGTAGTGCTTACGTTGTCCCGCA
TTTGGTACAGCGCAGTAACCGGCAAAATCGCGCCGAAGGATGTCGCTGCCGAC
TGGGCAATGGAGCGCCTGCCGGCCCAGTATCAGCCCGTCATACTTGAAGCTAG
ACAGGCTTATCTTGGACAAGAAGAAGATCGCTTGGCCTCGCGCGCAGATCAGTT
GGAAGAATTTGTCCACTACGTGAAAGGCGAGATCACCAAGGTAGTCGGCAAATA
ATGTCTAGCTAGAAATTCGTTCAAGCCGACGCCGCTTCGCCGGCGTTAACTCAA
GCGATTAGATGCACTAAGCACATAATTGCTCACAGCCAAACTATCAGGTCAAGT
CTGCTTTTATTATTTTTAAGCGTGCATAATAAGCCCTACACAAATTGGGAGATATA
TCATGCATGACCAAAATCCCTTAACGTGAGTTTTCGTTCCACTGAGCGTCAGAC
CCCGTAGAAAGATCAAAGGATCTTCTTGAGATCCTTTTTTTCTGCGCGTAATCT
GCTGCTTGCAAACAAAAAAACCACCGCTACCAGCGGTGGTTTGTTTGCCGGATC
AAGAGCTACCAACTCTTTTTCCGAAGGTAACTGGCTTCAGCAGAGCGCAGATAC
CAAATACTGTCCTTCTAGTGTAGCCGTAGTTAGGCCACCACTTCAAGAACTCTGT
AGCACCGCCTACATACCTCGCTCTGCTAATCCTGTTACCAGTGGCTGCTGCCAG
TGGCGATAAGTCGTGTCTTACCGGGTTGGACTCAAGACGATAGTTACCGGATAA
GGCGCAGCGGTCGGGCTGAACGGGGGGTTCGTGCACACAGCCCAGCTTGGAG
CGAACGACCTACACCGAACTGAGATACCTACAGCGTGAGCTATGAGAAAGCGC
CACGCTTCCCGAAGGGAGAAAGGCGGACAGGTATCCGGTAAGCGGCAGGGTC
GGAACAGGAGAGCGCACGAGGGAGCTTCCAGGGGGAAACGCCTGGTATCTTTA
TAGTCCTGTCGGGTTTCGCCACCTCTGACTTGAGCGTCGATTTTGTGATGCTC

FIG. 39E

>JD16 SEQ ID N°: 84 CONTINUED

```
GTCAGGGGGGCGGAGCCTATGGAAAAACGCCAGCAACGCGGCCTTTTTACGGT
TCCTGGCCTTTTGCTGGCCTTTTGCTCACATGTTCTTTCCTGCGTTATCCCCTGA
TTCTGTGGATAACCGTATTACCGCCTTTGAGTGAGCTGATACCGCTCGCCGCAG
CCGAACGACCGAGCGCAGCGAGTCAGTGAGCGAGGAAGCGGAAGAGCGCCTG
ATGCGGTATTTTCTCCTTACGCATCTGTGCGGTATTTCACACCGCATATGGTGCA
CTCTCAGTACAATCTGCTCTGATGCCGCATAGTTAAGCCAGTATACACTCCGCT
ATCGCTACGTGACTGGGTCATGGCTGCGCCCCGACACCCGCCAACACCCGCTG
ACGCGCCCTGACGGGCTTGTCTGCTCCCGGCATCCGCTTACAGACAAGCTGTG
ACCGTCTCCGGGAGCTGCATGTGTCAGAGGTTTTCACCGTCATCACCGAAACG
CGCGAGGCAGGGTGCCTTGATGTGGGCGCCGGCGGTCGAGTGGCGACGGCG
CGGCTTGTCCGCGCCCTGGTAGATTGCCTGGCCGTAGGCCAGCCATTTTTGAG
CGGCCAGCGGCCGCGATAGGCCGACGCGAAGCGGCGGGGCGTAGGGAGCGC
AGCGACCGAAGGGTAGGCGCTTTTTGCAGCTCTTCGGCTGTGCGCTGGCCAGA
CAGTTATGCACAGGCCAGGCGGGTTTTAAGAGTTTTAATAAGTTTTAAAGAGTTT
TAGGCGGAAAAATCGCCTTTTTTCTCTTTTATATCAGTCACTTACATGTGTGACC
GGTTCCCAATGTACGGCTTTGGGTTCCCAATGTACGGGTTCCGGTTCCCAATGT
ACGGCTTTGGGTTCCCAATGTACGTGCTATCCACAGGAAAGAGACCTTTTCGAC
CTTTTTCCCCTGCTAGGGCAATTTGCCCTAGCATCTGCTCCGTACATTAGGAAC
CGGCGGATGCTTCGCCCTCGATCAGGTTGCGGTAGCGCATGACTAGGATCGGG
CCAGCCTGCCCCGCCTCCTCCTTCAAATCGTACTCCGGCAGGTCATTTGACCC
GATCAGCTTGCGCACGGTGAAACAGAACTTCTTGAACTCTCCGGCGCTGCCACT
GCGTTCGTAGATCGTCTTGAACAACCATCTGGCTTCTGCCTTGCCTGCGGCGC
GGCGTGCCAGGCGGTAGAGAAAACGGCCGATGCCGGGATCGATCAAAAGTAA
TCGGGGTGAACCGTCAGCACGTCCGGGTTCTTGCCTTCTGTGATCTCGCGGTA
CATCCAATCAGCTAGCTCGATCTCGATGTACTCCGGCCGCCCGGTTTCGCTCTT
TACGATCTTGTAGCGGCTAATCAAGGCTTCACCCTCGGATACCGTCACCAGGCG
GCCGTTCTTGGCCTTCTTCGTACGCTGCATGGCAACGTGCGTGGTGTTTAACCG
AATGCAGGTTTCTACCAGGTCGTCTTTCTGCTTTCCGCCATCGGCTCGCCGGCA
GAACTTGAGTACGTCCGCAACGTGTGGACGGAACACGCGGCCGGGCTTGTCTC
CCTTCCCTTCCCGGTATCGGTTCATGGATTCGGTTAGATGGGAAACCGCCATCA
GTACCAGGTCGTAATCCCACACACTGGCCATGCCGGCCGGCCCTGCGGAAACC
TCTACGTGCCCGTCTGGAAGCTCGTAGCGGATCACCTCGCCAGCTCGTCGGTC
ACGCTTCGACAGACGGAAAACGGCCACGTCCATGATGCTGCGACTATCGCGGG
```

FIG. 39F

>JD16 SEQ ID N°: 84 CONTINUED

TGCCCACGTCATAGAGCATCGGAACGAAAAAATCTGGTTGCTCGTCGCCCTTGG
GCGGCTTCCTAATCGACGGCGCACCGGCTGCCGGCGGTTGCCGGGATTCTTTG
CGGATTCGATCAGCGGCCGCTTGCCACGATTCACCGGGGCGTGCTTCTGCCTC
GATGCGTTGCCGCTGGGCGGCCTGCGCGGCCTTCAACTTCTCCACCAGGTCAT
CACCCAGCGCCGCGCCGATTTGTACCGGGCCGGATGGTTTGCGACCGTCACG
CCGATTCCTCGGGCTTGGGGGTTCCAGTGCCATTGCAGGGCCGGCAGACAACC
CAGCCGCTTACGCCTGGCCAACCGCCCGTTCCTCCACACATGGGGCATTCCAC
GGCGTCGGTGCCTGGTTGTTCTTGATTTTCCATGCCGCCTCCTTTAGCCGCTAA
AATTCATCTACTCATTTATTCATTTGCTCATTTACTCTGGTAGCTGCGCGATGTAT
TCAGATAGCAGCTCGGTAATGGTCTTGCCTTGGCGTACCGCGTACATCTTCAGC
TTGGTGTGATCCTCCGCCGGCAACTGAAAGTTGACCCGCTTCATGGCTGGCGT
GTCTGCCAGGCTGGCCAACGTTGCAGCCTTGCTGCTGCGTGCGCTCGGACGG
CCGGCACTTAGCGTGTTTGTGCTTTTGCTCATTTTCTCTTTACCTCATTAACTCAA
ATGAGTTTTGATTTAATTTCAGCGGCCAGCGCCTGGACCTCGCGGGCAGCGTC
GCCCTCGGGTTCTGATTCAAGAACGGTTGTGCCGGCGGCGGCAGTGCCTGGG
TAGCTCACGCGCTGCGTGATACGGGACTCAAGAATGGGCAGCTCGTACCCGGC
CAGCGCCTCGGCAACCTCACCGCCGATGCGCGTGCCTTTGATCGCCCGCGACA
CGACAAAGGCCGCTTGTAGCCTTCCATCCGTGACCTCAATGCGCTGCTTAACCA
GCTCCACCAGGTCGGCGGTGGCCCATATGTCGTAAGGGCTTGGCTGCACCGG
AATCAGCACGAAGTCGGCTGCCTTGATCGCGGACACAGCCAAGTCCGCCGCCT
GGGGCGCTCCGTCGATCACTACGAAGTCGCGCCGGCCGATGGCCTTCACGTC
GCGGTCAATCGTCGGGCGGTCGATGCCGACAACGGTTAGCGGTTGATCTTCCC
GCACGGCCGCCCAATCGCGGGCACTGCCCTGGGGATCGGAATCGACTAACAG
AACATCGGCCCCGGCGAGTTGCAGGGCGCGGGCTAGATGGGTTGCGATGGTC
GTCTTGCCTGACCCGCCTTTCTGGTTAAGTACAGCGATAACCTTCATGCGTTCC
CCTTGCGTATTTGTTTATTTACTCATCGCATCATATACGCAGCGACCGCATGACG
CAAGCTGTTTTACTCAAATACACATCACCTTTTTAGACGGCGGCGCTCGGTTTCT
TCAGCGGCCAAGCTGGCCGGCCAGGCCGCCAGCTTGGCATCAGACAAACCGG
CCAGGATTTCATGCAGCCGCACGGTTGAGACGTGCGCGGGCGGCTCGAACAC
GTACCCGGCCGCGATCATCTCCGCCTCGATCTCTTCGGTAATGAAAACGGTTC
GTCCTGGCCGTCCTGGTGCGGTTTCATGCTTGTTCCTCTTGGCGTTCATTCTCG
GCGGCCGCCAGGGCGTCGGCCTCGGTCAATGCGTCCTCACGGAAGGCACCGC
GCCGCCTGGCCTCGGTGGGCGTCACTTCCTCGCTGCGCTCAAGTGCGCGGTA

FIG. 39G

>JD16 SEQ ID N°: 84 CONTINUED

CAGGGTCGAGCGATGCACGCCAAGCAGTGCAGCCGCCTCTTTCACGGTGCGG
CCTTCCTGGTCGATCAGCTCGCGGGCGTGCGCGATCTGTGCCGGGGTGAGGG
TAGGGCGGGGGCCAAACTTCACGCCTCGGGCCTTGGCGGCCTCGCGCCCGCT
CCGGGTGCGGTCGATGATTAGGGAACGCTCGAACTCGGCAATGCCGGCGAAC
ACGGTCAACACCATGCGGCCGGCCGGCGTGGTGGTGTCGGCCCACGGCTCTG
CCAGGCTACGCAGGCCCGCGCCGGCCTCCTGGATGCGCTCGGCAATGTCCAG
TAGGTCGCGGGTGCTGCGGGCCAGGCGGTCTAGCCTGGTCACTGTCACAACG
TCGCCAGGGCGTAGGTGGTCAAGCATCCTGGCCAGCTCCGGGCGGTCGCGCC
TGGTGCCGGTGATCTTCTCGGAAAACAGCTTGGTGCAGCCGGCCGCGTGCAGT
TCGGCCCGTTGGTTGGTCAAGTCCTGGTCGTCGGTGCTGACGCGGGCATAGCC
CAGCAGGCCAGCGGCGGCGCTCTTGTTCATGGCGTAATGTCTCCGGTTCTAGT
CGCAAGTATTCTACTTTATGCGACTAAAACACGCGACAAGAAAACGCCAGGAAA
AGGGCAGGGCGGCAGCCTGTCGCGTAACTTAGGACTTGTGCGACATGTCGTTT
TCAGAAGACGGCTGCACTGAACGTCAGAAGCCGACTGCACTATAGCAGCGGAG
GGGTTGGATCAAAGTACT

FIG. 40A

>RER32 SEQ ID N°: 85

TTGATCCCGAGGGGAACCCTGTGGTTGGCATGCACATACAAATGGACGAACGG
ATAAACCTTTTCACGCCCTTTTAAATATCCGTTATTCTAATAAACGCTCTTTTCTC
TTAGGTTTACCCGCCAATATATCCTGTCAAACACTGATAGTTTAAACTGAAGGCG
GGAAACGACAATCTGATCCAAGCTCAAGCTGCTCTAGCCAATACGCAAACCGCC
TCTCCCCGCGCGTTGGCCGATTCATTAATGCAGCTGGCACGACAGGTTTCCCG
ACTGGAAAGCGGGCAGTGAGCGCAACGCAATTAATGTGAGTTAGCTCACTCATT
AGGCACCCCAGGCTTTACACTTTATGCTTCCGGCTCGTATGTTGTGTGGAATTG
TGAGCGGATAACAATTTCACACAGGAAACAGCTATGACCATGATTACG<ins>AAttgaaa</ins>
<ins>acgcaggcccatttacATCCTCCAAAACAAAAGAAGCAATAGAATCCGGAACTGAATTA</ins>
<ins>AAAACATACAAACCAAGAGGTAAAGAAAACGCATAGTTAGCTAACCCGTCCGCA</ins>
<ins>AGACGATTGACCTCCCTATACACGTGAGAAATACGGACTAACCAGTCCCTTGAT</ins>
<ins>ATGAAGCCATAACACAAACGTAGTAGGAAAGATAGAGGATGAGAATCCGGTATC</ins>
<ins>CCTGTCTGTAAAAACCCAACCACGATCTTCGAATCCACTTCCAGCTCAAGGCGT</ins>
<ins>GTTATTCCTTGCTCCAGACTATGTGTAACCCATAGTAGAGTCCCCACAACTCTG</ins>
<ins>CTAGTGGCGCTGAACAGATTTCGATATTCAAAGCAAAAACCCCAACCCAGTTCT</ins>
<ins>CGTTCCCATCACGCACCGCACCTCCCGCTGCTGCTAACCCGGGATTCTCTCTC</ins>
<ins>GAGGCTCCATCCAT</ins>gttcaactagcctgatgaatttattaaactcatgtttccatttttttttcccaccagttatgttagt
ttgattaattttcagtcaattttggcataacgctttaaaataattatatcaaaataatattttcagtttttctgcaacagattcatt
ccaccaagaattcagccgattctacccgaattaatattaccattttcggactagatctatgaacgaaggtacaaaattaa
tcagttaaaaagaaaatagagtggcaagtactacatctagtgccgtatgatatgataatataggaacctaaacgaat
tttatactaattcaaatttaaaagtagttaggtttgtcacaaatgcaaattacaaattatatcgacgtaacgcttactcattaa
ataatctaaattacttggttaaaagactaattaaatattcttaacaagtaggcttttgttttcattataaaacaaattaaaaag
ctatactaatataaaaatggagattggtatttccaaagcagcaaagacagaaaaactgcaggttattatctctccatctt
catcttgcagagtggttctttctgggttttctgacttgcttttcatttttttattgatacaaatgttaaaccaattattttaaatagtctt
tgagattaatgaagagagatttgtgaacacaattaataaagagttatactatagtagtagtctttttttactgtatagtattttct
ccccgcatctgtcttgtctcactgtcttttctcgcaagtctctctattaaaaacctctttccctctactctgtcctttctctctc*tgc*
*agaagaagctcagatacagaaactgactaccaagaacaaagcttttccttcgagcaaagaaagttctttttttcttctttt*
*gctcttcgtaacccaaccaacaagactttcataagctattaaatcagaaccctggaagacaaaaaaggggaaaaac*
*cattatccttaaagtaaccaacacttctctctctcttcttca**ATGGATTTGCAACTGAAACAATGGAGA*
*AGCCAGCAGCAGCAACAACATCAGACAGAGTCAGAAGAACAACCTTCTGCAG*
*CTAAGATACCAAAACATGTCTTTGACCAGATTCATTCTCACACTGCAACTTCTA*
*CTGCTCTTCCTCTCTTTACCCCTGAGCCTACTTCTTCTAAACTCTCCTCTTTGTC*
*TCCTGATTCTTCCTCCAGGTTCCCCA*gtgagtcttttcttcctcttatcttatctttcttgataaagaa

FIG. 40B

>RER32 SEQ ID N°: 85 CONTINUED ttagacttttcattcatatagtttgtgtttaattgattttgattccttttgtagAGATGGGGAGCTTCTTTAG
CTGGGCACAGTGGCAAGAACTTGAACTACAAGCTCTGATCTACAGGTACATGT
TGGCTGGTGCTGCTGTTCCTCAGGAGCTCCTTTTACCAATCAAGAAAAGCCTT
CTCCATCTATCTCCTTCCTACTTTCTTCACCATCCTCTTCAACACCTACCTCATT
ACCAACCTGCTTgtgagtctcgagaacagtcttcatctatctattttttaaatataaatgggttttgtgctact
ggtgttggagttgtgttcccaagatccagactttcaatattagtatattatctcgttttgccaatcttgaagatctaa
acatgtgtgaatgggattaagtaggattagaatcttgttattgatctgatatgtgatatgaatgttgaaaacagG
GTATTTGGGAAGGGCAGCGATGGATCCTGAGCCAGGCAGATGCAGGAGAAC
GGATGGTAAGAAGTGGAGATGTTCAAGAGACGTCTTCGCTGGCCACAAGTAT
TGCGAGCGCCACATGCACCGTGGCCGCAACCGTTCtAGAAAaCCaGTaGAgAC
TCCAACCACCGTCAATGCAACTGCCACGTCCATGGCTTCATCAGTAGCAGCCG
CAGCCACCACTACAACAGCAACAACAACATCTACGTTTGCTTTTGGTGGTGGT
GGTGGTAGTGAGGAAGTGGTTGGTCAAGGAGGATCTTTCTTCTTCTCTGGCTC
TTCTAACTCTTCATCTGAACTTCTCCACCTTAGTCAAAGgtaataaaagaaactgttttt
tttctcttaggtctgtctgttttagctgttgaactttatggtcaaaacattaaacttaaacacattgactttttattctt
tagtgttgagccaataagattcatggttgagattttagacaattgttttgaataataatgaaatcgatttaaagcaa
tactgattcttgatttattagtatgaagtatgaactaatgatatacacaacttggtttgtatgttcatagcgatgttgt
gaagagagggtaatgttggaaattgagagacacatccttatcattttagggttggttggtttgtttgtttgttgaa
ttatgagtttgatttcattgtgaaaatatctttctttcttttttcttattgtgttgagagataatgataacattggatttgat
agaatctataatttgaagctaggtgtgagacttttcaaacagagaaaatagaaagagagagaaatggtagga
ccttagtgaaagctgacccatatatgtctcatatcttgcagaaaagttaaagcttttagattcttctgcacccacc
tcccctatccacacacaacacatgatatacaaaacactcactttataattctatttctatttactgcttaatcaattc
ttataaaacccacattaaaaggtacttttaaagcctataaactaatataaaggctactactgtctgcaactttgttg
ttgaagcctaaatgtggtttctcttttgacaaattattgcttttgtgctttgttttcaccaatgagatgtggattctgtta
acagTTGTTCGGAGATGAAGCAAGAAAGCAACAACATGAACAACAAGAGGCCA
TACGAGTCCCACATCGGATTCAGTAACAACAGATCAGATGGAGGACACATCC
TGAGGCCCTTCTTTGACGATTGGCCTCGTTCTTCGCTCCAAGAAGCTGACAAT
AGTTCAAGCCCCATGAGCTCAGCCACTTGTCTCTCCATCTCCATGCCCGGGAA
CTCTTCCTCAGACGTCTCTCTGAAGCTGTCCACAGGCAACGAAGAGGGAGCC
CGGAGCAACAACAATGGGAGAGATCAGCAAAACATGAGCTGGTGGAGCGGT
GGAGGTTCCAACCACCATCATCACAACATGGGCGGACCATTGGCCGAAGCCC
TGAGATCTTCTTCCTCATCTTCCCCAACCAGTGTTCTCCATCAGCTTGGTGTCT
CGACACAAGCCTTTCATTGAccagtgtaaaaccaacacaacaatgcggttttactgtgttttggttttatc

FIG. 40C

>RER32 SEQ ID N°: 85 CONTINUED

*caaatttcctgtataaagagggaggcttttgttgtcctcttccctttttcttttaagatttcccttgtatctgtagcctttctctgca gattttatatcctcaaagatttgtttttggaaattcatgtctaaataggatctacgatgaagcttaggcaaaat*<u>gTCGAC CTGCAGAGCTTTCGTTCGTATCATCGGTTTCGACAACGTTCGTCAAGTTCAATG CATCAGTTTCATTGCGCACACACCAGAATCCTACTGAGTTCGAGTATTATGGC ATTGGGAAACATGTTTTTCTTGTACCATTTGTTGTGCTTGTAATTTACTGTGTTT TTTATTCGGTTTTCGCTATCGAACTGTGAAATGGAAATGGATGGAGAAGAGTT AATGAATGATATGGTCCTTTTGTTCATTCTCAAATTAATATTATTTGTTTTTTCTC TTATTTGTTGTGTGTTGAATTTGAAAATATAAGAGATATGCAAACATTTTGTTTT GAGTAAAAATGTGTCAAATCGTGGCCTCTAATGACCGAAGTTAATATGAGGAG TAAAACACTTGTAGTTGTACCATTATGCTTATTCACTAGGCAACAAATATATTTT CAGACCTAGAAAAGCTGCAAATGTTACTGAATACAAGTATGTCCTCTTGTGTTT TAGACATTTATGAACTTTCCTTTATGTAATTTTCCAGAATCCTTGTCAGATTCTA ATCATTGCTTTATAATTATAGTTATACTCATGGATTTGTAGTTGAGTATGAAAAT ATTTTTTAATGCATTTTATGACTTGCCAATTGATTGACAACATGCATCAATCG</u>AA GCTTGGCACTGGCCGTCGTTTTACAACGTCGTGACTGGGAAAACCCTGGCGTT ACCCAACTTAATCGCCTTGCAGCACATCCCCCTTTCGCCAGCTGGCGTAATAGC GAAGAGGCCCGCACCGATCGCCCTTCCCAACAGTTGCGCAGCCTGAATGGCGA ATGCTAGAGCAGCTTGCCAACATGGTGGAGCACGACACTCTCGTCTACTCCAAG AATATCAAAGATACAGTCTCAGAAGACCAAAGGGCTATTGAGACTTTTCAACAAA GGGTAATATCGGGAAACCTCCTCGGATTCCATTGCCCAGCTATCTGTCACTTCA TCAAAAGGACAGTAGAAAAGGAAGGTGGCACCTACAAATGCCATCATTGCGATA AAGGAAAGGCTATCGTTCAAGATGCCTCTGCCGACAGTGGTCCCAAAGATGGA CCCCCACCCACGAGGAGCATCGTGGAAAAGAAGACGTTCCAACCACGTCTTC AAAGCAAGTGGATTGATGTGATAACATGGTGGAGCACGACACTCTCGTCTACTC CAAGAATATCAAAGATACAGTCTCAGAAGACCAAAGGGCTATTGAGACTTTTCAA CAAAGGGTAATATCGGGAAACCTCCTCGGATTCCATTGCCCAGCTATCTGTCAC TTCATCAAAAGGACAGTAGAAAAGGAAGGTGGCACCTACAAATGCCATCATTGC GATAAAGGAAAGGCTATCGTTCAAGATGCCTCTGCCGACAGTGGTCCCAAAGAT GGACCCCCACCCACGAGGAGCATCGTGGAAAAGAAGACGTTCCAACCACGTC TTCAAAGCAAGTGGATTGATGTGATATCTCCACTGACGTAAGGGATGACGCACA ATCCCACTATCCTTCGCAAGACCCTTCCTCTATATAAGGAAGTTCATTTCATTTG GAGAGGACACGCTGAAATCACCAGTCTCTCTACAAATCTATCTCTCTCGATTC GCAGATCTGTCGATCGACCATGGGGATTGAACAAGATGGATTGCACGCAGGTT

FIG. 40D

>RER32 SEQ ID N°: 85 CONTINUED

CTCCGGCCGCTTGGGTGGAGAGGCTATTCGGCTATGACTGGGCACAACAGACA
ATCGGCTGCTCTGATGCCGCCGTGTTCCGGCTGTCAGCGCAGGGGCGCCCGG
TTCTTTTTGTCAAGACCGACCTGTCCGGTGCCCTGAATGAACTCCAGGACGAGG
CAGCGCGGCTATCGTGGCTGGCCACGACGGGCGTTCCTTGCGCAGCTGTGCT
CGACGTTGTCACTGAAGCGGGAAGGGACTGGCTGCTATTGGGCGAAGTGCCG
GGGCAGGATCTCCTGTCATCTCACCTTGCTCCTGCCGAGAAAGTATCCATCATG
GCTGATGCAATGCGGCGGCTGCATACGCTTGATCCGGCTACCTGCCCATTCGA
CCACCAAGCGAAACATCGCATCGAGCGAGCACGTACTCGGATGGAAGCCGGTC
TTGTCGATCAGGATGATCTGGACGAAGAGCATCAGGGGCTCGCGCCAGCCGAA
CTGTTCGCCAGGCTCAAGGCGCGCATGCCCGACGGCGAGGATCTCGTCGTGA
CACATGGCGATGCCTGCTTGCCGAATATCATGGTGGAAAATGGCCGCTTTTCTG
GATTCATCGACTGTGGCCGGCTGGGTGTGGCGGACCGCTATCAGGACATAGCG
TTGGCTACCCGTGATATTGCTGAAGAGCTTGGCGGCGAATGGGCTGACCGCTT
CCTCGTGCTTTACGGTATCGCCGCTCCCGATTCGCAGCGCATCGCCTTCTATCG
CCTTCTTGACGAGTTCTTCTGAGCGGGACTCTGGGGTTCGGATCGATCCTCTAG
CTAGAGTCGATCGACATCGAGTTTCTCCATAATAATGTGTGAGTAGTTCCCAGAT
AAGGGAATTAGGGTTCTTATAGGGTTTCGCTCACGTGTTGAGCATATAAGAAAC
CCTTAGTATGTATTTGTATTTGTAAAATACTTCTATCAATAAAATTTCTAATTCCTA
AAACCAAAATCCAGTACTAAAATCCAGATCACCTAAAGTCCCTATAGATCCCCCG
AATTAATTCGGCGTTAATTCAGTACATTAAAAACGTCCGCAATGTGTTATTAAGTT
GTCTAAGCGTCAATTTGTTTACACCACAATATATCCTGCCACCAGCCAGCCAACA
GCTCCCCGACCGGCAGCTCGGCACAAAATCACCACTCGATACAGGCAGCCCAT
CAGTCCGGGACGGCGTCAGCGGGAGAGCCGTTGTAAGGCGGCAGACTTTGCT
CATGTTACCGATGCTATTCGGAAGAACGGCAACTAAGCTGCCGGGTTTGAAACA
CGGATGATCTCGCGGAGGGTAGCATGTTGATTGTAACGATGACAGAGCGTTGC
TGCCTGTGATCAATTCGGGCACGAACCCAGTGGACATAAGCCTCGTTCGGTTC
GTAAGCTGTAATGCAAGTAGCGTAACTGCCGTCACGCAACTGGTCCAGAACCTT
GACCGAACGCAGCGGTGGTAACGGCGCAGTGGCGGTTTTCATGGCTTCTTGTT
ATGACATGTTTTTTTGGGGTACAGTCTATGCCTCGGGCATCCAAGCAGCAAGCG
CGTTACGCCGTGGGTCGATGTTTGATGTTATGGAGCAGCAACGATGTTACGCAG
CAGGGCAGTCGCCCTAAAACAAAGTTAAACATCATGGGGGAAGCGGTGATCGC
CGAAGTATCGACTCAACTATCAGAGGTAGTTGGCGTCATCGAGCGCCATCTCGA
ACCGACGTTGCTGGCCGTACATTTGTACGGCTCCGCAGTGGATGGCGGCCTGA

FIG. 40E

>RER32 SEQ ID N°: 85 CONTINUED

AGCCACACAGTGATATTGATTTGCTGGTTACGGTGACCGTAAGGCTTGATGAAA
CAACGCGGCGAGCTTTGATCAACGACCTTTTGGAAACTTCGGCTTCCCCTGGAG
AGAGCGAGATTCTCCGCGCTGTAGAAGTCACCATTGTTGTGCACGACGACATCA
TTCCGTGGCGTTATCCAGCTAAGCGCGAACTGCAATTTGGAGAATGGCAGCGC
AATGACATTCTTGCAGGTATCTTCGAGCCAGCCACGATCGACATTGATCTGGCT
ATCTTGCTGACAAAAGCAAGAGAACATAGCGTTGCCTTGGTAGGTCCAGCGGC
GGAGGAACTCTTTGATCCGGTTCCTGAACAGGATCTATTTGAGGCGCTAAATGA
AACCTTAACGCTATGGAACTCGCCGCCCGACTGGGCTGGCGATGAGCGAAATG
TAGTGCTTACGTTGTCCCGCATTTGGTACAGCGCAGTAACCGGCAAAATCGCGC
CGAAGGATGTCGCTGCCGACTGGGCAATGGAGCGCCTGCCGGCCCAGTATCA
GCCCGTCATACTTGAAGCTAGACAGGCTTATCTTGGACAAGAAGAAGATCGCTT
GGCCTCGCGCGCAGATCAGTTGGAAGAATTTGTCCACTACGTGAAAGGCGAGA
TCACCAAGGTAGTCGGCAAATAATGTCTAGCTAGAAATTCGTTCAAGCCGACGC
CGCTTCGCCGGCGTTAACTCAAGCGATTAGATGCACTAAGCACATAATTGCTCA
CAGCCAAACTATCAGGTCAAGTCTGCTTTTATTATTTTTAAGCGTGCATAATAAG
CCCTACACAAATTGGGAGATATATCATGCATGACCAAAATCCCTTAACGTGAGTT
TTCGTTCCACTGAGCGTCAGACCCCGTAGAAAAGATCAAAGGATCTTCTTGAGA
TCCTTTTTTTCTGCGCGTAATCTGCTGCTTGCAAACAAAAAAACCACCGCTACCA
GCGGTGGTTTGTTTGCCGGATCAAGAGCTACCAACTCTTTTTCCGAAGGTAACT
GGCTTCAGCAGAGCGCAGATACCAAATACTGTCCTTCTAGTGTAGCCGTAGTTA
GGCCACCACTTCAAGAACTCTGTAGCACCGCCTACATACCTCGCTCTGCTAATC
CTGTTACCAGTGGCTGCTGCCAGTGGCGATAAGTCGTGTCTTACCGGGTTGGA
CTCAAGACGATAGTTACCGGATAAGGCGCAGCGGTCGGGCTGAACGGGGGGT
TCGTGCACACAGCCCAGCTTGGAGCGAACGACCTACACCGAACTGAGATACCT
ACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTC
CAGGGGGAAACGCCTGGTATCTTTATAGTCCTGTCGGGTTTCGCCACCTCTGAC
TTGAGCGTCGATTTTTGTGATGCTCGTCAGGGGGCGGAGCCTATGGAAAAAC
GCCAGCAACGCGGCCTTTTTACGGTTCCTGGCCTTTTGCTGGCCTTTTGCTCAC
ATGTTCTTTCCTGCGTTATCCCCTGATTCTGTGGATAACCGTATTACCGCCTTTG
AGTGAGCTGATACCGCTCGCCGCAGCCGAACGACCGAGCGCAGCGAGTCAGT
GAGCGAGGAAGCGGAAGAGCGCCTGATGCGGTATTTTCTCCTTACGCATCTGT
GCGGTATTTCACACCGCATATGGTGCACTCTCAGTACAATCTGCTCTGATGCCG

FIG. 40F

>RER32 SEQ ID N°: 85 CONTINUED

CATAGTTAAGCCAGTATACACTCCGCTATCGCTACGTGACTGGGTCATGGCTGC
GCCCCGACACCCGCCAACACCCGCTGACGCGCCCTGACGGGCTTGTCTGCTC
CCGGCATCCGCTTACAGACAAGCTGTGACCGTCTCCGGGAGCTGCATGTGTCA
GAGGTTTTCACCGTCATCACCGAAACGCGCGAGGCAGGGTGCCTTGATGTGGG
CGCCGGCGGTCGAGTGGCGACGGCGCGGCTTGTCCGCGCCCTGGTAGATTGC
CTGGCCGTAGGCCAGCCATTTTTGAGCGGCCAGCGGCCGCGATAGGCCGACG
CGAAGCGGCGGGGCGTAGGGAGCGCAGCGACCGAAGGGTAGGCGCTTTTTGC
AGCTCTTCGGCTGTGCGCTGGCCAGACAGTTATGCACAGGCCAGGCGGGTTTT
AAGAGTTTTAATAAGTTTTAAAGAGTTTTAGGCGGAAAAATCGCCTTTTTTCTCTT
TTATATCAGTCACTTACATGTGTGACCGGTTCCCAATGTACGGCTTTGGGTTCCC
AATGTACGGGTTCCGGTTCCCAATGTACGGCTTTGGGTTCCCAATGTACGTGCT
ATCCACAGGAAAGAGACCTTTTCGACCTTTTTCCCCTGCTAGGGCAATTTGCCC
TAGCATCTGCTCCGTACATTAGGAACCGGCGGATGCTTCGCCCTCGATCAGGTT
GCGGTAGCGCATGACTAGGATCGGGCCAGCCTGCCCCGCCTCCTCCTTCAAAT
CGTACTCCGGCAGGTCATTTGACCCGATCAGCTTGCGCACGGTGAAACAGAAC
TTCTTGAACTCTCCGGCGCTGCCACTGCGTTCGTAGATCGTCTTGAACAACCAT
CTGGCTTCTGCCTTGCCTGCGGCGCGGCGTGCCAGGCGGTAGAGAAAACGGC
CGATGCCGGGATCGATCAAAAAGTAATCGGGGTGAACCGTCAGCACGTCCGGG
TTCTTGCCTTCTGTGATCTCGCGGTACATCCAATCAGCTAGCTCGATCTCGATGT
ACTCCGGCCGCCCGGTTTCGCTCTTTACGATCTTGTAGCGGCTAATCAAGGCTT
CACCCTCGGATACCGTCACCAGGCGGCCGTTCTTGGCCTTCTTCGTACGCTGC
ATGGCAACGTGCGTGGTGTTTAACCGAATGCAGGTTTCTACCAGGTCGTCTTTC
TGCTTTCCGCCATCGGCTCGCCGGCAGAACTTGAGTACGTCCGCAACGTGTGG
ACGGAACACGCGGCCGGGCTTGTCTCCCTTCCCTTCCCGGTATCGGTTCATGG
ATTCGGTTAGATGGGAAACCGCCATCAGTACCAGGTCGTAATCCCACACACTGG
CCATGCCGGCCGGCCCTGCGGAAACCTCTACGTGCCCGTCTGGAAGCTCGTAG
CGGATCACCTCGCCAGCTCGTCGGTCACGCTTCGACAGACGGAAAACGGCCAC
GTCCATGATGCTGCGACTATCGCGGGTGCCCACGTCATAGAGCATCGGAACGA
AAAAATCTGGTTGCTCGTCGCCCTTGGGCGGCTTCCTAATCGACGGCGCACCG
GCTGCCGGCGGTTGCCGGGATTCTTTGCGGATTCGATCAGCGGCCGCTTGCCA
CGATTCACCGGGGCGTGCTTCTGCCTCGATGCGTTGCCGCTGGGCGGCCTGC
GCGGCCTTCAACTTCTCCACCAGGTCATCACCCAGCGCCGCGCCGATTTGTAC
CGGGCCGGATGGTTTGCGACCGTCACGCCGATTCCTCGGGCTTGGGGGTTCC

FIG. 40G

>RER32 SEQ ID N°: 85 CONTINUED

AGTGCCATTGCAGGGCCGGCAGACAACCCAGCCGCTTACGCCTGGCCAACCG
CCCGTTCCTCCACACATGGGGCATTCCACGGCGTCGGTGCCTGGTTGTTCTTG
ATTTTCCATGCCGCCTCCTTTAGCCGCTAAAATTCATCTACTCATTTATTCATTTG
CTCATTTACTCTGGTAGCTGCGCGATGTATTCAGATAGCAGCTCGGTAATGGTC
TTGCCTTGGCGTACCGCGTACATCTTCAGCTTGGTGTGATCCTCCGCCGGCAAC
TGAAAGTTGACCCGCTTCATGGCTGGCGTGTCTGCCAGGCTGGCCAACGTTGC
AGCCTTGCTGCTGCGTGCGCTCGGACGGCCGGCACTTAGCGTGTTTGTGCTTT
TGCTCATTTTCTCTTTACCTCATTAACTCAAATGAGTTTTGATTTAATTTCAGCGG
CCAGCGCCTGGACCTCGCGGGCAGCGTCGCCCTCGGGTTCTGATTCAAGAAC
GGTTGTGCCGGCGGCGGCAGTGCCTGGGTAGCTCACGCGCTGCGTGATACGG
GACTCAAGAATGGGCAGCTCGTACCCGGCCAGCGCCTCGGCAACCTCACCGC
CGATGCGCGTGCCTTTGATCGCCCGCGACACGACAAAGGCCGCTTGTAGCCTT
CCATCCGTGACCTCAATGCGCTGCTTAACCAGCTCCACCAGGTCGGCGGTGGC
CCATATGTCGTAAGGGCTTGGCTGCACCGGAATCAGCACGAAGTCGGCTGCCT
TGATCGCGGACACAGCCAAGTCCGCCGCCTGGGGCGCTCCGTCGATCACTAC
GAAGTCGCGCCGGCCGATGGCCTTCACGTCGCGGTCAATCGTCGGGCGGTCG
ATGCCGACAACGGTTAGCGGTTGATCTTCCCGCACGGCCGCCCAATCGCGGGC
ACTGCCCTGGGGATCGGAATCGACTAACAGAACATCGGCCCCGGCGAGTTGCA
GGGCGCGGGCTAGATGGGTTGCGATGGTCGTCTTGCCTGACCCGCCTTTCTGG
TTAAGTACAGCGATAACCTTCATGCGTTCCCCTTGCGTATTTGTTTATTTACTCAT
CGCATCATATACGCAGCGACCGCATGACGCAAGCTGTTTTACTCAAATACACAT
CACCTTTTTAGACGGCGGCGCTCGGTTTCTTCAGCGGCCAAGCTGGCCGGCCA
GGCCGCCAGCTTGGCATCAGACAAACCGGCCAGGATTTCATGCAGCCGCACGG
TTGAGACGTGCGCGGGCGGCTCGAACACGTACCCGGCCGCGATCATCTCCGC
CTCGATCTCTTCGGTAATGAAAAACGGTTCGTCCTGGCCGTCCTGGTGCGGTTT
CATGCTTGTTCCTCTTGGCGTTCATTCTCGGCGGCCGCCAGGGCGTCGGCCTC
GGTCAATGCGTCCTCACGGAAGGCACCGCGCCGCCTGGCCTCGGTGGGCGTC
ACTTCCTCGCTGCGCTCAAGTGCGCGGTACAGGGTCGAGCGATGCACGCCAAG
CAGTGCAGCCGCCTCTTTCACGGTGCGGCCTTCCTGGTCGATCAGCTCGCGGG
CGTGCGCGATCTGTGCCGGGGTGAGGGTAGGGCGGGGGCCAAACTTCACGCC
TCGGGCCTTGGCGGCCTCGCGCCCGCTCCGGGTGCGGTCGATGATTAGGGAA
CGCTCGAACTCGGCAATGCCGGCGAACACGGTCAACACCATGCGGCCGGCCG
GCGTGGTGGTGTCGGCCCACGGCTCTGCCAGGCTACGCAGGCCCGCGCCGGC

FIG. 40H

>RER32 SEQ ID N°: 85 CONTINUED

CTCCTGGATGCGCTCGGCAATGTCCAGTAGGTCGCGGGTGCTGCGGGCCAGG
CGGTCTAGCCTGGTCACTGTCACAACGTCGCCAGGGCGTAGGTGGTCAAGCAT
CCTGGCCAGCTCCGGGCGGTCGCGCCTGGTGCCGGTGATCTTCTCGGAAAAC
AGCTTGGTGCAGCCGGCCGCGTGCAGTTCGGCCCGTTGGTTGGTCAAGTCCTG
GTCGTCGGTGCTGACGCGGGCATAGCCCAGCAGGCCAGCGGCGGCGCTCTTG
TTCATGGCGTAATGTCTCCGGTTCTAGTCGCAAGTATTCTACTTTATGCGACTAA
AACACGCGACAAGAAAACGCCAGGAAAAGGGCAGGGCGGCAGCCTGTCGCGT
AACTTAGGACTTGTGCGACATGTCGTTTTCAGAAGACGGCTGCACTGAACGTCA
GAAGCCGACTGCACTATAGCAGCGGAGGGG

FIGURE 47

>CpGRF (*Carica papaya*) (SEQ ID No. 88)
ATGGACTTGCATCTGAAACAATGGAGGAACCAGCATGAGTCAGAGCAACAACCTTCT
GCGAAGATACCAAAACTTCTCCTTGATCCACATCAACAAAACCCATCTGCCTCAGCT
TCTGCTTCTCTTGCACTCCCTTTGTTTGTACCTGAACAGCCCTCTACCAAACTCACC
AACCTGTCAGCGTTGCCAGATTCATCCTCTAGATTTCCCAAGATGGGAAGCTACTTT
AGTTTGGCTCAGTGGCAGGAGCTGGAGTTGCAGGCTTTGATCTACAGATACATGTTA
GCTGGTGCTGCCGTTCCTCCCGAGCTCCTCCAGCCAATCAAGAAAAGTCTCCTTCAC
TCTTCTCCATATTTCCTCCATCATCCTCTTCAACATTACGCTCATTATCAGCCTGCT
TGGTATTGGAGCAGAGCTGCCCTGGATCCGGAGCCGGGTCGGTGCCGGAGAACAGAT
GGAAAGAAATGGAGGTGCTCAAGAGATGTGGTGGCTGGCCAGAAATATTGCGAGCGC
CACATGCACCGTGGCCGCAACCGTTCAAGAAAGCCTGTGGAAATCCCCACGCCGAAC
ACCACCGCCGCCGTCACTCCACTCTCCGTAGCCGCCTCAACGGTTTCTTCTCTGGGT
GCTGGTGGTGGTGGTCTCGGTGGCAGCGACACTTTCAAATCCACCGGTCCAATCTCC
ATGACATTGCCGGCAATGGTGGCTAATGGGCCGAGCTTCGGCCTCGCCGGACCGGCT
AGCTCCGCTGATCTCCTGCACCTGAATCATAGTTCCTCAGAGTTCAGGATTGAGAAC
AAGGGCCTCTTTGAAGCCCAAAACGAAGTTGACAACAGACCTGACGGCCACATTCTA
AGGCATTTTTTTGATGATTGGCCCCGATCACTTCAAGAACCTGATAATGCTGGGAGG
AATGCTAGCCCTATGAGCTCCTCCACCTGTCTCACAATTTCATCCTCCGATGTGTCG
TTGAAACTGTCAACTGGTAATGCAGATGAACTCACCACCAGGGACGGCGAAAGGGAT
CAACTGCAGTTGAATTGGGCTGCCGGATGGGCGACAAACCAAATGGGAGGACCTCTA
GCTGAGGCATTGCGTTCCTCCACTTCAAATTCTTCACCCACCAGTGTCTTACATCAG
TTGCCGCGGAACTCTGCCACAGAATCTAGTTACGTTAGCACCTGTGTTTAG

FIGURE 48

>CpGRF (*Carica papaya*) (SEQ ID No. 89)
MDLHLKQWRNQHESEQQPSAKIPKLLLDPHQQNPSASASASLALPLFVPEQPSTKLT
NLSALPDSSSRFPKMGSYFSLAQWQELELQALIYRYMLAGAAVPPELLQPIKKSLLH
SSPYFLHHPLQHYAHYQPAWYWSRAALDPEPGRCRRTDGKKWRCSRDVVAGQKYCER
HMHRGRNRSRKPVEIPTPNTTAAVTPLSVAASTVSSLGAGGGGLGGSDTFKSTGPIS
MTLPAMVANGPSFGLAGPASSADLLHLNHSSSEFRIENKGLFEAQNEVDNRPDGHIL
RHFFDDWPRSLQEPDNAGRNASPMSSSTCLTISSSDVSLKLSTGNADELTTRDGERD
QLQLNWAAGWATNQMGGPLAEALRSSTSNSSPTSVLHQLPRNSATESSYVSTCV FIGURE 50
A
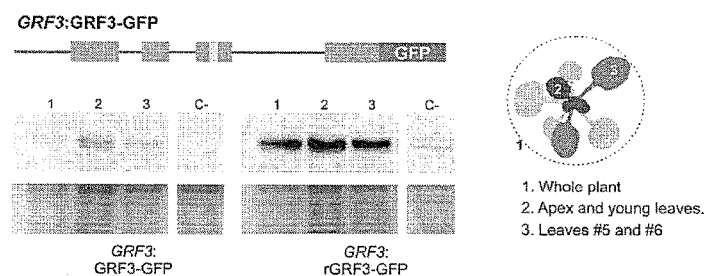
1. Whole plant
2. Apex and young leaves.
3. Leaves #5 and #6
B
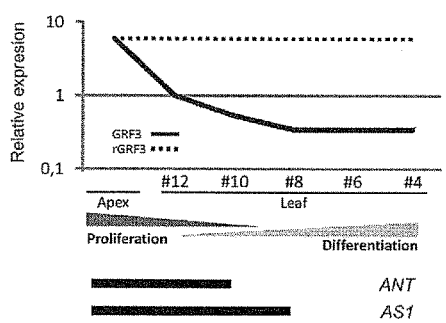
C
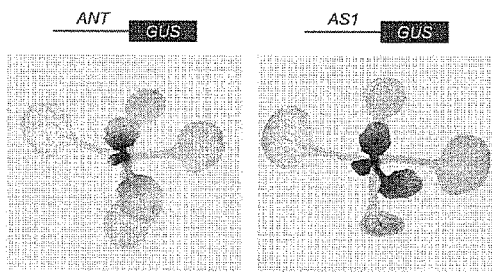

FIGURE 56

| Construct | Copy No. | Glass house randomised position order | widest stem width at Flowering mm | 10cm stem weight (g) |
|---|---|---|---|---|
| rGRF3 | 1 | 3 | 18.67 | 3.5 |
| rGRF3 | 1 | 4 | 17.60 | 2.0 |
| rGRF3 | 2 | 7 | 15.88 | 2.4 |
| rGRF3 | 1 | 13 | 14.46 | 1.9 |
| rGRF3 | 2 | 14 | 16.31 | 2.2 |
| rGRF3 | 2 | 15 | 17.18 | 2.9 |
| rGRF3 | 1 | 16 | 17.81 | 2.4 |
| rGRF3 | 2 | 20 | 17.47 | 2.3 |
| rGRF3 | 2 | 21 | 16.71 | 2.7 |
| rGRF3 | 1 | 31 | 16.87 | 2.4 |
| rGRF3 | 2 | 33 | 14.92 | 2.5 |
| rGRF3 | 1 | 38 | 17.40 | 3.0 |
| rGRF3 | 2 | 40 | 20.92 | 2.4 |
| rGRF3 | 1 | 41 | 16.08 | 3.5 |
| rGRF3 | 2 | 42 | 14.20 | 2.6 |
| rGRF3 | 1 | 55 | 19.75 | 3.7 |
| rGRF3 | 2 | 56 | 17.56 | 3.7 |
| TC | 0 | 1 | 16.29 | 2.4 |
| TC | 0 | 6 | 15.34 | 3.0 |
| TC | 0 | 8 | 16.36 | 2.3 |
| TC | 0 | 9 | 16.63 | 2.7 |
| TC | 0 | 10 | 15.34 | 2.5 |
| TC | 0 | 19 | 12.80 | 2.5 |
| TC | 0 | 23 | 13.02 | 1.8 |
| TC | 0 | 26 | 15.29 | 2.3 |
| TC | 0 | 28 | 16.60 | 1.7 |
| TC | 0 | 29 | 16.38 | 2.1 |
| TC | 0 | 32 | 15.88 | 2.2 |
| TC | 0 | 34 | 17.67 | 2.2 |
| TC | 0 | 36 | 15.41 | 3.2 |
| TC | 0 | 37 | 16.36 | 1.9 |
| TC | 0 | 43 | 16.02 | 2.4 |
| TC | 0 | 47 | 15.86 | 2.0 |
| TC | 0 | 48 | 14.02 | 3.7 |
| TC | 0 | 49 | 16.72 | 3.2 |
| TC | 0 | 51 | 15.02 | 3.2 |
| TC | 0 | 39 | 16.38 | 3.4 |

GRF3 MUTANTS, METHODS AND PLANTS

The instant application contains a Sequence Listing which has been submitted via EFS-web and is hereby incorporated by reference in its entirety.

FIELD OF THE INVENTION

Plants exhibiting improved productivity and/or yield phenotypes and/or increased drought tolerance by introducing into such plants mutations in the GRF3 growth factor, or in a GRF3 orthologue, which mutants deregulate the GRF3 or GRF3 orthologue from miR396 control (optionally in combination with overexpression of at least one GIF gene).

BACKGROUND OF THE INVENTION

In contrast to animals, plants continue to produce new organs throughout their life cycle. The above-ground organs are derived from the shoot apical meristem (SAM), which includes a pool of stem cells residing at the growing tip of the plant. Proliferating SAM cells produce an excess of daughter cells that are either incorporated into the developing leaf primordia at the SAM periphery or become part of the shoot. The core machinery controlling the progression of the cell cycle in plants, as well as in other eukaryotes, relies on the activity of cyclin-dependent kinases (Inze and De Veylder, 2006). Many aspects of cell cycle regulation are highly conserved among eukaryotes. It is, however, the integration of the basic cell cycle mechanisms with the developmental program that generates the enormous phenotypic variation among multicellular organisms, a process that is much less understood (Inze and De Veylder, 2006).

In contrast to the indeterminate SAM in *Arabidopsis thaliana*, leaves are determinate organs that have a defined morphology. Leaf development involves the concerted action of various hormone signalling pathways and transcription factor networks. Some of the major transcriptional regulators involved in the control of cell proliferation in leaves include AINTEGUMENTA (Mizukami and Fischer, 2000), PEAPOD (White, 2006), JAGGED (Dinneny et al., 2004; Ohno et al., 2004), BLADE ON PETIOLE (Ha et al., 2003), TCPs (Nath et al., 2003) and GROWTH-REGULATING FACTORs (GRFs) (Kim et al., 2003).

To obtain their characteristic final size and shape, growth of the developing leaf needs to be tightly coordinated first through cell proliferation and then by cell expansion (Piazza et al., 2005; Tsukaya, 2006). Initially, cell proliferation is observed throughout the developing leaf (Donnelly et al., 1999). Then, the cell cycle stops at the tip of the leaf and a mitotic arrest front moves towards the base of the organ (Donnelly et al., 1999). Once cells cease to divide, they begin to enlarge and cell growth becomes the driving force regulating organ size (Piazza et al., 2005; Tsukaya, 2006).

Currently, little is known about the molecular mechanisms that coordinate cell proliferation throughout a developing leaf. A known regulator is the TCP gene CINCINNATA (CIN), which controls the progression of the mitotic arrest front in snapdragon (Nath et al., 2003). Mutations such as cin (Nath et al., 2003) and triple knock-outs of its *Arabidopsis* homologues tcp2/4/10 (Schommer et al., 2008) cause changes in leaf morphogenesis and uneven organ curvature due to excess cell proliferation at the leaf margins. Interestingly, five *Arabidopsis* TCPs (TCP2, 3, 4, 10 and 24), as well as CIN, have a target site for microRNA (miRNA) miR319 (Palatnik at al., 2003). Overexpression of miR319 causes the degradation of these TCPs and the generation of crinkled leaves similar to those observed in tcp loss-of-function mutants (Palatnik et al., 2003). Mutations in the target site of the TCPs that diminish the interaction with the miRNA affect leaf morphology in *Arabidopsis* (Palatnik et al., 2003; Palatnik at al., 2007) and leaf complexity in tomato (Ori at al., 2007), and are lethal in extreme cases (Palatnik at al., 2003).

The GRF family of transcription factors comprises nine members in *Arabidopsis* (Kim et al., 2003). Seven of them have a target site for miR396 (Jones-Rhoades and Bartel, 2004). Loss-of-function mutations in different GRFs or overexpression of miR396, which decreases GRF levels, have been shown to reduce cell number in *Arabidopsis* leaves (Horiguchi et al., 2005; Kim et al., 2003; Kim and Kende, 2004; Liu at al., 2009). The GRFs work together with GRF-INTERACTING FACTORs (GIFs), a small gene family encoding proteins with homology to the human SYT transcriptional co-activator (Horiguchi at al., 2005; Kim and Kende, 2004). Inactivation of GIF1 (Kim and Kende, 2004), also known as ANGUSTIFOLIA 3 (AN3) (Horiguchi at al., 2005), produces narrower leaves as a result of a reduction in cell proliferation.

It has been disclosed by Rodriguez at al., Development 137, 103-112 (2010), that a microRNA, miR396, plays a role in the coordination of cell proliferation in *Arabidopsis* leaves. They showed that in leaf primordia, miR396 is expressed at low levels, but its expression steadily increases during organ development. They showed that miR396 antagonizes the expression pattern of its targets, the GROWTH-REGULATING FACTOR (GRF) transcription factors. miR396 was shown to accumulate preferentially in the distal part of young developing leaves, restricting the expression of GRF2 to the proximal part of the organ. This, in turn, was shown to coincide with the activity of the cell proliferation marker CYCLINB1;1. miR396 was shown to attenuate cell proliferation in developing leaves through the repression of GRF activity and a decrease in the expression of cell cycle genes. Furthermore, they reported that overexpression of miR396 in a mutant lacking GRF-INTERACTING FACTOR 1 (GIF1) severely compromised the shoot meristem. miR396 was found to be expressed at low levels throughout the meristem, overlapping with the expression of its target, GRF2. In addition, it was shown that overexpression of miR396 can reduce cell proliferation and the size of the meristem. *Arabidopsis* plants with an increased activity of the transcription factor TCP4, which reduces cell proliferation in leaves, were shown to have higher miR396 and lower GRF levels. Modified GRF2, which was mutated to interfere with the interaction with miR396, was shown to be independent of miR396 regulation to which the wild-type GRF2 was subject. These plants were reported to have slightly bigger leaves than those of wild-type, however these leaves were curved downwards which could be detrimental for light capture and photosynthesis. Those results indicated that miR396 levels can significantly restrict cell proliferation in plants.

In the present disclosure, it is shown that a mutant GRF3 (sometimes referred to herein as rGRF3) and mutant GRF3 orthologues (sometimes referred to herein as rGRF3 orthologues) are relieved of miR396 regulation, and that plants comprising the mutant GRF3 or mutant GRF3 orthologues have improved productivity and/or yield (including greater leaf area, greater cell numbers, increased biomass, increased stress resistance, delayed leaf senescence, increased seed production, increased seed yield, increased root growth, increased root elongation speed and greater tolerance to drought), whether compared to wild-type plants or to plants comprising a mutant GRF2 relieved of miR396 regulation. Furthermore, the leaves from mutant GRF3 plants or mutant GRF3 orthologue plants were not curved downwards as those of mutant GRF2. The slight increase in leaf area observed in mutant GRF2 plants were caused by increasing its level at least twenty-fold compared with the level of GRF2 in wild-type plants; however, just three to five times more mutant GRF3 compared with the level of GRF3 in wild-type plants has been observed to cause a much larger impact on leaf size and plant biomass.

When the GRF3 modification or GRF3 orthologue modification is combined in a plant overexpressing GIF1, these effects are greatly enhanced.

BRIEF DESCRIPTION OF THE DRAWINGS

In the cross between rGRF3 and 35S:GIF1 plants, the rGRF3 expression is slightly (but not significantly) lower than the five-fold expression level seen in the rGRF3 plants. By comparison, the expression levels of GIF1, again representing levels in wild-type plants as 1, it is not significantly altered in the 35S:miR396 expressing plants, but is almost forty times the wild-type level in both rGRF3 plants and crosses between rGRF3×GIF1 plants. The measurements are triplicates±SEM

FIG. 16 shows that maize GRFs are co-expressed with mitosis-specific genes.

FIG. 17 shows an increase in plant size caused by Arabidopsis miR396-resistant GRF3.

A) 30 days old plants corresponding to independent transgenic plant lines: empty vector (WT, left), miR396-resistant GRF3 (rGRF3 centre) and wild-type GRF3 (GRF3, right). Note the bigger size of the rosettes transformed with the rGRF3.

B) Fully expanded first leaf area of the different transgenic plants depicted in (A). At least 50 independent plants were scored for each vector. Bars marked with different letters are significantly different as determined by ANOVA and Duncan's multiple range test (P<0.05).

Figure 18:
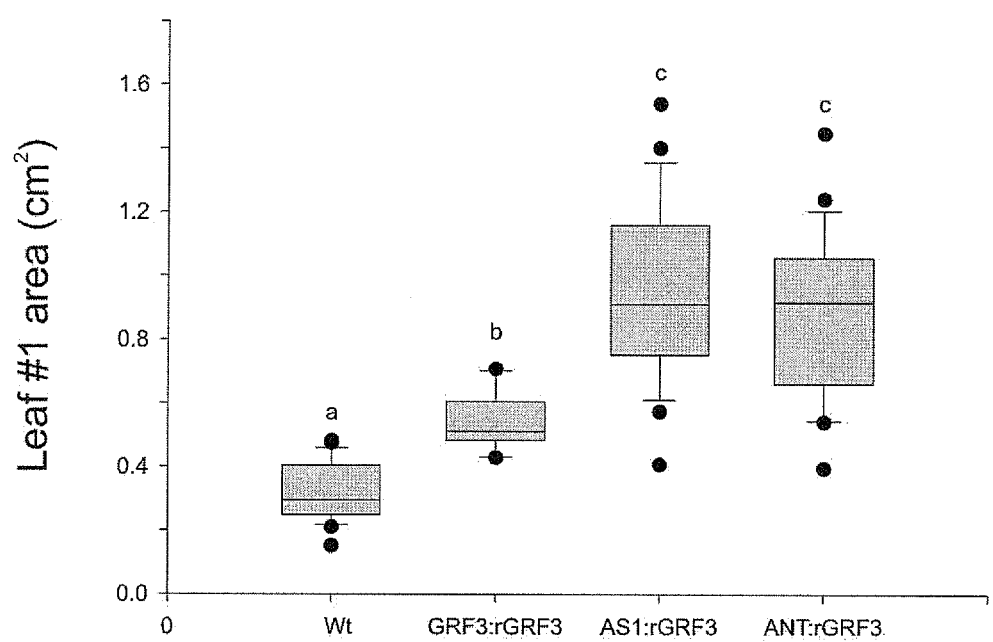

FIG. 18 shows that tissue-specific expression improves rGRF3 performance in plant productivity. Area of fully expanded first leaf of transgenic plants expressing rGRF3 from different promoters: GRF3, ASYMMETRIC LEAVES 1 (AS1) or AINTEGUMENTA (ANT). At least 50 plants were scored for each vector. For AS1:rGRF3 and ANT: rGRF3 the data represent independent primary transgenics, whereas for GRF3:rGRF3 a representative line was used. Bars marked with different letters are significantly different as determined by Kruskal-Wallis and Dunn's multiple range test (P<0.05).

Figure 19:
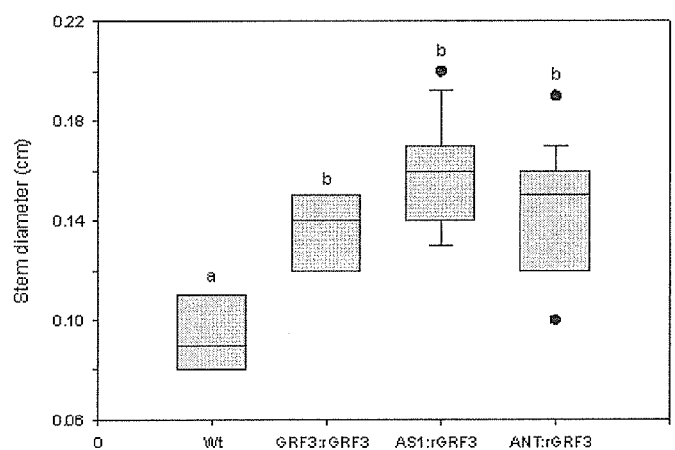

FIG. 19 shows an increase in stem diameter due to rGRF3. Stem diameter of transgenic plants expressing rGRF3 from different promoters: GRF3, ASYMMETRIC LEAVES 1 (AS1) and AINTEGUMENTA (ANT). Bars marked with different letters are significantly different as determined by Kruskal-Wallis and Dunn's multiple range test (P<0.05).

Figure 20:
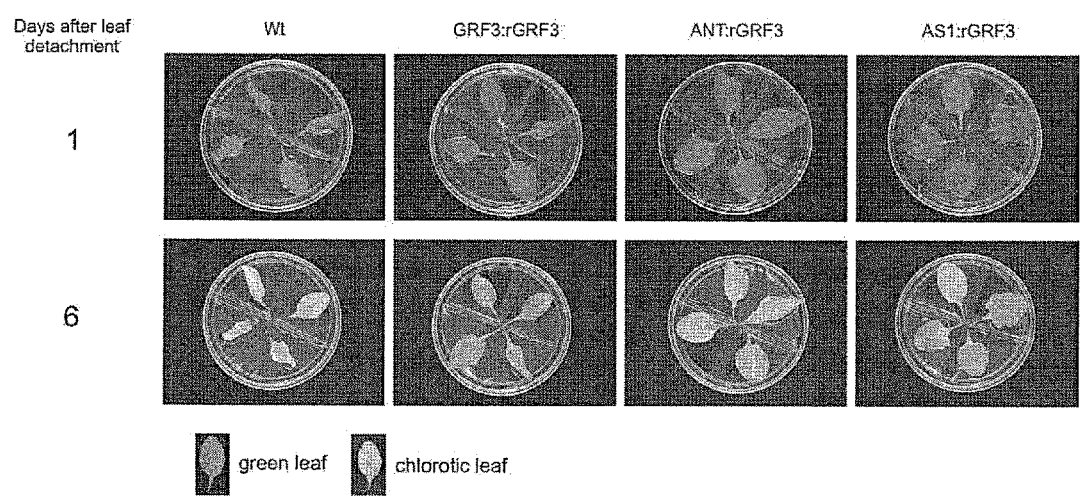

FIG. 20 shows uncoupling of effects on leaf size from those on timing of leaf-senescence using tissue specific promoters. As shown herein GRF3:rGRF3 increases leaf size and delays leaf senescence. The latter effect can be decoupled from the increase in leaf size if desired. Expression of rGRF3 from ANT and AS1 promoters significantly increased leaf size with a minor effect on leaf senescence. Dark-induced senescence of fully expanded leaf #5. Pictures were taken immediately after the full expanded leaves were cut from the rosette (Day 1) and after they were incubated 6 days in darkness (Day 6). For GRF3:rGRF3 a representative line was used, and for AS1:rGRF3 and ANT:rGRF3 vector the 4 primary transgenic plants with the biggest leaf area were selected.

FIGS. 21A to 21I show the nucleotide sequences of the *Arabidopsis thaliana* GRFs of which there are 9, namely: FIG. 21A, AtGRF1 (SEQ ID No. 40); FIG. 21B, AtGRF2 (SEQ ID No. 87); FIG. 21C, AtGRF3 (SEQ ID No. 2); FIG. 21D, AtGRF4 (SEQ ID No. 19); FIG. 21E, AtGRF5 (SEQ ID No. 41); FIG. 21F, AtGRF6 (SEQ ID No. 42); FIG. 21G, AtGRF7 (SEQ ID No. 43); FIG. 21H, AtGRF8 (SEQ ID No. 44), and; FIG. 21I, AtGRF9 (SEQ ID No. 45). The underlined section of the sequences represent the portion of the nucleotide sequence encoding the WRC (Trp, Arg, Cys) domain; and the underlined and bolded section of the sequences represent the miR396 target site, if one is present.

FIGS. 22A to 22I shows the amino acid sequences of the *A. thaliana* GRFs of which there are 9: FIG. 22A, AtGRF1 (SEQ ID No. 46); FIG. 22B, AtGRF2 (SEQ ID No. 47); FIG. 22C, AtGRF3 (SEQ ID No. 20); FIG. 22D, AtGRF4 (SEQ ID No. 21); FIG. 22E, AtGRF5 (SEQ ID No. 48); FIG. 22F, AtGRF6 (SEQ ID No. 49); FIG. 22G, AtGRF7 (SEQ ID No. 50); FIG. 22H, AtGRF8 (SEQ ID No. 51), and; FIG. 22I, AtGRF9 (SEQ ID No. 52), the underlined section of the sequences represent the portion of the amino acid sequence known as the WRC (Trp, Arg, Cys) domain; and the underlined and bolded section of the sequences represent the FFD motif.

FIGS. 23A to 23L show the nucleotide sequences of the *Oryza sativa* (rice) GRFs of which there are 12: FIG. 23A, OsGRF1 (SEQ ID No. 3); FIG. 23B, OsGRF2 (SEQ ID No. 4); FIG. 23C, OsGRF3 (SEQ ID No. 5); FIG. 23D, OsGRF4 (SEQ ID No. 6); FIG. 23E, OsGRF5 (SEQ ID No. 53); FIG. 23F, OsGRF6 (SEQ ID No. 54); FIG. 23G, OsGRF7 (SEQ ID No. 55); FIG. 23H, OsGRF8 (SEQ ID No. 56); FIG. 23I, OsGRF9 (SEQ ID No. 57); FIG. 23J, OsGRF10 (SEQ ID No. 58); FIG. 23K, OsGRF11 (SEQ ID No. 59), and; FIG. 23L, OsGRF12 (SEQ ID No. 60). The underlined and bolded section of the sequences represent the miR396 target site, if one is present.

FIGS. 24A-24L show the amino acid sequences of the *Oryza sativa* (rice) GRFs of which there are 12: FIG. 24A, (OsGRF1 (SEQ ID No. 22); FIG. 24B, OsGRF2 (SEQ ID No. 23); FIG. 24C, OsGRF3 (SEQ ID No. 24); FIG. 24D, OsGRF4 (SEQ ID No. 25); FIG. 24E, OsGRF5 (SEQ ID No. 61); FIG. 24F, OsGRF6 (SEQ ID No. 62); FIG. 24G, OsGRF7 (SEQ ID No. 63); FIG. 24H, OsGRF8 (SEQ ID No. 64); FIG. 24I, OsGRF9 (SEQ ID No. 65); FIG. 24J, OsGRF10 (SEQ ID No. 66); FIG. 24K, OsGRF11 (SEQ ID No. 67), and; FIG. 24L, OsGRF12 (SEQ ID No. 68).

FIGS. 25A to 25N show the nucleotide sequences of the *Zea mays* (maize) GRFs of which there are 14; FIG. 25A, ZmGRF1 (SEQ ID No. 7); FIG. 25B, ZmGRF2 (SEQ ID No. 69); FIG. 25C, ZmGRF3 (SEQ ID No. 8); FIG. 25D, ZmGRF4 (SEQ ID No. 70); FIG. 25E, ZmGRF5 (SEQ ID No. 9); FIG. 25F, ZmGRF6 (SEQ ID No. 10); FIG. 25G, ZmGRF7 (SEQ ID No. 11); FIG. 25H, ZmGRF8 (SEQ ID No. 71); FIG. 25I, ZmGRF9 (SEQ ID No. 12); FIG. 25J, ZmGRF10 (SEQ ID No. 72); FIG. 25K, ZmGRF11 (SEQ ID No. 13); FIG. 25L, ZmGRF12 (SEQ ID No. 73); FIG. 25M, ZmGRF13 (SEQ ID No. 74), and; FIG. 25N, ZmGRF14 (SEQ ID No. 14). The underlined and bolded section of the sequences represent the miR396 target site, if one is present.

FIGS. 26A to 26N show the amino acid sequences of the *Zea mays* (maize) GRFs of which there are 12; FIG. 26A, ZmGRF1 (SEQ ID No. 26); FIG. 26B, ZmGRF2 (SEQ ID No. 75); FIG. 26C, ZmGRF3 (SEQ ID No. 27); FIG. 26D, ZmGRF4 (SEQ ID No. 76); FIG. 26E, ZmGRF5 (SEQ ID No. 28); FIG. 26F, ZmGRF6 (SEQ ID No. 29); FIG. 26G, ZmGRF7 (SEQ ID No. 30); FIG. 26H, ZmGRF8 (SEQ ID No. 77); FIG. 26I, ZmGRF9 (SEQ ID No. 31); FIG. 26J, ZmGRF10 (SEQ ID No. 78); FIG. 26K, ZmGRF11 (SEQ ID No. 32); FIG. 26L, ZmGRF12 (SEQ ID No. 79); FIG. 26M, ZmGRF13 (SEQ ID No. 80), and; FIG. 26N, ZmGRF14 (SEQ ID No. 33).

FIG. 27 shows the nucleotide sequence for a GRF with high similarity to AtGRF3, namely *Glycine max* (soybean) GRF (GmGRF) (SEQ ID No. 16). The underlined and bolded section of the sequences represent the miR396 target site, if one is present.

FIG. 28 shows the nucleotide sequence for a GRF with high similarity to AtGRF3, namely *Medicago truncatula* GRF (MtGRF) (SEQ ID No. 17).

FIG. 29 shows the nucleotide sequence for a GRF with high similarity to AtGRF3, namely *Populus trichocarpa* GRF (PtGRF) (SEQ ID No. 18).

FIG. 30 shows the nucleotide sequence for a GRF with high similarity to AtGRF3, namely *Prunus persica* GRF (PpGRF) (SEQ ID No. 15).

FIG. 31 shows the amino acid sequence for a *Medicago truncatula* GRF (MtGRF) (SEQ ID No. 36); the underlined section of the sequences represent the portion of the amino acid sequence known as the WRC (Trp, Arg, Cys) domain; and the underlined and bolded section of the sequences represent the FFD motif.

FIG. 32 shows the amino acid sequence for a *Glycine max* (soybean) GRF (GmGRF) (SEQ ID No. 35); the underlined section of the sequences represent the portion of the amino acid sequence known as the WRC (Trp, Arg, Cys) domain; and the underlined and bolded section of the sequences represent the FFD motif.

FIG. 33 shows the amino acid sequence for a *Populus trichocarpa* GRF (PtGRF) (SEQ ID No. 37); the underlined section of the sequences represent the portion of the amino acid sequence known as the WRC (Trp, Arg, Cys) domain; and the underlined and bolded section of the sequences represent the FFD motif.

FIG. 34 shows the amino acid sequence for a *Prunus persica* GRF (PpGRF) (SEQ ID No. 34); the underlined section of the sequences represent the portion of the amino acid sequence known as the WRC (Trp, Arg, Cys) domain; and the underlined and bolded section of the sequences represent the FFD motif.

FIG. 35 shows the nucleotide sequence for the *Arabidopsis* GRF3 with a mutated miR396-target site (At-rGRF3) (SEQ ID No. 81); the shaded and underlined portion of the sequence is the mutated miR396-target site. The lower case refers to base substitutions to make the GRF resistant to miR396. For the avoidance of doubt when the mutant AtGRF3 is referred to herein unless stated otherwise it is this sequence that is being referred to. This sequence is also referred to herein as At-rGRF3 and rGRF3. This mutated At-rGRF3 was used herein to generate inter alia transgenic *Arabidopsis* plants.

FIG. 36 shows the nucleotide sequence for a *Glycine max* GRF with a mutated miR396-target site (Gm-rGRF) (SEQ ID No. 82); the shaded and underlined portion of the sequence is the mutated miR396-target site. The lower case refers to base substitutions to make the GRF resistant to miR396. This mutated Gm-rGRF was used herein to generate transgenic *Arabidopsis* plants.

FIG. 37 shows the nucleotide sequence for an *Oryza sativa* GRF4 with a mutated miR396-target site (Os-rGRF4.1) (SEQ ID No. 83); the shaded and underlined portion of the sequence is the mutated miR396-target site. The lower case refers to base substitutions to make the GRF resistant to miR396. This mutated Os-rGRF4 was used herein to generate transgenic *Arabidopsis* plants. This sequence is also referred to herein as Os-rGRF4.1 and rOsGRF4.1.

FIG. 38 shows similarity tables between At-GRF3 and GRFs from other plant species based on primary amino acid sequence. The global similarity between GRF3 and every GRF from At, Os and Zm (plus other highly similar GRFs from selected species) was scored using Needle (EMBOSS: http://www.ebi.ac.uk/Tools/psa/). Identity relates to when an identical amino acid is in the corresponding position; whereas similarity relates to when a conservative substitution of an amino acid is found in a corresponding position.

FIGS. 39A to 39G show the nucleotide sequence encoding JD16_GIF1 (including 35S promoter (nt 427-1295)—underlined section; GIF1 coding Sequence (nt 1310-1942)—section in italics and bold; and Terminator (nt 2106-2755)—section in bold and underline.

FIGS. 40A to 40H show the nucleotide sequence encoding RER32 GRF3 (SEQ ID No. 85) (including GRF3 Promoter (427-1707)—underlined section; 5'UTR (1708-1913)—lower case and italics; GRF3 Coding Sequence+ Introns [in lower case] (1914-4231)—italics & bold; 3'UTR (4232-4454)—lower case and italics; and Terminator (4455-5105)—section in bold and underlined.

Figure 41:
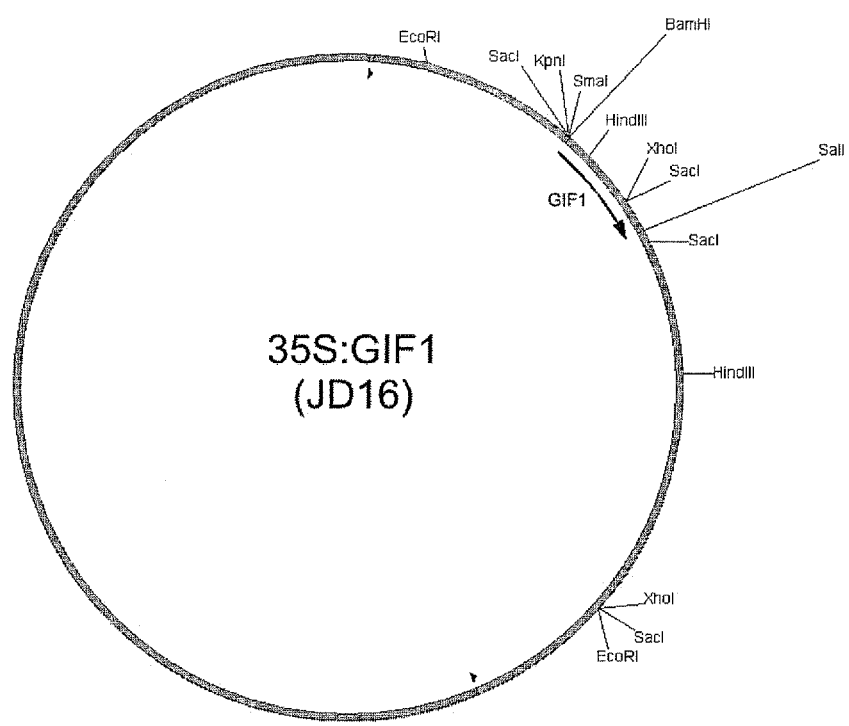

FIG. 41 shows a map of the vector 35S:GIF1 (JD16) (SEQ ID No. 84)—Vector size: 11332 pb Digest with bamHI and SalI. Products: 10682 and 650 pb.

Figure 42:
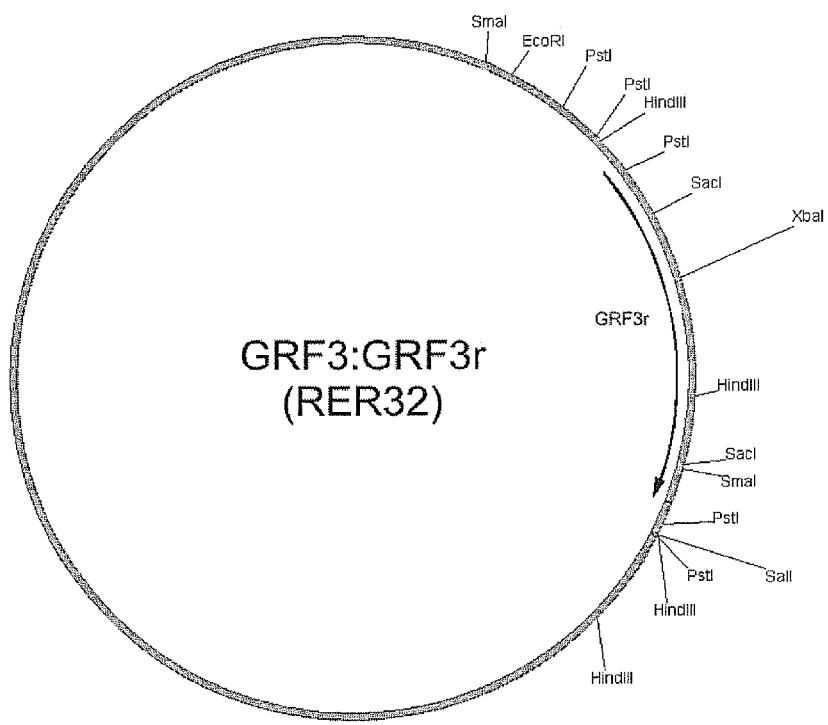

FIG. 42 shows a map of the vector GRF3:GRF3r (RER32)—Vector size: 13642 pb Digest with XbaI and SalI. Products: 11962 and 1680 pb.

Figure 9:
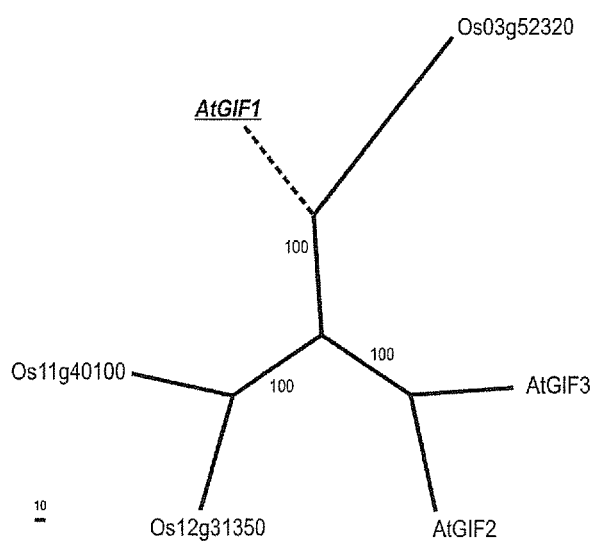
FIG. 9 shows a neighbour joining analysis of GIF from Arabidopsis thaliana and Oryza sativa shown as an unrooted cladogram: Sequences were retrieved from PlantTFDB 2.0 (http://planttfdb.cbi.pku.edu.cn).
Figure 43:
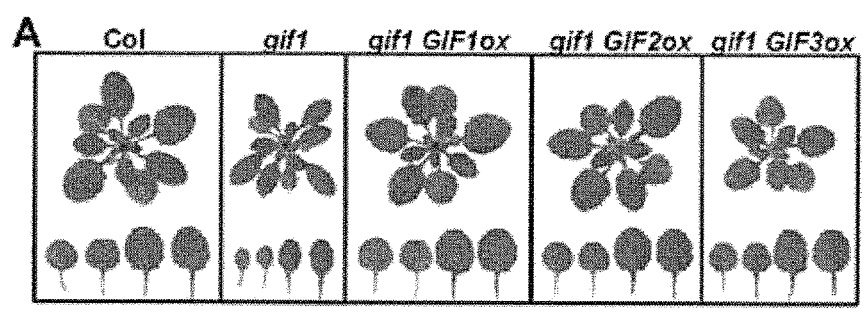

FIG. 43 shows that overexpression of GIF1, GIF2, and GIF3 promotes cell proliferation and leaf size and that GIF2 and GIF3 proteins are functional equivalents of GIF1 (see FIG. 43 in combination with FIG. 9).

Figure 44:
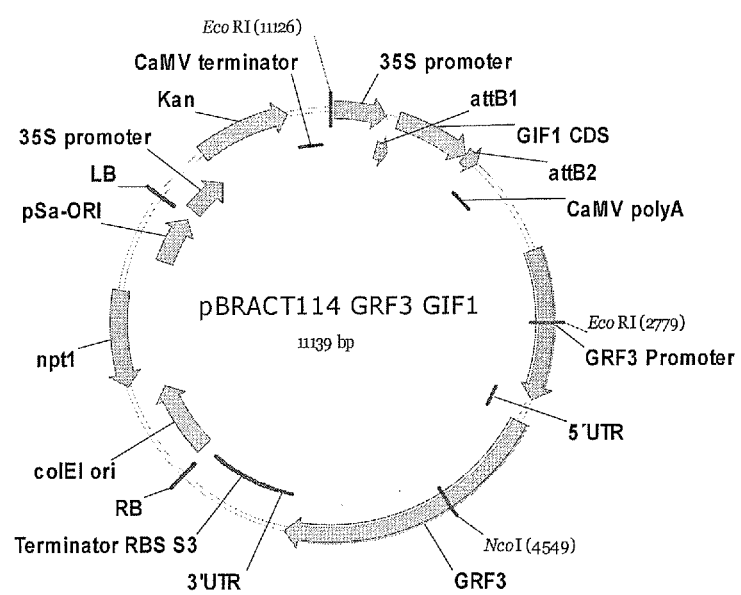

FIG. 44 shows the maps of the two plasmids comprising rGRF3:GIF1 in pBRACT114. pBRACT114 is available from www.bract.org. The pBRACTs are based on the pGreen/pSoup vector system and the original reference for pGreen is: Hellens et al 2000.

Figure 45:
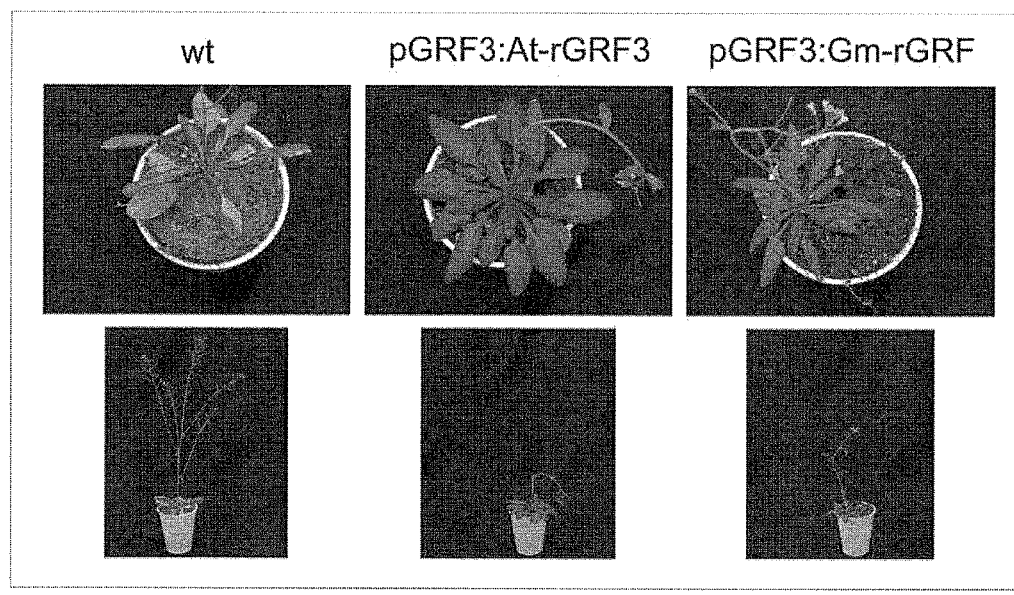

FIG. 45 shows delayed leaf senescence in primary transgenic *Arabidopsis* plants by a mutated *Arabidopsis* GRF (At-rGRF3) and by a mutated soybean GRF (Gm-rGRF).

Figure 46:
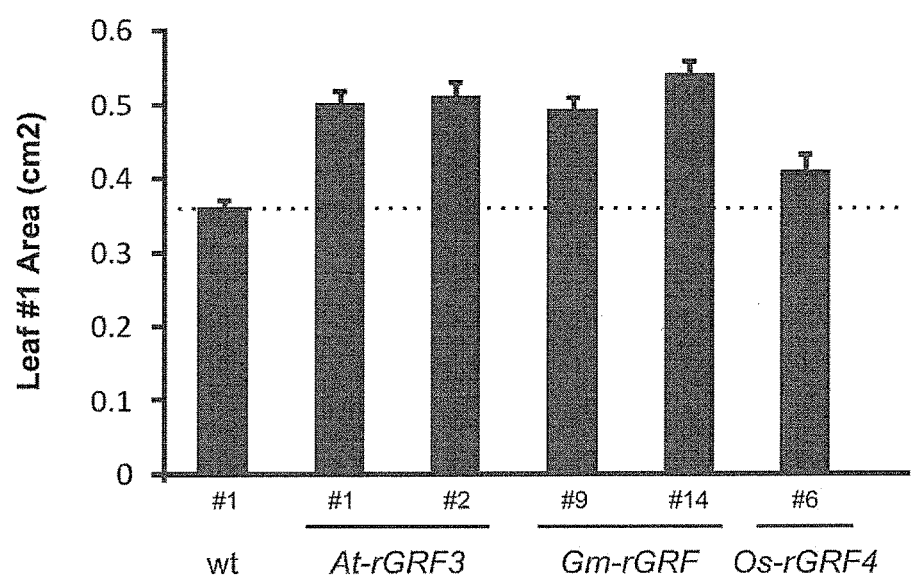

FIG. 46 shows that expression in *Arabidopsis* of GRF3 orthologues from soybean and from rice, when decoupled from miR396 regulation also increase plant biomass. The area of fully expanded first leaf of transgenic plants expressing GRF from *Arabidopsis*, soybean or rice was measured.

FIG. 47 shows the nucleotide sequence for a GRF with high similarity to AtGRF3, namely *Carica papaya* GRF (CpGRF) (SEQ ID No. 88).

FIG. 48 shows the amino acid sequence for a *Carica papaya* GRF (CpGRF) (SEQ ID No. 89); the underlined section of the sequences represent the portion of the amino acid sequence known as the WRC (Trp, Arg, Cys) domain; and the underlined and bolded section of the sequences represent the FFD motif.

Figure 49:
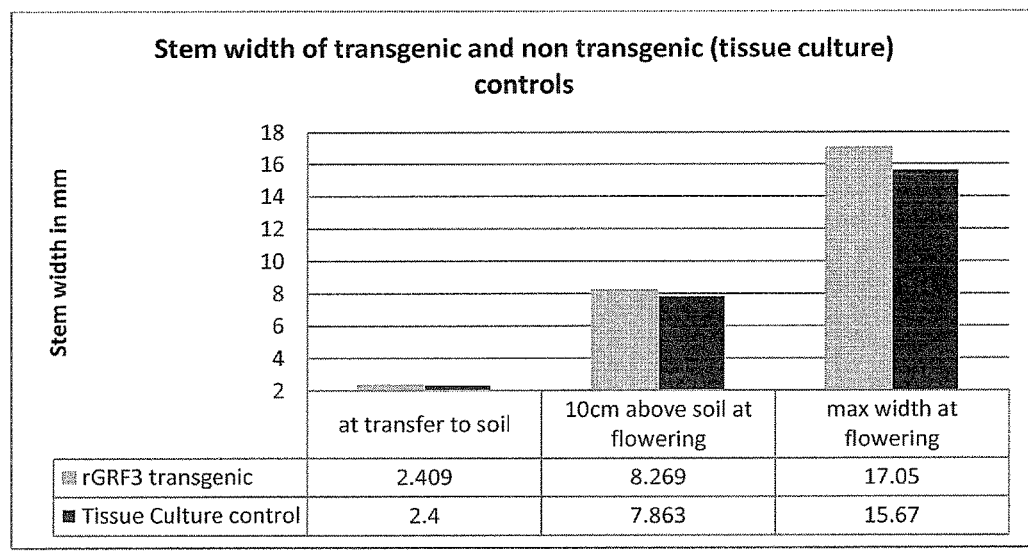

FIG. 49 shows data comparing stem width 10 cm above soil level at flowering and maximum stem width at flowering in *Brassica oleracea* plants transformed with *Arabidopsis* rGRF3 and control plants (without the At rGRF3).

FIG. 50 shows expression of rGRF3 from tissue-specific promoters.
A) Top: Schematic representation of a construct expressing GRF3 as a translational fusion to GFP. Bottom: Expression pattern of GRF3-GFP fusion protein in leaves of different ages collected from GRF3:GRF3-GFP and GRF3:rGRF3-GFP plants. B) Expression level of GRF3 mRNA in apex and leaves of different ages. C) GUS staining of plants transformed with ANT:GUS and AS1:GUS reporters. Upper part, schematic representation of the reporters.

Figure 51:
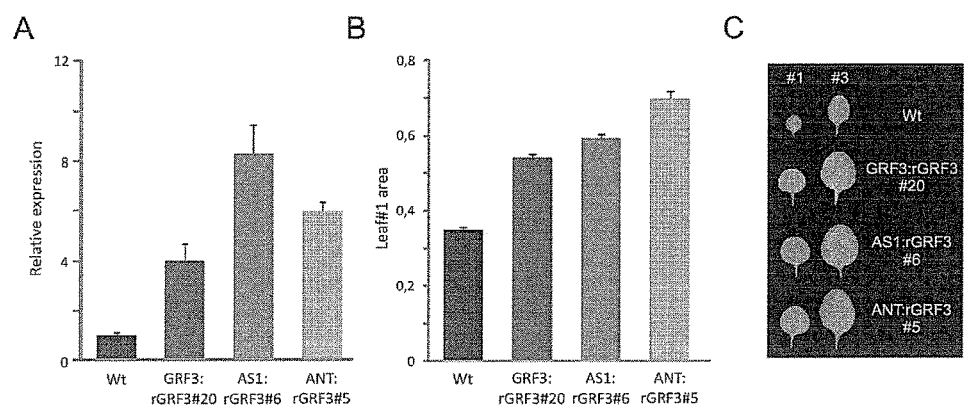

FIG. 51 shows the expression levels of rGRF3 under tissue-specific promoters and leaf area of transformants.
A) Expression levels of GRF3 in transgenic seedlings expressing GRF3 from different promoters. Determinations were carried out by RT-qPCR and normalized to wild-type plants. B) Area of fully expanded first and second leaves. C) Fully expanded first (left) and third (right) leaves.

Figure 52:
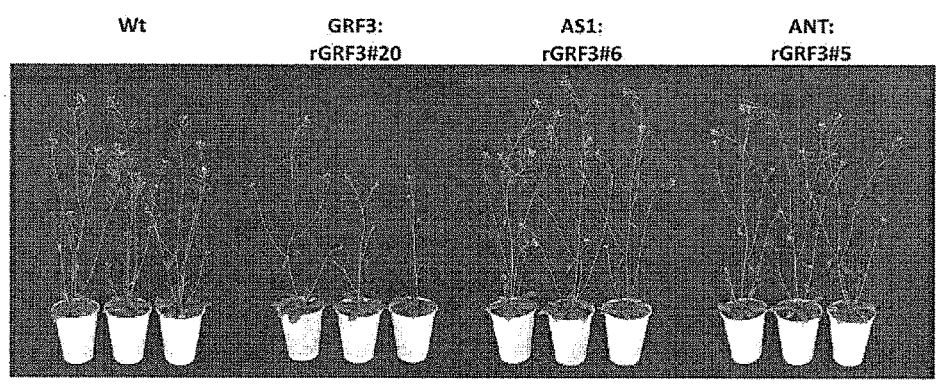

FIG. 52 shows pictures of 40 day old plants expressing rGRF3 from their endogenous promoters and from the ANT and AS1 promoters.

Figure 53:
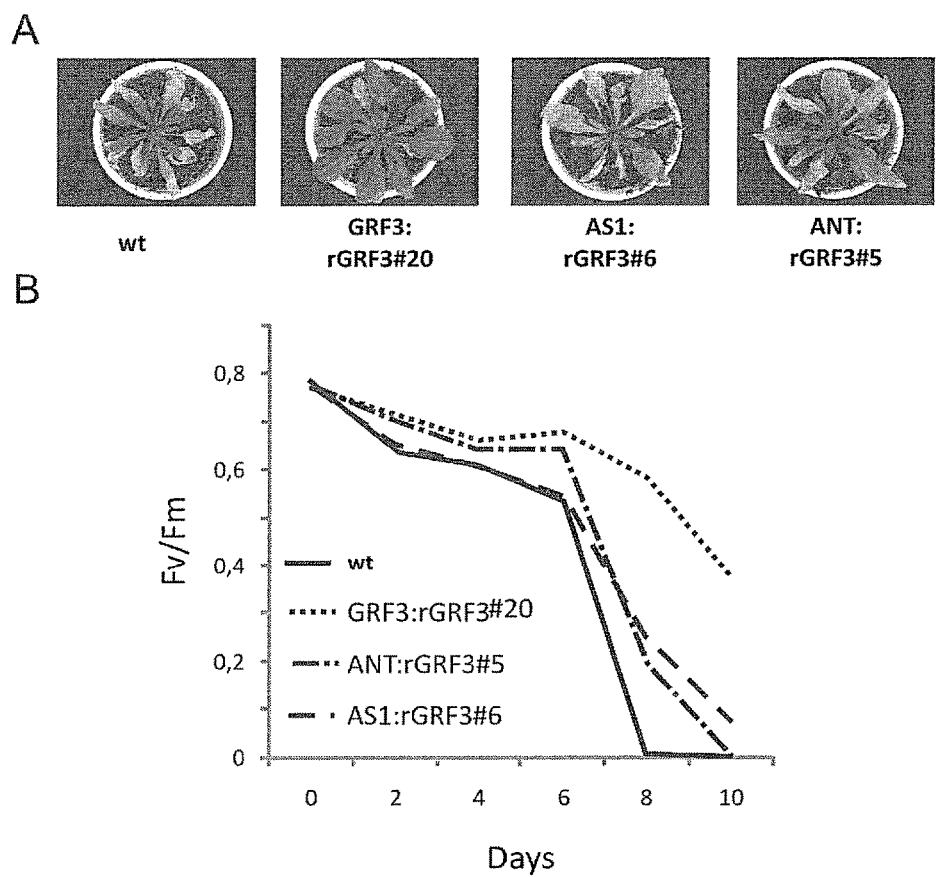
Figure 54:
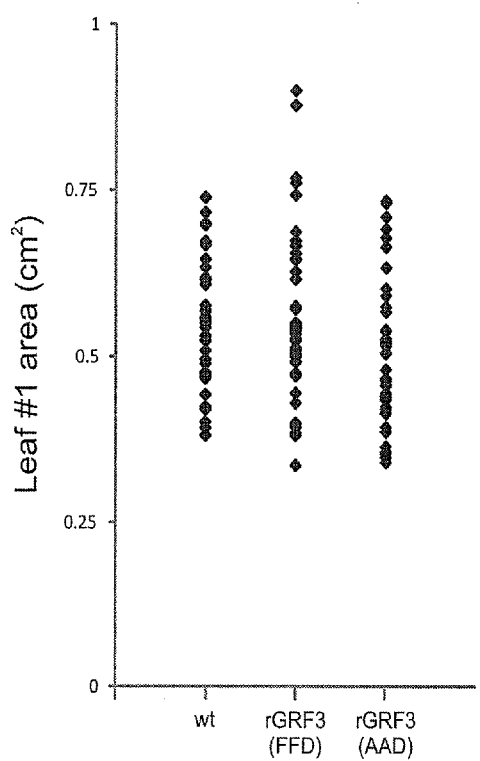

FIG. 53 shows delayed senescence when rGRF3 is expressed under the control of its own promoter. Senescence is evident in wild-type and when rGRF3 is expressed under the control of AS1 and/or ANT.
A) Pictures of 50 day old rosettes. Note the delayed senescence of GRF3: rGRF3 plants and the normal development of AS1:GRF3 and ANT:GRF3. B) Senescence of an individual leaf is shown for fully expanded leaf 5, which was detached and incubated in the dark (dark induced senescence). The progression of senescence was quantitated by determining Fv/Fm FIG. 54 shows leaf area plotted for independent primary transgenic plants. CHF3 is an empty vector control, rGRF3 with the FFD motif is the rGRF3 cDNA expressed from its own promoter. rGRF3 AAD is the cDNA of rGRF3 with three mutations in the FFD motif (FFDDW) that replace the two phenylalanine amino acids and the tryptophan with three alanine amino acids (AADDA).

Figure 55:
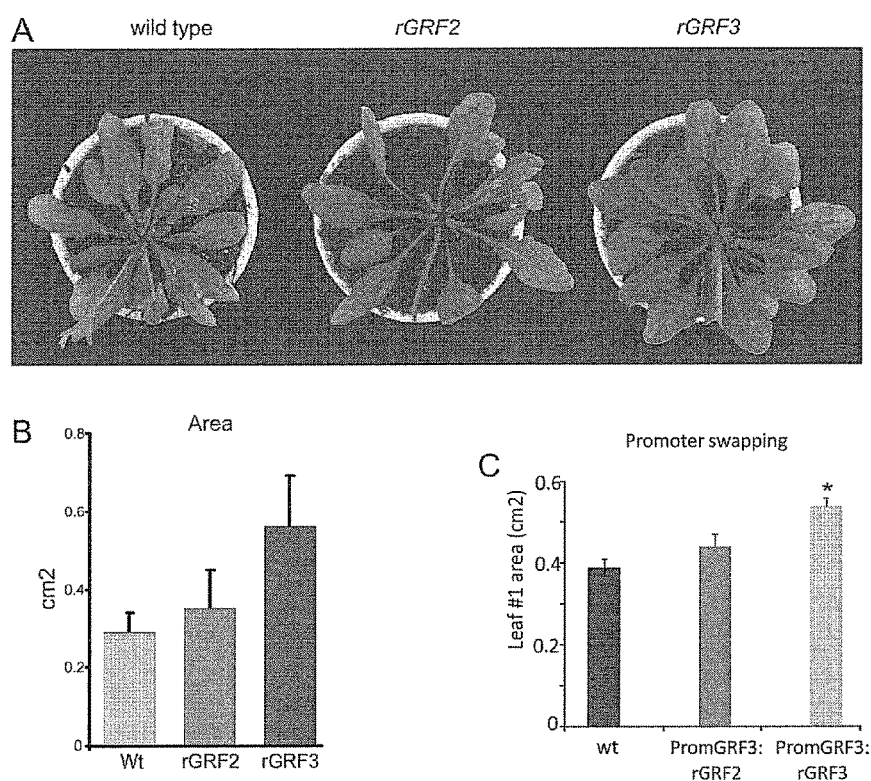

FIG. 55 shows a comparison between plants expressing rGRF2 and rGRF3. As shown herein rGRF3 expression leads to the production of bigger plants than wild-type or rGRF2 expression. rGRF2 also generates distorted rosettes.

FIG. 56 is a table showing widest stem width at flowering and 10 cm stem weight for *Brassica oleracea* transformants expressing rGRF3 and control plants (TC).

Figure 57:
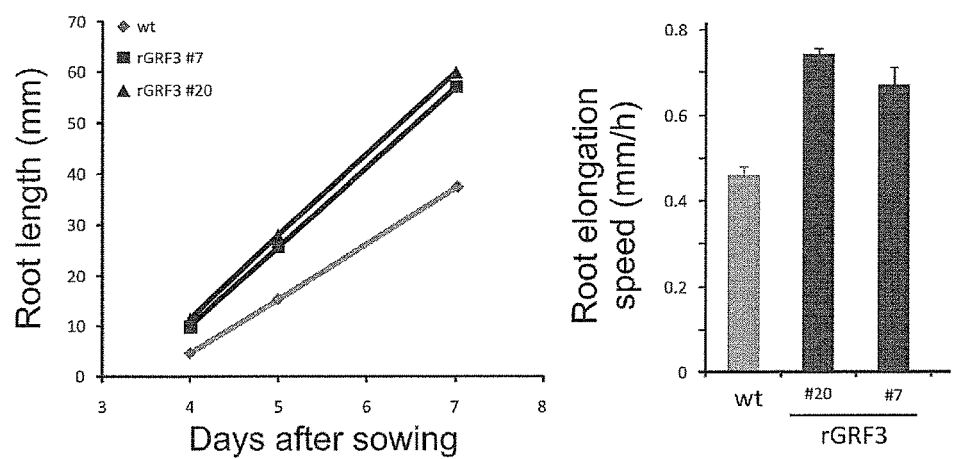

FIG. 57 left, a graph showing root length at various days after sowing for wild-type *Brassica oleracea*, and two transgenic *Brassica oleracea* plants expressing rGRF3. Right, a graph showing root elongation speed for wild-type or two transgenic plants expressing rGRF3.

SUMMARY OF THE INVENTION

The present invention is predicated upon the surprising finding that a novel modified GRF3 gene, rGRF3, which is shown to be decoupled from control by miR396, particularly in the presence of over-expression of GIF1, can be used to significantly improve the biomass, improve stress resistance, improve drought tolerance, delay leaf senescence in plants. The improvement in biomass accumulation is surprisingly high and unexpectedly better than the only other reported miRNA decoupled GRF, namely rGRF2, while the tolerance to drought is unexpected from previously reported data.

The present inventors have also surprisingly found that orthologues of GRF3 which are also modified to be decoupled from control by miR396 also provide these surprising and unexpected effects.

In a first aspect there is provided an isolated nucleic acid encoding a modified growth regulatory factor (GRF)-3 or an orthologue thereof which nucleic acid is decoupled from control by miR396.

In another aspect there is provided a construct comprising the nucleic acid according to the present invention operably linked with a promoter and a terminator.

The present invention further provides a vector comprising the nucleic acid of the present invention or the construct according to the present invention.

In a further aspect the present invention provides a plant, plant cell or plant tissue comprising the nucleic acid according to the present invention, the construct according to the present invention or the vector according to the present invention.

In yet another aspect there is provided a method for using the nucleic acid according to the present invention which comprises introducing said nucleic acid according to the present invention or a construct according to the present invention or a vector according to the present invention into a plant.

In another aspect of the present invention there is provided nucleic acid according to the present invention or a construct according to the present invention or a vector according to the present invention for use in the manufacture of a plant with increased productivity and/or yield (including for example increased biomass, increased stress resistance, increased drought tolerance, increased seed production, increased seed yield, increased root growth, increased root elongation speed, delayed leaf senescence and combinations thereof).

In another aspect of the present invention there is provided a method of producing a plant with increased productivity and/or yield (including for example one or more of increased biomass, increased stress resistance, increased drought tolerance, delayed leaf senescence, increased seed production, increased seed yield, increased root growth, increased root elongation speed and combinations thereof) comprising transforming the plant with nucleic acid according to the present invention or a construct according to the present invention or a vector according to the present invention.

A further aspect provides the use of a nucleic acid according to the present invention or a construct according to the present invention or a vector according to the present invention in the manufacture of a plant for increasing productivity and/or yield (for example one or more of increasing biomass, increasing stress resistance, increasing drought tolerance, delaying leaf senescence, increasing seed production, increasing seed yield, increasing root growth, increasing root elongation speed or combinations thereof).

In another aspect the present disclosure provides a novel modified gene, rGRF3, which is shown to be decoupled from control by miR396, particularly in the presence of over-expression of GIF1.

Accordingly, it is an object of this invention to provide a novel modified GRF3 gene or a novel modified GRF3 orthologue gene.

It is a further object of this invention to provide novel plants comprising a modified GRF3 gene or a modified GRF3 orthologue gene.

It is a further object of this invention to provide novel plants comprising a modified GRF3 or a modified GRF3 orthologue in the presence of over-expression of GIF1.

It is yet a further object of this invention to provide a method for using the modified GRF3 or modified GRF3 orthologue disclosed herein.

It is a further object of this invention to provide a method for producing plants with a phenotype of increased productivity and/or yield (for example a phenotype of delayed leaf senescence, increased biomass, increased stress response, increased drought tolerance, increased seed production, increased seed yield increased root growth, increased root elongation speed or combinations thereof), as compared with either wild-type plants or plants comprising a modified GRF2 (rGRF2).

A further object of the present invention is to provide plants with a phenotype of increased productivity and/or yield (for example a phenotype of delayed leaf senescence, increased biomass, increased stress response, increased drought tolerance, increased seed production, increased seed yield increased root growth, increased root elongation speed or combinations thereof) without adverse side effects observed in plants expressing modified GRF2 (rGRF2), such as detrimental leave shape changes, e.g. curved leaves or downwardly rolling leaves.

Further objects and advantages of this invention will be appreciated by referring to the entire disclosure provided herein, and the appended claims.

DETAILED DISCLOSURE OF THE PREFERRED EMBODIMENTS OF THE INVENTION

Rodriguez et al. (2010) followed the expression pattern of miR396 directly using small RNA blots and in situ hybridization in apices, and indirectly through the differential expression of wild-type and miRNA-resistant GRF2-GUS reporters. miR396 was expressed at low levels in the meristem and leaf primordia, and then it steadily accumulated with the development of the leaf. In contrast, the GRFs, which are highly expressed in the SAM and young leaves, decreased during leaf development, in concert with the retreat of cell proliferation.

Temporal antagonistic patterns of expression have been observed for miR156 and miR172 and their targets, the SPL and AP2-like transcription factors, respectively (Chuck et al., 2007; Wu and Poethig, 2006). The heterochronic miR156 and miR172 networks correspondingly regulate juvenile to adult, and vegetative to reproductive phase transitions, which require decisions implicating the whole plant (Aukerman and Sakai, 2003; Chen, 2004; Chuck et al., 2007; Schmid et al., 2005; Wu and Poethig, 2006). The observations on miR396 indicated that this miRNA is also involved in the coordination of developmental events in plants; however, its role would be restricted to individual organs.

The *Arabidopsis* developmental program directs a basiplastic pattern, whereby leaf maturation begins at the tip and then proceeds towards the base of the organ (Donnelly et al., 1999). Cell division occurs first throughout the primordia and then a mitotic arrest front moves from the tip to the base of the leaf, so that cells in the distal part of the leaf stop cycling and begin to expand, while cells at the base continue to proliferate (Donnelly et al., 1999). Rodriguez et al.'s results showed that the distal part of the leaf accumulates more miR396 and a gradient of miRNA activity proceeds towards the base of the organ. That result was supported by small RNA blots and the observed retreat of the wild-type GRF2-GUS reporter, which then matched the pattern of a CYCB1;1 reporter. Those observations prompted those authors to implicate the repression of GRF expression by miR396 as a component of the mitotic arrest front.

Similar spatial patterns of expression for GRF2 mRNA and miR396 in the meristem and leaf primordial have been observed, indicating that there is co-expression of the miRNA and its target at this early stage. The situation was different, however, at later stages of leaf development. The wild-type GRF2-GUS reporter was active only in the proximal part of young developing leaves, whereas the rGRF2-GUS reporter was expressed throughout the leaf. This qualitative change in the expression of wild-type GRF2-GUS was paralleled by a large increase in miR396, whose levels change by up to 10-30-fold in leaves with different developmental ages. Interestingly, the decrease in GRF expression occurred before miR396 reached its maximum level, indicating that a partial increase in the miRNA is sufficient to repress the GRFs in vivo; however, it cannot be ruled out that additional factors that act in concert with miR396 may participate in this process.

It has been proposed that miRNAs could have both qualitative effects, leading to complete elimination of their targets, and more subtle quantitative effects (Bartel and Chen, 2004). In plants, these quantitative interactions have been proposed for miR169 (Cartolano et al., 2007) and miR156 (Wang et al., 2008), miR319 (Ori et al., 2007) and miR164 (Baker et al., 2005; Nikovics et al., 2006), and their targets. From a mechanistic point of view, it is tempting to speculate that miR396 has dual functions during leaf development: it might quantitatively regulate GRF expression in the SAM and leaf primordia, while causing a large qualitative effect contributing to the clearance of GRF activity from older organs. This latter functional role in clearing GRF transcripts might explain the continued rise in miR396 levels, even after cell proliferation has ceased. On the other hand, the potential quantitative regulation of GRF activity during early leaf development might play a relevant role in the fine-tuning of cell proliferation, it has been shown that modifications of the balance between miR396 and GRF2 levels have important consequences for the final number of cells in the organ.

miR396 was first identified because of its conservation between *A. thaliana* and rice (Jones-Rhoades and Bartel, 2004). miR396 and GRFs with an miR396 target site are present in many plant species (Axtell and Bartel, 2005; Jones-Rhoades and Bartel, 2004), indicating an ancient origin for the miR396-GRF regulatory network. The function of the GRFs as regulators of cell number in leaves is well established based on the phenotypes of grf (Horiguchi et al., 2005; Kim et al., 2003; Kim and Lee, 2006) and gif (Horiguchi et al., 2005; Kim and Kende, 2004) mutants, and plants with high miR396 levels (Liu et al., 2009).

Rodriguez et al. (2010) extended these observations and found that the GRFs regulate cell proliferation in the SAM, which at least partially explains the lack of a functional meristem in an3-1 mutants overexpressing miR396 (this study) and in grf multiple knock-outs (Kim et al., 2003; Kim and Lee, 2006). Analysis of the transcriptome of moderate miR396 overexpressers has shown that the downregulation of mitosis-specific genes is one of the main molecular effects of high miR396 levels. However, the GRFs themselves do not change their expression during the cell cycle (Menges et al., 2005) and future work will be required to identify the mechanisms underlying the activity of the GRFs.

Measurements of the GRFs by RT-qPCR indicated that miR396 targets and non-targets are turned off at similar stages of leaf development, and that they act redundantly. Previous studies in which promoters have been fused directly to a GUS reporter have shown that the transcription of the GRF genes can occur in different regions of the leaf (Horiguchi et al., 2005). Rodriguez et al. observed that the post-transcriptional control of GRF2 by miR396 contributes significantly to its final expression pattern, and concluded that it is possible that the miRNA also plays a key role in adjusting the expression of other GRFs.

The snapdragon TCP gene CIN has been shown to be expressed in a dynamic pattern during leaf development and to regulate cyclin expression (Nath et al., 2003). CIN-like genes from *Arabidopsis*, which are regulated by miR319, have also been implicated in the coordination of cell proliferation and differentiation in leaves (Efroni et al., 2008; Koyama et al., 2007; Masuda et al., 2008; Palatnik et al., 2003; Schommer et al., 2008). An increase of TCP4 levels due to mutations that impair the interaction with miR319 produces smaller leaves (Efroni et al., 2008; Palatnik et al., 2003; Schommer et al., 2008).

Rodriguez et al. observed that plants expressing miR319-resistant forms of TCP4 induced miR396. As the quantitative balance between miR396 and the GRFs regulates cell number in leaves, the increase in miR396 caused by TCP4 might be responsible for at least part of the reduction in cell number in soj8 mutants. They observed, however, that the increase in TCP4 levels also caused a reduction in the GRFs that were not regulated by miR396 and GIF1, indicating an effect at the transcriptional level. Regulatory circuits in which a transcription factor causes both the transcriptional repression of target genes and the induction of an miRNA that in turn post-transcriptionally inhibits the same group of genes are well described in animals, where they are referred to as coherent feed-forward loops (Hornstein and Shomron, 2006).

miR319 overexpressers (Efroni et al., 2008; On et al., 2007; Palatnik et al., 2003) and tcp knock-outs (Nath et al., 2003; Schommer et al., 2008) have large changes in leaf morphology, as well as other phenotypic defects, such as a delay in flowering time (Palatnik et al., 2003). This indicates that the TCPs have functions that go beyond leaf development. However, it may be possible that the miR319-regulated TCPs recruit the miR396 network as part of their biological function. Rodriguez et al. proposed that the miR396 network could be a link between different developmental inputs or environmental stimuli and the components of the cell cycle machinery.

In this disclosure, the effects in plants of mutating GRF3 (and orthologues thereof) to produce a novel molecule, rGRF3 (or orthologues thereof), in a manner analogous to that for GRF2 reported by Rodriguez et al. are shown.

Surprisingly, however, it is reported here that the result is a plant with a pronounced increase in productivity and/or yield (for example with a pronounced increase in biomass, increased stress response, delayed leaf senescence, increased seed production, increased seed yield, increased root growth, increased root elongation speed and/or increased tolerance to drought), whether compared to plants with wild-type (e.g. non-mutated) GRF3, wild type GRF2 or the mutated GRF2 (rGRF2) described in Rodriguez et al.

In addition, it is shown that where at least one GIF (e.g. GIF1) is overexpressed in the presence of the mutated GRF3 (rGRF3) or an orthologue thereof, these effects are enhanced.

Furthermore, the leaves from mutant GRF3 plants and/or mutant GRF3 orthologue plants were not curved downwards as those of mutant GRF2 (rGRF2) reported in Rodriguez et al.

A slight increase in leaf area can be observed in rGRF2 plants if its level is increased to at least twenty times the level of GRF2; however, a much larger impact on productivity (for example leaf size and plant biomass) can be seen in rGRF3 plants and rGRF3-orthologue plants with only three to five times more GRF3 or GRF3-orthologue.

Thus, per this disclosure, as shown in detail in the examples and experimental methods provided below, rGRF3 or orthologues thereof is/are produced comprising several synonymous mutations in the nucleic acid sequence—i.e. there is no change in the amino acid sequence of GRF3.

The result is a plant in which the repression otherwise achieved by miR396 is uncoupled from the rGRF3, and plants with increased productivity and/or yield (including with increased biomass, increased stress resistance, delayed leaf senescence and increased drought tolerance or combinations thereof) are thereby producible.

In a first aspect there is provided an isolated nucleic acid encoding a modified growth regulatory factor (GRF)-3 or an orthologue thereof which nucleic acid is decoupled from control by miR396.

The nucleic acid may be decoupled from control by miR396 by mutating the miR396 target site.

Preferably the mutated or modified nucleic acid is only modified in the miR396 target site, e.g. with the remainder of the gene being unmodified or not being mutated.

In a preferred embodiment, the modified nucleic acid is modified in such a way as to comprise conserved nucleic acid changes. In other words, the nucleic acid is modified such that there is no change in the amino acid sequence of the GRF3 or the GRF3 orthologue expressed by the nucleic acid.

The modification to the nucleic acid essentially decouples the nucleic acid (e.g. gene) from control by miR396.

Preferably the nucleic acid is decoupled from control by miR396 by mutating the nucleic acid in the miR396 target site.

Preferably the nucleic acid according to the present invention encodes a protein having the FFD motif.

In some embodiments preferably the nucleic acid according to the present invention encodes a protein having the FFD(D/E)WP motif.

For the avoidance of doubt "(D/E)" means that at that position there is either a D or an E residue. In other workds, FFD(D/E)WP (SEQ ID NO: 117) means FFDDWP (SEQ ID NO: 127) or FFDEWP (SEQ ID NO: 128).

In order to determine whether a GRF is a GRF3-orthologue in accordance with the persnt invention one may look for GRFs which encode a protein having the FFD, (e.g. FFD(D/E)WP) (SEQ ID NO: 117) motif.

GRF3-orthologues in accordance with the present invention will be GRFs which at least comprise a miR396 target site.

Suitably the miR396 target site (e.g. in the nucleic acid according the present invention, such as in the GRF3 gene or in the GRF3-orthologue gene) may have, comprise or consist of the following nucleotide sequence CGT-TCAAGAAAGCCTGTGGAA (SEQ ID No. 1). In some embodiments this nucleotide sequence may be considered the wild-type miR396 target site sequence.

The GRF3-orthologue according to the present invention is preferably one or more of the following GRFs selected from the group consisting of: *Arabidopsis thaliana* GRF4; *Oryza sativa* GRF 1, 2, 3, 4, or 5; *Zea mays* GRF 1, 3, 5, 6, 7, 9, 11 or 14; *Glycine max* GRF; *Medicago truncatula* GRF; *Populus trichocarpa* GRF, *Carica papaya* GRF and *Prunus persica* GRF which have been decoupled from control by miR396.

Figure 7:
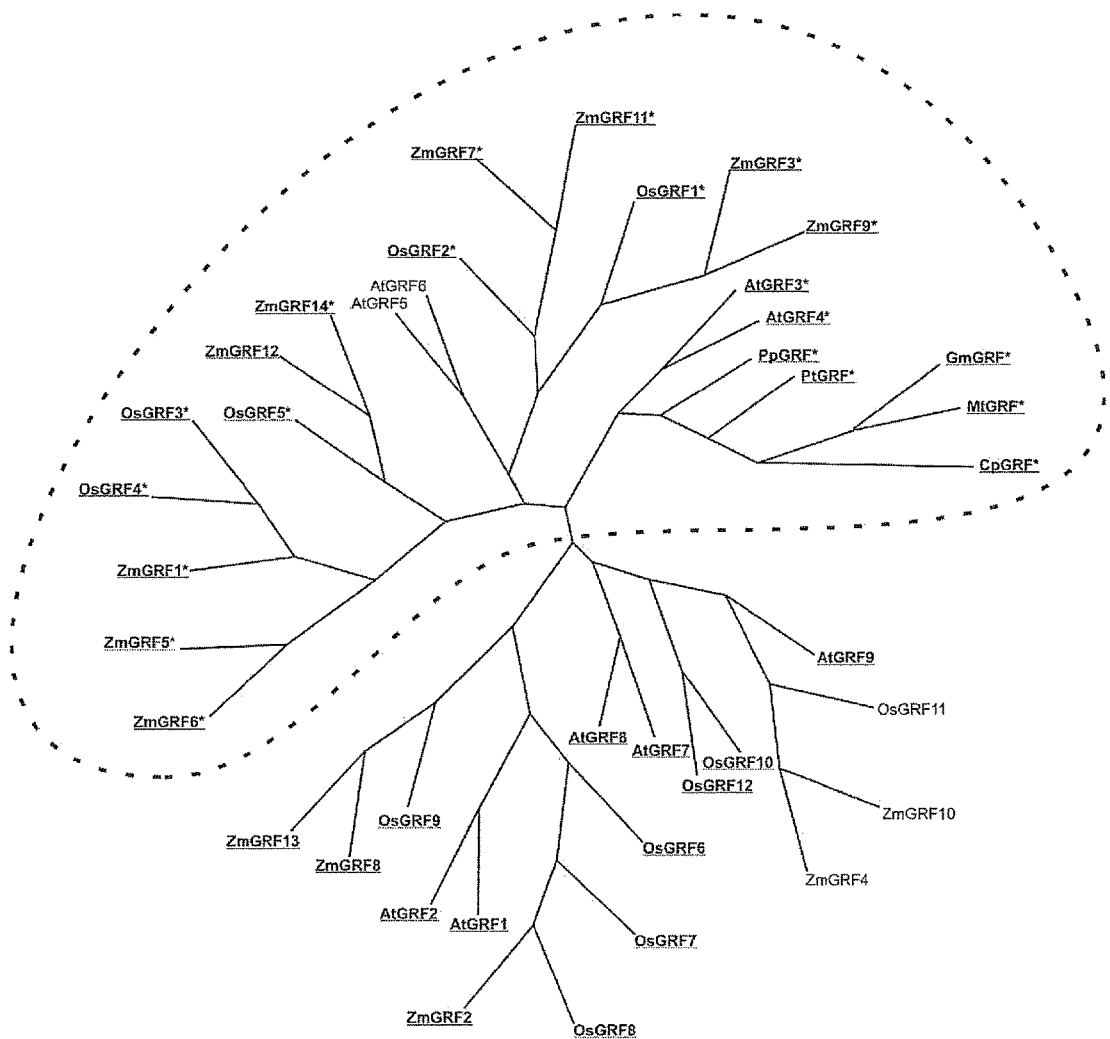
FIG. 7 shows a neighbour joining analysis of GRFs from Arabidopsis thaliana (AtGRF#), Oryza sativa (OsGRF#), Zea mays (ZmORF#), Glycine max (GmGRF), Populus trichocarpa (PtGRF), Prunus persica (PpGRF), Medicago truncatula (MtGRF) and Carica papaya (CpCRF) shown as an unrooted cladogram. Underlined: GRFs with a miR396 binding site: Labelled with an asterisk: GRFs with a FFD conserved motif.

In one embodiment, the GRF3-orthologues are ones which cluster with AtGRF3 in the cladogram depicted in FIG. 7. It has been found that these GRF3-orthologues function similarly to AtGRF3.

For the avoidance of doubt GRFs which cluster with either AtGRF2 or AtGRF9 are not of interest in the present application as it has been found that these GRFs do not function like AtGRF3.

A GRF3-orthologue in accordance with the present invention is one which has the same functionality as AtGRF3.

The term "orthologue" as used herein means genes of similar or same function but occurring in different species.

As shown in FIG. 7 the GRF3-orthologue may be preferably one that comprises a miR396 target site and which encodes for a protein having the FFD (e.g. FFD(D/E)WP) (SEQ ID NO: 117) motif.

The GRF3-orthologues in accordance with the present invention will be GRFs which at least comprise a miR396 target site.

The present invention relates to isolated nucleic acid according to any one of the preceding claims comprising i) a nucleotide sequence shown as SEQ ID No. 2 (AtGRF3); ii) or a nucleotide sequence which is at least 45%, preferably at least 50%, preferably at least 60%, preferably at least 65%, identical to SEQ ID No. 2; or iii) a nucleotide sequence which hybridises under stringent conditions with a nucleotide sequence of either i) or ii) wherein the nucleotide sequence comprises a modification in the miR396 target site to decouple the nucleic acid from control by miR396.

The isolated nucleic acid according to the present invention may comprise i) a nucleotide sequence shown as SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 11, SEQ ID No. 12, SEQ ID No. 13, SEQ ID No. 14, SEQ ID No. 15, SEQ ID No. 16, SEQ ID No. 17, SEQ ID No. 18, or SEQ ID No. 19; ii) or a nucleotide sequence which is at least 45%, preferably at least 50%, preferably at least 60%, preferably at least 65%, identical to SEQ ID No. SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 11, SEQ ID No. 12, SEQ ID No. 13, SEQ ID No. 14, SEQ ID No. 15, SEQ ID No. 16, SEQ ID No. 17, SEQ ID No. 18, or SEQ ID No. 19; or iii) a nucleotide sequence which hybridises under stringent conditions with a nucleotide sequence of either i) or ii) wherein the nucleotide sequence of i), ii) or iii) comprises a modification in the miR396 target site to decouple the nucleic acid from control by miR396.

The isolated nucleic acid according the present invention may comprise i) a nucleotide sequence encoding a polypeptide shown herein as SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36 or SEQ ID No. 37; ii) or a nucleotide sequence having at least 45%, preferably at least 50%, preferably at least 60%, preferably at least 65%, identity with the nucleotide sequence of i); or iii) a nucleotide sequence which hybridises under stringent conditions with a nucleotide sequence of either i) or ii) wherein the nucleotide sequence of i), ii) or iii) comprises a modification in the miR396 target site to decouple the nucleic acid from control by miR396.

Preferably the nucleic acid decoupled of miR396 control according to the present invention exhibits further enhancement in the presence of over-expression of at least one GIF gene (e.g. GIF1).

Over-expression of at least one GIF (e.g. GIF1) may be accomplished by transforming a plant, or a plant cell, or a plant tissue, with a construct comprising at least one GIF (e.g. GIF1) encoding sequence operably linked to a promoter.

In one embodiment the plant, plant cell or plant tissue comprises at least two, e.g. 2 or 3, over-expressed GIF genes.

The GIF gene in accordance with the present invention may be any suitable GIF gene, including AtGIF1 (sometimes referred to herein as GIF1), AtGIF 2, AtGIF 3, Os11g40100, Os12g31350, Os03g52320 or combinations thereof.

The GIF (e.g. GIF1) coding sequence may be under the control of a constitutive promoter, such as CaMV 35S promoter, or may be a tissue specific promoter.

As shown in detail in the examples and experimental methods provided below, rGRF3 or orthologues thereof may be produced comprising several synonymous nucleic acid changes—i.e. there is no change in the amino acid sequence of GRF3.

In one embodiment the modified GRF3 or orthologue thereof may comprise comprising at least one or all of the following base changes in the miR396 target site an A→U, a G→A, a U→G, a U→A, a G→C, a A→T, a G→A, a T→A, a G→A, a A→G modification. These changes may retain the native amino acid sequence, but substantially destabilize the interaction of miR396 with said rGRF3.

In one embodiment the modified GRF3 or orthologue thereof may comprise comprising at least one or all of the following base changes in the miR396 target site an A→U, a G→A, a U→A, a G→A, a A→G modification. These changes may retain the native amino acid sequence, but substantially destabilize the interaction of miR396 with said rGRF3.

In a preferred embodiment the modified GRF 3 or orthologue thereof comprises a modified miR396 target site having the following sequence: CGTTCnAGAAAnCCnGTnGAn (SEQ ID No. 86), wherein n designates bases that have been modified (e.g. mutated) (e.g. compared with the wild-type sequence).

The modified GRF 3 or orthologue thereof comprises a modified miR396 target site having the following sequence: CGTTCtAGAAAaCCaGTaGAg (SEQ ID No. 38), wherein the lower case letters designates modified bases (e.g. compared with the wild-type sequence).

Mutant sequences can be produced by any known method and various methods are readily available to one of ordinary skill in the art. As one skilled in the art will appreciate, it is possible to produce numerous site directed or random mutations into a nucleotide sequence and to subsequently screen for improved functionality of the encoded polypeptide by various means.

Mutations may be introduced using synthetic oligonucleotides. These oligonucleotides contain nucleotide sequences flanking the desired mutation sites.

A suitable method is disclosed in Morinaga et al., (*Biotechnology* (1984) 2, p 646-649). Another method of introducing mutations in nucleotide sequences is described in Nelson and Long (*Analytical Biochemistry* (1989), 180, p 147-151).

One method for introducing mutations into a nucleotide sequence would be to use QuikChange® Site Directed Mutagenesis Kit from Stratagene.

In some embodiments Targeted Induced Local Lesions IN Genomes (TILLING) technology described in Colbert et al 2001 (Plant Physiology June 2001, Vol. 126, pp 480-484) may be used to screen for induced mutations, e.g. induced point mutations.

In another aspect there is provided a construct comprising the nucleic acid according to the present invention operably linked with a promoter and/or a terminator.

The promoter may be a constitutive promoter, such as CaMV 35S promoter, the native AtGRF3 promoter, or the native GRF3 orthologue promoter, or may be a tissue specific promoter.

In one embodiment the promoter may be a tissue specific promoter.

When it is desired to decouple the different functions of GRF3 (such as to decouple the increased biomass from delayed leaf senescence), preferably the nucleic acid according to the present invention is operably linked with a tissue specific promoter.

In addition the use of a tissue specific promoter can improve the performance of plant production and further improve productivity.

In some embodiments the tissues specific promoter may comprise a (or may be a) promoter which is transiently expressed during early leaf development.

In one embodiment the tissue specific promoter may comprise a (or may be a) ASYMMETRIC LEAVES 1 (AS-1) promoter or a AINTEGUMENTA (ANT) promoter.

A person skilled in the art would be aware of other suitable tissue specific promoters to target expression of the nucleic acid according to the present invention in the appropriate location of the plant. Without wishing to be bound by theory, a mutant GRF3 or mutant GRF3 orthologue uncoupled of miR396 control with or without the co-overexpression of GIF may modify cell number in leaves or other organs when the nucleic acids are expressed specifically in those tissues. Therefore, rGRF3 will only affect that part of the plant where expression occurs.

A person skilled in the art would also be aware that the temporal pattern and level of expression might also be modified. For example, the AS-1 promoter is active for a longer period of time than the ANT promoter, and thus generates bigger leaves when expressing the mutated GRF3 (rGRF3) or mutated GRF3 orthologue sequences.

Therefore the tissue specific promoter may be one which is spatially and/or temporally regulating expression.

The present invention further provides a vector comprising the nucleic acid of the present invention or the construct according to the present invention.

In a further aspect the present invention provides a plant, plant cell or plant tissue comprising the nucleic acid according to the present invention, the construct according to the present invention or the vector according to the present invention.

In one embodiment the plant, plant cell or plant tissue according the present invention may further comprise a modified GRF2 (rGRF2) which modified GRF2 is also decoupled from control by miR396. In other words, the GRF2 may also be mutated in miR396 target site in accordance with the present invention. For the avoidance of doubt this embodiment only relates the combination of the rGRF3 or rGRF3-orthologue in accordance with the present invention in combination with rGRF2.

AtGRF2 and AtGRF9 are not GRF3-orthologues in accordance with the present invention.

Hence there term "GRF3-orthologue" as used herein does not include AtGRF2 or AtGRF9.

Hence the nucleotide sequence according to the present invention does not comprise a nucleotide sequence comprising the nucleotide sequence shown herein as SEQ ID No. 87 or SEQ ID No. 45.

Likewise, the term "modified GRF3-orthologue" or "rGRF3-orthologue" as used herein does not include modified AtGRF2 or modified AtGRF9.

In one embodiment of the present invention the plant, plant cell or plant tissue may in addition over-express at least one GIF (e.g. GIF1).

Over-expression of at least one GIF (e.g. GIF1) may be accomplished by transforming said plant, or a plant cell, or a plant tissue, with a construct comprising the at least one GIF (e.g. GIF1) encoding sequence operably linked to a promoter.

In some embodiments the plant, plant cell or plant tissue according to the present invention may comprise more than one (e.g. two, for example three) nucleic acids according to the present invention.

By way of example only, the plant, plant cell or plant tissue according to the present invention may comprise more than one (e.g. two, for example three) rGRF3 genes and/or rGRF3-orthologues. For example the plant, plant cell or plant tissue according to the present invention may comprise rGRF3 in combination with one or more rGRF3-orthologues.

The term "GRF3" as used herein means the GROWTH-REGULATING FACTOR 3 obtainable (preferably obtained) from *Arabidopsis thaliana*.

The term "rGRF3" as used herein means a mutated or modified GROWTH-REGULATING FACTOR 3 obtainable (preferably obtained) from *Arabidopsis thaliana*. Preferably the mutated or modified GROWTH-REGULATING FACTOR 3 has been mutated or modified to decouple it from control by miR396.

The term "GRF3-orthologue" as used herein may encompass one or more of the following GRFs selected from the group consisting of: *Arabidopsis thaliana* GRF4; *Oryza sativa* GRF 1, 2, 3, 4, or 5 *Zea mays* GRF 1, 3, 5, 6, 7, 9, 11 or 14; *Glycine max* GRF; *Medicago truncatula* GRF; *Populus trichocarpa* GRF; *Carica papaya* GRF and *Prunus persica* GRF.

The term "rGRF3-orthologue" as used herein may encompass one or more of the following GRFs selected from the group consisting of *Arabidopsis thaliana* GRF4; *Oryza sativa* GRF 1, 2, 3, 4 or 5; *Zea mays* GRF 1, 3, 5, 6, 7, 9, 11 or 14; *Glycine max* GRF; *Medicago truncatula* GRF; *Populus trichocarpa* GRF; *Carica papaya* GRF and *Prunus persica* GRF which have been decoupled from control by miR396.

The nucleic acid encoding a modified GRF-3 or an orthologue thereof may comprise introns or may exclude introns.

In one embodiment the nucleic acid encoding a modified GRF-3 or an orthologue thereof comprises introns. Without wishing to be bound by theory introns may enhance the expression of the transgenes.

In yet another aspect there is provided a method for using the nucleic acid according to the present invention which comprises introducing said nucleic acid according to the present invention or a construct according to the present invention or a vector according to the present invention into a plant.

In another aspect of the present invention there is provided nucleic acid according to the present invention or a construct according to the present invention or a vector according to the present invention for use in the manufacture of a plant with increased biomass, increased stress resistance, increased drought tolerance, delayed leaf senescence and combinations thereof.

In another aspect of the present invention there is provided a method of producing a plant with increased biomass, increased stress resistance, increased drought tolerance, delayed leaf senescence and combinations thereof comprising transforming the plant with nucleic acid according to the present invention or a construct according to the present invention or a vector according to the present invention.

A further aspect provides the use of a nucleic acid according to the present invention or a construct according to the present invention or a vector according to the present invention in the manufacture of a plant for increasing biomass, increasing stress resistance, increasing drought tolerance, delaying leaf senescence or combinations thereof.

Preferably plants in accordance with the present invention have increased biomass, increased stress resistance, increased drought tolerance, delayed leaf senescence or combinations thereof.

The term "increased biomass" may comprise one or more of the following selected from the group consisting of: increased overall plant biomass, increased fresh weight, increased leaf area or size, increased root length, increased dry weight, increased stem growth, increased stem biomass, increased stem diameter, and increased stem width at flowering.

A surprising technical advantage of the use of rGRF3 or rGRF3 orthologues (which differs from use of rAtGRF2) is that the increased biomass, increased drought tolerance, delayed leaf senescence or combinations thereof occurs without detrimental leaf shape changes, e.g. downward rolling.

In some embodiments it may be preferable to uncouple increased biomass from delayed leaf senescence. The inventors have surprisingly found that this can be achieved by using tissue specific promoters.

The term "increased stress resistance" as used herein means the ability of a plant to remain productive (e.g. maintain or increase biomass, etc.) even in conditions which place the plant under stress, e.g. drought etc.

The terms "increased biomass", "increased stress resistance", "increased drought tolerance", "delayed leaf senescence" "increased root growth", "increased root elongation speed" mean increased or delayed compared with either wild-type plants (e.g. plants comprising a non-modified GRF3 or GRF3-orthologue) or plants comprising a modified GRF2 (rGRF2).

The terms "increased overall plant biomass", "increased fresh weight", "increased leaf area or size", "increased dry weight", "increased stem growth", "increased stem biomass", "increased stem diameter", and "increased stem width at flowering" mean increased or delayed compared with either wild-type plants (e.g. plants comprising a non-modified GRF3 or GRF3-orthologue) or plants comprising a modified GRF2 (rGRF2).

The term "modified" as used herein may mean mutated. The term "modified" as used herein mean different from the wild-type.

The term "wild type" as used herein means a naturally-occurring nucleic acid. That is to say a nucleic acid found in an endogenous genetic code and isolated from its endogenous host organism which has not been mutated (i.e. does not contain base deletions, additions or substitutions) when compared with the genetic code of the host organism.

The vector according to the present invention may be an expression vector. The term "expression vector" means a construct capable of in vivo or in vitro expression.

Preferably, the expression vector is incorporated into the genome of a suitable host organism, e.g. plant. The term "incorporated" preferably covers stable incorporation into the genome.

The nucleotide sequence of the present invention may be present in a vector in which the nucleotide sequence is operably linked to regulatory sequences capable of providing for the expression of the nucleotide sequence by a suitable host organism, e.g. plant.

The vectors for use in the present invention may be transformed into a suitable host cell, e.g. plant cell, as described below.

The vectors for use in the present invention may contain one or more selectable marker genes such as a gene which confers antibiotic resistance e.g. ampicillin, kanamycin, chloramphenicol or tetracyclin resistance.

Vectors may be used in vitro, for example for the production of RNA or used to transfect, transform, transduce or infect a host cell.

Thus, in a further embodiment, the invention provides a method of making nucleotide sequences of the present invention by introducing a nucleotide sequence of the present invention into a replicable vector, introducing the vector into a compatible host (e.g. plant) cell, and growing the host (e.g. plant) under conditions which bring about replication of the vector.

The term "operably linked" as used herein refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals.

The term "promoter" is used in the normal sense of the art, e.g. an RNA polymerase binding site.

The term "construct"—which is synonymous with terms such as "conjugate", "cassette" and "hybrid"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, preferably the construct of the present invention comprises at least the nucleotide sequence of the present invention operably linked to a promoter.

A host organism suitable for transformation with the nucleic acid of the present invention may be a plant. In this respect, the basic principle in the construction of genetically modified plants is to insert genetic information in the plant genome so as to obtain a stable maintenance of the inserted genetic material. A review of the general techniques may be found in articles by Potrykus (*Annu Rev Plant Physiol Plant Mol Biol* [1991] 42:205-225) and Christou (Agro-Food-Industry Hi-Tech March/April 1994 17-27).

Direct infection of plant tissues by *Agrobacterium* is a simple technique which has been widely employed and which is described in Butcher D. N. et al., (1980), *Tissue Culture Methods for Plant Pathologists*, eds.: D. S. Ingrams and J. P. Helgeson, 203-208.

Other techniques for transforming plants include ballistic transformation, the silicon whisker carbide technique (see Frame B R, Drayton P R, Bagnaall S V, Lewnau C J, Bullock W P, Wilson H M, Dunwell J M, Thompson J A & Wang K (1994) Production of fertile transgenic maize plants by silicon carbide whisker-mediated transformation, *The Plant Journal* 6: 941-948) and viral transformation techniques (e.g. see Meyer P, Heidmann I & Niedenhof I (1992) The use of cassava mosaic virus as a vector system for plants, *Gene* 110: 213-217).

Further teachings on plant transformation may be found in EP-A-0449375.

Plant cells may be grown and maintained in accordance with well-known tissue culturing methods such as by culturing the cells in a suitable culture medium supplied with the necessary growth factors such as amino acids, plant hormones, vitamins, etc.

In a further aspect, the present invention relates to a vector system which carries a nucleotide sequence or construct according to the present invention and which is capable of introducing the nucleotide sequence or construct into the genome of an organism, such as a plant. The vector system may comprise one vector, but it may comprise two vectors. In the case of two vectors, the vector system is normally referred to as a binary vector system. Binary vector systems are described in further detail in Gynheung An et al., (1980), Binary Vectors, *Plant Molecular Biology Manual* A3, 1-19.

One extensively employed system for transformation of plant cells uses the Ti plasmid from *Agrobacterium tumefaciens* or a Ri plasmid from *Agrobacterium rhizogenes* An et al., (1986), *Plant Physiol*. 81, 301-305 and Butcher D. N. et al., (1980), *Tissue Culture Methods for Plant Pathologists*, eds.: D. S. Ingrams and J. P. Helgeson, 203-208. After each introduction method of the desired promoter or construct or nucleotide sequence according to the present invention in the plants, the presence and/or insertion of further DNA sequences may be necessary. If, for example, for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985, Chapter V; Fraley, et al., *Crit. Rev. Plant Sci.*, 4:1-46; and An et al., *EMBO J.* (1985) 4:277-284.

The term GIF as used herein means GRF-INTERACTING FACTORs (GIFs), a small gene family encoding proteins with homology to the human SYT transcriptional co-activator (Horiguchi et al., 2005; Kim and Kende, 2004).

GIF1 (Kim and Kende, 2004) is also known as ANGUSTIFOLIA 3 (AN3).

In one embodiment preferably the GIF used in accordance with the present invention is GIF1. GIF1 may also be referred to herein as AtGIF1.

In one embodiment the GIF used in accordance with the present invention may be GIF1, wherein GIF1 i) comprises the amino acid shown herein as MQQHLMQMQPMMAGYYPSNVTSDHIQQYLDENKSLILKIVESQNSGKLSECAENQ ARLQRNLMYLAAIADSQPQPPSVHSQYGSAGGGMIQGEGGSHYLQQQQATQQQQMTQQSLMAARSSMLYAQQQQQQQPYATLQHQQLHHSQLGMSSSSGGGGSSGLH ILQGEAGGFHDFGRGKPEMGSGGGEGRGGSSGDGGETLYLKSSDDGN (SEQ ID No. 95) or an amino acid sequence having at least 80% identity therewith; or ii) is encoded by the nucleotide sequence:
ATGCAACAGCACCTGATGCAGATGCAGCCCATGATGGCTGGTTACTACCCCAG CAATGTTACCTCTGATCATATCCAACAGTACTTGGACGAAAACAAATCGTTGATT
CTGAAGATTGTTGAGTCTCAAAACTCTGGAAAGCTTAGCGAATGCGCCGAGAAT CAAGCAAGGCTTCAACGCAACCTAATGTACCTAGCTGCAATAGCAGATTCTCAG
CCTCAGCCACCAAGTGTGCATAGCCAGTATGGATCTGCTGGTGGTGGGATGAT TCAGGGAGAAGGAGGGTCACACTATTTGCAGCAGCAACAAGCGACTCAACAGC
AACAGATGACTCAGCAGTCTCTAATGGCGGCTCGATCTTCAATGTTGTATGCTC AGCAACAGCAGCAGCAGCCTTACGCGACGCTTCAGCATCAGCAATTGCAC
CATAGCCAGCTTGGAATGAGCTCGAGCAGCGGAGGAGGAGGAAGCAGTGGTC TCCATATCCTTCAGGGAGAGGCTGGTGGGTTTCATGATTTTGGCCGTGGGAAG
CCGGAAATGGGAAGTGGTGGTGGCGGTGAAGGCAGAGGAGGAAGTTCAGGGG ATGGTGGAGAAACCCTTTACTTGAAATCATCAGATGATGGGAATTGA (SEQ ID No. 39); or
iii) is encoded by a nucleotide sequence which is at least 70%, preferably 80%, more preferably 90%, even more preferably 95% identical with SEQ ID No. 39; or
iv) is encoded by a nucleotide sequence which hybridizes under stringent conditions with SEQ ID No. 39.

As can be seen from FIG. 9 a number of GIF sequences from *Arabidopsis thaliana* and *Oryza sativa* cluster together. It is envisaged that any one of these GIFs may be used in accordance with the present invention. Therefore the GIF for use in accordance with the present invention may be one or more of the GIFs designated Os11g40100, Os12g31350, Os03g52320 obtainable (preferably obtained) from *Oryza sativa* or may be one or more of the GIFs designated AtGIF1, AtGIF2 or AtGIF3 obtainable (preferably obtained) from *Arabidopsis thaliana*.

In one embodiment the GIF used in accordance with the present invention may be AtGIF2, wherein AtGIF2 i) comprises the amino acid shown herein as MQQQQSPQMFPMVPSIPPANNITTEQIQKYLDENKKLIMAIMENQNLGKLAECAQY
QALLQKNLMYLAAIADAQPPPPPTPGPSPSTAVAAQMATPHSGMQPPSYFMQHPQA SPAGIFAPRGPLQFGSPLQFQDPQQQQQIHQQAMQGHMGIRPMGMTNNGMQHA
MQQPETGLGGNVGLRGGKQDGADGQGKDDGK (SEQ ID No. 96) or an amino acid sequence having at least 80% identity therewith; or
ii) is encoded by the nucleotide sequence:
ATGCAGCAGCAGCAGTCTCCGCAAATGTTTCCGATGGTTCCGTCGATTCCCCCT GCTAACAACATCACTACCGAACAGATCCAAAAGTACCTTGATGAGAACAAGAAG
CTGATTATGGCCATCATGGAAAACCAGAATCTCGGTAAACTTGCTGAGTGCGCC CAGTACCAAGCTCTTCTCCAGAAGAACTTGATGTATCTTGCTGCAATTGCTGATG
CTCAACCCCCACCACCTACGCCAGGACCTTCACCATCTACAGCTGTCGCTGCC CAGATGGCAACACCGCATTCTGGGATGCAACCACCTAGCTACTTCATGCAACAC
CCACAAGCATCCCCTGCAGGGATTTTCGCTCCAAGGGGTCCTTTACAGTTTGGT AGCCCACTCCAGTTTCAGGATCCGCAACAGCAGCAGCAGATACATCAGCAAGC
TATGCAAGGACACATGGGGATTAGACCAATGGGTATGACCAACAACGGGATGC AGCATGCGATGCAACAACCAGAAACCGGTCTTGGAGGAAACGTGGGGCTTAGA
GGAGGAAAGCAAGATGGAGCAGATGGACAAGGAAAAGATGATGGCAAGTGA (SEQ ID No. 90), or
iii) is encoded by a nucleotide sequence which is at least 70%, preferably 80%, more preferably 90%, even more preferably 95% identical with SEQ ID No. 90; or
iv) is encoded by a nucleotide sequence which hybridizes under stringent conditions with SEQ ID No. 90.

In one embodiment the GIF used in accordance with the present invention may be AtGIF3 wherein AtGIF3 i) comprises the amino acid shown herein as MQQSPQMIPMVLPSFPPTNNITTEQIQKYLDENKKLIMAILENQNLGKLAECAQYQA
LLQKNLMYLAAIADAQPQPPAATLTSGAMTPQAMAPNPSSMQPPPSYFMQQHQAV GMAQQIPPGIFPPRGPLQFGSPHQFLDPQQQLHQQAMQGHMGIRPMGLNNNNGL
QHQMHHHETALAANNAGPNDASGGGKPDGTNMSQSGADGQGGSAARHGGGDA KTEGK (SEQ ID No. 97) or an amino acid sequence having at least 80% identity therewith; or
ii) is encoded by the nucleotide sequence:
ATGCAGCAATCTCCACAGATGATTCCGATGGTTCTTCCTTCATTTCCGCCCACCA ATAATATCACCACCGAACAGATCCAAAAGTATCTTGATGAGAACAAGAAGCTGAT
AATGGCGATCTTGGAAAATCAGAACCTCGGTAAACTTGCAGAATGTGCTCAGTA TCAAGCTCTTCTCCAGAAGAATTTGATGTATCTCGCTGCAATTGCGGATGCTCAA
CCTCAGCCACCAGCAGCTACACTAACATCAGGAGCCATGACTCCCCAAGCAAT GGCTCCTAATCCGTCATCAATGCAGCCACCACCAAGCTACTTCATGCAGCAACA
TCAAGCTGTGGGAATGGCTCAACAAATACCTCCTGGGATTTTCCCTCCTAGAGG TCCATTGCAATTTGGTAGCCCGCATCAGTTTCTGGATCCGCAGCAACAGTTACA TCAACAAGCTATGCAAGGGCACATGGGGATTA-GACCAATGGGTTTGAATAATAA CAACGGACTG-CAACATCAAATGCACCACCATGAAACTGCTCTTGC-CGCAAACAA
TGCGGGTCCTAACGATGCTAGTGGAGGAGG-TAAACCGGATGGGACCAATATGA GCCAGAGTG-GAGCTGATGGGCAAGGTGGCTCAGCCGCTAGA-CATGGCGGTGG
TGATGCAAAAACTGAAGGAAAATGA (SEQ ID No. 91), or
iii) is encoded by a nucleotide sequence which is at least 70%, preferably 80%, more preferably 90%, even more preferably 95% identical with SEQ ID No. 91; or
iv) is encoded by a nucleotide sequence which hybridizes under stringent conditions with SEQ ID No. 91.

In one embodiment the GIF used in accordance with the present invention may be the GIF designated Os11g40100 wherein Os11g401001) comprises the amino acid shown herein as:
MQQQMAMPAGAAAAAVPPAAGITTEQIQKYLDEN-KQLILAILENQNLGKLAECAQY QAQLQKNLLY-LAAIADAQPPQNPGSRPQMMQPGATPGAGHYM-SQVPMFPPRTPL
TPQQMQEQQQQQLQQQQAQALAFPGQMLMRPGT-VNGMQSIPVADPARAADLQT AAPGSVDGRGNKQ-DATSEPSGTESHKSAGADNDAGGDIAEKS (SEQ ID No. 98) or an amino acid sequence having at least 80% identity therewith; or
ii) is encoded by the nucleotide sequence:
ATGCAGCAGCAGATGGCCATGCCGGCGGGGGC-CGCCGCCGCCGCGGTGCCG CCGGCGGCCGGCAT-CACCACCGAGCAGATCCAAAAGTATTTGGAT-GAAAATAA
ACAGCTAATTTTGGCCATCCTGGAAAATCAAAAC-CTAGGGAAGTTGGCTGAATG TGCTCAGTAC-CAAGCTCAGCTTCAAAAGAATCTCTTGTATCTG-GCTGCCATTGCA
GATGCCCAACCACCTCAGAATCCAGGAAGTCGC-CCTCAGATGATGCAGCCTGG TGCTACCCCAGGT-GCTGGGCATTACATGTCCCAAGTACCGATGTTC-CCTCCAAG
AACTCCCTTAACCCCACAACAGATGCAAGAGCA-GCAGCAGCAGCAACTCCAGC AACAGCAAGCTCA-GGCTCTAGCCTTCCCCGGCCAGATGCTAATGAGAC-CAGGT
ACTGTCAATGGCATGCAATCTATCCCAGTTGCT-GACCCTGCTCGCGCAGCCGAT CTTCAGACGGCAG-CACCGGGCTCGGTAGATGGCCGAGGAAACAAGCA-GGATG
CAACCTCGGAGCCTTCCGGGACCGAGAGCCA-CAAGAGTGCGGGAGCAGATAACGACGCAGGCGGT-GACATAGCGGAGAAGTCCTGA (SEQ ID No. 92)), or
iii) is encoded by a nucleotide sequence which is at least 70%, preferably 80%, more preferably 90%, even more preferably 95% identical with SEQ ID No. 92; or
iv) is encoded by a nucleotide sequence which hybridizes under stringent conditions with SEQ ID No. 92.

In one embodiment the GIF used in accordance with the present invention may be the GIF designated Os12g31350 wherein Os12g313501) comprises the amino acid shown herein as:
MQQQPMPMPAQAPPTAGITTEQIQKYLDEN-KQLILAILENQNLGKLAECAQYQAQL QKNLLY-LAAIADTQPQTTISRPQMVPHGASPGLGGQYMSQVP-MFPPRTPLTPQQM
QEQQLQQQQAQLLSFGGQMVMRPGWN-GIPQLLQGEMHRGADHQNAGGATSEP SESHRSTG-TENDGGSDFGDQS (SEQ ID No. 99) or an amino acid sequence having at least 80% identity therewith; or
ii) is encoded by the nucleotide sequence:
ATGCAGCAGCAGCCGATGCCGATGCCCGCGCAG-GCGCCGCCGACGGCCGGAA TCACCACCGAGCA-GATCCAAAAGTATCTGGATGAAAACAAGCAGCTT-ATTTTGG
CTATTTTGGAAAATCAGAATCTGGGAAAGTTGGCA-GAATGTGCTCAGTATCAAG CGCAGCTTCA-GAAGAATCTCTTGTACTTGGCTGCAATTGCTGA-TACTCAACCGC
AGACCACTATAAGCCGTCCCCAGATGGTGCCG-CATGGTGCATCGCCGGGGTTA GGGGGGCAATACAT-GTCGCAGGTGCCAATGTTCCCCCCCAGGAC-CCCTCTAAC
GCCCCAGCAGATGCAGGAGCAGCAGCTGCAG-CAACAGCAAGCCCAGCTGCTC TCGTTCGGCG-GTCAGATGGTTATGAGGCCTGGCGTTGTGAATG-GCATTCCTCA
GCTTCTGCAAGGCGAAATGCACCGCGGAGCAGAT-CACCAGAACGCTGGCGGG GCCACCTCGGAGCCT-TCCGAGAGCCACAGGAGCACCGGCACCGAAAAT-GACG GTGGAAGCGACTTCGGCGATCAATCCTAA (SEQ ID No. 93), or
iii) is encoded by a nucleotide sequence which is at least 70%, preferably 80%, more preferably 90%, even more preferably 95% identical with SEQ ID No. 93; or
iv) is encoded by a nucleotide sequence which hybridizes under stringent conditions with SEQ ID No. 93.

In one embodiment the GIF used in accordance with the present invention may be the GIF designated Os03g52320 wherein Os03g523201) comprises the amino acid shown herein as:
MQQQHLMQMNQGMMGGYASPTT-VTTDLIQQYLDENKQLILAILDNQNNGKVEECA RNQAKLQHNLMYLAAIADSQPPQTAAMSQYPSN-LMMQSGARYMPQQSAQMMAP QSLMAARSSM-MYAQPALSPLQQQQQQQAAAAHGQLGMGSGGTTS-GFSILHGEAS
MGGGGGGGGAGNSMMNAGVFSDFGRGGGGGG-KEGSTSLSVDVRGANSGAQSG DGEYLKGTEEEGS (SEQ ID No. 100) or an amino acid sequence having at least 80% identity therewith; or
ii) is encoded by the nucleotide sequence:
ATGCAGCAGCAACACCTGATGCAGATGAACCA-GGGCATGATGGGGGGATATGC TTCCCCTACCAC-CGTCACCACTGATCTCATTCAGCAGTATCTGGAT-GAGAACAA
GCAGCTGATCCTGGCCATCCTTGACAACCA-GAACAATGGGAAGGTGGAAGAGT GCGCTCG-GAACCAAGCTAAGCTCCAGCACAATCTCATGTAC-CTCGCCGCCATC
GCCGACAGCCAGCCGCCGCAGACGGCCGCCAT-GTCCAGTATCCGTCGAACC TGATGATGCAGTC-CGGGGCGAGGTACATGCCGCAGCAGTCGGCGCA-GATGAT
GGCGCCGCAGTCGCTGATGGCGGCGAGGTCTTC-GATGATGTACGCGCAGCCG GCGCTGTCGCCGCTC-CAGCAGCAGCAGCAGCAGCAGGCGGCGGCGGCG-CAC
GGGCAGCTGGGCATGGGCTCGGGGGGCACCACCA-GCGGGTTCAGCATCCTCC ACGGCGAGGCCAG-CATGGGCGGCGGCGGCGGCGGCGGTGGCGCCGG-TAACA
GCATGATGAACGCCGGCGTGTTCTCCGACTTCG-GACGCGGCGGCGGCGGCGG CGGCAAGGAGGGGTCCACCTCGCTGTCCGTC- GACGTCCGGGGCGCCAACTCC GGCGCCCA-
GAGCGGCGACGGGGAGTACCTCAAGGGCAC-
CGAGGAGGAAGGC AGCTAG (SEQ ID No. 94), or iii) is encoded by a nucleotide sequence which is at least 70%, preferably 80%, more preferably 90%, even more preferably 95% identical with SEQ ID No. 94; or iv) is encoded by a nucleotide sequence which hybridizes under stringent conditions with SEQ ID No. 94.

Furthermore, the inventors have demonstrated that overexpression of GIF1, GIF2, and GIF3 promotes cell proliferation and leaf size and that GIF2 and GIF3 proteins are functional equivalents of GIF1 (se FIG. 43 in combination with FIG. 9).

Previously Horiguchi et al. (2005) have shown that overexpression of the GIF1/AN3 gene stimulates cell proliferation as well, leading to enlarged leaves by about 20%.

These results suggest that all of the GIF genes function redundantly as positive regulators of cell proliferation, thereby determining plant organ size.

Therefore the use of any GIF gene in accordance with the present invention is contemplated herein.

In addition combinations of GIF genes are also contemplated herein.

In one aspect, preferably the sequence is in an isolated form. The term "isolated" means that the sequence is at least substantially free from at least one other component with which the sequence is naturally associated in nature and as found in nature.

In one aspect, preferably the sequence is in a purified form. The term "purified" means that the sequence is in a relatively pure state—e.g. at least about 90% pure, or at least about 95% pure or at least about 98% pure.

The terms "nucleotide sequence" or "nucleic acid" as used herein refers to an oligonucleotide sequence or polynucleotide sequence, and variants, homologues, fragments and derivatives thereof (such as portions thereof). The nucleotide sequence may be of genomic or synthetic or recombinant origin, which may be double-stranded or single-stranded whether representing the sense or anti-sense strand.

The terms "nucleotide sequence" or "nucleic acid" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention does not include the native nucleotide sequence according to the present invention when in its natural environment and when it is linked to its naturally associated sequence(s) that is/are also in its/their natural environment. For ease of reference, this preferred embodiment shall be called the "non-native nucleotide sequence" or "non-native nucleic acid"

Typically, the nucleotide sequence or nucleic acid encompassed by scope of the present invention is prepared using recombinant DNA techniques (i.e. recombinant DNA). However, in an alternative embodiment of the invention, the nucleotide sequence or nucleic acid could be synthesised, in whole or in part, using chemical methods well known in the art (see Caruthers M H et al., (1980) Nuc Acids Res Symp Ser 215-23 and Horn T et al., (1980) Nuc Acids Res Symp Ser 225-232).

Due to degeneracy in the genetic code, nucleotide sequences may be readily produced in which the triplet codon usage, for some or all of the amino acids encoded by the original nucleotide sequence, has been changed thereby producing a nucleotide sequence with low homology to the original nucleotide sequence but which encodes the same, or a variant, amino acid sequence as encoded by the original nucleotide sequence. For example, for most amino acids the degeneracy of the genetic code is at the third position in the triplet codon (wobble position) (for reference see Stryer, Lubert, Biochemistry, Third Edition, Freeman Press, ISBN 0-7167-1920-7) therefore, a nucleotide sequence in which all triplet codons have been "wobbled" in the third position would be about 66% identical to the original nucleotide sequence. However, the amended nucleotide sequence would encode for the same, or a variant, primary amino acid sequence as the original nucleotide sequence.

Therefore, the present invention in some embodiments further relates to any nucleotide sequence that has alternative triplet codon usage for at least one amino acid encoding triplet codon, but which encodes the same, or a variant, polypeptide sequence as the polypeptide sequence encoded by the original nucleotide sequence.

Furthermore, specific organisms typically have a bias as to which triplet codons are used to encode amino acids. Preferred codon usage tables are widely available, and can be used to prepare codon optimised genes. Such codon optimisation techniques are routinely used to optimise expression of transgenes in a heterologous host.

The present invention also encompasses the use of sequences which have identity or similarity with the sequences according to the present invention.

Here, the term "identity" means an entity having a certain identity with the amino acid sequences and the nucleotide sequences. Identity means the percentage of amino acids or bases that are the same in one sequence when compared with another sequence.

Here, the term "similarity" means an entity having similar chemical properties/functions. Hence the term similarity takes into account conservative changes.

In the present context, a sequence which has a certain percentage identity or similarity is taken to include a sequence which may be at least 90% identical, preferably at least 95, 96, 97, 98 or 99% identical to a sequence of the present invention (the subject sequence). Typically, the sequences will comprise the same sequences that code for the active sites etc. as the subject sequence.

Identity or similarity comparisons can be conducted by eye, or more usually, with the aid of readily available sequence comparison programs. The available computer programs can calculate % identity and % similarity between two or more sequences.

% identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap.

This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % identity therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p 387). Examples of other software than can perform sequence comparisons include, but are not limited to, the BLAST package (see Ausubel et al., 1999 Short Protocols in Molecular Biology, 4$^{th}$ Ed—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60).

However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final % identity can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage identity may be calculated using the multiple alignment feature in DNASIS™ (Hitachi Software), based on an algorithm, analogous to CLUSTAL (Higgins D G & Sharp P M (1988), Gene 73(1), 237-244).

Generally percentage identity is calculated over at least 50, preferably at least 100, preferably at least 200 contiguous bases or residues. Preferably the percentage identity is calculated using the full length sequence.

Once the software has produced an optimal alignment, it is possible to calculate % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids can be grouped together based on the properties of their side chain alone. However it is more useful to include mutation data as well. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" Comput. Appl Biosci. 9: 745-756) (Taylor W. R. (1986) "The classification of amino acid conservation" J. Theor. Biol. 119; 205-218). Conservative substitutions may be made, for example according to the table below which describes a generally accepted Venn diagram grouping of amino acids.

| SET | | | SUB-SET | |
|---|---|---|---|---|
| Hydrophobic | Phe, Trp, Tyr, His, Lys, Met, Ile, Leu, Val, Ala, Gly, Cys | | Aromatic | Phe, Trp, Tyr, His |
| | | | Aliphatic | Ile, Leu, Val |
| Polar | Trp, Tyr, His, Lys, Arg, Glu, Asp, Cys, Ser, Thr, Asn, Gln | | Charged | His, Lys, Arg, Glu, Asp |
| | | | Positively Charged | His, Lys, Arg |
| | | | Negatively Charged | Glu, Asp |
| Small | Val, Cys, Ala, Gly, Ser, Thr, Asn, Asp | | Tiny | Ala, Gly, Ser |

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% identical to the sequences of the present invention but fall within the scope of the invention can be obtained in a number of ways. Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species orthologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated procedures are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector.

The present invention also encompasses sequences that are complementary to the nucleic acid sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

Preferably, the hybridisation is determined under stringent conditions (e.g. 50° C. and 0.2×SSC {1×SSC=0.15 M NaCl, 0.015 M Na$_3$citrate pH 7.0}).

Suitably, the hybridisation may be determined under high stringent conditions (e.g. 65° C. and 0.1×SSC {1×SSC=0.15 M NaCl, 0.015 M Na$_3$citrate pH 7.0}).

The present invention also relates to nucleotide sequences that can hybridise to the nucleotide sequences of the present invention (including complementary sequences of those presented herein).

A skilled person will understand that the modified GRF3-orthologue may be obtainable from any plant. In a preferred embodiment the GRF3-orthologue is obtainable, preferably obtained, from one or more of the plants selected from the group consisting of: *Arabidopsis thaliana, Oryza sativa, Zea mays, Glycine max, Medicago truncatula, Populus trichocarpa, Prunus persica, Carica papaya, Triticum aestivum, Sorghum bicolor, Gossypium hirstutum*, sugar cane (*Saccharum* spp.), *Panicum virgatum, Helianthis annus, Beta vulgaris*, and *Brassica* species.

In an even more preferred embodiment the GRF3-orthologue is obtainable, preferably obtained, from one or more of the plants selected from the group consisting of: *Arabidopsis thaliana, Oryza sativa, Zea mays, Glycine max, Medicago truncatula, Populus trichocarpa, Prunus persica, Carica papaya,*

The nucleic acid, vector or construct according to the present invention may be transformed in to any (host) plant.

The plant, plant cell or plant tissue according to the present invention may be a monocotyledonous (monocot) plant or a dicotyledonous (dicot) plant.

In one embodiment the plant, plant cell or plant tissue according to the present invention may be a dicot.

A monocot plant may, for example, be selected from the families Arecaceae, Amaryllidaceae or Poaceae. For example, the plant may be a cereal crop, such as wheat, rice, barley, maize, oat, sorghum, rye, onion, leek, millet, buckwheat, turf grass, Italian rye grass, switchgrass, *Miscanthus*, sugarcane grass, false oat grass, fescue, Bermuda grass, brome, heath grass, meadow grasses (e.g. naturally mixed grassland swards, orchard grass, rye grass, Timothy-grass) or *Festuca* species A dicot plant which may be selected from the families including, but not limited to Asteraceae, Brassicaceae (e.g. *Brassica napus*), Chenopodiaceae, Cucurbitaceae, Leguminosae (Caesalpiniaceae, Aesalpiniaceae Mimosaceae, Papilionaceae or Fabaceae), Malvaceae, Rosaceae or Solanaceae. For example, the plant may be selected from lettuce, sunflower, *Arabidopsis*, spinach, water melon, squash, oilseed rapeseed (including canola), cabbage, broccoli, kale, turnip, rutabaga (swede), tomato, potato, *capsicum*, tobacco, cotton, legumes sugar beet, okra, apple, rose, strawberry, alfalfa (lucerne), birdsfoot trefoil, bean, soybean, field (fava) bean, pea, lentil, peanut, chickpea, coffee, cocoa, apricots, apples, pears, peach, grape vine or citrus species.

Also included are biofuel and bioenergy crops such as sugar cane, oilseed rape/oil-seed rape, linseed, jatropha, oil-palm, copra and willow, eucalyptus, poplar, poplar hybrids. *Miscanthus* or gymnosperms, such as loblolly pine. Also included are crops for silage (e.g. forage grass species or forage maize), grazing or fodder (pasture grasses, clover, alsike clover, red clover, subterranean clover, white clover, sanfoin, alfalfa), fibres (e.g. cotton, flax), building materials (e.g. pine, oak), pulping (e.g. poplar), feeder stocks for the chemical industry (e.g. high erucic acid oil seed rape, linseed), rubber plants, and crops for amenity purposes (e.g. turf grasses for sports and amenity surfaces), ornamentals for public and private gardens (e.g. species of *Angelonia, Begonia, Catharanthus, Euphorbia, Gazania, Impatiens, Nicotiana, Pelargonium, Petunia, Rosa, Verbena*, and *Viola*) and flowers of any plants for the cut-flower market (such as tulips, roses, daffodils, lilies, stallions, gerbera, carnations, chrysanthemums, irises, gladioli, alstromerias, marigold, sweet pea, freesia, anemone poppy).

Preferably, the plant, plant cell or plant tissue, or host plant is a crop plant. By crop plant is meant any plant which is grown on a commercial scale for human or animal consumption or use for other non-food/feed use. Preferred plants are corn (maize), millet, wheat, Durum wheat, rice, oilseed rape (or canola), sorghum, sugar cane, soybean, sunflower, potato, tomato, barley, rye, oats, pea, bean, field bean, sugar beet, oil-palm, groundnut, peanut, cassava, alfalfa, clover, copra, raisin, coffee, cotton, lettuce, banana, broccoli or other vegetable brassicas.

In one embodiment the plant, pant cell or plant tissue, or host plant is Brassica, suitably Brassica oleracea (e.g. broccoli or other vegetable Brassicas).

The plant may be a tree such as eucalyptus, poplar, or conifer such as *Picea* species (e.g. spruce) or *Pinus* species (pines), a hardwood tree species such as teak, a plantation tree such as rubber (*Hevea*), palm tree (date- or oil-palm) or jatropha or an orchard fruit tree (such as plum, peach, apple and pear).

EXAMPLES

While the invention disclosed herein is described in general above, and those skilled in the art based on that disclosure would be enabled to practice this invention, including its best mode, the following examples are provided to further support this written description and enabling disclosure. The details of these examples are, however, non-limiting. For an understanding of the scope of this invention, reference should be had to the appended claims and their equivalents.

Transgenes

See Table 1 for a list of binary plasmids used.

Expression Analysis

First, 0.5-1.0 µg of total RNA was treated with RQ1 RNase-free DNase (Promega). Then, first-strand cDNA synthesis was carried out using SuperScript III reverse transcriptase (Invitrogen). PCR reactions were performed in a Mastercycler ep realplex thermal cycler (Eppendorf) using SYBR Green I (Roche) to monitor double-stranded (ds) DNA synthesis. Quantitative (q)PCR of each gene was carried out for at least three biological replicates, with technical duplicates for each biological replicate. The relative transcript level was determined for each sample, normalized using PROTEIN PHOSPHATASE 2A cDNA level (Czechowski et al., 2005). Primer sequences are given in Table 2:

TABLE 2

Relevant Locus IDs and oligonucleotide primers used in RT-qPCR.

| Gene | Locus ID | Forward primer | Reverse primer |
|---|---|---|---|
| AtGRF3 | AT2G36400 | GTCTTCGCTGGCCACAAGTATT SEQ ID NO: 104 | TGTTGCTGTTGTAGTGGTGGCT SEQ ID NO: 105 |
| AtGRF2 | AT4G37740 | CACATCAACAGAGGCCGTCATcg SEQ ID NO: 106 | AACCGGAGATTCCTTGGGTTGTAAG SEQ ID NO: 107 |
| AtGIF1 | AT5G28640 | TTGGACGAAAACAAATCGTTGA SEQ ID NO: 108 | CTGTTGCTGTTGAGTCGCTTGT SEQ ID NO: 109 |

Small RNA Analysis

RNA was extracted using TRIzol reagent (Invitrogen). Total RNA was resolved on 17% polyacrylamide gels under denaturing conditions (7 M urea). Blots were hybridized using either radioactively labelled or digoxigenin end-labelled locked nucleic acid (LNA) oligonucleotide probes designed against miR396 (Exiqon, Denmark).

Alternatively, miR396 levels were determined by stem-loop RT-qPCR, as described previously (Chen et al., 2005). The sequences of the oligonucleotides used were: retrotranscription stem-loop oligo, 5'GTCTCCTCTGGTGCAGGGTCCGAGGTATTCGCAC-CAGAGGAGACMAAAGTTC3' (SEQ ID NO: 110); PCR forward primer, 5'GGCGGTTCCACAGCTTTCTT3' (SEQ ID NO: 111); and PCR reverse primer, 5'TGGTGCAGGGTCCGAGGTATT3' (SEQ ID NO: 112).

Microarray Analyses

Total RNA was extracted from the aerial part of seedlings grown on plates for 10 days using the RNeasy plant mini kit

TABLE 1

| Vector | Construct | Arabidopsis Chromosome: start-end[a] | Purpose |
|---|---|---|---|
| pJP123 | 35S:miR396b | 5: 13628907-13629319 | Overexpression of miR396b stem-loop |
| pRER31 | GRF3 | 2: 15274101-15270081 CGC AAC CGT TCA AGA AAG CCT GTG GAA ACT CCA (SEQ ID NO: 122) | Genomic GRF3 |
| pRER32 | rGRF3 | 2: 15274101-15270081 CGC AAC CGT TCT AGA AAA CCA GTA GAG ACT CCA (SEQ ID NO: 123) | Genomic mutant GRF3 |
| pRER35 | rGRF2 | 4: 17729683-17725302 CGT CAT CGT TCT AGA AAA CCG GTC GAA CTC CAA (SEQ ID NO: 124) | Genomic mutant GRF2 |
| pJD16 | 35S:GIF1 | 5: 10647830-10649620 | Overexpression of AtGIF1 |

[a]The nucleotides annealing with miR396 are 8-19, 21-27 of GRF3 construct; 8-11, 13-17, 19, 22-23, 25-27 of rGRF3 construct and 8-11, 13-17, 19, 22-23, 25-27 of rGRF2. Underlined, mutagenized residues are 12, 18, 21 and 24 of rGRF3 construct and 12, 18, 21 and 24 of rGRF2 construct. The upstream and downstream codons are 1-6, 28-33 of GRF3 construct; 1-6, 28-33 of rGFR3 construct and 1-6, 28-33 of rGRF2 construct.

(QIAGEN). Microarray analyses using the Affymetrix ATH1 platform were performed on two biological replicates as described (Schmid et al., 2005). Differentially expressed genes were identified using per-gene variance, calculated using logit-T (Lemon et al., 2003). The corresponding fold change of the transcripts was obtained by expression estimates using gcRMA (www.bioconductor.org), a modification of the robust multi-array analysis (RMA) algorithm (Irizarry et al., 2003). The expression of gene groups was assessed by gene set enrichment analysis using GSEA-P 2.0 (Subramanian et al., 2007; Subramanian et al., 2005).

Microscopic Observations

Tissue was fixed in FAA and embedded in paraffin. Sections 10 μm thick were stained with Toluidine Blue.

To obtain paradermal views of palisade cells, leaves were fixed with FAA and cleared with chloral hydrate solution as described (Horiguchi et al., 2005). Palisade leaf cells were observed using differential interference contrast (DIC) microscopy.

In Situ Hybridization

DIG-labelled sense and antisense probes were synthesized by transcription with T7 or SP6 RNA polymerase with the DIG RNA labelling kit (SP6/T7) (Roche) using cloned cDNAs of GRF2 and HISTONE H4 as templates. For the miR396 probe, LNA oligonucleotides (Exiqon) were end labelled with the DIG oligonucleotide 3'-end labelling kit (Roche). Shoot apices from 15-day-old plants grown in short photoperiods were dissected and fixed in FAA. Paraffin-embedded material was sectioned to 8 μm thickness. Hybridization and detection were performed as previously described (Palatnik et al., 2003).

GUS Assays

To visualize the activity of the reporters, transgenic plants were subjected to GUS staining, according to Donnelly et al. (Donnelly et al., 1999). Stained tissue was paraffin embedded, sectioned and mounted in Canada balsam.

Accession Numbers

A list of relevant AGI locus identifiers is provided in Table 2. The accession number for the microarray experiments is GSE11250.

TABLE 3

GRF expression in 35S:miR396b plants compared to that in wild type, as estimated by Affymetrix microarray

| Description | Relative expression* |
| --- | --- |
| GRF1 | 0.81 |
| GRF2 | 0.58 |
| GRF3 | 0.73 |
| GRF4 | WA |
| GRF5 | 0.89 |
| GRF6 | A |
| GRF7 | 0.57 |
| GRF8 | A |
| GRF9 | NP |

*Fold change relative to wild type, normalized with gcRMA. The average of two biological replicates for each genotype is shown.
A, a gene termed 'absent' by MAS 5.0 software (Affymetrix);
NP, not present in ATH1 arrays;
WA, wrongly annotated in ATH1 arrays.

Example #1

A miR396 Resistant Version of GRF3 Increases Plant Size and Biomass Accumulation The GRF family of transcription factors comprises nine members in *Arabidopsis* (Kim et al., 2003). Seven of them, including GRF3, have a target site for miR396 (Jones-Rhoades and Bartel, 2004). GRF loss-of-function or over-expression of miR396 have been shown to reduce cell number in *Arabidopsis* leaves (Horiguchi et al., 2005) (Kim et al., 2003) (Kim and Kende, 2004; Liu et al., 2009).

To study the importance of miR396 in restricting GRF3 expression, two GRF3 genomic fragments were introduced into *Arabidopsis thaliana* plants. One of them contained the wild-type GRF3 gene (FIG. 1, top panel), while the second harbored a modified GRF3 sequence in which the miRNA-targeting motif was altered through synonymous mutations that prevent miR396 targeting (named rGRF3, FIG. 1, middle panel).

The wild-type sequence of GRF3 contains a region complementary to miR396 with a high interaction energy ($\Delta G = -33.9$ kcal/mol). In contrast, the modified GRF3 sequence (rGRF3), which includes five changes from the wild-type sequence (A→U, G→A, U→A, a G→A and a A→G modifications) does not have a clear miR396 interacting site, as the interaction energy is reduced from $-33.9$ kcal/mol to $-14.4$ kcal/mol. The complete sequence of GRF3 is detailed in FIGS. 21 and 22. The complete sequence of rGRF3 is detailed in FIG. 35. The full sequence and a map of the binary vector used (named RER32, see Table 1) can be found in FIGS. 40 and 42, respectively.

Figure 3:
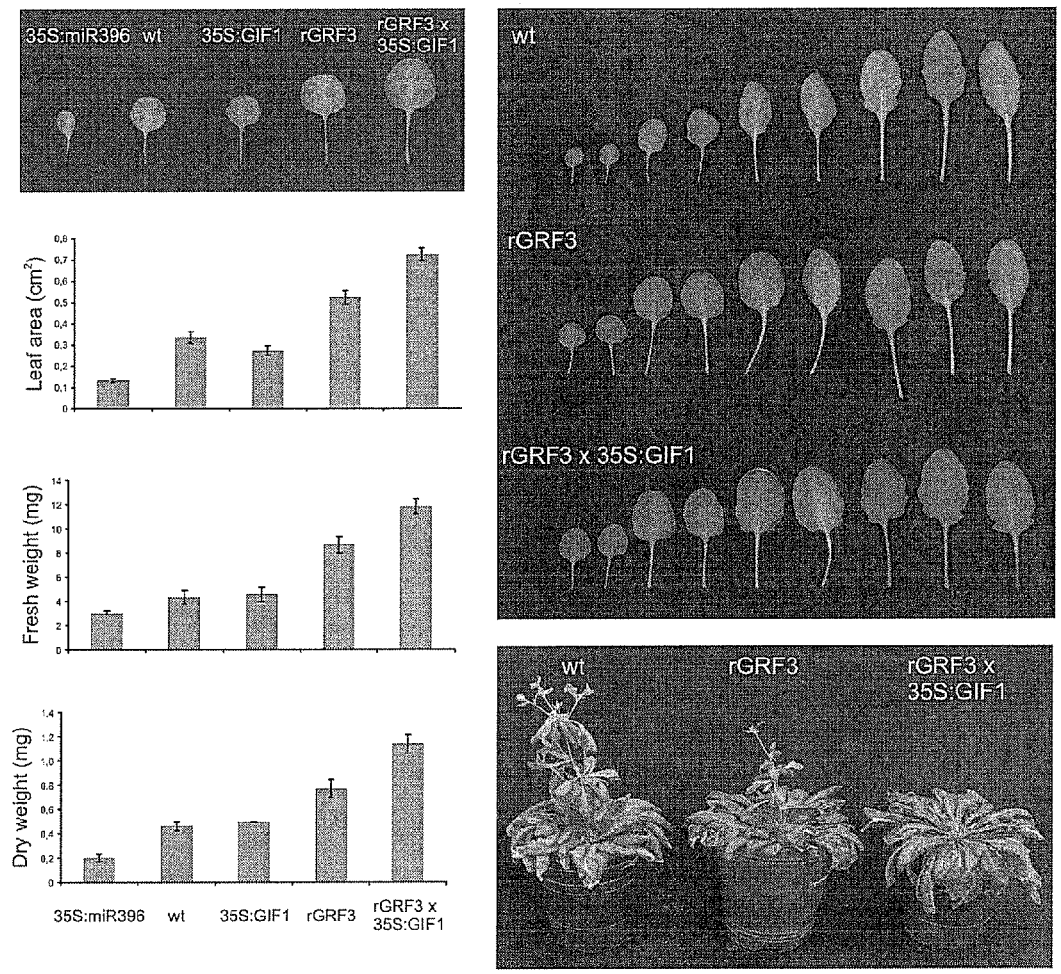
FIG. 3 shows the modification in leaf development observed in rGRF3 plants, 35S:GIF1 plants and rGRF3× 35S:GIF1 plants. In the left panel, leaf area, fresh weight and dry weight were determined for fully expanded first leaves, which show the most easily observed changes; the right panel shows leaf phenotypes of developing plants in short days, while the bottom right panel shows plants grown in large pots in short day conditions.
Figure 6:
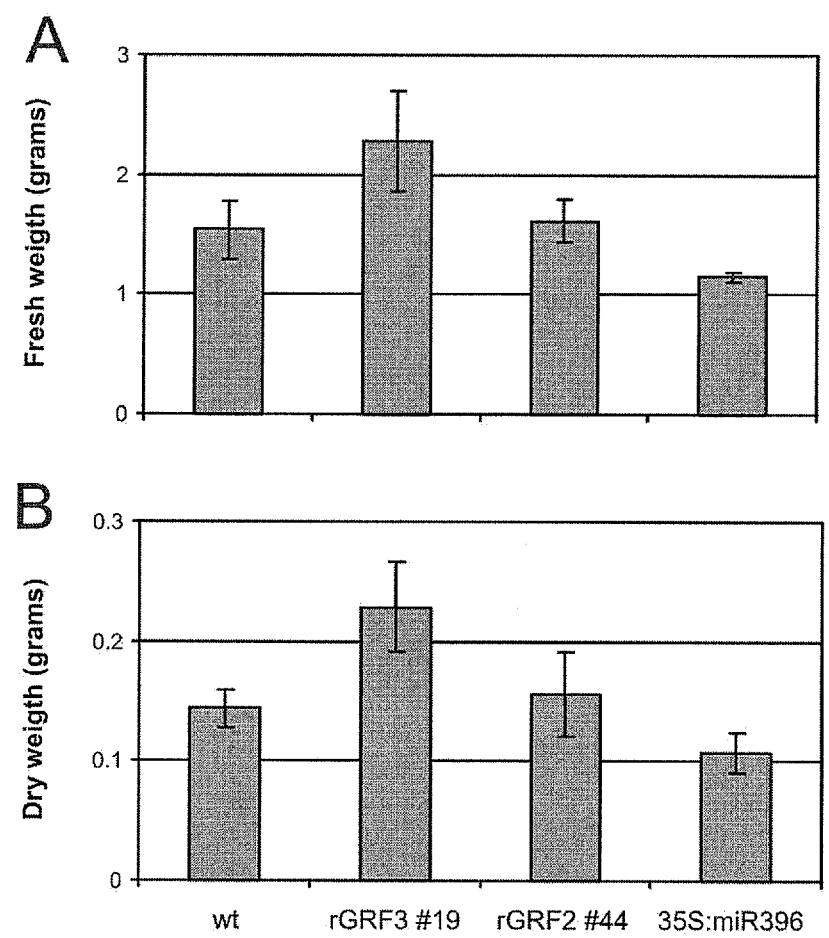
FIG. 6 shows the fresh weight (FIG. 6A) and dry weight (FIG. 6B) of rGRF3, GRF2 and 35S:miR396 plants, all in long day conditions, with the vertical axis being in units of grams.

Transgenic *Arabidopsis* plants expressing rGRF3 had bigger leaves and rosettes than wild-type or transgenic plants expressing the miR396-regulated GRF3 sequence (FIGS. 3, 5, 13 and 17). They also accumulate more biomass, as judged by the fresh and dry weight of leaves and rosettes (FIG. 6). In general, it was observed that rGRF3 nearly doubled the size and weight of the first leaf with respect to wild-type plants (FIG. 3). The FFD domain of rGRF3 increased the activity of the protein (FIG. 54).

Figure 12:
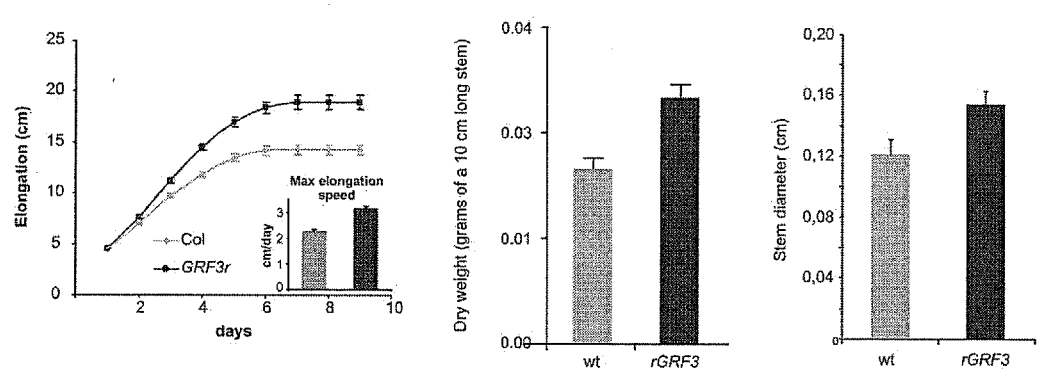
FIG. 12 shows that rGRF3 plants display higher rates of stem growth and stem biomass accumulation. Left: elongation of a 4.5 cm long stem segment in 10 days of wild type (wt) and rGRF3 plants.

Plants expressing rGRF3 also had a thicker stem with higher dry weight and growth speed than wild-type plants (FIG. 12). It was observed that the stem diameter increased 20% in rGRF3 plants with respect to wild type (FIG. 12).

Materials and Methods

The *Arabidopsis thaliana* Columbia (Col-0) accession was used as a wild type. All transgenics are in the Col-0 background. Plants were grown in long photoperiods (16 hr light/8 hr dark) or in short photoperiods (8 hr light/16 hr dark) at 23° C. See Table 1 for a list of binary plasmids generated and details on how transgenic plants were prepared. The miRNA target motif in AtGRF3 was altered introducing synonymous mutations in a cloned AtGRF3 wild type genomic fragment using the QuikChange® Site Directed Mutagenesis Kit (Stratagene).

All constructs were cloned in the binary vector pCHF3 (Jarvis et al., 1998). T-DNA constructs were introduced into *Agrobacterium tumefaciens* strain ASE and *Arabidopsis* transgenic plants were obtained by floral-dip.

Leaf area was measured by first taking a photograph of detached fully-expanded leaves, and then measuring the foliar area with the NIH software ImageJ.

To determine biomass accumulation, complete rosettes or individual leafs were weighed to measure fresh weight. Then, tissue was dried at 60° C. during 2 days and dry weight was measured. To determine stem growth, elongation was measured starting with 5 cm long stems during 10 days until full extension was reached. Maximum elongation speed was calculated from the elongation plot. Stem biomass accumulation was estimated by measuring the dry weight of 10 cm long fully elongated stem segments. Finally stem diameter was measured in the lower part of the stem, 0.5 cm above the rosette.

The FFD motif in AtGRF3 was altered introducing mutations in a cloned AtGRF3 cDNA using the QuikChange® Site Directed Mutagenesis Kit (Stratagene). The rGRF3 cDNA native sequence "TTC TTT GAC GAT TGG" (SEQ ID NO: 113) coding for FFDDW (amino acids 1-5 of SEQ ID NO: 127) was mutagenized to "GCT GCT GAC GAT GCT" (SEQ ID NO: 115) coding for AADDA (SEQ ID NO: 116), replacing all aromatic amino acids for alanines in the FFD motif. The wt (rGRF3 (FFD)) and mutagenized (rGRF3 (AAD)) genes were placed under the AtGRF3 promoter Conclusions Transgenic Arabidopsis plants transformed with the miR396-resistant version of GRF3 (named rGRF3) show a striking increase in leaf size and biomass accumulation in comparison to wild-type plants or transgenic plants expressing a GRF3 sequence with a miR396 binding site.

rGRF3 promotes growth of other tissues as well, such as the stems.

The FFD domain increases the activity of rGRF3.

Example #2

Overexpression of GIF1 Enhances the Effect of rGRF3

The GRF family of transcription factors comprises nine members in Arabidopsis (Kim et al., 2003). Seven of them have a target site for miR396 (Jones-Rhoades and Bartel, 2004). Mutations in different GRFs or overexpression of miR396 have been shown to reduce cell number in Arabidopsis leaves (Horiguchi et al., 2005; Kim and Kende, 2004; Rodriguez et al., 2010). The GRFs interact with GRF-INTERACTING FACTORs (GIFs), a small gene family composed by three members (GIF1, GIF2 and GIF3) encoding proteins with homology to the human SYT transcriptional co-activator (Kim and Kende, 2004). Inactivation of GIF1, also known as ANGUSTIFOLIA 3 (AN3), produces narrower leaves as a result of a reduction in cell proliferation in a similar way to GRF-deficient plants (Horiguchi et al., 2005).

Figure 1:
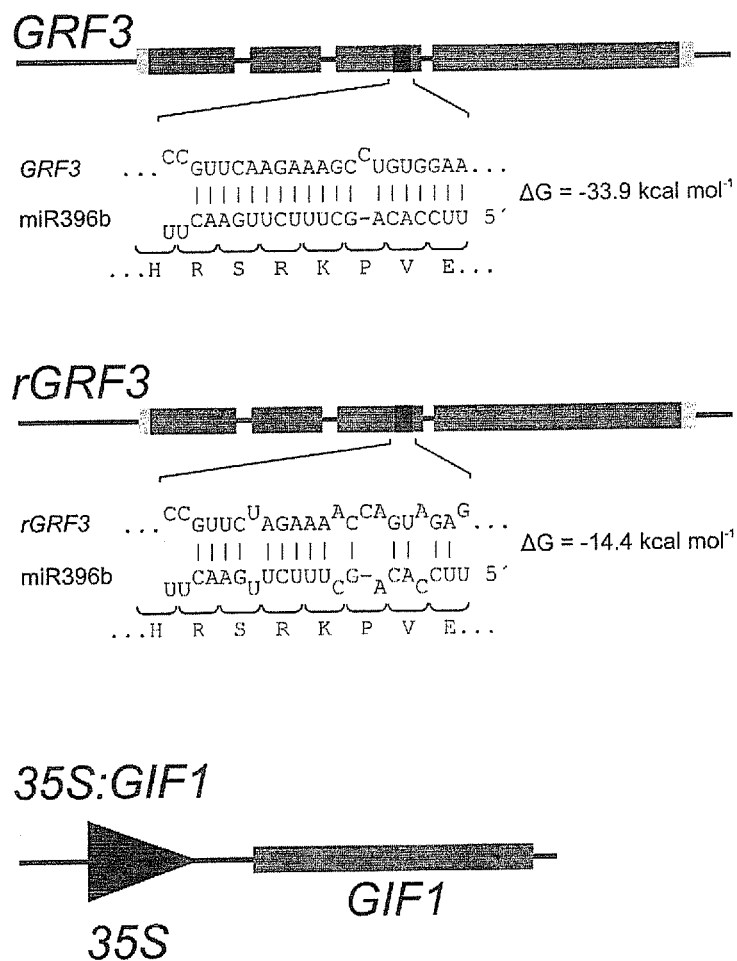
FIG. 1 shows nucleic acid constructs and sequences of relevance to this invention; top panel shows the sequence of GRF3 wild-type sequence in the region that is substantially complementary to miR396b, showing the binding affinity (L1G=−33.9 kcal/mole)(Upper nucleotide sequence SEQ ID NO: 118, lower nucleotide sequence SEQ ID NO: 125, and amino acid sequence SEQ ID NO: 120); middle panel shows the modified GRF3 sequence (rGRF3), which includes five base changes from the wild-type sequence {an A→U, a G→A, a U→A, a G→A and a A→G modification), all of which retain the native amino acid sequence, but which substantially destabilizes the interaction with the miR396b microRNA, (reducing the L1G to −14.4 kcal/mole)(Upper nucleotide sequence SEQ ID NO: 121, lower nucleotide sequence SEQ ID NO: 126 and amino acid sequence SEQ ID NO: 120); and the bottom panel shows a graphic of a 35S:G/F1 expression construct.
Figure 2:
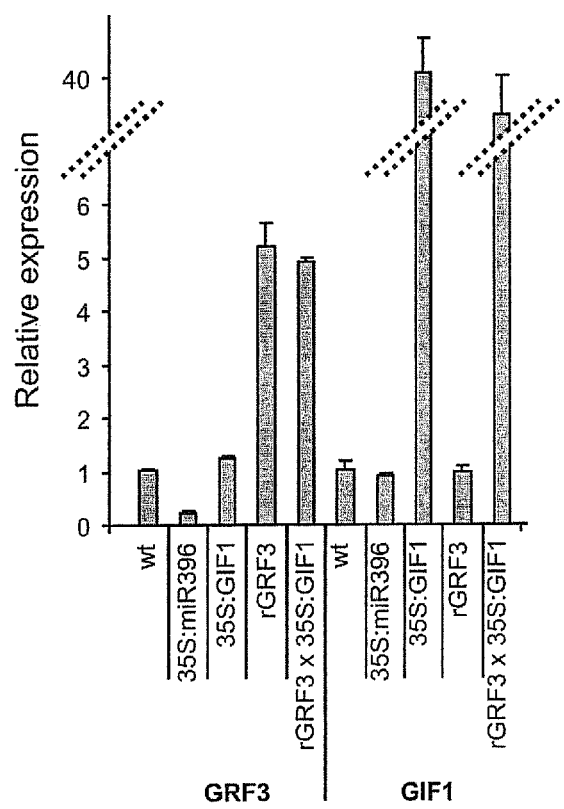
FIG. 2 shows the relative expression levels of GRF3 and GIF1 in transgenic Arabidopsis plants as estimated by RT-qPCR as well as in crosses between such transgenic plants, representing GRF3 levels in wild-type plants as having a relative value of 1, it can be seen that overexpression of miR396 (under the control of the 35S promoter), reduces the GRF3 expression, while the level of expression of GRF3 in rGRF3 transgenics is approximately five-fold the level of expression of GRF3 in wild type plants. This increase of GRF3 in transgenic plants expressing the mutant version is caused by the relief of the miRNA repression.

Transgenic plants overexpressing GIF1 (FIGS. 1 and 2) from the 35S viral promoter (named 35S:GIF1) were prepared. The full sequence and a map of the binary vector used (named JD16, see Table 1) can be found in FIGS. 39 and 41, respectively. These plants were similar to wild-type plants. Later, 35S:GIF1 was crossed to plants expressing rGRF3 (GRF3 insensitive to miR396, described in example #1). The resulting plants co-overexpressing rGRF3 and GIF1 (named rGRF3×35S:GIF1) were analyzed in more detail (FIGS. 1 and 2).

Figure 13:
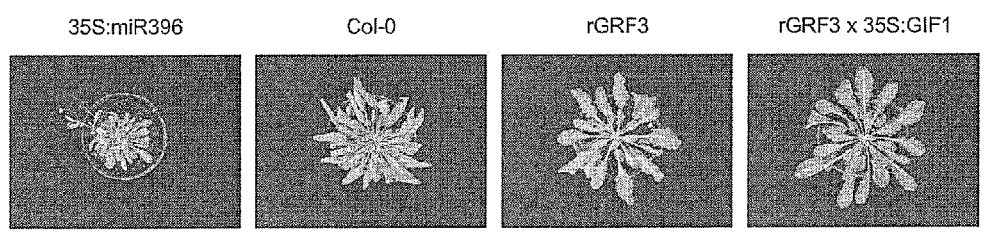
FIG. 13 shows—rosette phenotypes of short-day grown plants. Note increased leaf size and biomass accumulation with plants according to the present invention.

Upon analysing the biomass productivity of these plants it was found that rGRF3 in combination with GIF1 overexpression produce plants with larger leaves and accumulate more than double fresh and dry weight than wild-type plants (FIGS. 3 and 13). The performance of rGRF3×GIF was better than rGRF3 alone.

Materials and Methods

The Arabidopsis thaliana Columbia (Col-0) accession was used as a wild type. All transgenics are in the Col-0 background. Plants were grown in long photoperiods (16 hr light/8 hr dark) or in short photoperiods (8 hr light/16 hr dark) at 23° C. See Table 1 for a list of binary plasmids generated and details on how transgenic plants were prepared. The miRNA target motif in AtGRF3 was altered introducing synonymous mutations in a cloned AtGRF3 wild type genomic fragment using the QuikChange® Site Directed Mutagenesis Kit (Stratagene). All constructs were cloned in the binary vector pCHF3 (Jarvis et al., 1998). T-DNA constructs were introduced into Agrobacterium tumefaciens strain ASE and Arabidopsis transgenic plants were obtained by floral-dip.

For expression analysis by RT-PCR, RNA was prepared from apices of 20-day-old plants grown in short photoperiods, including developing leaves smaller than 3 mm. 0.5 to 1.0 μg of total RNA was treated with RQ1 RNase-free Dnase (Promega). Then, first-strand cDNA synthesis was carried out using SuperScript™ III Reverse Transcriptase (Invitrogen). PCR reactions were performed in a Mastercycler® ep realplex thermal cycler (Eppendorf) using SYBRGreen I (Roche) to monitor dsDNA synthesis. qPCR for each gene was done on at least 3 biological replicates with technical duplicates for each biological replicate. The relative transcript level was determined for each sample, normalized using PROTEIN PHOSPHATASE 2A cDNA level (Czechowski et al., 2005).

Leaf area and fresh and dry weight measurements were made as in Example#1.

Conclusions

The rGRF3 performance in plant productivity can be enhanced by co-overexpression of GIF1.

Example #3

Delayed Leaf Senescence and Increased Drought Resistance of rGRF3 Plants

Figure 4:
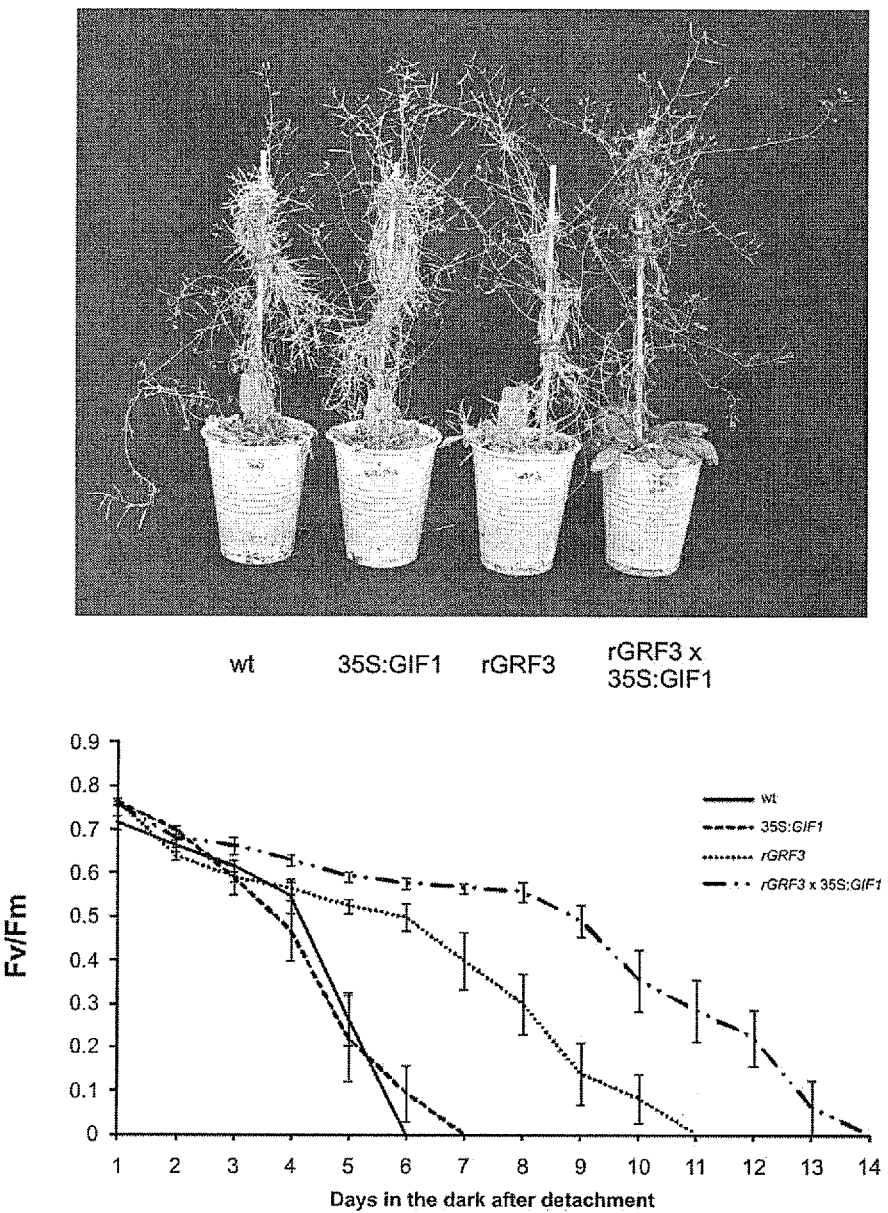
FIG. 4 shows, in the top panel, delayed leaf senescence of rGRF3×35S:GIF1 crossed plants; in the bottom panel, delayed leaf senescence of an individual leaf is shown for fully expanded leaf 5, which was detached and incubated in the dark (dark induced senescence). The progression of senescence was followed by measuring chlorophyll fluorescence (Fv/Fm).
Figure 5:
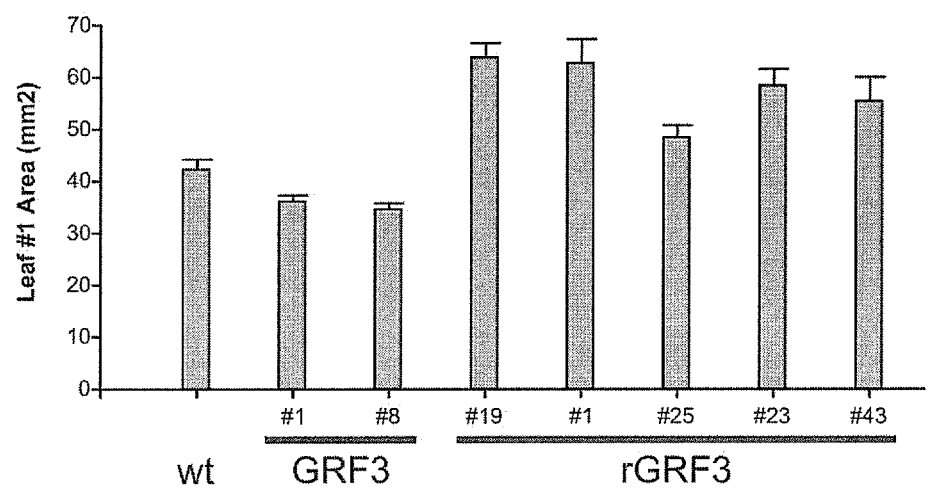
FIG. 5 shows leaf area of plants transformed with the wild-type version of GRF3 (GRF3) and/or with the miR396 resistant version of GRF3 (rGRF3).

As shown in Example #1, rGRF3 plants produces bigger leaves than wild-type plants, accumulating more biomass. This effect is enhanced by co-overexpression of rGRF3 and GIF1 (rGRF3×35S:GIF1) (see example #2 for further details). In addition, the inventors observed that rGRF3 and rGRF3/35S:GIF1 stay green for a longer period of time than wild-type plants (FIG. 4).

To test whether there this delay in leaf senescence in rGRF3 and rGRF3×35S: GIF1 transgenic plants, a dark-induced senescence experiment was performed. Incubation of detached leaves in the dark induces senescence and this process can be followed by measuring the decrease in the maximum efficiency of photosystem II (PSII) photochemistry (Fv/Fm) as described previously (Baker, 2008; Schommer et al., 2008). To do this, the fifth leaf of wild-type, rGRF3, 35S:GIF1 and rGRF3×35S:GIF1 were collected and kept in the dark, and Fv/Fm was measured every day. As detailed in FIG. 4, there is no difference between wild-type and 35S:GIF1 plants. However, senescence in rGRF3 leaves starts 2 days after the wild-type leaves. Interestingly, leaves that co-overexpress high levels of both rGRF3 and GIF1 showed an even larger delay in Fv/Fm decay, indicating that overexpression of GIF1 enhances even further the senescence delay of rGRF3 plants.

Figure 14:
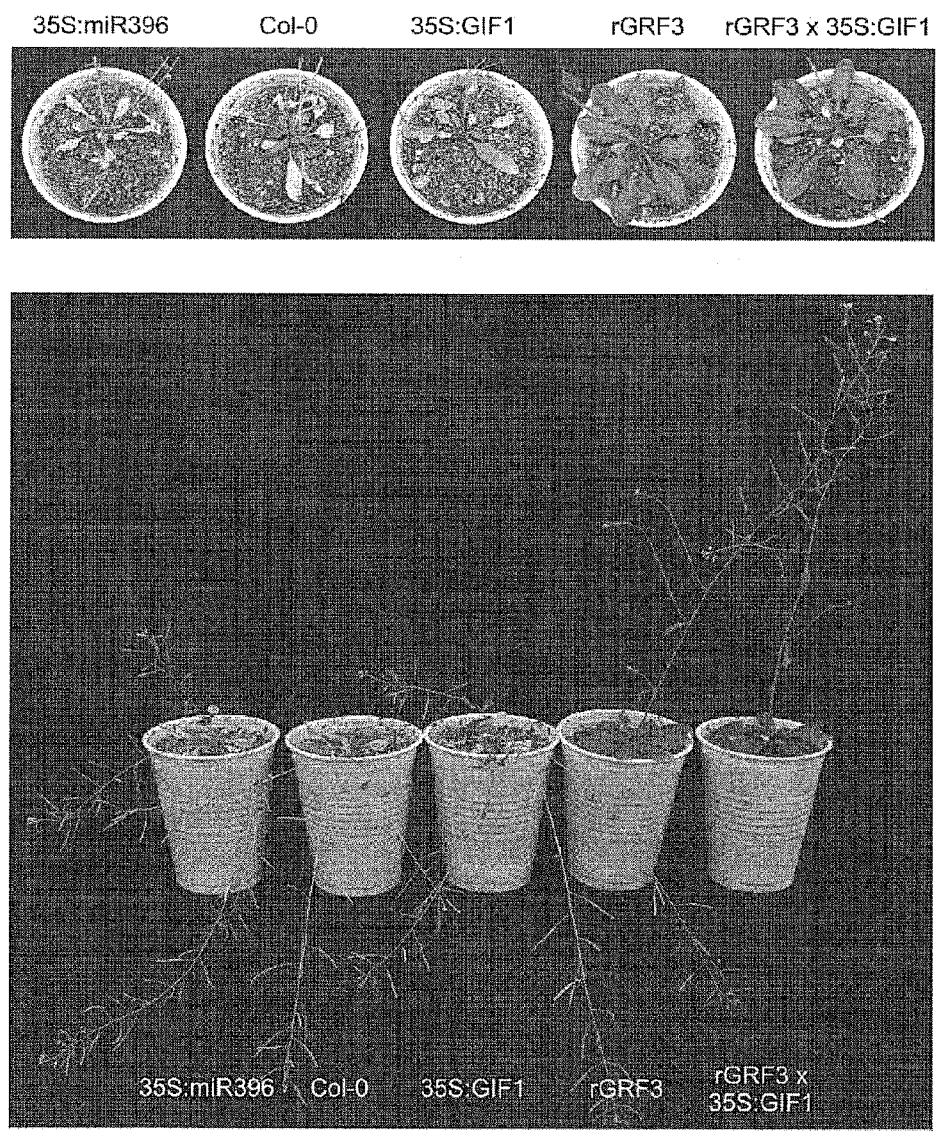
FIG. 14 shows drought effects in the different transgenic plants.

Furthermore, the performance of the transgenic under water deprivation (FIG. 14) was assayed. 25 days-old plant of 35S:miR396, wild-type, rGRF3, 35S:GIF1 and rGRF3× 35S:GIF1 were deprived of water for 2 weeks. Then, the plants were irrigated once a week. MiR396 over-expressers, wild-type and 35S:GIF1 were severely affected in their growth by the end of the water deprivation and subsequently to it (FIG. 14). In contrast, both rGRF3 and rGRF3×35S: GIF1 lines recovered and developed well following the water deprivation (FIG. 14).

Materials and Methods

To study leaf senescence, fifth-fully expanded leaves were detached and stored in darkness. Dark-induced senescence was followed by measuring Maximal Photochemical Efficiency (Fv/Fm) of Photosystem II, as described (Baker, 2008). In the water deprivation assays, plants were grown in long photoperiods (16 hour light/8 hour dark) at 23° C. When the plants were 25 day-old, they were deprived of water for two weeks. After that, the plants were irrigated once a week. Pictures were taken when the plants were 50 day-old.

Conclusions rGRF3 plants have a delay in leaf senescence. This effect is further enhanced by the co-overexpression of GIF1. rGRF3 plants are more tolerant to water deprivation.

Example #4

Expression from Tissue Specific Promoters Improves rGRF3 Performance in Plant Productivity The GRF family of transcription factors comprises nine members in *Arabidopsis* (Kim et al., 2003). Seven of them, including GRF3, have a target site for miR396 (Jones-Rhoades and Bartel, 2004). MiR396 is expressed at low levels in the meristem and leaf primordia, and then it steadily accumulates with the development of the leaf, in concert with the retreat of cell proliferation (Rodriguez et al., 2010). It is shown in Examples #1 and #2 that the abolishment of miR396-repression of GRF3 in *Arabidopsis* generates plants with a significant increase in biomass accumulation and a delay in senescence.

To study if it is possible to improve further performance of rGRF3 this miR396 resistant version of GRF3 was expressed from tissue specific promoters. The promoters of AS1 (ASYMMETRIC LEAVES 1) and ANT (AINTEGUMENTA), which are known to be specifically expressed in the proliferative stages of leaf development, were selected (FIG. 50).

Transgenic *Arabidopsis* plants transformed with the vectors AS1:rGRF3 and ANT:rGRF3 had bigger leaves than wild-type plants and even than plants expressing the rGRF3 from the native GRF3 promoter (FIGS. 18 and 51). These plants also had thicker stems (FIG. 19).

Interestingly, the expression of rGRF3 from ANT and AS1 promoters had only a minor effect on leaf senescence, and less than that observed in rGRF3 plants expressing plants from the endogenous promoter (FIGS. 20 and 54).

Expression of rGRF3 from the ANT and AS1 promoters shows similar apical dominance (FIG. 52) to wild-type plants.

Materials and Methods

The *Arabidopsis thaliana* Columbia (Col-0) accession was used as a wild type. All transgenics are in the Col-0 background. Plants were grown in long photoperiods (16 hr light/8 hr dark) or in short photoperiods (8 hr light/16 hr dark) at 23° C. See Table 1 for a list of binary plasmids generated and details on how transgenics plants were prepared. The miRNA target motif in AtGRF3 was altered introducing synonymous mutations in a cloned AtGRF3 wild type genomic fragment using the QuikChange® Site Directed Mutagenesis Kit (Stratagene).

Leaf area was measured by first taking a photograph of detached fully expanded leaves, and then measuring the foliar area with the NIH software ImageJ. Finally stem diameter was measured in the lower part of the stem, 0.5 cm above the rosette.

Senescence phenotype was analyzed by dark-induced senescence experiments on fully expanded leaves #5. Pictures were taken just after the full expanded leaves were detached from the rosette (Day 1) and after they were incubated 6 days in darkness (Day 6). Chlorophyll degradation is an indicator of senescence (Schommer et al., 2008).

Conclusions

Expression of rGRF3 form tissue specific promoters can improve its performance in plant productivity.

Expression of rGRF3 from tissue specific promoters can uncouple the different functions of GRF3, such as the control of leaf size and senescence.

Example #5 rGRF3 Outperforms rGRF2 in Increasing Plant Size and Biomass Accumulation

As was previously showed, high levels of miR396 reduce considerably leaf (Rodriguez et al., 2010). On the other hand, plants expressing a miR396 resistant version of GRF2 (rGRF2) accumulate high levels of GRF2 that cause a slight decrease of leaf size (Rodriguez et al., 2010). It has been shown in Examples #1 and #2 that rGRF3 plants also accumulate more biomass than wild-type plants. This example shows that rGRF3 significantly outperforms rGRF2 in increasing plant size and biomass accumulation.

To compare biomass accumulation in rGRF2 and rGRF3 lines, we measured fresh and dry weight of 40 day-old rosettes of 35S:miR396, wild-type, rGRF2 and rGRF3 plants (FIG. 6). Plants with high levels of miR396 had a reduction of plant biomass of 25%. rGRF2 plants have only a minor increase in biomass accumulation that was not statistically significant (FIG. 6). rGRF3 rossettes accumulated nearly 40% more biomass compared to wild-type plants, which is statistically significant (FIG. 6).

Figure 10:
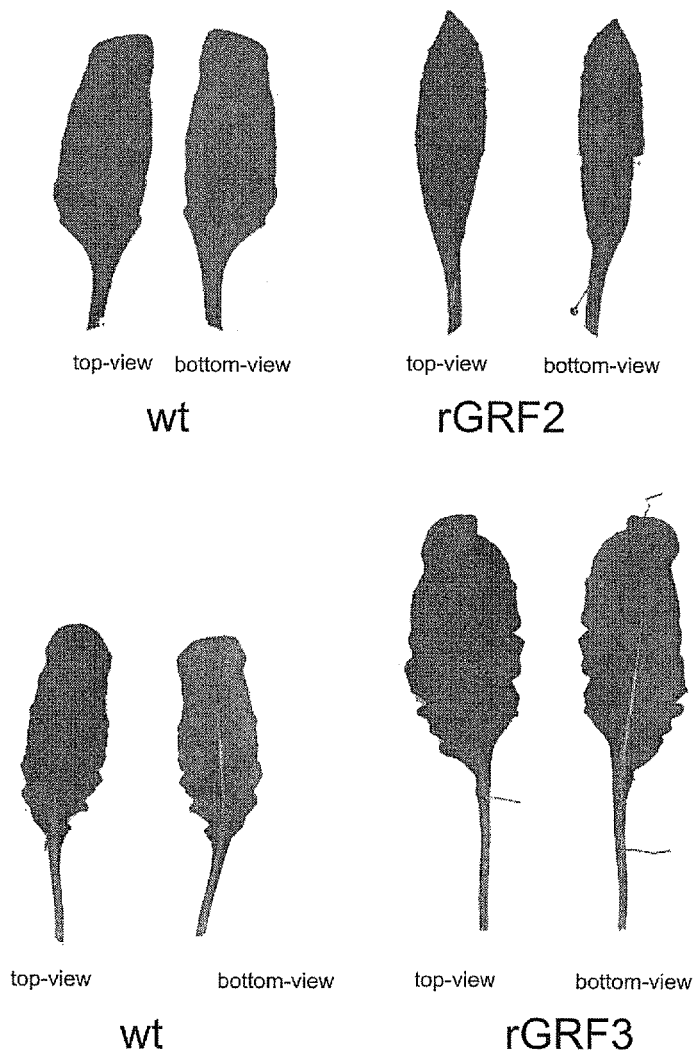
FIG. 10 shows the detrimental leaf-shape changes (downward "rolling") which are found with rGRF2, but not in rGRF3.

Another remarkable difference between rGRF2 and rGRF3 plants was observed when comparing leaf morphology. Leaves of rGRF2 plants have downward "rolling" shape, while leaves of rGRF3 plants are bigger than wild-type leaves with no major change in leaf morphology (FIG. 10). In this way, rGRF3 produced plants with bigger leaves without affecting leaf morphology.

Figure 11:
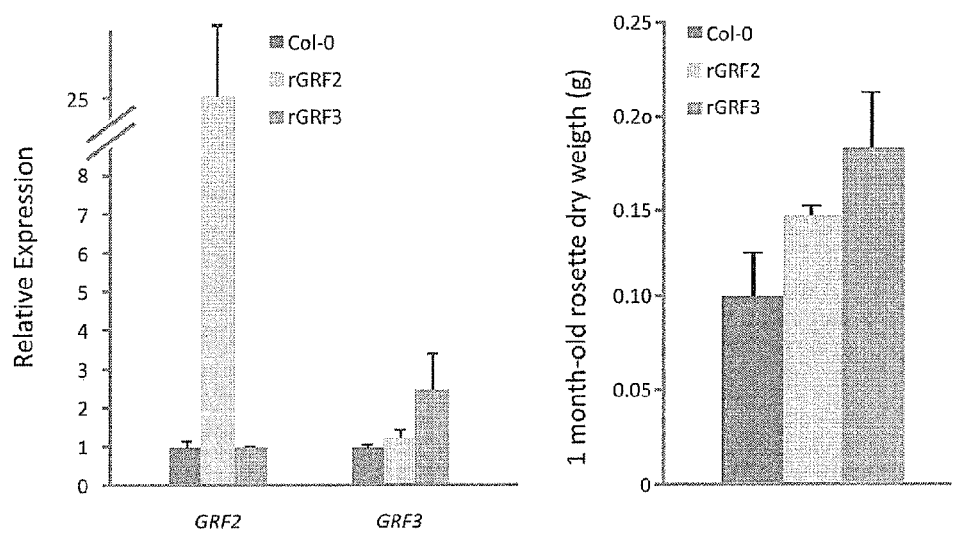
FIG. 11 shows that a mild increase in GRF3 (3×) causes a higher increase in productivity, e.g. biomass compared with a large accumulation of GRF2 (25×).

To analyze the correlation between biomass accumulation and GRF levels in rGRF2 and rGRF3 plants, one independent line of each rGRF transgenic line was selected. Then, GRF2 and GRF3 mRNA levels were measured by RT-PCR and the dry weight of 1 month-old rosettes of rGRF2 and rGRF3 plants. It was observed that a 25-fold increase in GRF2 mRNA levels in rGRF2 plants produced a biomass increase of only 30% (FIG. 11). On the contrary, only a 2.5 fold increase in GRF3 mRNA levels in rGRF3 plants resulted in almost twice as much biomass accumulation compared with wild type Col-0 (FIG. 11).

As a further comparison the effect of rGRF2 or rGRF3 expression with wild-type (FIG. 55) was compared. Leaf area in rGRF3 expressing plants was almost double that of wild-type and increased compared to rGRF2 (FIG. 55). When rGRF2 was placed under the control of the GRF3 promoter the increase in leaf area was not as significant as in rGRF3-expressing plants, showing that the differential activity of rGRF3 and rGRF2 is caused by their different primary sequences and not promoter strength and/or expression levels (FIG. 55).

Materials and Methods

The *Arabidopsis thaliana* Columbia (Col-0) accession was used as a wild-type. All transgenics are in the Col-0 background. Plants were grown in long photoperiods (16 hr light/8 hr dark) or in short photoperiods (8 hr light/16 hr dark) at 23° C. See Table 1 for a list of binary plasmids generated and details on how transgenics plants were prepared. The miRNA target motif in AtGRF3 or AtGRF2 was altered introducing synonymous mutations in a cloned AtGRF3 wild type genomic fragment using the QuikChange® Site Directed Mutagenesis Kit (Stratagene).

All constructs were cloned in the binary vector pCHF3 (Jarvis et al., 1998). T-DNA constructs were introduced into *Agrobacterium tumefaciens* strain ASE and *Arabidopsis* transgenics plants were obtained by floral-dip.

To determine biomass accumulation, complete rosettes were weighed to measure fresh weight. Then, tissue was dried at 60° C. during 2 days and dry weight was measured.

For expression analysis by RT-PCR, RNA was prepared from apices of 20-day-old plants grown in short photoperiods, including developing leaves smaller than 3 mm. 0.5 to 1.0 μg of total RNA was treated with RQ1 RNase-free Dnase (Promega).

Then, first-strand cDNA synthesis was carried out using SuperScript™ III Reverse Transcriptase (Invitrogen). PCR reactions were performed in a Mastercycler® ep realplex thermal cycler (Eppendorf) using SYBRGreen I (Roche) to monitor dsDNA synthesis. qPCR for each gene was done on at least 3 biological replicates with technical duplicates for each biological replicate. The relative transcript level was determined for each sample, normalized using PROTEIN PHOSPHATASE 2A cDNA level (Czechowski et al., 2005).

Conclusions
- High levels of rGRF2 are required to slightly increase plant biomass (e.g., 25 times more GRF2 caused 30% biomass increase).
- Moderate increases of GRF3 expression in rGRF3 plants caused a high increase in biomass accumulation (e.g., 2.5 times more GRF3 caused 85% biomass increase).
- High levels of rGRF2 affect leaf development.
- Expression of rGRF3 in plants leads to approximately 2 times increase in leaf area compared to wild-type
- Increased leaf area in rGRF3 compared to rGRF2 is dependent on the primary sequence of the genes and not a result of promoter strength Example #6

*Arabidopsis* GRF3 and GIF1 Homologues are Found in Crop Plants: GRF Family in *Arabidopsis thaliana* and Other Plant Species The GROWTH-REGULATING FACTOR (GRF) family of transcription factors is a plant specific family of proteins defined by the presence of two highly conserved protein motifs, the QLQ and WRC (Kim et al., 2003). The QLQ domain is involved in protein-protein interactions with GRF-INTERACTING FACTORS proteins, and the WRC domain contains a functional nuclear localization signal and a DNA-binding motif consisting of three conserved cysteines and one histidine (Kim and Kende, 2004). The GRF family of transcription factors comprises nine members in *Arabidopsis* (Kim et al., 2003) (FIGS. 21 and 22), 12 in *Oryza sativa* (Choi et al., 2004) (FIGS. 23 and 24) and 14 in *Zea mays* (Zhang et al., 2008) (FIGS. 25 and 26). Besides, GRFs can be found in many other plant species (Zhang et al., 2011) (See selected examples from *Glycine max, Medicago truncatula, Prunus persica, Carica papaya* and *Populus trichocarpa* in FIGS. 27 to 34).

At least two other conserved regions can be found in GRF coding sequences. First, at the nucleotide level, only a subgroup of the GRFs from each species contains a miR396-target site. For example, only 7 of the nine GRFs found in *Arabidopsis* are miR396 targets (FIGS. 7 and 8) (Jones-Rhoades and Bartel, 2004).

Figure 8:
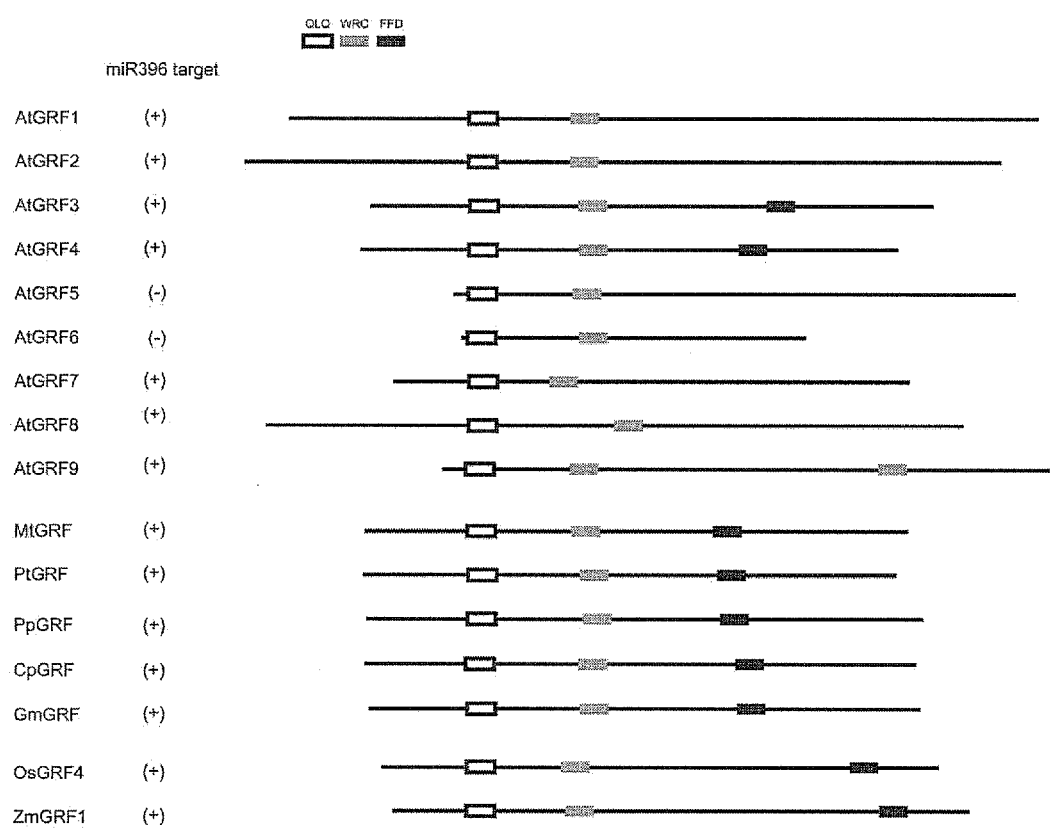
FIG. 8 shows the distribution of QLQ, WRC and FDD protein motifs in GRFs from Arabidopsis thaliana (AtGRF#), Oryza sativa (OsGRF#), Zea mays (ZmORF#), Glycine max (GmGRF), Populus trichocarpa (PtGRF), Prunus persica (PpGRF), Medicago truncatula (MtGRF), and Carica papaya (CpGRF)

Second, only a subgroup of the GRFs of each species contains the FFD conserved motif (FIG. 8). For example, in *Arabidopsis* only GRF3 and GRF4 have the FFD motif. Furthermore, GRFs containing the miR396-targeting motif and the FFD motif, and with high homology to *Arabidopsis* GRF3 can be found in rice, maize and many other plant species (FIGS. 7, 8, 22, 24, 26 31-34, 38).

GRFs Expression Patterns in *Arabidopsis thaliana* and *Zea mays*

Figure 15:
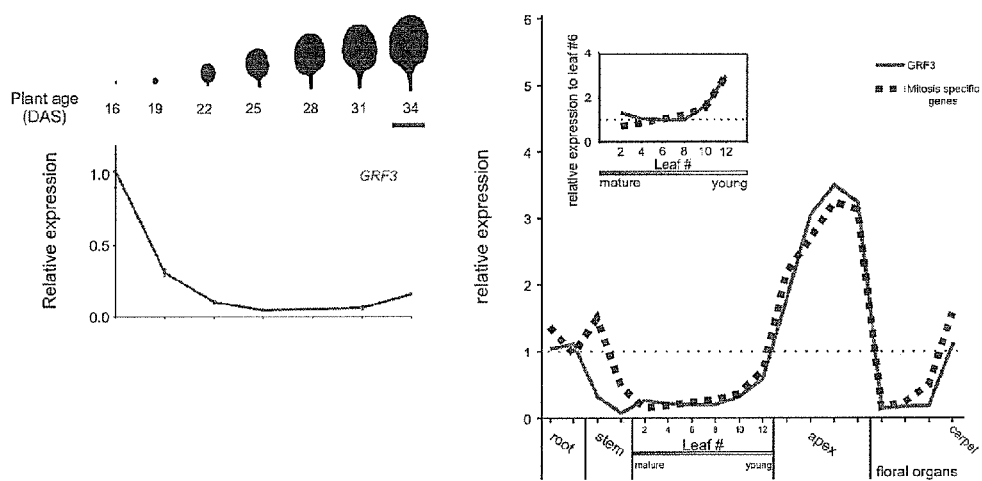
FIG. 15 shows Arabidopsis GRFs are expressed in proliferative tissues. Left panel: GRF3 expression pattern during leaf development (DAS=days after sowing). Right panel: GRF3 is coexpressed with mitosis-specific genes during Arabidopsis development.

GRF3 expression pattern was analyzed by RT-qPCR in developing leaves (FIG. 15, left). The fifth rosette leaf was collected at three-day intervals, starting from the day that it first became visible (~1 mm) to the naked eye, which was 16 days after sowing (DAS). Next, the level of GRF3 was determined by RT-qPCR. It was observed that this transcription factor was expressed during the early stages of leaf development (FIG. 15, left). An expression atlas of *Arabidopsis* development (Schmid et al., 2005) indicates that mitosis specific genes are expressed in proliferating tissues (FIG. 15, right). Consistent with a role of the GRFs as positive regulators of cell proliferation during organ growth, their expression profile is very similar to that of the mitosis specific genes (shown for GRF3 in FIG. 15, right).

To confirm the functional equivalency between *Arabidopsis* and *Zea mays* GRFs their expression patterns during maize leaf development were analysed using the Maize eFP browser (Li et al., 2010; Winter et al., 2007). As detailed in FIG. 16, maize GRFs, in the same way as *Arabidopsis* GRFs, are coexpressed with mitosis specific genes.

GRF-INTERACTING FACTORS in *Arabidopsis* and Crop Plants

As described in example #2, rGRF3 performance in plant productivity can be greatly enhanced by cooverexpression of GRF-INTERACTING FACTOR 1. This gene belongs to a small gene family composed by three members (GIF1, GIF2 and GIF3) in *Arabidopsis*. Also, GIF1 homologs are readily found in other plant species, such as rice (FIG. 9). The three GIFs in *Arabidopsis* are highly redundant, as mutants in GIF1 can be complemented by the overexpression of GIF2 or GIF3 (FIG. 43) (Lee et al., 2009). These results suggest that the enhancement of the rGRF3 phenotype by overexpression of GIF1 is also achieved by co-overexpression of GIF2 and GIF3.

Materials and Methods

RNA was prepared from apices of 20-day-old plants grown in short photoperiods, including developing leaves smaller than 3 mm. 0.5 to 1.0 μg of total RNA was treated with RQ1 RNase-free Dnase (Promega). Then, first-strand cDNA synthesis was carried out using SuperScript™ III Reverse Transcriptase (Invitrogen). PCR reactions were performed in a Mastercycler® ep realplex thermal cycler (Eppendorf) using SYBRGreen I (Roche) to monitor dsDNA synthesis. qPCR for each gene was done on at least 3 biological replicates with technical duplicates for each biological replicate. The relative transcript level was determined for each sample, normalized using PROTEIN PHOSPHATASE 2A cDNA level. Primer sequences are given in Table 2.

GRFs sequences from *Arabidopsis thaliana, Oryza sativa* and *Zea maize* were obtained from Genebank using the accession numbers provided in the literature (Choi et al., 2004; Kim et al., 2003; Zhang et al., 2008). Pairwise sequence alignments and calculations of percentage of identity and similarity were performed with NEEDLE using the Needleman-Wunche alignment algorithm (Rice et al., 2000). Multiple sequence alignments of protein sequences were performed using MCOFFE (Moretti et al., 2007). The PHYLIP package version 3.67 (Felsenstein, 1989) was used to perform 100 bootstrap replicas of a neighbor joining (NJ) tree based on a JTT distance matrix. Trees were visualized using TreeView 1.6.6. (Page, 1996).

Conclusions
- GRFs in general and homologs (orthologues) of GRF3 in particular exist in many plant species.
- GIFs also exist in many plant species.
- According to its function as a positive regulator of cell proliferation, GRF3 is co-expressed with mitosis genes during leaf development in *Arabidopsis*. As expected for functional equivalent genes, *Zea mays* GRFs expression also co-expressed with mitosis genes during leaf development.
- The enhancement of the rGRF3 phenotype by overexpression of GIF1 might also be achieved by homologs (orthologues) from *Arabidopsis* and crop plants.

Example #7

Introduction of rGRF3 and rGRF3+GIF into *Brassica oleracea*

Materials and Methods
Plant Material

A genetically uniform doubled haploid *Brassica oleracea* genotype, DH 1012 (Sparrow et al., 2004) was used in this study. This genotype is derived from a cross between a rapid cycling *B. oleracea* alboglabra (A12) and a *B. oleracea* Italica Green Duke (GD33).

Bacterial Strains

Transformations were carried out using the *Agrobacterium tumefaciens* strain AGL1 harbouring the appropriate plasmids pBRACT114 rGRF3 and pBRACT114 rGRF3:GIF1 and (see FIG. 44) containing the neomycin phosphotransferase (nptII) selectable marker gene driven by the 35S promoter and the gene(s) of interest (namely rGRF3 driven by its own promoter; or the combined construct which contained both rGRF3 driven by its own promoter, and additionally GIF driven by the 35S promoter, respectively).

The cloning procedure used to make the transformation vector pBRACT114-rGRF3 GIF1 is described below. pBRACT114-rGRF3 GIF1 contains both the rGRF3 gene driven by its native promoter and the coding region of GIF1 over-expressed by the CaMV 35S promoter.

Digestion of ~1.7 µg of pGRF3:GRF3r DNA in a 20 µl total volume reaction with PvuII (Invitrogen) in the appropriate buffer was performed at 37° C. for 1 hour in a water bath. A 4950 bp fragment containing the rGRF3 native promoter, coding region, 3'UTR and terminator was isolated by gel extraction.

The *Brassica* transformation vector pBRACT114 (www.bract.org) is based on pGreen (Hellens et al., 2000) and is Gateway™ (Invitrogen) compatible. Approximately 1 µg of pBract114 was digested with restriction enzyme StuI (Roche) in the appropriate buffer for 1 hour at 37° C. The linearised vector was dephosphorylated by incubation at 37° C. for a further hour with shrimp alkaline phosphatase (SAP). The SAP was denatured by heating to 65° C. for 15 minutes.

An overnight ligation reaction was performed at 14° C. and contained the rGRF3 fragment and the linear pBRACT114 at a 3:1 ratio respectively. Five units of T4 ligase (Invitrogen) were used in the 10 µl blunt end ligation. To 50 µl of ccdB competent *E. coli* cells (Invitrogen) 2 µl of the ligation reaction was added and transformation by heat shock. The cells were grown in 250 µl of SOC medium for 1 hour at 37° C. and shaken at 200 rpm. 20 µl and 100 µl of the culture was spread onto plates of solid LB medium (Sambrook and Russel, 2001) containing appropriate selection and incubated overnight at 37° C.

*E. coli* colonies were screened by direct colony PCR to ensure that they contained pBRACT114 with the insert in the desired orientation. Twelve PCR positive single colonies were transferred to 10 ml of liquid LB media containing the appropriate selection and incubated at 37° C. shaken 220 rpm overnight. Plasmid DNA was isolated using a mini-prep kit (Qiagen). The integrity of the construct known as pBRACT114-rGRF3 was confirmed by enzyme digestion and sequencing of the insertion sites.

Phase two of the cloning process to create pBRACT-rGRF3 GIF1 used the Gateway™ (Invitrogen) system to recombine the coding region of GIF1 downstream of the CaMV 35S promoter. The coding region of GIF1 was amplified by PCR using high fidelity Platinum™ polymerase (Invitrogen) and Topo T/A cloned into the Gateway™ entry vector pCR8/GW/Topo® TA (Invitrogen). To 50 µl of chemically competent *E. coli* DH5-α cells (Invitrogen) 2 µl of the Topo reaction was added and transformation by heat shock. The cells were grown in 250 µl of SOC medium for 1 hour at 37° C. and shaken at 200 rpm. 20 µl and 100 µl of the culture was spread onto plates of solid LB medium (Sambrook and Russel, 2001) containing appropriate selection and incubated overnight at 37° C.

*E. coli* colonies were screened by direct colony PCR to ensure that they contained pCR8 with the GIF1 amplicon in the desired orientation. Six PCR positive single colonies were transferred to 10 ml of liquid LB medium containing the appropriate selection and incubated at 37° C. shaken 220 rpm overnight. Plasmid DNA was isolated using a plasmid mini-prep kit (Qiagen). The entry vector pCR8-GIF1 was checked by enzyme digestion. Sequencing of the entire GIF1 coding region was performed to ensure its integrity.

A Gateway™ LR recombination reaction was performed to insert the GIF1 coding region into pBRACT114-rGRF3 between the gateway sites downstream of the CaMV 35S promoter. The 10 µl LR reaction contained ~100 ng of pBRACT114-rGRF3+35 ng of pCR8-GIF1 with 2 µl Gateway® LR Clonase™ II enzyme Mix™ (Invitrogen) in TE buffer. The LR reaction was incubated at room temperature overnight. A proteinase K treatment was performed a 37° C. for 10 minutes. To 50 µl of chemically competent *E. coli* DH5-α cells (Invitrogen) 1 µl of the LR reaction was added and transformation by heat shock. The cells were grown in 250 µl of SOC medium for 1 hour at 37° C. and shaken at 200 rpm. 20 µl and 100 µl of the culture was spread onto plates of solid LB medium (Sambrook and Russel, 2001) containing appropriate selection and incubated overnight at 37° C.

Twelve single colonies were transferred to 10 ml of liquid LB media containing the appropriate selection and incubated at 37° C. shaken 220 rpm overnight. Plasmid DNA was isolated using a mini-prep kit (Qiagen). The integrity of the construct known as pBRACT114-rGRF3 GIF1 was confirmed by enzyme digestion and sequencing of the GIF1 insertion sites.

The plasmid pBRACT-rGRF3 GIF1 along with its helper plasmid pSoup (Hellens et al., 2000) was transformed into *Agrobacterium tumefaciens* strain AGL1 by electroporation. The plasmid pGRF3:rGRF3 was also transformed by electroporation into *A. tumefaciens*. Briefly, 100 ng of plasmid DNA was added to 40 μl of electro-competent *A. tumefaciens* cells in a pre-chilled electroporation cuvette with 2 mm electrode separation. The cells were electroporated in a GenePulser (Biorad) with the following settings 2.50 kV, 25 uFD and 400 Ohms. Immediately 300 μl of liquid LB medium was added to recover the cells, these were grown at room temperature, shaken at 180 rpm for 6 hours. The *A. tumefaciens* cultures were spread onto solid LB medium (Sambrook and Russel, 2001) containing appropriate selection and incubated at 28° C. for 48 hours. Single colonies were selected and used to inoculate 10 ml of liquid LB media containing the appropriate antibiotics and incubated at 28° C., shaken at 200 rpm for 48 hours. Glycerol stocks and standard inoculums were prepared and stored at −80° C. The plasmids were checked once again, by enzyme digestion, prior to embarking on the *Brassica* transformation experiments.

The *A. tumefaciens* was streaked onto solid LB medium (Sambrook and Russel, 2001) containing appropriate selection (and incubated at 28° C. for 48 hours. A single colony was transferred to 10 ml of liquid LB media containing the appropriate selection and transferred to a 28° C. shaker for 48 hours. A 50 μl aliquot of the resulting bacterial suspension was transferred to 10 ml of MGL liquid medium with selection and grown over night in a 28° C. shaker. Overnight cultures were spun down at 3,000 rpm for 5 minutes at R.T. before being re suspended in liquid MS medium. Suspensions of $O.D_{650}=0.3$ were used for inoculations (dilutions made using liquid MS medium).

Plant Transformation

Seeds were surface sterilised in 100% ethanol for 2 minutes, 15% sodium hypochlorite plus 0.1% Tween-20 for 15 minutes and rinsed three times for 10 minutes in sterile distilled water. Seeds were germinated on full strength MS (Murashige and Skoog, 1962) plant salt base, containing 3% sucrose and 0.8% phytagar (Difco) at pH 5.6. Prior to pouring, filter-sterilised vitamins were added to the medium; myo-Inositol (100 mg/l), Thiamine-HCL (10 mg/l), Pyridoxine (1 mg/l) and Nicotinic acid (1 mg/l). Seeds were sown at a density of 15 seed per 90 mm petri dish and transferred to a 10° C. cold room overnight before being transferred to a 23° C. culture room under 16 hour day length with 70 μmol $m^{-2}$ $sec^{-1}$ illumination.

Based on the transformation protocol developed for *Brassica napus* (Moloney et al. 1989), and further developed by BRACT (www.bract.org), cotyledonary petioles excised from 4-day-old seedlings were dipped into an overnight suspension of *Agrobacterium*. Explants were maintained, 10 explants per plate, on co-cultivation medium (germination medium supplemented with 2 mg/l 6-benzylaminopurine); with the petioles embedded and ensuring the cotyledonary lamella were clear of the medium. Cultures were maintained in growth rooms at 23° C. with 16 hour day length, under scattered light of 40 μmol $m^{-2}$ $sec^{-1}$ for 72 hours. After 72 hours explants were transferred to selection medium (co-cultivation medium supplemented with 160 mg/l timentin (or appropriate *Agrobacterium* eliminating antibiotic) and 15 mg/l kanamycin as the selection agent. Controls were established on kanamycin-free medium, as explants that had, and had not, been inoculated with *Agrobacterium*.

Shoot Isolation and Plant Regeneration

Regenerating green shoots were excised and transferred to Gamborgs B5 medium (Gamborg et al. 1968), containing 1% sucrose, 0.8% Phytagar, 160 mg/l timentin and 50 mg/l kanamycin. Where dense multiple shoots were isolated, further sub-culturing was made after shoot elongation to ensure a main stem was isolated thus reducing the likelihood of escapes and the frequency of multi-stemmed plants when transferred to the glasshouse. Shoots were maintained on Gamborgs B5 medium until roots developed. Plantlets were then transferred to sterile peat pots (Jiffy No. 7) to allow further root development, before being transferred to the glasshouse.

Plant Maintenance and Seed Production

Transgenic plants were maintained in a containment lit glasshouse (of 16-hour photoperiod, +18/12° C. day/night) and self-pollinated, to generate the $T_1$ seed. Plants were covered with clear, perforated 'bread-bags' (Cryovac (UK) Ltd) as soon as they came into flower to prevent cross-pollination. The background genotype DH1012 is a self-compatible genotype and daily shaking of the 'bread-bag' was carried out to facilitate pollination. Pods were allowed to develop on the plant until fully swollen and were harvested when pods had dried and turned brown. Harvested pods were threshed when dry, and seed stored in the John Innes Centre seed store (+1.5° C., 7-10 relative humidity).

Molecular Analysis

Leaf tissue from putative transgenic shoots (in vitro) was used for initial DNA extractions to PCR test for presence of the transgenes.

Copy Number Analysis by Multiplexed Real Time PCR

The copy number of the transgene was measured using multiplexed real time PCR (TaqMan) assays, carried out by 'iDNA genetics' (www.idnagenetics.com). The nptII target gene was detected using a Fam labelled, Tamra quenched probe, and simultaneously an internal positive control gene was detected using a Vic labelled, Tamra quenched probe. The reactions were carried out using 5-20 ng of genomic DNA from each sample, in a 20 μl reaction volume, with each sample assayed twice. The cycle threshold (Cts) for the Fam and Vic signals were found for each tube, and the average DeltaCt (CtFam−CtVIC) calculated for each sample. The samples were ranked by DeltaCt (where high delta Ct relates to samples with low numbers of copies, and low DeltaCt to high numbers of copies). Plant samples were classified with respect to reference samples (of known copy number).

Preliminary investigations show that enhanced growth and improved plant productivity is obtained in *Brassica* plants comprising the AtrGRF3 or AtrGRF3:GIF1

FIG. 49 shows data comparing *Brassica oleracea* plants transformed with *Arabidopsis* rGRF3 and control plants (without the At rGRF3). Transforming *Brassica oleracea* plants with At rGRF3 significantly improved growth and productivity of the plants. For example, at flowering the stem width 10 cm above soil level and the maximum stem width at flowering were both significantly greater in *Brassica oleracea* plants transformed with At rGRF3 compared with control plants. These results were significant using either the t-test ($p<0.01$) or regression analysis ($p=0.008$).

FIG. 56 shows data for *Brassica oleracea* plants transformed with *Arabidopsis* rGRF3 (rGRF3) and a control of regeneration (TC). The widest stem width at flowering is increased in rGRF3 when compared to the control (FIG. 56). The figure also shows that the 10 cm stem weight is increased in rGRF3 when compared to the control (FIG. 56).

Root growth of transgenic *Brassica oleracea* plants expressing *Arabidopsis* rGRF3 was measured. To do this, wild-type and transgenic plants were grown in vertical MS plates. Root length was measured in at least 10 plants for each genotype from 4 to 7 days after sowing (FIG. 57, left). From the slope of these lines, the root growth rate was estimated (FIG. 57, right).

Conclusions

Transgenic *Brassica oleracea* plants expressing *Arabidopsis* rGRF3 and rGRF3:GIF1 show enhanced growth and improved plant productivity.

Transgenic *Brassica oleracea* plants transformed with the miR396-resistant version of GRF3 (named rGRF3) show a striking increase in root growth.

Example #8

Expression in *Arabidopsis* of GRF3 Orthologues from Soybean and Rice Also Increases Plant Biomass In Example #6, GRFs from other species than *Arabidopsis* were described. To test if these GRFs behave in a similar way to *Arabidopsis* rGRF3, selected sequences were introduced into *Arabidopsis*. The GRFs with the highest homology to At-rGRF3 and containing a FFD motif and a miR396 target site were selected from rice (FIG. 37) and soybean (FIG. 36). The GRF3 from soybean and rice were uncoupled from miR396 control by introducing mutations in the miRNA binding site as described previously for *Arabidopsis* GRF3.

A vector expressing these sequences from the *Arabidopsis* GRF3 promoter was prepared and then, *Arabidopsis* transgenic plants were obtained. In a similar way to plants expressing At-rGRF3, transgenic *Arabidopsis* plants expressing Os-rGRF4 and Gm-rGRF had bigger leaves than wild-type plants (FIG. 46). These transgenic plants expressing the soybean and rice rGRF3 orthologues also had a delay in leaf senescence (not shown).

Materials and Methods

The *Arabidopsis thaliana* Columbia (Col-0) accession was used as a wild type control. All transgenics are in the Col-0 background. Plants were grown in long photoperiods (16 hr light/8 hr dark) or in short photoperiods (8 hr light/16 hr dark) at 23° C. See Table 1 for a list of binary plasmids generated and details on how transgenics plants were prepared. The miRNA target motif in OsGRF4 and Gm-GRF was altered introducing mutations using the QuikChange® Site Directed Mutagenesis Kit (Stratagene) as described previously for *Arabidopsis* GRF3. The mutated miR396 motif in Os-GRF4 and Gm-GRF is shown FIG. 37 and FIG. 36 respectively.

All constructs were cloned in the binary vector pCHF3 (Jarvis et al., 1998). T-DNA constructs were introduced into *Agrobacterium tumefaciens* strain ASE and *Arabidopsis* transgenics plants were obtained by floral-dip.

Leaf area was measured by first taking a photograph of detached fully expanded leaves, and then measuring the foliar area with the NIH software ImageJ (as described in Example #1 and other examples above).

Conclusions rGRF3 orthologues from species other than *Arabidopsis* (e.g. at least rice and soybean) species can also increase plant size and biomass accumulation.

REFERENCES

Aukerman M. J., Sakai H. (2003). Regulation of flowering time and floral organ identity by a microRNA and its APETALA2-like target genes. Plant Cell 15, 2730-2741

Ausubel F M, Brent R, Kingston R E, Moore D D, Seidman J G, Smith J A and Struhl K. (1998). Current protocols in molecular biology. John Wiley and Sons. Inc. publication.

Axtell M. J., Bartel D. P. (2005). Antiquity of microRNAs and their targets in land plants. Plant Cell 17, 1658-1673

Baker C. C., Sieber P., Wellmer F., Meyerowitz E. M. (2005). The early extra petals1 mutant uncovers a role for microRNA miR164c in regulating petal number in *Arabidopsis*. Curr. Biol. 15, 303-315

Baker, N. R. (2008). Chlorophyll fluorescence: a probe of photosynthesis in vivo. Annu Rev Plant Biol 59, 89-113.

Bartel D. P., Chen C. Z. (2004). Micromanagers of gene expression: the potentially widespread influence of metazoan microRNAs. Nat. Rev. Genet. 5, 396-400

Cartalano M., Castillo R., Efremova N., Kuckenberg M., Zethof J., Gerats T., Schwarz-Sommer Z., Vandenbussche M. (2007). A conserved microRNA module exerts homeotic control over *Petunia hybrida* and *Antirrhinum majus* floral organ identity. Nat. Genet. 39, 901-905

Chen C., Ridzon D. A., Broomer A. J., Zhou Z., Lee D. H., Nguyen J. T., Barbisin M., Xu N. L., Mahuvakar V. R., Andersen M. R., et al. (2005). Real-time quantification of microRNAs by stem-loop RT-PCR. Nucleic Acids Res. 33, e179

Chen X. (2004). A microRNA as a translational repressor of APETALA2 in *Arabidopsis* flower development. Science 303, 2022-2025

Choi, D., Kim, J. H., and Kende, H. (2004). Whole genome analysis of the OsGRF gene family encoding plant-specific putative transcription activators in rice (*Oryza sativa* L.). Plant & cell physiology 45, 897-904.

Chuck G., Cigan A. M., Saeteurn K., Hake S. (2007). The heterochronic maize mutant Corngrass1 results from overexpression of a tandem microRNA. Nat. Genet. 39, 544-549

Czechowski T., Stitt M., Altmann T., Udvardi M. K., Scheible W. R. (2005). Genome-wide identification and testing of superior reference genes for transcript normalization in *Arabidopsis*. Plant Physiol. 139, 5-17

De Veylder L., Beeckman T., Beemster G. T., Krols L., Terras F., Landrieu I., van der Schueren E., Maes S., Naudts M., Inze D. (2001). Functional analysis of cyclin-dependent kinase inhibitors of *Arabidopsis*. Plant Cell 13, 1653-1668

Dinneny J. R., Yadegari R., Fischer R. L., Yanofsky M. F., Weigel D. (2004). The role of JAGGED in shaping lateral organs. Development 131, 1101-1110

Donnelly P. M., Bonetta D., Tsukaya H., Dengler R. E., Dengler N. G. (1999). Cell cycling and cell enlargement in developing leaves of *Arabidopsis*. Dev. Biol. 215, 407-419

Efroni I., Blum E., Goldshmidt A., Eshed Y. (2008). A protracted and dynamic maturation schedule underlies *Arabidopsis* leaf development. Plant Cell 20, 2293-2306

Felsenstein, J. (1989). Mathematics vs. Evolution: Mathematical Evolutionary Theory. Science (New York, N.Y. 246, 941-942.

Ferjani A., Horiguchi G., Yano S., Tsukaya H. (2007). Analysis of leaf development in fugu mutants of *Arabidopsis* reveals three compensation modes that modulate cell expansion in determinate organs. Plant Physiol. 144, 988-999

Fujikura U., Horiguchi G., Ponce M. R., Micol J. L, Tsukaya H. (2009). Coordination of cell proliferation and cell expansion mediated by ribosome-related processes in the leaves of *Arabidopsis thaliana*. Plant J. 59, 499-508

Gamborg, O L., R. B. Miller and K. Ojima. 1968. Nutrient requirements of suspension cultures of soybean root cells. Experimental Cell Research. 50: 151-158.

Gaudin V., Lunness P. A., Fobert P. R., Towers M., Riou-Khamlichi C., Murray J. A., Coen E., Doonan J. H. (2000). The expression of D-cyclin genes defines distinct developmental zones in snapdragon apical meristems and is locally regulated by the Cycloidea gene. Plant Physiol. 122, 1137-1148

Ha C. M., Kim G. T., Kim B. C., Jun J. H., Soh M. S., Ueno Y., Machida Y., Tsukaya H., Nam H. G. (2003). The BLADE-ON-PETIOLE 1 gene controls leaf pattern formation through the modulation of meristematic activity in *Arabidopsis*. Development 130, 161-172

Haga N., Kato K., Murase M., Araki S., Kubo M., Demura T., Suzuki K., Muller I., Voss U., Jurgens G., et al. (2007). R1R2R3-Myb proteins positively regulate cytokinesis through activation of KNOLLE transcription in *Arabidopsis thaliana*. Development 134, 1101-1110

Hellens, R. P, Edwards E. A., Leyland, N. R., Bean, S, and Mullineaux P. M. (2000) "pGreen: a versatile and flexible binary Ti vector for *Agrobacterium*-mediated plant transformation", *Plant Mol. Bio.* 42: 819-832.

Horiguchi G., Kim G. T., Tsukaya H. (2005). The transcription factor AtGRF5 and the transcription coactivator AN3 regulate cell proliferation in leaf primordia of *Arabidopsis thaliana*. Plant J. 43, 68-78

Horiguchi G., Ferjani A., Fujikura U., Tsukaya H. (2006). Coordination of cell proliferation and cell expansion in the control of leaf size in *Arabidopsis thaliana*. J. Plant Res. 119, 37-42

Hornstein E., Shomron N. (2006). Canalization of development by microRNAs. Nat. Genet. 38Suppl, S20-S24

Inze D., De Veylder L. (2006). Cell cycle regulation in plant development. Annu. Rev. Genet. 40, 77-105

Irizarry R. A., Bolstad B. M., Collin F., Cope L. M., Hobbs B., Speed T. P. (2003). Summaries of Affymetrix GeneChip probe level data. Nucleic Acids Res. 31, e15

Jarvis, P., Chen, L. J., Li, H., Peto, C. A., Fankhauser, C., and Chory, J. (1998). An *Arabidopsis* mutant defective in the plastid general protein import apparatus. Science 282, 100-103.

Jones-Rhoades M. W., Bartel D. P. (2004). Computational identification of plant microRNAs and their targets, including a stress-induced miRNA. Mol. Cell 14, 787-799

Kim J. H., Kende H. (2004). A transcriptional coactivator, AtGIF1, is involved in regulating leaf growth and morphology in *Arabidopsis*. Proc. Natl. Acad. Sci. USA 101, 13374-13379

Kim J. H., Lee B. H. (2006). GROWTH-REGULATING FACTOR4 of *Arabidopsis thaliana* is required for development of leaves, cotyledons, and shoot apical meristem. J. Plant Biol. 49, 463-468

Kim J. H., Choi D., Kende H. (2003). The AtGRF family of putative transcription factors is involved in leaf and cotyledon growth in *Arabidopsis*. Plant J. 36, 94-104

Koyama T., Furutani M., Tasaka M., Ohme-Takagi M. (2007). TCP transcription factors control the morphology of shoot lateral organs via negative regulation of the expression of boundary-specific genes in *Arabidopsis*. Plant Cell 19, 473-484

Krizek B. A. (1999). Ectopic expression of AINTEGUMENTA in *Arabidopsis* plants results in increased growth of floral organs. Dev. Genet. 25, 224-236

Lee, B. H., Ko, J. H., Lee, S., Lee, Y., Pak, J. H., and Kim, J. H. (2009). The *Arabidopsis* GRF-INTERACTING FACTOR Gene Family Performs an Overlapping Function in Determining Organ Size as well as Multiple Developmental Properties. Plant physiology.

Lemon W. J., Liyanarachchi S., You M. (2003). A high performance test of differential gene expression for oligonucleotide arrays. Genome Biol. 4, R67

Li, P., Ponnala, L., Gandotra, N., Wang, L., Si, Y., Tausta, S. L., Kebrom, T. H., Provart, N., Patel, R., Myers, C. R., et al. (2010). The developmental dynamics of the maize leaf transcriptome. Nature genetics 42, 1060-1067.

Liu D., Song Y., Chen Z., Yu D. (2009). Ectopic expression of miR396 suppresses GRF target gene expression and alters leaf growth in *Arabidopsis*. Physiol. Plant 136, 223-236

Lukowitz W., Mayer U., Jurgens G. (1996). Cytokinesis in the *Arabidopsis* embryo involves the syntaxin-related KNOLLE gene product. Cell 84, 61-71

Masuda H. P., Cabral L. M., De Veylder L., Tanurdzic M., de Almeida Engler J., Geelen D., Inze D., Martienssen R. A., Ferreira P. C., Hemerly A. S. (2008). ABAP1 is a novel plant Armadillo BTB protein involved in DNA replication and transcription. EMBO J. 27, 2746-2756

Menges M., de Jager S. M., Gruissem W., Murray J. A. (2005). Global analysis of the core cell cycle regulators of *Arabidopsis* identifies novel genes, reveals multiple and highly specific profiles of expression and provides a coherent model for plant cell cycle control. Plant. J. 41, 546-566

Moloney, M M., J. M. Walker, and K. K. Sharma. 1989. High-efficiency transformation of *Brassica napus* using *Agrobacterium* vectors. Plant Cell Reports 8:238-242.

Moretti, S., Armougom, F., Wallace, I. M., Higgins, D. G., Jongeneel, C. V., and Notredame, C. (2007). The M-Coffee web server: a meta-method for computing multiple sequence alignments by combining alternative alignment methods. Nucleic acids research 35, W645-648.

Mizukami Y., Fischer R. L. (2000). Plant organ size control: AINTEGUMENTA regulates growth and cell numbers during organogenesis. Proc. Natl. Acad. Sci. USA 97, 942-947

Murashige, T., and F. Skoog. 1962. A revised medium for rapid growth and bioassays and tobacco tissue culture. Physiol Plant 15:437-497.

Nath U., Crawford B. C., Carpenter R., Coen E. (2003). Genetic control of surface curvature. Science 299, 1404-1407

Nikovics K., Blein T., Peaucelle A., Ishida T., Morin H., Aida M., Laufs P. (2006). The balance between the MIR164A and CUC2 genes controls leaf margin serration in *Arabidopsis*. Plant Cell 18, 2929-2945

Ohno C. K., Reddy G. V., Heisler M. G., Meyerowitz E. M. (2004). The *Arabidopsis* JAGGED gene encodes a zinc finger protein that promotes leaf tissue development. Development 131, 1111-1122

Ori N., Cohen A. R., Etzioni A., Brand A., Yanai O., Shleizer S., Menda N., Amsellem Z., Efroni I., Pekker I., et al. (2007). Regulation of LANCEOLATE by miR319 is required for compound-leaf development in tomato. Nat. Genet. 39, 787-791

Page, R. D. (1996). TreeView: an application to display phylogenetic trees on personal computers. Comput Appl Biosci 12, 357-358.

Palatnik J. F., Allen E., Wu X., Schommer C., Schwab R., Carrington J. C., Weigel D. (2003). Control of leaf morphogenesis by microRNAs. Nature 425, 257-263

Palatnik J. F., Wollmann H., Schommer C., Schwab R., Boisbouvier J., Rodriguez R., Warthmann N., Allen E., Dezulian T., Huson D., et al. (2007). Sequence and expression differences underlie functional specialization of *Arabidopsis* microRNAs miR159 and miR319. Dev. Cell 13, 115-125

Piazza P., Jasinski S., Tsiantis M. (2005). Evolution of leaf developmental mechanisms. New Phytol. 167, 693-710

Rice, P., Longden, I., and Bleasby, A. (2000). EMBOSS: the European Molecular Biology Open Software Suite. Trends Genet 16, 276-277.

Rodriguez, R., Mecchia, M., Debernardi, J., Schommer, C., Weigel, D., and Palatnik, J. (2010). Control of cell proliferation in *Arabidopsis thaliana* by microRNA miR396, Development 137, 103-112

Sambrook J and Russell D W (2001). Molecular Cloning: A Laboratory Manual. Third Edition. Cold Spring. Harbour Laboratory Press Schmid M., Davison T. S., Henz S. R., Pape U. J., Demar M., Vingron M., Scholkopf B., Weigel D., Lohmann J. U. (2005). A gene expression map of *Arabidopsis thaliana* development. Nat. Genet. 37, 501-506

Schommer C., Palatnik J. F., Aggarwal P., Chetelat A., Cubas P., Farmer E. E., Nath U., Weigel D. (2008). Control of jasmonate biosynthesis and senescence by miR319 targets. PLoS Biol. 6, e230

Schwab R., Palatnik J. F., Riester M., Schommer C., Schmid M., Weigel D. (2005). Specific effects of microRNAs on the plant transcriptome. Dev. Cell 8, 517-527

Sparrow P A C, Dale P J and Irwin J A (2004). The use of phenotypic markers to identify *Brassica oleracea* genotypes for routine high-throughput *Agrobacterium*-mediated transformation. Plant Cell Reports. 23:64-70

Subramanian A., Tamayo P., Mootha V. K., Mukherjee S., Ebert B. L., Gillette M. A., Paulovich A., Pomeroy S. L., Golub T. R., Lander E. S., et al. (2005). Gene set enrichment analysis: a knowledge-based approach for interpreting genome-wide expression profiles. Proc. Natl. Acad. Sci. USA 102, 15545-15550

Subramanian A., Kuehn H., Gould J., Tamayo P., Mesirov J. P. (2007). GSEA-P: a desktop application for Gene Set Enrichment Analysis. Bioinformatics 23, 3251-3253

Tsukaya H. (2005). Leaf shape: genetic controls and environmental factors. Int. J. Dev. Biol. 49, 547-555

Tsukaya H. (2006). Mechanism of leaf-shape determination. Annu. Rev. Plant Biol. 57, 477-496

Wang J. W., Schwab R., Czech B., Mica E., Weigel D. (2008). Dual effects of miR156-tTargeted SPL genes and CYP78A5/KLUH on plastochron length and organ size in *Arabidopsis thaliana*. Plant Cell. 5, 1231-1243

White D. W. (2006). PEAPOD regulates lamina size and curvature in *Arabidopsis*. Proc. Natl. Acad. Sci. USA 103, 13238-13243

Wu G., Poethig R. S. (2006). Temporal regulation of shoot development in *Arabidopsis thaliana* by miR156 and its target SPL3. Development 133, 3539-3547

Winter, D., Vinegar, B., Nahal, H., Ammar, R., Wilson, G. V., and Provart, N.J. (2007). An "Electronic Fluorescent Pictograph" browser for exploring and analyzing large-scale biological data sets. PloS one 2, e718.

Zhang, D.-F., Li, B., Jia, G.-Q., Zhang, T.-F., Dai, J.-R., Li, J.-S., and Wang, S.-C. (2008). Isolation and characterization of genes encoding GRF transcription factors and GIF transcriptional coactivators in Maize (*Zea mays* L.). Plant Science 175, 809-817.

Zhang, H., Jin, J., Tang, L., Zhao, Y., Gu, X., Gao, G., and Luo, J. (2011). PlantTFDB 2.0: update and improvement of the comprehensive plant transcription factor database. Nucleic acids research 39, D1114-1117.

---

The invention claimed is:

1. A method of producing a plant with increased productivity compared to a wild-type plant, comprising transforming a plant with a construct comprising an isolated nucleic acid encoding a growth regulatory factor (AtGRF-3) of SEQ ID NO: 20, which nucleic acid comprises a modification in the miRNA396 target site as set forth in SEQ ID NO: 86, operably linked with a native AtGRF3 promoter and a terminator.

2. The method of claim 1 wherein the increased productivity is selected from the group consisting of increased yield, increased biomass, increased stress resistance, increased drought tolerance, delayed leaf senescence, increased seed production, increased seed yield, increased root growth and increased root elongation speed and combinations thereof, compared to the wild-type plant.

3. The method according to claim 2 wherein the increased biomass compared to the wild-type plant comprises one or more of the following selected from the group consisting of: increased overall plant biomass, increased fresh weight, increased leaf area or size, increased root length, increased stem growth, increased stem biomass, increased stem diameter, and increased stem width at flowering compared to the wild-type plant.

4. The method according to claim 2 wherein the increased productivity compared to the wild-type plant occurs without leaf shape changes.

5. The method according to claim 2 wherein the increased biomass compared to the wild-type plant is uncoupled from delayed leaf senescence by using tissue specific promoters.

6. The method of claim 1 wherein the method further comprises overexpressing a nucleic acid encoding a GRF-interacting factor (GIF), wherein the GIF comprises SEQ ID NO: 95.

7. The method of claim 1, wherein the nucleic acid encoding said growth regulatory factor (atGRF-3) comprises SEQ ID NO: 81.

8. The method of claim 6, wherein the nucleic acid encoding said growth regulatory factor (atGRF-3 comprises SEQ ID NO: 81.

9. The method of claim 7, wherein the increased productivity compared to the wild-type plant is selected from the group consisting of increased yield, increased biomass, increased stress resistance, increased drought tolerance, delayed leaf senescence, increased seed production, increased seed yield, increased root growth, increased root elongation speed and combinations thereof.

10. The method of claim 8, wherein the increased productivity compared to the wild-type plant is selected from the group consisting of increased yield, increased biomass, increased stress resistance, increased drought tolerance, delayed leaf senescence, increased seed production, increased seed yield, increased root growth, increased root elongation speed and combinations thereof.

* * * * *

SEQUENCE LISTING

```
<160> NUMBER OF SEQ ID NOS: 128

<210> SEQ ID NO 1
<211> LENGTH: 21
<212> TYPE: DNA
<213> ORGANISM: Artificial Sequence
<220> FEATURE:
<223> OTHER INFORMATION: miR396 target site

<400> SEQUENCE: 1
cgttcaagaa agcctgtgga a                                              21

<210> SEQ ID NO 2
<211> LENGTH: 1197
<212> TYPE: DNA
<213> ORGANISM: Arabidopsis thaliana

<400> SEQUENCE: 2
atggatttgc aactgaaaca atggagaagc cagcagcagc aacaacatca gacagagtca      60
gaagaacaac cttctgcagc taagatacca aaacatgtct ttgaccagat tcattctcac     120
actgcaactt ctactgctct tcctctcttt accctgagc ctacttcttc taaactctcc     180
tctttgtctc ctgattcttc ctccaggttc cccaagatgg ggagcttctt tagctgggca     240
cagtggcaag aacttgaact acaagctctg atctacaggt acatgttggc tggtgctgct     300
gttcctcagg agctcctttt accaatcaag aaaagccttc tccatctatc tccttcctac     360
tttcttcacc atcctcttca acacctacct cattaccaac ctgcttggta tttgggaagg     420
gcagcgatgg atcctgagcc aggcagatgc aggagaacgg atggtaagaa gtggagatgt     480
```

```
tcaagagacg tcttcgctgg ccacaagtat tgcgagcgcc acatgcaccg tggccgcaac      540
cgttcaagaa agcctgtgga aactccaacc accgtcaatg caactgccac gtccatggct      600
tcatcagtag cagccgcagc caccactaca acagcaacaa caacatctac gtttgctttt      660
ggtggtggtg gtggtagtga ggaagtggtt ggtcaaggag gatctttctt cttctctggc      720
tcttctaact cttcatctga acttctccac cttagtcaaa gttgttcgga gatgaagcaa      780
gaaagcaaca acatgaacaa caagaggcca tacgagtccc acatcggatt cagtaacaac      840
agatcagatg gaggacacat cctgaggccc tcttttgacg attggcctcg ttcttcgctc      900
caagaagctg acaatagttc aagcccatg agctcagcca cttgtctctc catctccatg       960
cccgggaact cttcctcaga cgtctctctg aagctgtcca caggcaacga agagggagcc      1020
cggagcaaca caatgggag agatcagcaa acatgagct ggtggagcgg tggaggttcc        1080
aaccaccatc atcacaacat gggcggacca ttggccgaag ccctgagatc ttcttcctca      1140
tcttccccaa ccagtgttct ccatcagctt ggtgtctcga cacaagcctt tcattga        1197
```

<210> SEQ ID NO 3
<211> LENGTH: 1194
<212> TYPE: DNA
<213> ORGANISM: Oryza sativa

<400> SEQUENCE: 3

```
atgatgatga tgagcggtcg cccgagcggc ggcgccggcg gaggtcggta cccgttcacg       60
gcgtcgcagt ggcaggagct ggagcaccag gcgctcatct acaagtacat ggcgtccggg      120
actcccatcc cctccgacct catcctcccc ctccgccgca gcttcctcct cgactccgcc      180
ctcgccacct cccttccct cgccttccct ccccaacctt cactggggtg gggttgcttt      240
ggcatggggt ttgggcggaa ggcggaggac ccggagccag ggcgatgccg gcgtacggac      300
ggcaagaagt ggcggtgctc caaggaggcg taccccggact ccaagtactg cgagaagcac     360
atgcaccgtg gcaagaaccg ttcaagaaag cctgtggaaa tgtccttggc cacgccgccg     420
ccgccgtcct cctccgccac ctccgccgcg tcgaacacct ccgccggcgt cgccccacc      480 accaccacca cctcctcccc ggcgccctcc tacagccgcc cggcgccgca cgacgcggcg      540
ccgtaccagg cgctctacgg cgggccctac gccgcggcca ccgcgcgcac ccccgccgcc      600
gcggcgtacc acgcgcaggt gagcccgttc cacctccagc tcgacaccac ccacccgcac      660
ccgccgccgt cctactactc catggaccac aaggagtacg cgtacgggca cgccaccaag      720
gaggtgcacg cgagcacgc cttcttctcc gatggcaccg agagggagca ccaccacgcc      780
gccgccgggc acggccagtg gcagttcaag cagctcggca tggagcccaa gcagagcacc     840
acgcctctct tcccgggcgc cggctacggc cacaccgcgg cgtcgccgta cgccattgat      900
ctttcaaaag aggacgacga tgagaaagag aggcggcaac agcagcagca gcagcagcag     960
cagcactgct tcctcctggg cgccgacctc cgtctggaga agccggcggg ccacgaccac    1020
gcggcggcgg cgcagaaacc tctccgccac ttcttcgacg agtggccgca tgagaagaac    1080
agcaagggct cctggatggg gctcgaaggc gagacgcagc tgtccatgtc catccccatg    1140
gccgccaacg acctcccgat caccaccacc tcccgctacc acaatgatga ttaa          1194
```

<210> SEQ ID NO 4
<211> LENGTH: 1164
<212> TYPE: DNA
<213> ORGANISM: Oryza sativa

```
<400> SEQUENCE: 4
atggcgatgc cctttgcctc cctgtcgccg gcagccgacc accggccctc cttcatcttc      60
cccttctgcc gctcctcccc tctctccgcg gtcggggagg aggcgcagca gcacatgatg     120
ggcgcgaggt gggcggcggc ggtggccagg ccgccgccct tcacggcggc gcagtacgag     180
gagctggagc agcaggcgct catatacaag tacctcgtcg ccggcgtgcc cgtcccggcg     240
gatctcctcc tccccatccg ccgtggcctc gactcactcg cctcgcgctt ctaccaccac     300
cctgtccttg gatacggttc ctacttcggc aagaagctgg accggagcc cggacggtgc      360 cggcgtacgg acggcaagaa gtggcggtgc tccaaggagg ccgcgccgga ctccaagtac     420
tgtgagcgac acatgcaccg cggccgcaac cgttcaagaa agcctgtgga agcgcagctc     480
gtcgcccccc actcgcagcc ccccgccacg gcgccggccg ccgccgtcac ctccaccgcc     540
ttccagaacc actcgctgta cccggcgatt gctaatggcg gcggcgccaa cggaggcggt     600
ggtggtggtg gcggtggcgg cagcgcgcct ggctcgttcg ccttggggtc taatactcag     660
ctgcacatgg acaatgctgc gtcttactcg actgttgctg ctggtgccgg aaacaaagat     720
ttcaggtatt ctgcttatgg agtgagacca ttggcagatg agcacagccc actcatcact     780
ggagctatgg atacctctat tgacaattcg tggtgcttgc tgccttctca gacctccaca     840
ttttcagttt cgagctaccc tatgcttgga aatctgagtg agctggacca gaacaccatc     900
tgctcgctgc cgaaggtgga gagggagcca ttgtcattct cgggagcga ctatgtgacc      960 gtcgactccg ggaagcagga gaaccagacg ctgcgccect ttttcgacga gtggccaaag    1020
gcaagggact cctggcctga tctagctgat gacaacagcc ttgccacctt ctctgccact    1080
cagctctcga tctccattcc aatggcaacc tctgacttct cgaccaccag ctcacgatca    1140
cacaacggta tatactcccg atga                                            1164

<210> SEQ ID NO 5
<211> LENGTH: 1164
<212> TYPE: DNA
<213> ORGANISM: Oryza sativa

<400> SEQUENCE: 5
atggcgatgc cctttgcctc cctgtcgccg gcagccgacc accggccctc cttcatcttc      60
cccttctgcc gctcctcccc tctctccgcg gtcggggagg aggcgcagca gcacatgatg     120
ggcgcgaggt gggcggcggc ggtggccagg ccgccgccct tcacggcggc gcagtacgag     180
gagctggagc agcaggcgct catatacaag tacctcgtcg ccggcgtgcc cgtcccggcg     240
gatctcctcc tccccatccg ccgtggcctc gactcactcg cctcgcgctt ctaccaccac     300
cctgtccttg gatacggttc ctacttcggc aagaagctgg accggagcc cggacggtgc      360 cggcgtacgg acggcaagaa gtggcggtgc tccaaggagg ccgcgccgga ctccaagtac     420
tgtgagcgac acatgcaccg cggccgcaac cgttcaagaa agcctgtgga agcgcagctc     480
gtcgcccccc actcgcagcc ccccgccacg gcgccggccg ccgccgtcac ctccaccgcc     540
ttccagaacc actcgctgta cccggcgatt gctaatggcg gcggcgccaa cggaggcggt     600
ggtggtggtg gcggtggcgg cagcgcgcct ggctcgttcg ccttggggtc taatactcag     660
ctgcacatgg acaatgctgc gtcttactcg actgttgctg ctggtgccgg aaacaaagat     720
ttcaggtatt ctgcttatgg agtgagacca ttggcagatg agcacagccc actcatcact     780
ggagctatgg atacctctat tgacaattcg tggtgcttgc tgccttctca gacctccaca     840
ttttcagttt cgagctaccc tatgcttgga aatctgagtg agctggacca gaacaccatc     900
```

```
tgctcgctgc cgaaggtgga gagggagcca ttgtcattct tcgggagcga ctatgtgacc    960
gtcgactccg ggaagcagga gaaccagacg ctgcgcccct ttttcgacga gtggccaaag   1020
gcaagggact cctggcctga tctagctgat gacaacagcc ttgccacctt ctctgccact   1080
cagctctcga tctccattcc aatggcaacc tctgacttct cgaccaccag ctcacgatca   1140
cacaacggta tatactcccg atga                                          1164
```

<210> SEQ ID NO 6
<211> LENGTH: 1185
<212> TYPE: DNA
<213> ORGANISM: Oryza sativa

<400> SEQUENCE: 6

```
atggcgatgc cgtatgcctc cctgtctccg gcggtggccg accaccgctc gtccccggca     60
gccgcgaccg cctccctcct cccttctgc cgctccaccc cgctctccgc gggcggtggt    120
ggcgtcgcga tgggggagga cgcgccgatg accgcgaggt ggccgccggc ggcggcggcg    180
aggctgccgc cgttcaccgc ggcgcagtac gaggagctgg agcagcaggc gctcatatac    240
aagtacctgg tggcaggcgt gcccgtcccg ccggatctcg tgctccccat cgccgcggga    300
ctcgactccc tcgccgcccg cttctacaac catcccgccc ttggatatgg tccgtacttc    360
ggcaagaagc tggacccaga gccagggcgg tgccggcgta cggacggcaa gaaatggcgg    420
tgctcgaagg aggccgcgcc ggattccaag tactgcgagc gccacatgca ccgcggccgc    480
aaccgttcaa gaaagcctgt ggaaacgcag ctggtcgccc agtcccaacc gccctcatct    540
gttgtcggtt ctgcggcggc gcccttgct gctgcctcca atggcagcag cttccaaaac    600
cactctcttt accctgctat tgccggcagc aatggcgggg cgggggggag gaacatgccc    660
agctcatttg gctcggcgtt gggttctcag ctgcacatgg ataatgctgc cccttatgca    720
gctgttggtg gtggaacagg caaagatctc aggtatactg cttatggcac aagatctttg    780
gcggatgagc agagtcaact cattactgaa gctatcaaca catctattga aaatccatgg    840
cggctgctgc catctcagaa ctcgccattt cccctttcaa gctattctca gctggggca    900 ctaagtgacc ttggtcagaa cacccccagc tcactttcaa aggttcagag gcagccactt    960
tcgttctttg ggaacgacta tgcggctgtc gattctgtga agcaagagaa ccagacgctg   1020
cgtcccttct ttgatgagtg gccaaaggga agggattcat ggtcagacct cgctgatgag   1080
aatgctaatc tttcgtcatt ctcaggcacc caactgtcga tctccatacc aatggcatcc   1140
tctgacttct cggcggccag ttctcgatca actaatggtg actga                  1185
```

<210> SEQ ID NO 7
<211> LENGTH: 1388
<212> TYPE: DNA
<213> ORGANISM: Zea mays

<400> SEQUENCE: 7

```
gacaggttga gatggcgatg ccgtatgcct ctctttcccc ggcaggcgcc gccgaccacc     60
gctcctccac agccacggcg tccctcgtcc ccttctgccg ctccacccg ctctccgcgg    120 gcggcgggct gggggaggag gacgcccagg cgagcgcgag gtggcggcc gcgaggccgg    180 tggtgccgtt cacgccggcg cagtaccagg agctggagca gcaggcgctc atatacaagt    240
acctggtggc cggcgtgccc gttcgccgg atctcgtggt ccaatccgc gcggcctcg    300 actccctcgc taccgcttc tacggccaac ccacactcgg gtacgaccg tacctgggga    360
```

```
ggaaactgga tccggagccc ggccggtgcc ggcgaacgga cggcaagaag tggcggtgct      420
ccaaggaagc cgccccggac tccaagtact gcgagcgcca catgcaccgc ggccgcaacc      480
gttcaagaaa gcctgtggaa acgcagctcg cgcccagtc ccaaccgccc gccgccgcgg       540
ccgtctccgc cgctccgccc ctggcagccg ccgccgccgc cgccaccaac ggcagcggct      600
tccagaacca ctctctctac ccggccatcg ccggcagcac tggtggtgga ggaggagttg      660
gcgggtccgg caatatctcc tccccgttct cctcgtcgat gggggatcg tctcagctgc       720 acatggacag tgttgccagc tactcctacg cagctcttgg tggtggaact gcaaaggatc      780
tcaggtacaa cgcttacgga ataagatctc tggcggacga gcacaaccag ctgatcgcag      840
aagccatcga ctcgtcgata gagagccaga ggcgcctccc cagctcgtcg ttcccgctct      900
cgagctaccc acatctcggg gcgctgggcg acctgggcgg ccagaacagc acggtgagct      960
cgctgccgaa gatggagaag cagcagccgc cctcgtcctt cctagggaac gacaccgggg     1020
ccggcatggc catgggctcc gcctccgcga agcaggaggg ccagacgctg cggcacttct     1080
tcgacgagtg gcccaaggcg cgggactcct ggccgggcct ctccgacgag accgccagcc     1140
tcgcctcgtc cccccggcg acccagctgt cgatgtccat acccatggcg tcctccgact      1200
tctccgtggc cagctcccag tcgcccaacg atgactaatg gtgcgtggat cgtcgcgttc     1260 tggcccttg tctatctccc ctccagtcct ccacccaccg cgcagtagta gctgcggaaa      1320
cagcccatgc tcctgtatat ttgtcggtca ttttccgtgt cagatctgtg taccaaacca     1380
agcggcgg                                                               1388

<210> SEQ ID NO 8
<211> LENGTH: 1350
<212> TYPE: DNA
<213> ORGANISM: Zea mays

<400> SEQUENCE: 8
tagccgtgct ccgctcacct tctctcgcgc tacagtctca aggggtagct agccaagcta       60
ccaagctcgt caggaacgag agaaagaggc cggcggtgcg cggggatgat gatgatgagc      120
agcggccggg cgggcggcgg ggccaccgcg gggcggtacc cgttcacggc gtcgcagtgg      180
caggagctgg agcaccaggc gctcatctac aagtgcctgg cgtccggcaa gcccatccct      240
tcctacctca tgccgccgct ccgccgcatc ctcgactccg ccctcgccac gtcgccgtcc      300
ctcgcctacc cgccgcaacc ctcgctgggc tggggctgct tcgggatggg cttcacccgg      360
aaggccgacg aggacccgga gcccggcggg tgccggcgca cggacggcaa gaagtggcgc      420
tgctccaagg aggcgtaccc ggactccaag tactgcgaga gcacatgcca ccggggcaag      480
aaccgttcaa gaaagcctgt ggaaatgtcc ttggccacgc cggccccggc gccggccccc      540
gccgccgcca caaccgccac cgccacctca tccccggcgc cgtcctacca ccgcccggcc      600
cacgacgcca cgccgtctcc gtaccacgcg ctgtatggag gcggcggcgg cggcggcggt      660
agcccttact cggcgtcggc acgcccagga gcaaccggag cggcggcgc gtaccaccac       720 gcgcagcatg tgagcccctt ccacctccac ctcgagacca cccacccgca cccgccgccg      780
ccctacaact actccgccga ccagagggac tacgcgtacg gcacgcggc cgccaaggag       840 gtcggcgagc acgccttctt ctcggacggc gcgggcgagc gggtcgaccg ccaggccgcg      900
gcggggcagt ggcagttcag gcagctcggg gtggagacga agcccgggccc cacgccgctg    960 ttccccgtcg ccgggtacgg gcacggcgcg gcgtcgccgt acggcgtcga gctgggcaag     1020
gacgacgacg agcaggagga gaggcgccgc cagcactgct tcgttcttgg agccgacctg     1080
```

```
cggctggagc ggccgtcgtc gggccatggc catggccatg gccatgacca tgacgacgcc    1140
gccgccgcgc agaagccgct ccggcccttc ttcgacgagt ggccgcacca gaaggggac     1200 aaggccgggt cgtggatggg gctcgacggc gagacgcagc tctccatgtc catccccatg    1260
gccgctaccg acctccccgt cacctcccgc ttccgtaacg acgagtgatg ccacatcaaa    1320
cctggcgctg gaaactcgga acgtatggtg                                     1350
```

<210> SEQ ID NO 9
<211> LENGTH: 1374
<212> TYPE: DNA
<213> ORGANISM: Zea mays

<400> SEQUENCE: 9

```
cagccaggta aggcaaaaga gagagggcgg aagcagcggc agagcggaga gggagagaga     60
agagcatata tgggcatggc gatgcccttt gcctccccgt ctccggcagc cgaccaccgc    120
ccctcctccc tcctcccctt ctgccgcgcc gcccctctct ccgcggcggg agaggacgcc    180
gcgcagcagc acgcgatgag cggcaggtgg gccgcgaggc cggcgctctt cacggcggcg    240
cagtacgagg agctggagca ccaggcgctc atatacaagt acctcgtcgc cggcgtgccc    300
gtcccgccgg acctcctcct cccctgcgc cgaggcttcg tcttccacca gccacccgcc    360
cttgggtacg gccctactt cggcaagaag gtggaccggg agcccgggcg gtgccggcgt    420
acggacggca agaagtggcg gtgctccaag gaggccgccc cggactccaa gtactgcgag    480
cgccacatgc accgcggccg caaccgttca agaaagcctg tggaagcgca gctcgcgccc    540
ccgccgcacg cccagccgcc gcagcagcag caggccccg cgccgctgc tggcttccag     600 aaccactcgc tgtacccgtc gatcctcaac ggcaacggcg gcggcgggtt aggtgctggt    660
gctggtggtg gcacgttcgg cctggggccc acctctcagc tgcacatgga cagtgccgct    720
gcctacgcga ctgctgccgg tgagggggagc aaatatctca ggtactctgc atacggggtg    780
aaatctctgt cggacgagca cagcacgctc ttgtcgggcg gcatggatcc gtcgatgatg    840
gacaactcgt ggcgccttct gccatcccaa aacaacacat ccaagccac aagctaccct    900 gtgttcggca cgctgagtgg gctagacgag agcaccatcg cgtcgctgcc gaagacccag    960
agggagcccc tctctttctt cgggagcgac ttcgtgaccg ccgccaagca ggagaaccag    1020
acgctgcgcc ctttcttcga cgagtggccc aagtcgaggg actcgtggcc ggagctgggc    1080
gaggacggca gcctcggctt ctcggccacc cagctctcca tctccattcc catggcgacc    1140
tccgacttct ccaacaccag ctccagatcg ccgggtggaa taccgtcgag atgaacgagt    1200
accgtgcatg tggatcccag cgtcttaggg ttgacgactc ttcggtgctg gcctcatcgt    1260
atcatgctcc taaattttcg aacgatatat gccttatgta acgctatttc tctcattgtt    1320
acaacaccct ttacccgttt ggaattgtgt tgaagtggat ggtctgcgtt gctc          1374
```

<210> SEQ ID NO 10
<211> LENGTH: 1172
<212> TYPE: DNA
<213> ORGANISM: Zea mays

<400> SEQUENCE: 10

```
gatatatggc gatgcccttt gcctccctgt ctccggcagc cgaccaccgc ccctcctccc     60
tcctccccta ctgccgcgcc gcccctctct ccgcggtggg agaggacgcc gccgcgcagg    120
cgcagcagca gcagcagcag cacgctatga gcggcaggtg ggcagcgagg ccgccggcgc    180
```

```
tcttcacagc ggcgcagtac gaggagctgg agcaccaggc gctcatatac aagtacctcg     240
tcgccggcgt gcccgtcccg ccggacctcc tcctccccct acgccgaggc ttcgtctacc     300
accaacccgc ccttgggtac gggccctact tcggcaagaa ggtggacccg gagcccgggc     360
ggtgccggcg tacggacggc aagaagtggc ggtgctccaa ggaggccgcc ccggactcca     420
agtactgcga gcgccacatg caccgcggcc gcaaccgttc aagaaagcct gtggaagcgc     480
agctcgtgcc cccgccgcac gcccagccgc agcagcaggc cccgcgcccc accgctggct     540
tccagagcca ccccatgtac ccatccatcc tcgccggcaa cggcggcggc ggcggcgggg     600
taggtggcgg tgctggcggt ggcacgttcg gcctgggccc cacctctcag ctgcgcatgg     660
acagtgccgc tgcttacgcg actgctgctg atggagggag caaagatctc aggtactctg     720
cctacggggt gaagtcactg tcggacgagc acagccagct cttgcccggc ggcggcggcg     780
gcatggacgc gtcaatggac aactcgtggc gcctgttgcc gtcccaaacc gccgccacgt     840
tccaagccac aagctaccct ctgttcggcg cgctgagcgg tctggacgag agcaccatcg     900
cctcgctgcc caagacgcag agggagcccc tctccttctt cggagcgac  ttcgtgaccc     960 cgaagcagga gaaccagacg ctgcgcccct tcttcgacga gtggcccaag tcgagggact    1020
cgtggccgga gctgaacgag gacaacagcc tcggctcctc ggccacccag ctctccacct    1080
ccatccccat ggcgccctcc gacttcaaca ccagctccag atcgccgaat ggaataccgt    1140
caagatgaac ctgagtaacc atgcggaccc ca                                  1172
```

<210> SEQ ID NO 11
<211> LENGTH: 1154
<212> TYPE: DNA
<213> ORGANISM: Zea mays

<400> SEQUENCE: 11

```
agcgtgcatt gttgagcgag tgcggccaag caacgcgggc tcgaggagat gatgctgagc      60
gggcacggcg gcgggaggcg cctgttcacg gcgtcgcagt ggcaggagct cgagcaccag     120
gcgctcatct tcaagtacat ggcctcgggc gcgcccgtgc cgcacgacct cgtcctaccg     180
ctccgcctcg ccaccggcgt cgacaccgcg ccctcccctcg ccttcccgcc ccagccttcg    240
ccgtcgctgg cgtactgggg ctgctacggc gcggggggcgc cgttcgtcgg ccgcaaggcg    300
gcggaggaca cggagccggg gcggtgccgg cggacggacg caagaagtg gcggtgctcc     360 agggaggccc acggcgactc caagtactgc gagaagcaca ttcaccgcgg gaagagccgt    420
tcaagaaagc ctgtggaagt gacctcctcc ccgccgccg cgccgctgc ggcgtaccga     480 ccgtccgcga tctccaccat ctcgccgccc cgcgcggccg acgcgccgcc gccgagcctc    540
gcctacccgc agcagcatct cctccacggc gcctcctcct ccgcagcagc ccgcgccccc    600
gctggcgctc tccagctcca cctcgacgcg agcctgcacg cggcggcggc gtcgccatcg    660
ccgccgccgt cctaccacag gtacgccac tacacaccgc cagcgtcgtc gctcttcccg    720
ggcggcggct acggctacga ctacgactac gggcagtcca aggagctcag gcgacggcac    780
ttccacgcgc tcggggccga cctgagcctc gacaagccgc tgcccgagcc cgacaccggc    840
tccgacgaga gcagcccct gcggcgtttc ttcgacgagt ggccgcggga gagcggcgac    900
atggcggcgg acgacgcgac gcagctttcc atctccatcc ccgcggcttc gccctccgac    960
ctcgctgcta cctccgcctc cgccgccgcc gcgcgattcc acaacgggga gtgatcggtc   1020
catctcctag ctgcagccct gcaacagcgt ggattgaccg ctgcatttcc tggctgcaat   1080
gcaagcctgc aacagcgagc agtaagccag tgacgtggat gcatctcgta gcggcaaacc   1140
```
ctgcttctgc ctct                                                          1154

<210> SEQ ID NO 12
<211> LENGTH: 1139
<212> TYPE: DNA
<213> ORGANISM: Zea mays

<400> SEQUENCE: 12
gtaggtcgtt cgcaggtagg taaccgtaac ctagctagct cgtcgggatg atgatgatga        60
gcggtcgagc ggccaccgcg gggcggtacc cgttcacggc gtcgcagtgg caggagctgg       120
agcaccaggc gctcatctac aagtgcctgg cgtccggcaa gcccatcccg tcctacctca       180
tgccaccgct ccgccgcatc ctcgactccg ccctcgccac gtcgccgtcg ctcgccgcct       240
tccagccgca accctcgctg gggtgggggg gctgcttcgg gatgggcttc agcaggaagc       300
ccgccgacga ggacccggag cccgggcggt gccggcgcac ggacggcaag aagtggcgct       360
gctccaagga ggcgtacccg gactccaagt actgcgagaa gcacatgcac cggggcaaga       420
accgttcaag aaagcctgtg gaaatgtcct tggccacgcc ggcgccgccg gcctcctccg       480
ctgccaccac ctcgacgtcc ccggcgccgt cctaccaccg cccggccccc gccgcgcacg       540
acgccgtgcc gtaccacgcg ccctacggcg ccgcgtacca tcacacgcag acgcaggtga       600
tgagcccctt ccacctccac ctcgagacca cccaccccgca cccgccgccg ccgccgccct       660
actactacgc ggaccagagg gactacgcct acggcaagga ggtcggcgag cgcgccttct       720
tctccgacgg cgcgggggag agggaccgcc agcagcaggc cgcggggcag tggcagttca       780
agcagctcgg gacgatggag gcgacgaagc cgtgccccac cccacgccg ctgctccccg        840
ccgccgggta cggcgtcggt caggccaagg aagacgagga ggaggaaacg cggcggcagc       900
agcagcagca ctgcttcgtt cttggcgccg acctgcggct ggcggagcgg ccgtcggggg       960
cacatgacga cgccgcgcag aagccgctcc ggcatttctt cgacgagtgg ccgcacgaga      1020
aagggagcaa ggcggggtgg tggattgggg gactcgacgg cgagacgacg cagctctcca      1080
tgtccatccc gatggcggcc gctgccgacc tccccgtcac ctcccgctac cgtacgtga       1139

<210> SEQ ID NO 13
<211> LENGTH: 1372
<212> TYPE: DNA
<213> ORGANISM: Zea mays

<400> SEQUENCE: 13
gcctctgaca ccagcacaaa cctggagact actactagta ttggagtccc ctccacttcc        60
acctcccttg ccactgaagc gagagctctc ggagccgtcg tcctctgtct ctcatccttc       120
ttcgttgttg agcaaagcgg gctcgaggag gagatgatgc tgagcgggca cggcggcggg       180
aggcgcctgt tcacggcgtc gcagtggcag gagctggagc accaggcgct catcttcaaa       240
tacatggcct ccggcgcgcc cgtgccgcac gacctcgtcc tgccgctccg cctcgccacc       300
ggcgtcgaca ccgcgccctc cctcgccttc ccgccccagc cttcgccgtc gctggcgtac       360
tggggctgct atggcgcggg ggcgccgttc ggccgcaagg cggaggaccc ggagcccggg       420
cggtgccggc ggacggacgg caagaagtgg cgatgctcca gggaggccca ggagactcc        480
aagtactgcg agaagcacat ccaccgcggg aagagccgtt caagaaagcc tgtggaagtg       540
acctcccccg ccgcctaccg cccgtccgcg ttctccatct cgccgcctcg cgcggccgac       600
gcgccgccgc cgccgccggg cctcggccac ccgcagcagc agcatctccg ccacggcgct       660

```
ctctctccag caggccgcgc ccacgccgct ggcgctctcc agctccacct cgactcgagc      720
ctgcacgcgg cgtcgccgcc gccgtcctac cacaggtacg cccactccca cgctcactac      780
acgccgccgc cgccgccgtc gctctacgac tacgggcagt ccaaggagct tcgggaggcg      840
gcggagctca gcggcggca cttccacgcg ctcggggccg acctgagcct cgacaagccg       900
ctggccgacg ccggggccgc ggagaagccc ctgcggcgtt tcttcgacga gtggccgcgg      960
gagagaggcg acacgaggcc gtcgtgggcg ggggcggagg acgcgacgca gctctccatc     1020
tccatccccg cggcttcgcc ctcctctgac cacgctgcct ctgccgccgc gcgatgccac     1080
aacgatggga gtgatcggtg catctcctag ctgcaactgc aatgcaagcc tgcaaccgcg     1140
tggattgttg ttgattggtg tagtttccta gctgcaattc aagcctgcaa cagcgagcag     1200
tgagcagcaa atgcgtgggg agggcacgca gctcaggctg atgcgcaaaa tccgaagcga     1260
gtcaagcagc aataggactc taggtctatg atttgatctt cctttgtagc agtacgttac     1320
caaaatgtta gctcgttgtt gttcggtgtg acattttcgt tcaggttgct cc             1372
```

```
<210> SEQ ID NO 14
<211> LENGTH: 1440
<212> TYPE: DNA
<213> ORGANISM: Zea mays

<400> SEQUENCE: 14
```

```
gccaccaaga gccctccaac acacacctga cctccccttc cccctctct ccgccgcccg        60 ttccccgcgc ctccgcccgt acgtcccgtt cccggtcggc cggccggtcc aagggaggg      120 gaggaggagg ggcgcgggag tcggggcccg caccgatgct gagctcggca tcctcggccg     180
cgggggcggc catggggatg gcggcggcg ggtacgcgca ccagcccccg ccacagcgcg      240
cggtcttcac cgccgcgcag tgggcggagc tggagcagca ggcgctcatc tacaagtacc      300
tcatggccgg cgtccccgtc ccgcccgacc tcctcctccc cgtccgcccc ggccccgccg      360
ccgccttctc cttcgccggc cccgccgccg cgtcgccctt ctaccaccaa caccacccgt      420
ccctgagcta ctacgcctac tacggcaaga agctggaccc ggagccgtgg cggtgccgcc      480
gcaccgacgg caagaagtgg cggtgctcca aggaggcgca ccccgactcc aagtactgcg      540
agcgccacat gcaccgtggc cgcaaccgtt caagaaagcc tgtggaatcc aagaccgcct      600
cgtcgtcgtc gcccgcgcac ccgtcgccgc cccagctgtc caccgtcacc accaccgcgc      660
ctctcgagcc ccttgcagcg gcggggggca aggtccacgg cctgtccctc ggcggcggcg      720
ctgctggctc gtcgcacctc ggcgtcgatg cttcgaatgc tcactatcgt tatggtagca      780
acaggtaccc tctcggagct aaaccggacg gcggcgagtt gagcttcttc tcaggagcgt      840
catcggggaa caactcgagg ggtggcttca ccatcgactc tccatcagat aacaactcgt      900
ggcactccgc cctggcgtcc agcgtgcccc cgttcacgct gtcgacgaag agcggggact      960
ccggcctcct gccccggcgcc tacgcctcct actcccagtc ccactccac atggagccgc     1020 cgcgggagct cggggcaggtc accatcgcct cgctggcgca ggagcaggag cgccagcagc     1080
cgttcagtgg tgggatgctc gggaacgtga agcaggagaa ccagaaccag ccgctgcggc     1140
ccttcttcga cgagtggccc gggacgcggg cggactcgtg gccgcggag atggacggcg      1200 cgccgcgggc cggcaggacc tccttctcct cctccaccac ccagctctcc atctccatcc     1260
cgatgcccag atgtgagctg catctcagaa accagaactc ttaattctgt tcgctgcccg     1320
aatcatgctt gaccgaaact tgtttctgc aggcgactga cgaggaaccg tcgatcgggc      1380
ggccactaga cggtggacgc tcacgctcac tagtgcgctg tcgcctggag tggagatcga     1440
```

<210> SEQ ID NO 15
<211> LENGTH: 1173
<212> TYPE: DNA
<213> ORGANISM: Prunus persica

<400> SEQUENCE: 15

| | | | | | |
|---|---|---|---|---|---|
| atggactttc | acctcaagca | atggagaaac | cagcagcatg | agtcagagga | acaacattct | 60 |
| gcaaagatac | caaaacttca | ccttgagccc | catccacact | cagagccatc | tgggtatgct | 120 |
| ctccctctgt | ttgttcctga | gcccaacagc | aaaatgatca | gcaccctgtc | agcgttttct | 180 |
| gaatctacac | cagcatctgc | ctccaccaga | tttcccaaaa | tggggagcta | tttcagcttc | 240 |
| tcccagttgc | aggagcttga | gctgcaggct | tgatattca | ggtacatgtt | agctggtgct | 300 |
| gctgttcctc | ctgaacttct | tcagccaatc | aggaaaagcc | ttctccactc | tcctccatat | 360 |
| tttctccacc | accctcttca | acagtaccct | cattttcagc | ctgctttgtt | gcaatcaggg | 420 |
| tattggggaa | gagcagccat | ggatccgag | ccaacaaggt | gtagaaggac | agatggcaag | 480 |
| aaatggaggt | gttctagaga | tgtggtggct | ggtcagaagt | actgtgagcg | ccatgtgcac | 540 |
| cgtggcagaa | accgttcaag | aaagcctgtg | aagccacca | ctgctgctgc | tggtggtggt | 600 |
| ggtggaggga | caagtgatat | tgctaccaac | accaccacca | agacatcatc | tagtggggcc | 660 |
| cattttactc | tttctgggtc | atcatcatcc | ccttcaattg | atctgcttca | tctcaaccag | 720 |
| agttcctcag | agcccaaagc | tgagaatagg | agcctctttg | aaccccacag | tgaggtctcc | 780 |
| gggagtgcta | atccgacag | ccatgtcttg | cggcctttt | ttgatgactg | gccggggaag | 840 |
| ctccaagaac | tggacaatgc | acgaaccaat | gctggctcaa | tgaactctgc | caccagcctc | 900 |
| tccatttcga | tacggggaaa | ttcctcctcg | gatgtgtcac | tgaaattgtc | taccggcaat | 960 |
| ggagttgaga | cagggcgcct | ggacggccat | gctgagcgcg | agcagccaca | attgaattgg | 1020 |
| cctgccggat | ggggaacaaa | ccaaatggct | tccatgggag | gccgcttgc | ggaggccctt | 1080 |
| aggtcctcct | ccaactccaa | ttcctcacca | accagtgttc | tacatcagtt | gccccgcagc | 1140 |
| tccgcctcag | aaactagctt | tatcagcact | tga | | | 1173 |

<210> SEQ ID NO 16
<211> LENGTH: 1092
<212> TYPE: DNA
<213> ORGANISM: Glycine max

<400> SEQUENCE: 16

| | | | | | |
|---|---|---|---|---|---|
| atggacttcc | atctgaagca | atggagaaac | cagcacgagt | cagaggaaca | acattctaca | 60 |
| aagatgccaa | aacttctccc | tgaatcccat | caacaacaac | agccatcagc | ctctgcactc | 120 |
| cctttgtttg | tacctgaacc | caacagcagc | aaagtcagca | ccctattatt | tcccaggatg | 180 |
| gggagctact | tcagcttgtc | tcagtggcag | gagcttgagt | tgcaggcttt | gatattcagg | 240 |
| tacatgttgg | ctggtgctgc | tgttcctcct | gaactcctc | aaccaatcaa | gaaaagcctt | 300 |
| cttcattctc | cacactatta | cctccatcac | cctctccaac | attaccaacc | ttctgcttgg | 360 |
| tattggggta | gaggagcgat | ggatccggag | ccagggcggt | gccggagaac | cgacggcaag | 420 |
| aagtggcgct | gttcgaggga | cgtggtggct | ggcaaaagt | actgtgagcg | ccacatgcac | 480 |
| cgtggaagaa | accgttcaag | aaagcctgtg | aactaccca | caccaactag | tgctattaac | 540 |
| aattgtggtg | taactggagt | tggatcccta | ggaccaggtg | cttcatcatc | ttccatttgt | 600 |
| tcaccaccct | tagcttctgc | ttcattcaaa | tctccttttg | atcttcatct | tgatgaacgt | 660 |

| | |
|---|---|
| tcctctggga ccaagaatga agacgaagat catgtgggtg gggatggcag atcaggtgga | 720 |
| ggtggtggcc atatgctgag gcatttcttc gatgattggc cacgatcact ccaagactct | 780 |
| gacaacgttg aaaacaatgc tgctgctggc cgtagcctct ctatttcaat gcccggtgct | 840 |
| tcctcggatg tgtcattgaa attgtccacg ggctatggag aggactcggg cccaggaaat | 900 |
| gagaatgtaa gcctcgagcc agagcagctg cagttgaatt gggccggagg atgggcctcg | 960 |
| tctaatcaag tggcttcgat gggaggtcca cttgctgagg cactcagatc atctacttca | 1020 |
| acctcatctc ccactagtgt tttgcatcgt cacttgcctc gtggatctga gaccagcttt | 1080 |
| attagcacct ga | 1092 |

<210> SEQ ID NO 17
<211> LENGTH: 1155
<212> TYPE: DNA
<213> ORGANISM: Medicago truncatula

<400> SEQUENCE: 17

| | |
|---|---|
| atggactttc ctacgaaaca atggagaaac caacagcatg agtcagagaa acaacattcc | 60 |
| acaaagatgc caaaacttct tcaccctgct caatctcaat cccaatccca ttcccatcaa | 120 |
| caatcacctg cacttccttt gtttctacct caacccaaca ccaaagtcac caacttgtca | 180 |
| gattcagcat taccttccaa caacagattt cccagaatag aatgggaag ccatttcagc | 240 |
| ttatctcaat ggcaagaact tgagttacaa gctttgatat ttaggtacat gttggttggt | 300 |
| gcttctgttc ctcctgaact tcttcaacct atcaagaaaa gtcttcttca ttcatctcct | 360 |
| tatttccttc atcattatca acctacagca ttgttgcaaa gtgggtattg gggaagagga | 420 |
| gcaatggatc cagagccagg tcgttgccgg agaacagacg gtaaaaagtg cggtgtgcg | 480 |
| agggatgtgg tggctggaca aaagtactgt gaaagacaca tgcatcgtgg tagaaaccgt | 540 |
| tcaagaaagc ctgtggaact tcccacacca actagtaatg gcggtggatc tttctctgct | 600 |
| ttgtcttcta tttcttcaca gcctcttgtc acttcctcat tcaaatctcc ttttgatctt | 660 |
| cactttactg aacgctccac tgggaccaaa attgaagaga gagcttatg tgaaagcgat | 720 |
| gatcatgtgg gtggggatgg aagaccaggt gggcaaatgc taaggcattt cttttgacgat | 780 |
| tggccacgat cactgcaaga ctctgacaat gctgaaaaca atggtgggtc atcctccaca | 840 |
| tgtctctcaa tttcaatgcc aggaaataac aacacttctt cttcttcttc agatgtgtca | 900 |
| ttgaaattgt ccactggcta tggagaagaa ccatgtccaa gaaatgagaa tgtgggccta | 960 |
| gtacaaactg agcagcaaca acaacaactt caattgaatt ggatcggagg atggaattca | 1020 |
| ggtaatcaag tgtcttcaat ggaggaccca cttgctgagg cacttagatc atctacttca | 1080 |
| acttcttcac ctactagtgt tttacatcaa ttgccacgtt gttctggttc tcaaaccagc | 1140 |
| tacattagca cctaa | 1155 |

<210> SEQ ID NO 18
<211> LENGTH: 1134
<212> TYPE: DNA
<213> ORGANISM: Populus trichocarpa

<400> SEQUENCE: 18

| | |
|---|---|
| atggacttcc atctgaagca atggagaaac cagcatgagg agtcagggca acaaccctct | 60 |
| gcaaagatgc caaaactcct catggatccc catcaaccac aacaacatcc acactcatct | 120 |
| gggtctgctg ccttcccttt gtttctaccc gagcccagct gcaaaatag taacctgtca | 180 |
| gcatttcctg attcaaacac agctgcaaac accagacttc ctaagatcat ggggaattac | 240 |

-continued

```
tttagcctgg aacagtggca agagctagag ctgcaggctt tgatctacag attcatgtta      300
gccggtgcag ctattcctcc ggagctcctc caaccaatca agaaaaccct tcttcattct      360
cacccccctc catatttcct ccatcatcct cttcaattac attgctctta ttatcagcca      420
tcttggtatt ggggaagagc agccatggat ccggagccag gtcggtgccg agaacagat       480 gggaagaaat ggcggtgctc cagagacgtg gtggcagggc acaagtattg cgagcgccac      540
ttgcaccgtg gccgcaaccg ttcaagaaag cctgtggaaa atcccacacc tacaatatcc      600
actaacatca cttgcattgg tattggagaa ttggaccaaa ctaccttttc attgttttgt      660
ttttgcttta atcttcttgc tcacccttat tgcagctcca aaactgaaag caagggctta      720
attggaccac cacctccaaa tgaggttggt aacaggtctg atggccacat tctgtggcat      780
ttttttgatg actggccacg atccgttgat gaatccgaca atatgaatgc tggaagctca      840
atgaactctt taacctgcct ctccgtttca atgcctggaa actcaccagc atcagatgtg      900
tcattgaaat tgtccactgg gaataatatt gcagaggagg agccggagcc agtcccagcc      960
ccgatcccta gaggcaatac aagcaattgg gctgctgcag gatgggcac aaaaattaca      1020 aaccaggtgg tgacttcaat gggggggacct cttgctgagg cgctgaggtc ctccactacc     1080
aaactcatct cccacgaatg ttctgcacca gttatgtcgc cccactgttt ctga           1134
```

<210> SEQ ID NO 19
<211> LENGTH: 1143
<212> TYPE: DNA
<213> ORGANISM: Arabidopsis thaliana

<400> SEQUENCE: 19

```
atggacttgc aactgaaaca atggagaagt cagcagcaga atgagtcaga agaacaaggc       60
tctgctgcaa ctaagatatc aaactttttc tttgatcaga ttcagtccca aactgctact      120
tctgctgctg cggctcctct tcctctcttt gtccctgaac ccacttcttc ctcttctttc      180
tcttgcttct ctcctgactc ttctaattct tcttcttctt ccaggttcct caagatggga      240
aacttcttca gctgggcaca gtggcaagaa cttgagctac aagcactgat ctatagatac      300
atgttggctg gtgcttctgt tcctcaagag cttctcttac ctattaagaa aagtctcctc      360
catcaatctc ctatgcattt ccttcaccat cctcttcaac atagttttcc tcatcaccaa      420
ccttcttggt attggggaag aggagcaatg gatcctgagc agggaggtg taagagaact       480 gacggcaaga atggagatg ttcaagggat gttgtagcgg gccacaagta ttgtgaccgc       540
cacattcacc gtgaagaaa ccgttcaaga aagcctgtgg aaaccgccac aaccaccatc      600
acaacgacag ccacaacaac cgcatcttct tttgtcttag gtgaggagct tggtcatgga      660
ccaaacaaca accacttctt ctcctctggt tcatctcaac ctctccacct tagtcatcaa      720
caaagttgtt cttcagagat gaaacaagaa agcaacaaca acaagaggcc atatgaagct      780
aacagtggat tcagcaatgg aagatcagac gatggtcaca tcttgaggca tttctttgac      840
gattggccac gatcatcaga ctctacctcc agtccaatga gctcatccac ttgtcatctt      900
tcaatctcca tgcccggtaa caacacgtcc tcagatgttt ctctaaaact ttccacaggc      960
aatgaagaag aagaagagaa catgagaaat aacaacaatg agagggagca atgaattgg      1020 tggagcaatg gagggaatca ccacaacaat atgggaggac cattagctga ggctttgagg     1080
tcagcttctt cgacgtcaag tgttcttcat cagatgggaa tctctactca gttttttcat    1140
taa                                                                  1143
```

<210> SEQ ID NO 20
<211> LENGTH: 398
<212> TYPE: PRT
<213> ORGANISM: Arabidopsis thaliana

<400> SEQUENCE: 20

Met Asp Leu Gln Leu Lys Gln Trp Arg Ser Gln Gln Gln Gln His
1               5                   10                  15

Gln Thr Glu Ser Glu Glu Gln Pro Ser Ala Ala Lys Ile Pro Lys His
            20                  25                  30

Val Phe Asp Gln Ile His Ser His Thr Ala Thr Ser Thr Ala Leu Pro
        35                  40                  45

Leu Phe Thr Pro Glu Pro Thr Ser Ser Lys Leu Ser Ser Leu Ser Pro
    50                  55                  60

Asp Ser Ser Ser Arg Phe Pro Lys Met Gly Ser Phe Phe Ser Trp Ala
65                  70                  75                  80

Gln Trp Gln Glu Leu Glu Leu Gln Ala Leu Ile Tyr Arg Tyr Met Leu
                85                  90                  95

Ala Gly Ala Ala Val Pro Gln Glu Leu Leu Pro Ile Lys Lys Ser
            100                 105                 110

Leu Leu His Leu Ser Pro Ser Tyr Phe Leu His His Pro Leu Gln His
        115                 120                 125

Leu Pro His Tyr Gln Pro Ala Trp Tyr Leu Gly Arg Ala Ala Met Asp
    130                 135                 140

Pro Glu Pro Gly Arg Cys Arg Arg Thr Asp Gly Lys Lys Trp Arg Cys
145                 150                 155                 160

Ser Arg Asp Val Phe Ala Gly His Lys Tyr Cys Glu Arg His Met His
                165                 170                 175

Arg Gly Arg Asn Arg Ser Arg Lys Pro Val Glu Thr Pro Thr Thr Val
            180                 185                 190

Asn Ala Thr Ala Thr Ser Met Ala Ser Ser Val Ala Ala Ala Thr
        195                 200                 205

Thr Thr Thr Ala Thr Thr Thr Ser Thr Phe Ala Phe Gly Gly Gly Gly
    210                 215                 220

Gly Ser Glu Glu Val Val Gly Gln Gly Gly Ser Phe Phe Phe Ser Gly
225                 230                 235                 240

Ser Ser Asn Ser Ser Glu Leu Leu His Leu Ser Gln Ser Cys Ser
                245                 250                 255

Glu Met Lys Gln Glu Ser Asn Asn Met Asn Asn Lys Arg Pro Tyr Glu
            260                 265                 270

Ser His Ile Gly Phe Ser Asn Asn Arg Ser Asp Gly Gly His Ile Leu
        275                 280                 285

Arg Pro Phe Phe Asp Asp Trp Pro Arg Ser Ser Leu Gln Glu Ala Asp
    290                 295                 300

Asn Ser Ser Ser Pro Met Ser Ser Ala Thr Cys Leu Ser Ile Ser Met
305                 310                 315                 320

Pro Gly Asn Ser Ser Ser Asp Val Ser Leu Lys Leu Ser Thr Gly Asn
                325                 330                 335

Glu Glu Gly Ala Arg Ser Asn Asn Asn Gly Arg Asp Gln Gln Asn Met
            340                 345                 350

Ser Trp Trp Ser Gly Gly Gly Ser Asn His His His Asn Met Gly
        355                 360                 365

Gly Pro Leu Ala Glu Ala Leu Arg Ser Ser Ser Ser Ser Pro Thr
    370                 375                 380

Ser Val Leu His Gln Leu Gly Val Ser Thr Gln Ala Phe His
385                 390                 395

<210> SEQ ID NO 21
<211> LENGTH: 380
<212> TYPE: PRT
<213> ORGANISM: Arabidopsis thaliana

<400> SEQUENCE: 21

Met Asp Leu Gln Leu Lys Gln Trp Arg Ser Gln Gln Asn Glu Ser
1               5                   10                  15

Glu Glu Gln Gly Ser Ala Ala Thr Lys Ile Ser Asn Phe Phe Asp
                20                  25                  30

Gln Ile Gln Ser Gln Thr Ala Thr Ser Ala Ala Ala Pro Leu Pro
                35                  40                  45

Leu Phe Val Pro Glu Pro Thr Ser Ser Ser Phe Ser Cys Phe Ser
        50                  55                  60

Pro Asp Ser Ser Asn Ser Ser Ser Ser Arg Phe Leu Lys Met Gly
65                  70                  75                  80

Asn Phe Phe Ser Trp Ala Gln Trp Gln Glu Leu Glu Leu Gln Ala Leu
                85                  90                  95

Ile Tyr Arg Tyr Met Leu Ala Gly Ala Ser Val Pro Gln Glu Leu Leu
                100                 105                 110

Leu Pro Ile Lys Lys Ser Leu Leu His Gln Ser Pro Met His Phe Leu
                115                 120                 125

His His Pro Leu Gln His Ser Phe Pro His His Gln Pro Ser Trp Tyr
130                 135                 140

Trp Gly Arg Gly Ala Met Asp Pro Glu Pro Gly Arg Cys Lys Arg Thr
145                 150                 155                 160

Asp Gly Lys Lys Trp Arg Cys Ser Arg Asp Val Val Ala Gly His Lys
                165                 170                 175

Tyr Cys Asp Arg His Ile His Arg Gly Arg Asn Arg Ser Arg Lys Pro
                180                 185                 190

Val Glu Thr Ala Thr Thr Thr Ile Thr Thr Thr Ala Thr Thr Thr Ala
                195                 200                 205

Ser Ser Phe Val Leu Gly Glu Glu Leu Gly His Gly Pro Asn Asn Asn
210                 215                 220

His Phe Phe Ser Ser Gly Ser Ser Gln Pro Leu His Leu Ser His Gln
225                 230                 235                 240

Gln Ser Cys Ser Ser Glu Met Lys Gln Glu Ser Asn Asn Lys Arg
                245                 250                 255

Pro Tyr Glu Ala Asn Ser Gly Phe Ser Asn Gly Arg Ser Asp Asp Gly
                260                 265                 270

His Ile Leu Arg His Phe Phe Asp Asp Trp Pro Arg Ser Ser Asp Ser
                275                 280                 285

Thr Ser Ser Pro Met Ser Ser Thr Cys His Leu Ser Ile Ser Met
                290                 295                 300

Pro Gly Asn Asn Thr Ser Ser Asp Val Ser Leu Lys Leu Ser Thr Gly
305                 310                 315                 320

Asn Glu Glu Glu Glu Asn Met Arg Asn Asn Asn Glu Arg Glu
                325                 330                 335

Gln Met Asn Trp Trp Ser Asn Gly Gly Asn His His Asn Asn Met Gly
                340                 345                 350

Gly Pro Leu Ala Glu Ala Leu Arg Ser Ala Ser Ser Thr Ser Ser Val

```
            355                 360                 365
Leu His Gln Met Gly Ile Ser Thr Gln Val Phe His
    370                 375                 380

<210> SEQ ID NO 22
<211> LENGTH: 397
<212> TYPE: PRT
<213> ORGANISM: Oryza sativa

<400> SEQUENCE: 22

Met Met Met Met Ser Gly Arg Pro Ser Gly Ala Gly Gly Gly Arg
1               5                   10                  15

Tyr Pro Phe Thr Ala Ser Gln Trp Gln Glu Leu Glu His Gln Ala Leu
                20                  25                  30

Ile Tyr Lys Tyr Met Ala Ser Gly Thr Pro Ile Pro Ser Asp Leu Ile
            35                  40                  45

Leu Pro Leu Arg Arg Ser Phe Leu Leu Asp Ser Ala Leu Ala Thr Ser
    50                  55                  60

Pro Ser Leu Ala Phe Pro Pro Gln Pro Ser Leu Gly Trp Gly Cys Phe
65                  70                  75                  80

Gly Met Gly Phe Gly Arg Lys Ala Glu Asp Pro Glu Pro Gly Arg Cys
                85                  90                  95

Arg Arg Thr Asp Gly Lys Lys Trp Arg Cys Ser Lys Glu Ala Tyr Pro
            100                 105                 110

Asp Ser Lys Tyr Cys Glu Lys His Met His Arg Gly Lys Asn Arg Ser
        115                 120                 125

Arg Lys Pro Val Glu Met Ser Leu Ala Thr Pro Pro Pro Ser Ser
    130                 135                 140

Ser Ala Thr Ser Ala Ala Ser Asn Thr Ser Ala Gly Val Ala Pro Thr
145                 150                 155                 160

Thr Thr Thr Thr Ser Ser Pro Ala Pro Ser Tyr Ser Arg Pro Ala Pro
                165                 170                 175

His Asp Ala Ala Pro Tyr Gln Ala Leu Tyr Gly Gly Pro Tyr Ala Ala
            180                 185                 190

Ala Thr Ala Arg Thr Pro Ala Ala Ala Ala Tyr His Ala Gln Val Ser
        195                 200                 205

Pro Phe His Leu Gln Leu Asp Thr Thr His Pro His Pro Pro Ser
    210                 215                 220

Tyr Tyr Ser Met Asp His Lys Glu Tyr Ala Tyr Gly His Ala Thr Lys
225                 230                 235                 240

Glu Val His Gly Glu His Ala Phe Phe Ser Asp Gly Thr Glu Arg Glu
                245                 250                 255

His His His Ala Ala Gly His Gly Gln Trp Gln Phe Lys Gln Leu
            260                 265                 270

Gly Met Glu Pro Lys Gln Ser Thr Thr Pro Leu Phe Pro Gly Ala Gly
        275                 280                 285

Tyr Gly His Thr Ala Ala Ser Pro Tyr Ala Ile Asp Leu Ser Lys Glu
    290                 295                 300

Asp Asp Asp Glu Lys Glu Arg Arg Gln Gln Gln Gln Gln Gln Gln
305                 310                 315                 320

Gln His Cys Phe Leu Leu Gly Ala Asp Leu Arg Leu Glu Lys Pro Ala
                325                 330                 335

Gly His Asp His Ala Ala Ala Ala Gln Lys Pro Leu Arg His Phe Phe
            340                 345                 350
```

Asp Glu Trp Pro His Glu Lys Asn Ser Lys Gly Ser Trp Met Gly Leu
            355                 360                 365

Glu Gly Glu Thr Gln Leu Ser Met Ser Ile Pro Met Ala Ala Asn Asp
        370                 375                 380

Leu Pro Ile Thr Thr Thr Ser Arg Tyr His Asn Asp Asp
385                 390                 395

<210> SEQ ID NO 23
<211> LENGTH: 301
<212> TYPE: PRT
<213> ORGANISM: Oryza sativa

<400> SEQUENCE: 23

Met Met Ala Gly Gly Ser Gly Arg Cys Leu Phe Thr Ala Thr Gln
1               5                   10                  15

Trp Gln Glu Leu Glu His Gln Ala Leu Ile Tyr Lys Tyr Met Ala Ala
            20                  25                  30

Gly Ala Pro Val Pro Pro Asp Leu Leu His Leu Arg His Arg Ala
        35                  40                  45

Ala Ala Ala Ala Ala Ala Asp Val Asp Thr Val Pro Ser Leu Ala Phe
50                  55                  60

Pro Pro His His Leu Gly Trp Gly Cys Tyr Gly Ala Ala Ala Gln
65                  70                  75                  80

Tyr Gly Arg Arg Val Glu Asp Pro Glu Pro Gly Arg Cys Arg Arg Thr
            85                  90                  95

Asp Gly Lys Lys Trp Arg Cys Ser Arg Glu Ala Tyr Gly Glu Ser Lys
        100                 105                 110

Tyr Cys Glu Lys His Met His Arg Gly Lys Asn Arg Ser Arg Lys Pro
        115                 120                 125

Val Glu Met Pro Pro Ala Ala Ala Val Tyr Arg Pro Ser Ala
        130                 135                 140

Leu Ser Ile Ser Pro Pro His Asp Ala Asp Ala Pro Ser Tyr Gly
145                 150                 155                 160

Ala Gly Ala Gly Ala Pro Leu Gln Leu His Leu Asp Ser Phe His Ala
            165                 170                 175

Ser Thr Ser Pro Pro Ser Tyr His Arg Tyr Ala His Thr Ser Ser
        180                 185                 190

Ala Pro Leu Phe Pro Ser Ser Ala Ala Gly Tyr Gly Gly Gly Trp Ser
        195                 200                 205

Leu Ser Lys Glu His Cys Leu Thr Leu Gly Gly Ala Ala Ala Asp Leu
210                 215                 220

Ser Leu Asp Lys Pro Ala Asp His His His Asp Ala Thr Ser Ala Thr
225                 230                 235                 240

Thr Glu Lys Pro Leu Arg Arg Phe Phe Asp Glu Trp Pro Arg Ser Asp
            245                 250                 255

Asp Gly Arg Thr Pro Trp Asp Gly Thr Gln Leu Ser Ile Ser Ile Pro
        260                 265                 270

Thr Ala Ala Ala Ala Ser Pro Asp Leu Ala Ile Ala Gly Ala Ala Ser
        275                 280                 285

Arg Tyr His Ser Asn Gly Asp His Leu Arg Thr Ser Glu
        290                 295                 300

<210> SEQ ID NO 24
<211> LENGTH: 387
<212> TYPE: PRT
<213> ORGANISM: Oryza sativa

<400> SEQUENCE: 24

Met Ala Met Pro Phe Ala Ser Leu Ser Pro Ala Ala Asp His Arg Pro
1               5                   10                  15

Ser Phe Ile Phe Pro Phe Cys Arg Ser Ser Pro Leu Ser Ala Val Gly
            20                  25                  30

Glu Glu Ala Gln Gln His Met Met Gly Ala Arg Trp Ala Ala Ala Val
        35                  40                  45

Ala Arg Pro Pro Pro Phe Thr Ala Ala Gln Tyr Glu Leu Glu Gln
    50                  55                  60

Gln Ala Leu Ile Tyr Lys Tyr Leu Val Ala Gly Val Pro Val Pro Ala
65                  70                  75                  80

Asp Leu Leu Leu Pro Ile Arg Arg Gly Leu Asp Ser Leu Ala Ser Arg
                85                  90                  95

Phe Tyr His His Pro Val Leu Gly Tyr Gly Ser Tyr Phe Gly Lys Lys
                100                 105                 110

Leu Asp Pro Glu Pro Gly Arg Cys Arg Thr Asp Gly Lys Lys Trp
            115                 120                 125

Arg Cys Ser Lys Glu Ala Ala Pro Asp Ser Lys Tyr Cys Glu Arg His
130                 135                 140

Met His Arg Gly Arg Asn Arg Ser Arg Lys Pro Val Glu Ala Gln Leu
145                 150                 155                 160

Val Ala Pro His Ser Gln Pro Pro Ala Thr Ala Pro Ala Ala Val
                165                 170                 175

Thr Ser Thr Ala Phe Gln Asn His Ser Leu Tyr Pro Ala Ile Ala Asn
                180                 185                 190

Gly Gly Gly Ala Asn Gly Gly Gly Gly Gly Gly Gly Gly Gly Ser
            195                 200                 205

Ala Pro Gly Ser Phe Ala Leu Gly Ser Asn Thr Gln Leu His Met Asp
    210                 215                 220

Asn Ala Ala Ser Tyr Ser Thr Val Ala Ala Gly Ala Gly Asn Lys Asp
225                 230                 235                 240

Phe Arg Tyr Ser Ala Tyr Gly Val Arg Pro Leu Ala Asp Glu His Ser
                245                 250                 255

Pro Leu Ile Thr Gly Ala Met Asp Thr Ser Ile Asp Asn Ser Trp Cys
            260                 265                 270

Leu Leu Pro Ser Gln Thr Ser Thr Phe Ser Val Ser Ser Tyr Pro Met
                275                 280                 285

Leu Gly Asn Leu Ser Glu Leu Asp Gln Asn Thr Ile Cys Ser Leu Pro
    290                 295                 300

Lys Val Glu Arg Glu Pro Leu Ser Phe Phe Gly Ser Asp Tyr Val Thr
305                 310                 315                 320

Val Asp Ser Gly Lys Gln Glu Asn Gln Thr Leu Arg Pro Phe Phe Asp
                325                 330                 335

Glu Trp Pro Lys Ala Arg Asp Ser Trp Pro Asp Leu Ala Asp Asp Asn
            340                 345                 350

Ser Leu Ala Thr Phe Ser Ala Thr Gln Leu Ser Ile Ser Ile Pro Met
                355                 360                 365

Ala Thr Ser Asp Phe Ser Thr Thr Ser Ser Arg Ser His Asn Gly Ile
            370                 375                 380

Tyr Ser Arg
385

```
<210> SEQ ID NO 25
<211> LENGTH: 394
<212> TYPE: PRT
<213> ORGANISM: Oryza sativa

<400> SEQUENCE: 25
```

| | | | | | | | | | | | | | | | |
|---|---|---|---|---|---|---|---|---|---|---|---|---|---|---|---|
| Met | Ala | Met | Pro | Tyr | Ala | Ser | Leu | Ser | Pro | Ala | Val | Ala | Asp | His | Arg |
| 1 | | | | 5 | | | | | 10 | | | | | 15 | |
| Ser | Ser | Pro | Ala | Ala | Ala | Thr | Ala | Ser | Leu | Leu | Pro | Phe | Cys | Arg | Ser |
| | | | 20 | | | | | 25 | | | | | 30 | | |
| Thr | Pro | Leu | Ser | Ala | Gly | Gly | Gly | Val | Ala | Met | Gly | Glu | Asp | Ala | |
| | | | 35 | | | | 40 | | | | | 45 | | | |
| Pro | Met | Thr | Ala | Arg | Trp | Pro | Ala | Ala | Ala | Arg | Leu | Pro | Pro | | |
| | 50 | | | | | 55 | | | | 60 | | | | | |
| Phe | Thr | Ala | Ala | Gln | Tyr | Glu | Glu | Leu | Glu | Gln | Gln | Ala | Leu | Ile | Tyr |
| 65 | | | | | 70 | | | | 75 | | | | | 80 | |
| Lys | Tyr | Leu | Val | Ala | Gly | Val | Pro | Val | Pro | Pro | Asp | Leu | Val | Leu | Pro |
| | | | | 85 | | | | | 90 | | | | | 95 | |
| Ile | Arg | Arg | Gly | Leu | Asp | Ser | Leu | Ala | Ala | Arg | Phe | Tyr | Asn | His | Pro |
| | | | 100 | | | | | 105 | | | | | 110 | | |
| Ala | Leu | Gly | Tyr | Gly | Pro | Tyr | Phe | Gly | Lys | Lys | Leu | Asp | Pro | Glu | Pro |
| | | | 115 | | | | | 120 | | | | | 125 | | |
| Gly | Arg | Cys | Arg | Arg | Thr | Asp | Gly | Lys | Lys | Trp | Arg | Cys | Ser | Lys | Glu |
| | 130 | | | | | 135 | | | | | 140 | | | | |
| Ala | Ala | Pro | Asp | Ser | Lys | Tyr | Cys | Glu | Arg | His | Met | His | Arg | Gly | Arg |
| 145 | | | | | 150 | | | | | 155 | | | | | 160 |
| Asn | Arg | Ser | Arg | Lys | Pro | Val | Glu | Thr | Gln | Leu | Val | Ala | Gln | Ser | Gln |
| | | | | 165 | | | | | 170 | | | | | 175 | |
| Pro | Pro | Ser | Ser | Val | Val | Gly | Ser | Ala | Ala | Pro | Leu | Ala | Ala | Ala | |
| | | | 180 | | | | | 185 | | | | | 190 | | |
| Ser | Asn | Gly | Ser | Ser | Phe | Gln | Asn | His | Ser | Leu | Tyr | Pro | Ala | Ile | Ala |
| | | | 195 | | | | | 200 | | | | | 205 | | |
| Gly | Ser | Asn | Gly | Gly | Gly | Gly | Arg | Asn | Met | Pro | Ser | Ser | Phe | Gly | |
| | | 210 | | | | | 215 | | | | | 220 | | | |
| Ser | Ala | Leu | Gly | Ser | Gln | Leu | His | Met | Asp | Asn | Ala | Ala | Pro | Tyr | Ala |
| 225 | | | | | 230 | | | | | 235 | | | | | 240 |
| Ala | Val | Gly | Gly | Gly | Thr | Gly | Lys | Asp | Leu | Arg | Tyr | Thr | Ala | Tyr | Gly |
| | | | | 245 | | | | | 250 | | | | | 255 | |
| Thr | Arg | Ser | Leu | Ala | Asp | Glu | Gln | Ser | Gln | Leu | Ile | Thr | Glu | Ala | Ile |
| | | | 260 | | | | | 265 | | | | | 270 | | |
| Asn | Thr | Ser | Ile | Glu | Asn | Pro | Trp | Arg | Leu | Leu | Pro | Ser | Gln | Asn | Ser |
| | | 275 | | | | | 280 | | | | | 285 | | | |
| Pro | Phe | Pro | Leu | Ser | Ser | Tyr | Ser | Gln | Leu | Gly | Ala | Leu | Ser | Asp | Leu |
| | 290 | | | | | 295 | | | | | 300 | | | | |
| Gly | Gln | Asn | Thr | Pro | Ser | Ser | Leu | Ser | Lys | Val | Gln | Arg | Gln | Pro | Leu |
| 305 | | | | | 310 | | | | | 315 | | | | | 320 |
| Ser | Phe | Phe | Gly | Asn | Asp | Tyr | Ala | Ala | Val | Asp | Ser | Val | Lys | Gln | Glu |
| | | | | 325 | | | | | 330 | | | | | 335 | |
| Asn | Gln | Thr | Leu | Arg | Pro | Phe | Phe | Asp | Glu | Trp | Pro | Lys | Gly | Arg | Asp |
| | | | 340 | | | | | 345 | | | | | 350 | | |
| Ser | Trp | Ser | Asp | Leu | Ala | Asp | Glu | Asn | Ala | Asn | Leu | Ser | Ser | Phe | Ser |
| | | 355 | | | | | 360 | | | | | 365 | | | |
| Gly | Thr | Gln | Leu | Ser | Ile | Ser | Ile | Pro | Met | Ala | Ser | Ser | Asp | Phe | Ser |
| | | 370 | | | | | 375 | | | | | 380 | | | |

```
Ala Ala Ser Ser Arg Ser Thr Asn Gly Asp
385                 390
```

<210> SEQ ID NO 26
<211> LENGTH: 408
<212> TYPE: PRT
<213> ORGANISM: Zea mays

<400> SEQUENCE: 26

```
Met Ala Met Pro Tyr Ala Ser Leu Ser Pro Ala Gly Ala Ala Asp His
1               5                   10                  15

Arg Ser Ser Thr Ala Thr Ala Ser Leu Val Pro Phe Cys Arg Ser Thr
            20                  25                  30

Pro Leu Ser Ala Gly Gly Gly Leu Gly Glu Glu Asp Ala Gln Ala Ser
        35                  40                  45

Ala Arg Trp Pro Ala Ala Arg Pro Val Val Pro Phe Thr Pro Ala Gln
    50                  55                  60

Tyr Gln Glu Leu Glu Gln Gln Ala Leu Ile Tyr Lys Tyr Leu Val Ala
65                  70                  75                  80

Gly Val Pro Val Pro Pro Asp Leu Val Val Pro Ile Arg Arg Gly Leu
                85                  90                  95

Asp Ser Leu Ala Thr Arg Phe Tyr Gly Gln Pro Thr Leu Gly Tyr Gly
            100                 105                 110

Pro Tyr Leu Gly Arg Lys Leu Asp Pro Glu Pro Gly Arg Cys Arg Arg
        115                 120                 125

Thr Asp Gly Lys Lys Trp Arg Cys Ser Lys Glu Ala Ala Pro Asp Ser
    130                 135                 140

Lys Tyr Cys Glu Arg His Met His Arg Gly Arg Asn Arg Ser Arg Lys
145                 150                 155                 160

Pro Val Glu Thr Gln Leu Ala Pro Gln Ser Gln Pro Pro Ala Ala Ala
                165                 170                 175

Ala Val Ser Ala Ala Pro Pro Leu Ala Ala Ala Ala Ala Ala Ala Thr
            180                 185                 190

Asn Gly Ser Gly Phe Gln Asn His Ser Leu Tyr Pro Ala Ile Ala Gly
        195                 200                 205

Ser Thr Gly Gly Gly Gly Val Gly Gly Ser Gly Asn Ile Ser Ser
    210                 215                 220

Pro Phe Ser Ser Ser Met Gly Gly Ser Ser Gln Leu His Met Asp Ser
225                 230                 235                 240

Val Ala Ser Tyr Ser Tyr Ala Ala Leu Gly Gly Gly Thr Ala Lys Asp
                245                 250                 255

Leu Arg Tyr Asn Ala Tyr Gly Ile Arg Ser Leu Ala Asp Glu His Asn
            260                 265                 270

Gln Leu Ile Ala Glu Ala Ile Asp Ser Ser Ile Glu Ser Gln Arg Arg
        275                 280                 285

Leu Pro Ser Ser Ser Phe Pro Leu Ser Ser Tyr Pro His Leu Gly Ala
    290                 295                 300

Leu Gly Asp Leu Gly Gly Gln Asn Ser Thr Val Ser Ser Leu Pro Lys
305                 310                 315                 320

Met Glu Lys Gln Gln Pro Pro Ser Ser Phe Leu Gly Asn Asp Thr Gly
                325                 330                 335

Ala Gly Met Ala Met Gly Ser Ala Ser Ala Lys Gln Glu Gly Gln Thr
            340                 345                 350

Leu Arg His Phe Phe Asp Glu Trp Pro Lys Ala Arg Asp Ser Trp Pro
        355                 360                 365
```

Gly Leu Ser Asp Glu Thr Ala Ser Leu Ala Ser Ser Pro Pro Ala Thr
        370                 375                 380

Gln Leu Ser Met Ser Ile Pro Met Ala Ser Ser Asp Phe Ser Val Ala
385                 390                 395                 400

Ser Ser Gln Ser Pro Asn Asp Asp
                405

<210> SEQ ID NO 27
<211> LENGTH: 400
<212> TYPE: PRT
<213> ORGANISM: Zea mays

<400> SEQUENCE: 27

Met Met Met Met Ser Gly Arg Ala Gly Gly Ala Thr Ala Gly
1               5                   10                  15

Arg Tyr Pro Phe Thr Ala Ser Gln Trp Gln Glu Leu Glu His Gln Ala
                20                  25                  30

Leu Ile Tyr Lys Cys Leu Ala Ser Gly Lys Pro Ile Pro Ser Tyr Leu
            35                  40                  45

Met Pro Pro Leu Arg Arg Ile Leu Asp Ser Ala Leu Ala Thr Ser Pro
50                  55                  60

Ser Leu Ala Tyr Pro Pro Gln Pro Ser Leu Gly Trp Gly Cys Phe Gly
65                  70                  75                  80

Met Gly Phe Thr Arg Lys Ala Asp Glu Asp Pro Glu Pro Gly Arg Cys
                85                  90                  95

Arg Arg Thr Asp Gly Lys Lys Trp Arg Cys Ser Lys Glu Ala Tyr Pro
            100                 105                 110

Asp Ser Lys Tyr Cys Glu Lys His Met His Arg Gly Lys Asn Arg Ser
        115                 120                 125

Arg Lys Pro Val Glu Met Ser Leu Ala Thr Pro Ala Pro Ala Pro Ala
    130                 135                 140

Pro Ala Ala Ala Thr Thr Ala Thr Ala Thr Ser Ser Pro Ala Pro Ser
145                 150                 155                 160

Tyr His Arg Pro Ala His Asp Ala Thr Pro Ser Pro Tyr His Ala Leu
                165                 170                 175

Tyr Gly Gly Gly Gly Gly Gly Gly Ser Pro Tyr Ser Ala Ser Ala
            180                 185                 190

Arg Pro Gly Ala Thr Gly Gly Gly Ala Tyr His His Ala Gln His
        195                 200                 205

Val Ser Pro Phe His Leu His Leu Glu Thr Thr His Pro His Pro Pro
    210                 215                 220

Pro Pro Tyr Asn Tyr Ser Ala Asp Gln Arg Asp Tyr Ala Tyr Gly His
225                 230                 235                 240

Ala Ala Ala Lys Glu Val Gly Glu His Ala Phe Phe Ser Asp Gly Ala
                245                 250                 255

Gly Glu Arg Val Asp Arg Gln Ala Ala Gly Gln Trp Gln Phe Arg
            260                 265                 270

Gln Leu Gly Val Glu Thr Lys Pro Gly Pro Thr Pro Leu Phe Pro Val
        275                 280                 285

Ala Gly Tyr Gly His Gly Ala Ala Ser Pro Tyr Gly Val Glu Leu Gly
    290                 295                 300

Lys Asp Asp Asp Glu Gln Glu Glu Arg Arg Gln His Cys Phe Val
305                 310                 315                 320

Leu Gly Ala Asp Leu Arg Leu Glu Arg Pro Ser Ser Gly His Gly His

```
                           325                 330                 335
Gly His Gly His Asp His Asp Ala Ala Ala Gln Lys Pro Leu
                   340                 345                 350

Arg Pro Phe Phe Asp Glu Trp Pro His Gln Lys Gly Asp Lys Ala Gly
                   355                 360                 365

Ser Trp Met Gly Leu Asp Gly Glu Thr Gln Leu Ser Met Ser Ile Pro
370                 375                 380

Met Ala Ala Thr Asp Leu Pro Val Thr Ser Arg Phe Arg Asn Asp Glu
385                 390                 395                 400

<210> SEQ ID NO 28
<211> LENGTH: 374
<212> TYPE: PRT
<213> ORGANISM: Zea mays

<400> SEQUENCE: 28

Met Gly Met Ala Met Pro Phe Ala Ser Pro Ser Pro Ala Ala Asp His
1               5                   10                  15

Arg Pro Ser Ser Leu Leu Pro Phe Cys Arg Ala Ala Pro Leu Ser Ala
                20                  25                  30

Ala Gly Glu Asp Ala Ala Gln Gln His Ala Met Ser Gly Arg Trp Ala
            35                  40                  45

Ala Arg Pro Ala Leu Phe Thr Ala Ala Gln Tyr Glu Glu Leu Glu His
        50                  55                  60

Gln Ala Leu Ile Tyr Lys Tyr Leu Val Ala Gly Val Pro Val Pro Pro
65                  70                  75                  80

Asp Leu Leu Leu Pro Leu Arg Arg Gly Phe Val Phe His Gln Pro Pro
                85                  90                  95

Ala Leu Gly Tyr Gly Pro Tyr Phe Gly Lys Lys Val Asp Pro Glu Pro
            100                 105                 110

Gly Arg Cys Arg Arg Thr Asp Gly Lys Lys Trp Arg Cys Ser Lys Glu
        115                 120                 125

Ala Ala Pro Asp Ser Lys Tyr Cys Glu Arg His Met His Arg Gly Arg
130                 135                 140

Asn Arg Ser Arg Lys Pro Val Glu Ala Gln Leu Ala Pro Pro His
145                 150                 155                 160

Ala Gln Pro Pro Gln Gln Gln Gln Ala Pro Ala Pro Ala Ala Gly Phe
                165                 170                 175

Gln Asn His Ser Leu Tyr Pro Ser Ile Leu Asn Gly Asn Gly Gly Gly
            180                 185                 190

Gly Leu Gly Ala Gly Ala Gly Gly Thr Phe Gly Leu Gly Pro Thr
        195                 200                 205

Ser Gln Leu His Met Asp Ser Ala Ala Ala Tyr Ala Thr Ala Ala Gly
210                 215                 220

Gly Gly Ser Lys Tyr Leu Arg Tyr Ser Ala Tyr Gly Val Lys Ser Leu
225                 230                 235                 240

Ser Asp Glu His Ser Thr Leu Leu Ser Gly Gly Met Asp Pro Ser Met
                245                 250                 255

Met Asp Asn Ser Trp Arg Leu Leu Pro Ser Gln Asn Asn Thr Phe Gln
            260                 265                 270

Ala Thr Ser Tyr Pro Val Phe Gly Thr Leu Ser Gly Leu Asp Glu Ser
        275                 280                 285

Thr Ile Ala Ser Leu Pro Lys Thr Gln Arg Glu Pro Leu Ser Phe Phe
290                 295                 300
```

```
Gly Ser Asp Phe Val Thr Ala Ala Lys Gln Glu Asn Gln Thr Leu Arg
305                 310                 315                 320

Pro Phe Asp Glu Trp Pro Lys Ser Arg Asp Ser Trp Pro Glu Leu
            325                 330                 335

Gly Glu Asp Gly Ser Leu Gly Phe Ser Ala Thr Gln Leu Ser Ile Ser
            340                 345                 350

Ile Pro Met Ala Thr Ser Asp Phe Ser Asn Thr Ser Ser Arg Ser Pro
            355                 360                 365

Gly Gly Ile Pro Ser Arg
            370

<210> SEQ ID NO 29
<211> LENGTH: 380
<212> TYPE: PRT
<213> ORGANISM: Zea mays

<400> SEQUENCE: 29

Met Ala Met Pro Phe Ala Ser Leu Ser Pro Ala Ala Asp His Arg Pro
1               5                   10                  15

Ser Ser Leu Leu Pro Tyr Cys Arg Ala Ala Pro Leu Ser Ala Val Gly
            20                  25                  30

Glu Asp Ala Ala Ala Gln Ala Gln Gln Gln Gln Gln His Ala Met
        35                  40                  45

Ser Gly Arg Trp Ala Ala Arg Pro Pro Ala Leu Phe Thr Ala Ala Gln
50                  55                  60

Tyr Glu Glu Leu Glu His Gln Ala Leu Ile Tyr Lys Tyr Leu Val Ala
65                  70                  75                  80

Gly Val Pro Val Pro Pro Asp Leu Leu Leu Pro Leu Arg Arg Gly Phe
                85                  90                  95

Val Tyr His Gln Pro Ala Leu Gly Tyr Gly Pro Tyr Phe Gly Lys Lys
            100                 105                 110

Val Asp Pro Glu Pro Gly Arg Cys Arg Arg Thr Asp Gly Lys Lys Trp
        115                 120                 125

Arg Cys Ser Lys Glu Ala Ala Pro Asp Ser Lys Tyr Cys Glu Arg His
    130                 135                 140

Met His Arg Gly Arg Asn Arg Ser Arg Lys Pro Val Glu Ala Gln Leu
145                 150                 155                 160

Val Pro Pro His Ala Gln Pro Gln Gln Gln Ala Pro Ala Pro Thr
                165                 170                 175

Ala Gly Phe Gln Ser His Pro Met Tyr Pro Ser Ile Leu Ala Gly Asn
            180                 185                 190

Gly Gly Gly Gly Gly Val Gly Gly Ala Gly Gly Gly Thr Phe
        195                 200                 205

Gly Leu Gly Pro Thr Ser Gln Leu Arg Met Asp Ser Ala Ala Ala Tyr
    210                 215                 220

Ala Thr Ala Ala Asp Gly Gly Ser Lys Asp Leu Arg Tyr Ser Ala Tyr
225                 230                 235                 240

Gly Val Lys Ser Leu Ser Asp Glu His Ser Gln Leu Leu Pro Gly Gly
                245                 250                 255

Gly Gly Gly Met Asp Ala Ser Met Asp Asn Ser Trp Arg Leu Leu Pro
            260                 265                 270

Ser Gln Thr Ala Ala Thr Phe Gln Ala Thr Ser Tyr Pro Leu Phe Gly
        275                 280                 285

Ala Leu Ser Gly Leu Asp Glu Ser Thr Ile Ala Ser Leu Pro Lys Thr
290                 295                 300
```

```
Gln Arg Glu Pro Leu Ser Phe Phe Gly Ser Asp Phe Val Thr Pro Lys
305                 310                 315                 320

Gln Glu Asn Gln Thr Leu Arg Pro Phe Phe Asp Glu Trp Pro Lys Ser
            325                 330                 335

Arg Asp Ser Trp Pro Glu Leu Asn Glu Asp Asn Ser Leu Gly Ser Ser
        340                 345                 350

Ala Thr Gln Leu Ser Thr Ser Ile Pro Met Ala Pro Ser Asp Phe Asn
            355                 360                 365

Thr Ser Ser Arg Ser Pro Asn Gly Ile Pro Ser Arg
        370                 375                 380

<210> SEQ ID NO 30
<211> LENGTH: 321
<212> TYPE: PRT
<213> ORGANISM: Zea mays

<400> SEQUENCE: 30

Met Met Leu Ser Gly His Gly Gly Arg Arg Leu Phe Thr Ala Ser
1               5                   10                  15

Gln Trp Gln Glu Leu Glu His Gln Ala Leu Ile Phe Lys Tyr Met Ala
            20                  25                  30

Ser Gly Ala Pro Val Pro His Asp Leu Val Leu Pro Leu Arg Leu Ala
        35                  40                  45

Thr Gly Val Asp Thr Ala Pro Ser Leu Ala Phe Pro Pro Gln Pro Ser
    50                  55                  60

Pro Ser Leu Ala Tyr Trp Gly Cys Tyr Gly Ala Gly Ala Pro Phe Val
65                  70                  75                  80

Gly Arg Lys Ala Ala Glu Asp Thr Glu Pro Gly Arg Cys Arg Arg Thr
                85                  90                  95

Asp Gly Lys Lys Trp Arg Cys Ser Arg Glu Ala His Gly Asp Ser Lys
            100                 105                 110

Tyr Cys Glu Lys His Ile His Arg Gly Lys Ser Arg Ser Arg Lys Pro
        115                 120                 125

Val Glu Val Thr Ser Ser Pro Ala Ala Gly Ala Ala Ala Ala Tyr Arg
    130                 135                 140

Pro Ser Ala Ile Ser Thr Ile Ser Pro Pro Arg Ala Ala Asp Ala Pro
145                 150                 155                 160

Pro Pro Ser Leu Ala Tyr Pro Gln Gln His Leu Leu His Gly Ala Ser
                165                 170                 175

Ser Ser Ala Ala Ala Arg Ala Pro Ala Gly Ala Leu Gln Leu His Leu
            180                 185                 190

Asp Ala Ser Leu His Ala Ala Ala Ser Pro Ser Pro Pro Pro Ser
        195                 200                 205

Tyr His Arg Tyr Ala His Tyr Thr Pro Pro Ala Ser Ser Leu Phe Pro
    210                 215                 220

Gly Gly Gly Tyr Gly Tyr Asp Tyr Asp Tyr Gly Gln Ser Lys Glu Leu
225                 230                 235                 240

Arg Arg Arg His Phe His Ala Leu Gly Ala Asp Leu Ser Leu Asp Lys
                245                 250                 255

Pro Leu Pro Glu Pro Asp Thr Gly Ser Asp Glu Lys Gln Pro Leu Arg
            260                 265                 270

Arg Phe Phe Asp Glu Trp Pro Arg Glu Ser Gly Asp Met Ala Ala Asp
        275                 280                 285

Asp Ala Thr Gln Leu Ser Ile Ser Ile Pro Ala Ala Ser Pro Ser Asp
```

```
            290                 295                 300
Leu Ala Ala Thr Ser Ala Ser Ala Ala Ala Arg Phe His Asn Gly
305                 310                 315                 320

Glu

<210> SEQ ID NO 31
<211> LENGTH: 363
<212> TYPE: PRT
<213> ORGANISM: Zea mays

<400> SEQUENCE: 31

Met Met Met Met Ser Gly Arg Ala Ala Thr Ala Gly Arg Tyr Pro Phe
1               5                   10                  15

Thr Ala Ser Gln Trp Gln Glu Leu Glu His Gln Ala Leu Ile Tyr Lys
                20                  25                  30

Cys Leu Ala Ser Gly Lys Pro Ile Pro Ser Tyr Leu Met Pro Pro Leu
            35                  40                  45

Arg Arg Ile Leu Asp Ser Ala Leu Ala Thr Ser Pro Ser Leu Ala Ala
50                  55                  60

Phe Gln Pro Gln Pro Ser Leu Gly Trp Gly Gly Cys Phe Gly Met Gly
65                  70                  75                  80

Phe Ser Arg Lys Pro Ala Asp Glu Asp Pro Glu Pro Gly Arg Cys Arg
                85                  90                  95

Arg Thr Asp Gly Lys Lys Trp Arg Cys Ser Lys Glu Ala Tyr Pro Asp
            100                 105                 110

Ser Lys Tyr Cys Glu Lys His Met His Arg Gly Lys Asn Arg Ser Arg
        115                 120                 125

Lys Pro Val Glu Met Ser Leu Ala Thr Pro Ala Pro Pro Ala Ser Ser
130                 135                 140

Ala Ala Thr Thr Ser Thr Ser Pro Ala Pro Ser Tyr His Arg Pro Ala
145                 150                 155                 160

Pro Ala Ala His Asp Ala Val Pro Tyr His Ala Pro Tyr Gly Ala Ala
                165                 170                 175

Tyr His His Thr Gln Thr Gln Val Met Ser Pro Phe His Leu His Leu
            180                 185                 190

Glu Thr Thr His Pro His Pro Pro Pro Pro Pro Tyr Tyr Tyr Ala
        195                 200                 205

Asp Gln Arg Asp Tyr Ala Tyr Gly Lys Glu Val Gly Glu Arg Ala Phe
210                 215                 220

Phe Ser Asp Gly Ala Gly Glu Arg Asp Arg Gln Gln Ala Ala Gly
225                 230                 235                 240

Gln Trp Gln Phe Lys Gln Leu Gly Thr Met Glu Ala Thr Lys Pro Cys
                245                 250                 255

Pro Thr Pro Thr Pro Leu Leu Pro Ala Ala Gly Tyr Gly Val Gly Gln
            260                 265                 270

Ala Lys Glu Asp Glu Glu Glu Thr Arg Arg Gln Gln Gln His
        275                 280                 285

Cys Phe Val Leu Gly Ala Asp Leu Arg Leu Ala Glu Arg Pro Ser Gly
290                 295                 300

Ala His Asp Asp Ala Ala Gln Lys Pro Leu Arg His Phe Phe Asp Glu
305                 310                 315                 320

Trp Pro His Glu Lys Gly Ser Lys Ala Gly Trp Trp Ile Gly Gly Leu
                325                 330                 335

Asp Gly Glu Thr Thr Gln Leu Ser Met Ser Ile Pro Met Ala Ala Ala
```

```
                340             345             350
Ala Asp Leu Pro Val Thr Ser Arg Tyr Arg Thr
        355                 360

<210> SEQ ID NO 32
<211> LENGTH: 318
<212> TYPE: PRT
<213> ORGANISM: Zea mays

<400> SEQUENCE: 32

Met Met Leu Ser Gly His Gly Gly Arg Arg Leu Phe Thr Ala Ser
1               5                   10                  15

Gln Trp Gln Glu Leu Glu His Gln Ala Leu Ile Phe Lys Tyr Met Ala
            20                  25                  30

Ser Gly Ala Pro Val Pro His Asp Leu Val Leu Pro Leu Arg Leu Ala
        35                  40                  45

Thr Gly Val Asp Thr Ala Pro Ser Leu Ala Phe Pro Pro Gln Pro Ser
    50                  55                  60

Pro Ser Leu Ala Tyr Trp Gly Cys Tyr Gly Ala Gly Ala Pro Phe Gly
65                  70                  75                  80

Arg Lys Ala Glu Asp Pro Glu Pro Gly Arg Cys Arg Thr Asp Gly
                85                  90                  95

Lys Lys Trp Arg Cys Ser Arg Glu Ala His Gly Asp Ser Lys Tyr Cys
            100                 105                 110

Glu Lys His Ile His Arg Gly Lys Ser Arg Ser Arg Lys Pro Val Glu
        115                 120                 125

Val Thr Ser Pro Ala Ala Tyr Arg Pro Ser Ala Phe Ser Ile Ser Pro
    130                 135                 140

Pro Arg Ala Ala Asp Ala Pro Pro Pro Gly Leu Gly His Pro
145                 150                 155                 160

Gln Gln Gln His Leu Arg His Gly Ala Leu Ser Pro Ala Gly Arg Ala
                165                 170                 175

His Ala Ala Gly Ala Leu Gln Leu His Leu Asp Ser Ser Leu His Ala
            180                 185                 190

Ala Ser Pro Pro Ser Tyr His Arg Tyr Ala His Ser His Ala His
        195                 200                 205

Tyr Thr Pro Pro Pro Pro Ser Leu Tyr Asp Tyr Gly Gln Ser Lys
    210                 215                 220

Glu Leu Arg Glu Ala Ala Glu Leu Arg Arg His Phe His Ala Leu
225                 230                 235                 240

Gly Ala Asp Leu Ser Leu Asp Lys Pro Leu Ala Asp Ala Gly Ala Ala
                245                 250                 255

Glu Lys Pro Leu Arg Arg Phe Phe Asp Glu Trp Pro Arg Glu Arg Gly
            260                 265                 270

Asp Thr Arg Pro Ser Trp Ala Gly Ala Glu Asp Ala Thr Gln Leu Ser
        275                 280                 285

Ile Ser Ile Pro Ala Ala Ser Pro Ser Ser Asp His Ala Ala Ser Ala
    290                 295                 300

Ala Ala Arg Cys His Asn Asp Gly Ser Asp Arg Cys Ile Ser
305                 310                 315

<210> SEQ ID NO 33
<211> LENGTH: 382
<212> TYPE: PRT
<213> ORGANISM: Zea mays
```

<400> SEQUENCE: 33

```
Met Leu Ser Ser Ala Ser Ala Ala Gly Ala Ala Met Gly Met Gly
1               5                   10                  15

Gly Gly Gly Tyr Ala His Gln Pro Pro Gln Arg Ala Val Phe Thr
                20                  25                  30

Ala Ala Gln Trp Ala Glu Leu Glu Gln Gln Ala Leu Ile Tyr Lys Tyr
            35                  40                  45

Leu Met Ala Gly Val Pro Val Pro Pro Asp Leu Leu Leu Pro Val Arg
    50                  55                  60

Pro Gly Pro Ala Ala Ala Phe Ser Phe Ala Gly Pro Ala Ala Ala Ser
65                  70                  75                  80

Pro Phe Tyr His Gln His His Pro Ser Leu Ser Tyr Tyr Ala Tyr Tyr
                85                  90                  95

Gly Lys Lys Leu Asp Pro Glu Pro Trp Arg Cys Arg Thr Asp Gly
                100             105                 110

Lys Lys Trp Arg Cys Ser Lys Glu Ala His Pro Asp Ser Lys Tyr Cys
            115                 120                 125

Glu Arg His Met His Arg Gly Arg Asn Arg Ser Arg Lys Pro Val Glu
    130                 135                 140

Ser Lys Thr Ala Ser Ser Ser Pro Ala His Pro Ser Pro Pro Gln
145                 150                 155                 160

Leu Ser Thr Val Thr Thr Thr Ala Pro Leu Glu Pro Leu Ala Ala Ala
                165                 170                 175

Gly Gly Lys Val His Gly Leu Ser Leu Gly Gly Ala Ala Gly Ser
                180                 185                 190

Ser His Leu Gly Val Asp Ala Ser Asn Ala His Tyr Arg Tyr Gly Ser
    195                 200                 205

Asn Arg Tyr Pro Leu Gly Ala Lys Pro Asp Gly Glu Leu Ser Phe
    210                 215                 220

Phe Ser Gly Ala Ser Ser Gly Asn Asn Ser Arg Gly Gly Phe Thr Ile
225                 230                 235                 240

Asp Ser Pro Ser Asp Asn Asn Ser Trp His Ser Ala Leu Ala Ser Ser
                245                 250                 255

Val Pro Pro Phe Thr Leu Ser Thr Lys Ser Gly Asp Ser Gly Leu Leu
    260                 265                 270

Pro Gly Ala Tyr Ala Ser Tyr Ser Gln Ser His Ser His Met Glu Pro
        275                 280                 285

Pro Arg Glu Leu Gly Gln Val Thr Ile Ala Ser Leu Ala Gln Glu Gln
    290                 295                 300

Glu Arg Gln Gln Pro Phe Ser Gly Gly Met Leu Gly Asn Val Lys Gln
305                 310                 315                 320

Glu Asn Gln Asn Gln Pro Leu Arg Pro Phe Phe Asp Glu Trp Pro Gly
                325                 330                 335

Thr Arg Ala Asp Ser Trp Pro Pro Glu Met Asp Gly Ala Pro Arg Ala
            340                 345                 350

Gly Arg Thr Ser Phe Ser Ser Ser Thr Thr Gln Leu Ser Ile Ser Ile
        355                 360                 365

Pro Met Pro Arg Cys Glu Leu His Leu Arg Asn Gln Asn Ser
        370                 375                 380
```

<210> SEQ ID NO 34
<211> LENGTH: 390
<212> TYPE: PRT
<213> ORGANISM: Prunus persica

<400> SEQUENCE: 34

```
Met Asp Phe His Leu Lys Gln Trp Arg Asn Gln Gln His Glu Ser Glu
1               5                   10                  15

Glu Gln His Ser Ala Lys Ile Pro Lys Leu His Leu Glu Pro His Pro
            20                  25                  30

His Ser Glu Pro Ser Gly Tyr Ala Leu Pro Leu Phe Val Pro Glu Pro
        35                  40                  45

Asn Ser Lys Met Ile Ser Thr Leu Ser Ala Phe Ser Glu Ser Thr Pro
    50                  55                  60

Ala Ser Ala Ser Thr Arg Phe Pro Lys Met Gly Ser Tyr Phe Ser Phe
65                  70                  75                  80

Ser Gln Leu Gln Glu Leu Glu Leu Gln Ala Leu Ile Phe Arg Tyr Met
                85                  90                  95

Leu Ala Gly Ala Ala Val Pro Pro Glu Leu Leu Gln Pro Ile Arg Lys
            100                 105                 110

Ser Leu Leu His Ser Pro Pro Tyr Phe Leu His Pro Leu Gln Gln
        115                 120                 125

Tyr Pro His Phe Gln Pro Ala Leu Leu Gln Ser Gly Tyr Trp Gly Arg
    130                 135                 140

Ala Ala Met Asp Pro Glu Pro Thr Arg Cys Arg Arg Thr Asp Gly Lys
145                 150                 155                 160

Lys Trp Arg Cys Ser Arg Asp Val Val Ala Gly Gln Lys Tyr Cys Glu
                165                 170                 175

Arg His Val His Arg Gly Arg Asn Arg Ser Arg Lys Pro Val Glu Ala
            180                 185                 190

Thr Thr Ala Ala Ala Gly Gly Gly Gly Gly Thr Ser Asp Ile Ala
        195                 200                 205

Thr Asn Thr Thr Thr Lys Thr Ser Ser Ser Gly Ala His Phe Thr Leu
210                 215                 220

Ser Gly Ser Ser Ser Ser Pro Ser Ile Asp Leu Leu His Leu Asn Gln
225                 230                 235                 240

Ser Ser Ser Glu Pro Lys Ala Glu Asn Arg Ser Leu Phe Glu Pro His
                245                 250                 255

Ser Glu Val Ser Gly Ser Ala Lys Ser Asp Ser His Val Leu Arg Pro
            260                 265                 270

Phe Phe Asp Asp Trp Pro Gly Lys Leu Gln Glu Leu Asp Asn Ala Arg
        275                 280                 285

Thr Asn Ala Gly Ser Met Asn Ser Ala Thr Ser Leu Ser Ile Ser Ile
    290                 295                 300

Arg Gly Asn Ser Ser Ser Asp Val Ser Leu Lys Leu Ser Thr Gly Asn
305                 310                 315                 320

Gly Val Glu Thr Gly Arg Leu Asp Gly His Ala Glu Arg Glu Gln Pro
                325                 330                 335

Gln Leu Asn Trp Pro Ala Gly Trp Gly Thr Asn Gln Met Ala Ser Met
            340                 345                 350

Gly Gly Pro Leu Ala Glu Ala Leu Arg Ser Ser Ser Asn Ser Asn Ser
        355                 360                 365

Ser Pro Thr Ser Val Leu His Gln Leu Pro Arg Ser Ser Ala Ser Glu
    370                 375                 380

Thr Ser Phe Ile Ser Thr
385                 390
```

<210> SEQ ID NO 35
<211> LENGTH: 363
<212> TYPE: PRT
<213> ORGANISM: Glycine max

<400> SEQUENCE: 35

Met Asp Phe His Leu Lys Gln Trp Arg Asn Gln His Glu Ser Glu Glu
1               5                   10                  15

Gln His Ser Thr Lys Met Pro Lys Leu Leu Pro Glu Ser His Gln Gln
            20                  25                  30

Gln Gln Pro Ser Ala Ser Ala Leu Pro Leu Phe Val Pro Glu Pro Asn
        35                  40                  45

Ser Ser Lys Val Ser Thr Leu Leu Phe Pro Arg Met Gly Ser Tyr Phe
50                  55                  60

Ser Leu Ser Gln Trp Gln Glu Leu Glu Leu Gln Ala Leu Ile Phe Arg
65                  70                  75                  80

Tyr Met Leu Ala Gly Ala Val Pro Pro Glu Leu Leu Gln Pro Ile
                85                  90                  95

Lys Lys Ser Leu Leu His Ser Pro His Tyr Leu His His Pro Leu
                100                 105                 110

Gln His Tyr Gln Pro Ser Ala Trp Tyr Trp Gly Arg Gly Ala Met Asp
            115                 120                 125

Pro Glu Pro Gly Arg Cys Arg Arg Thr Asp Gly Lys Lys Trp Arg Cys
130                 135                 140

Ser Arg Asp Val Val Ala Gly Gln Lys Tyr Cys Glu Arg His Met His
145                 150                 155                 160

Arg Gly Arg Asn Arg Ser Arg Lys Pro Val Glu Leu Pro Thr Pro Thr
                165                 170                 175

Ser Ala Ile Asn Asn Cys Gly Val Thr Gly Val Gly Ser Leu Gly Pro
            180                 185                 190

Gly Ala Ser Ser Ser Ser Ile Cys Ser Pro Pro Leu Ala Ser Ala Ser
        195                 200                 205

Phe Lys Ser Pro Phe Asp Leu His Leu Asp Glu Arg Ser Ser Gly Thr
210                 215                 220

Lys Asn Glu Asp Glu Asp His Val Gly Gly Asp Gly Arg Ser Gly Gly
225                 230                 235                 240

Gly Gly Gly His Met Leu Arg His Phe Phe Asp Asp Trp Pro Arg Ser
                245                 250                 255

Leu Gln Asp Ser Asp Asn Val Glu Asn Asn Ala Ala Gly Arg Ser
            260                 265                 270

Leu Ser Ile Ser Met Pro Gly Ala Ser Ser Asp Val Ser Leu Lys Leu
        275                 280                 285

Ser Thr Gly Tyr Gly Glu Asp Ser Gly Pro Gly Asn Glu Asn Val Ser
290                 295                 300

Leu Glu Pro Glu Gln Leu Gln Leu Asn Trp Ala Gly Gly Trp Ala Ser
305                 310                 315                 320

Ser Asn Gln Val Ala Ser Met Gly Gly Pro Leu Ala Glu Ala Leu Arg
                325                 330                 335

Ser Ser Thr Ser Thr Ser Ser Pro Thr Ser Val Leu His Arg His Leu
            340                 345                 350

Pro Arg Gly Ser Glu Thr Ser Phe Ile Ser Thr
        355                 360

<210> SEQ ID NO 36
<211> LENGTH: 384

<212> TYPE: PRT
<213> ORGANISM: Medicago truncatula

<400> SEQUENCE: 36

```
Met Asp Phe Pro Thr Lys Gln Trp Arg Asn Gln Gln His Glu Ser Glu
1               5                   10                  15

Lys Gln His Ser Thr Lys Met Pro Lys Leu Leu His Pro Ala Gln Ser
            20                  25                  30

Gln Ser Gln Ser His Ser His Gln Gln Ser Pro Ala Leu Pro Leu Phe
        35                  40                  45

Leu Pro Gln Pro Asn Thr Lys Val Thr Asn Leu Ser Asp Ser Ala Leu
    50                  55                  60

Pro Ser Asn Asn Arg Phe Pro Arg Ile Gly Met Gly Ser His Phe Ser
65                  70                  75                  80

Leu Ser Gln Trp Gln Glu Leu Glu Leu Gln Ala Leu Ile Phe Arg Tyr
                85                  90                  95

Met Leu Val Gly Ala Ser Val Pro Pro Glu Leu Leu Gln Pro Ile Lys
            100                 105                 110

Lys Ser Leu Leu His Ser Ser Pro Tyr Phe Leu His His Tyr Gln Pro
        115                 120                 125

Thr Ala Leu Leu Gln Ser Gly Tyr Trp Gly Arg Gly Ala Met Asp Pro
    130                 135                 140

Glu Pro Gly Arg Cys Arg Arg Thr Asp Gly Lys Lys Trp Arg Cys Ala
145                 150                 155                 160

Arg Asp Val Val Ala Gly Gln Lys Tyr Cys Glu Arg His Met His Arg
                165                 170                 175

Gly Arg Asn Arg Ser Arg Lys Pro Val Glu Leu Pro Thr Pro Thr Ser
            180                 185                 190

Asn Gly Gly Gly Ser Phe Ser Ala Leu Ser Ser Ile Ser Ser Gln Pro
        195                 200                 205

Leu Val Thr Ser Ser Phe Lys Ser Pro Phe Asp Leu His Phe Thr Glu
    210                 215                 220

Arg Ser Thr Gly Thr Lys Ile Glu Glu Lys Ser Leu Cys Glu Ser Asp
225                 230                 235                 240

Asp His Val Gly Gly Asp Gly Arg Pro Gly Gly Gln Met Leu Arg His
                245                 250                 255

Phe Phe Asp Asp Trp Pro Arg Ser Leu Gln Asp Ser Asp Asn Ala Glu
            260                 265                 270

Asn Asn Gly Gly Ser Ser Ser Thr Cys Leu Ser Ile Ser Met Pro Gly
        275                 280                 285

Asn Asn Asn Thr Ser Ser Ser Ser Asp Val Ser Leu Lys Leu Ser
    290                 295                 300

Thr Gly Tyr Gly Glu Glu Pro Cys Pro Arg Asn Glu Asn Val Gly Leu
305                 310                 315                 320

Val Gln Thr Glu Gln Gln Gln Gln Leu Gln Leu Asn Trp Ile Gly
                325                 330                 335

Gly Trp Asn Ser Gly Asn Gln Val Ser Ser Met Gly Gly Pro Leu Ala
            340                 345                 350

Glu Ala Leu Arg Ser Ser Thr Thr Ser Ser Pro Thr Ser Val Leu
        355                 360                 365

His Gln Leu Pro Arg Cys Ser Gly Ser Gln Thr Ser Tyr Ile Ser Thr
    370                 375                 380
```

<210> SEQ ID NO 37

```
<211> LENGTH: 377
<212> TYPE: PRT
<213> ORGANISM: Populus trichocarpa

<400> SEQUENCE: 37

Met Asp Phe His Leu Lys Gln Trp Arg Asn Gln His Glu Glu Ser Gly
1               5                   10                  15

Gln Gln Pro Ser Ala Lys Met Pro Lys Leu Leu Met Asp Pro His Gln
            20                  25                  30

Pro Gln His Pro His Ser Gly Ser Ala Ala Phe Pro Leu Phe
        35                  40                  45

Leu Pro Glu Pro Ser Cys Lys Asn Ser Asn Leu Ser Ala Phe Pro Asp
50                  55                  60

Ser Asn Thr Ala Ala Asn Thr Arg Leu Pro Lys Ile Met Gly Asn Tyr
65                  70                  75                  80

Phe Ser Leu Glu Gln Trp Gln Glu Leu Glu Leu Gln Ala Leu Ile Tyr
                85                  90                  95

Arg Phe Met Leu Ala Gly Ala Ala Ile Pro Pro Glu Leu Leu Gln Pro
            100                 105                 110

Ile Lys Lys Thr Leu Leu His Ser His Pro Pro Tyr Phe Leu His
        115                 120                 125

His Pro Leu Gln Leu His Cys Ser Tyr Tyr Gln Pro Ser Trp Tyr Trp
    130                 135                 140

Gly Arg Ala Ala Met Asp Pro Glu Pro Gly Arg Cys Arg Arg Thr Asp
145                 150                 155                 160

Gly Lys Lys Trp Arg Cys Ser Arg Asp Val Val Ala Gly His Lys Tyr
                165                 170                 175

Cys Glu Arg His Leu His Arg Gly Arg Asn Arg Ser Arg Lys Pro Val
            180                 185                 190

Glu Asn Pro Thr Pro Thr Ile Ser Thr Asn Ile Thr Cys Ile Gly Ile
        195                 200                 205

Gly Glu Leu Asp Gln Thr Thr Phe Ser Leu Phe Cys Phe Cys Phe Asn
    210                 215                 220

Leu Leu Ala His Pro Tyr Cys Ser Ser Lys Thr Glu Ser Lys Gly Leu
225                 230                 235                 240

Ile Gly Pro Pro Pro Asn Glu Val Gly Asn Arg Ser Asp Gly His
                245                 250                 255

Ile Leu Trp His Phe Phe Asp Asp Trp Pro Arg Ser Val Asp Glu Ser
            260                 265                 270

Asp Asn Met Asn Ala Gly Ser Ser Met Asn Ser Leu Thr Cys Leu Ser
        275                 280                 285

Val Ser Met Pro Gly Asn Ser Pro Ala Ser Asp Val Ser Leu Lys Leu
    290                 295                 300

Ser Thr Gly Asn Asn Ile Ala Glu Glu Glu Pro Glu Pro Val Pro Ala
305                 310                 315                 320

Pro Ile Pro Arg Gly Asn Thr Ser Asn Trp Ala Ala Ala Gly Trp Gly
                325                 330                 335

Thr Lys Ile Thr Asn Gln Val Val Thr Ser Met Gly Gly Pro Leu Ala
            340                 345                 350

Glu Ala Leu Arg Ser Ser Thr Thr Lys Leu Ile Ser His Glu Cys Ser
        355                 360                 365

Ala Pro Val Met Ser Pro His Cys Phe
    370                 375
```

<210> SEQ ID NO 38
<211> LENGTH: 21
<212> TYPE: DNA
<213> ORGANISM: Artificial Sequence
<220> FEATURE:
<223> OTHER INFORMATION: Modified GRF3 miR396 target site

<400> SEQUENCE: 38
cgttctagaa aaccagtaga g                                              21

<210> SEQ ID NO 39
<211> LENGTH: 633
<212> TYPE: DNA
<213> ORGANISM: Arabidopsis thaliana

<400> SEQUENCE: 39
atgcaacagc acctgatgca gatgcagccc atgatggctg ttactaccc cagcaatgtt      60 acctctgatc atatccaaca gtacttggac gaaaacaaat cgttgattct gaagattgtt    120
gagtctcaaa actctggaaa gcttagcgaa tgcgccgaga tcaagcaag gcttcaacgc     180 aacctaatgt acctagctgc aatagcagat tctcagcctc agccaccaag tgtgcatagc    240
cagtatggat ctgctggtgg tgggatgatt caggagaag gagggtcaca ctatttgcag     300
cagcaacaag cgactcaaca gcaacagatg actcagcagt ctctaatggc ggctcgatct    360
tcaatgttgt atgctcagca acagcagcag cagcagcctt acgcgacgct tcagcatcag    420
caattgcacc atagccagct tggaatgagc tcgagcagcg gaggaggagg aagcagtggt    480
ctccatatcc ttcagggaga ggctggtggg tttcatgatt ttggccgtgg gaagccggaa    540
atgggaagtg gtggtggcgg tgaaggcaga ggaggaagtt caggggatgg tggagaaacc    600 cttttacttga aatcatcaga tgatgggaat tga                                633

<210> SEQ ID NO 40
<211> LENGTH: 1593
<212> TYPE: DNA
<213> ORGANISM: Arabidopsis thaliana

<400> SEQUENCE: 40
atggatcttg gagttcgtgt ttctggtcat gaaaccgttt cttctccggg tcaaactgaa      60
ctcggatctg gtttcagtaa caagcaagaa agatccggtt tcgatggtga agattgctgg    120
agaagttcaa agctctcacg aacatcaact gatggattcc cttcttcccc tgcctctgct    180
aaaacgctgt cgtttcatca aggcatcect ttactgagat ctaccactat taatgatcct    240
cgtaaaggac aagaacacat gcttagcttc tcttctgctt caggcaaatc agatgtctca    300
ccttatcttc agtactgtag aaactcagga tatggtttag gaggaatgat gaacacaagc    360
aacatgcatg gaaacttgtt gacaggagta aaaggacctt ttcattgac tcagtgggca     420 gagctagagc aacaggcgtt gatctataag tatatcacag ccaatgtccc tgttccatct    480
agtttacttc tctctctcaa gaaatctttt ttcccttatg gttccttgcc tcctaattct    540
tttggatggg gctctttttca tctgggcttt tccggtggta acatggatcc cgagccaggg   600
agatgtcgcc ggacagatgg aaagaaatgg cggtgctcga gggacgctgt tcccgatcaa    660
aagtactgtg aacgacatat taacagaggc cgccatcgtt caagaaagcc tgtggaaggc    720
caaaatggcc acaatactaa tgctgccgcc gctgcttctg ctgctgccgc ttctaccgct    780
gctgctgtgt ccaaagcggc agcggggact cagctgttg cgatgcgtgg atcagataat     840
aacaatagcc ttgccgctgc tgttggaaca caacatcata ccaataatca atctacagat    900

```
tctttggcta acagagttca aaattctcga ggggcttcgg ttttctgc cacgatgaac      960
ttacagtcga aggaaactca tccgaaacaa agcaataatc cctttgaatt cggactcatc   1020
tcttctgatt cgttacttaa tccgtcgcat aaacaagcct cgtatgcaac ctcttccaaa   1080
ggctttggat cgtatcttga cttcggcaac caagccaagc acgcgggaa tcacaacaat    1140
gtcgattctt ggcccgaaga gctgaaatcg gattggactc agctctcaat gtcaatccct  1200
atggctccat cttccctgt tcaagataaa cttgcactct cacctttaag gttatcgcgt   1260
gagtttgacc ccgcgatcca catgggatta ggcgtcaaca ccgagtttct tgaccccggg  1320
aaaaagacga ataactggat accaatctcc tggggtaata caactccat ggaggtcca    1380
ctcggcgagg tactaaacag cacgaccaat agtcccaagt ttggttcctc tccaacaggc  1440
gtcttgcaaa agtcgacatt tggttctctt tctaacagca gctcggcaag cagcaccatc  1500
attggcgata caacaataa gaacggtgat ggaaagatc cgcttggccc gaccacgctg    1560
atgaatactt ctgctactgc tccttctctg tga                               1593
```

<210> SEQ ID NO 41
<211> LENGTH: 1194
<212> TYPE: DNA
<213> ORGANISM: Arabidopsis thaliana

<400> SEQUENCE: 41

```
atgatgagtc taagtggaag tagcgggaga acaataggaa ggcctccatt tacaccaaca    60
caatgggaag aactggaaca tcaagcccta atctacaagt acatggtctc tggtgttcct  120
gtcccacctg agctcatctt ctccattaga agaagcttgg acattccctt ggtctctaga  180
ctccttcctc accaatccct tggatggggg tgttaccaga tgggatttgg gagaaaacca  240
gatccagagc caggaagatg cagaagaaca gatggtaaga aatggagatg ctcaagagaa  300
gcttacccag attcgaagta ctgtgaaaaa cacatgcaca gaggaagaaa ccgtgccaga  360
aaatctcttg atcagaatca gacaacaaca actcctttaa catcaccatc tctctcattc  420
accaacaaca caacccaag tcccaccttg tcttcttctt cttcctctaa ttcctcttct   480
actacttatt ctgcttcttc ttcttcaatg gatgcctaca gtaacagtaa taggtttggg  540
cttggtggaa gtagtagtaa cactagaggt tatttcaaca gccattctct tgattatcct  600
tatccttcta cttcacccaa acaacaacaa caaactcttc atcatgcttc cgctttgtca  660
cttcatcaaa atactaattc tacttctcag ttcaatgtct tagcctctgc tactgaccac  720
aaagacttca ggtactttca agggattggg gagagagttg gaggagttgg ggagagaacg  780
ttctttccag aagcatctag aagctttcaa gattctccat accatcatca ccaacaaccg  840
ttagcaacag tgatgaatga tccgtaccac cactgtagta ctgatcataa taagattgat  900
catcatcaca catactcatc ctcatcatca tctcaacatc ttcatcatga tcatgatcat  960
agacagcaac agtgttttgt tttgggcgcc gacatgttca acaaacctac aagaagtgtc  1020
cttgcaaact catcaagaca agatcaaaat caagaagaag atgagaaaga ttcatcagag  1080
tcgtccaaga agtctctaca tcacttcttt ggtgaggact gggcacagaa caagaacagt  1140
tcagattctt ggcttgacct ttcttcccac tcaagactcg acactggtag ctaa          1194
```

<210> SEQ ID NO 42
<211> LENGTH: 700
<212> TYPE: DNA
<213> ORGANISM: Arabidopsis thaliana

<400> SEQUENCE: 42

```
atggctacaa ggattccatt cacagaatca caatgggaag aacttgaaaa ccaagctctt        60
gtgttcaagt acttagctgc aaatatgcct gttccacctc atcttctctt cctcatcaaa       120 agacccttc tcttctcttc ttcttcttct tcatcttctt cttcaagctt cttctctccc        180
actctttctc cacactttgg gtggaatgtg tatgagatgg gaatgggaag aaagatagat       240
gcagagccag gaagatgtag aagaactgat ggcaagaaat ggagatgctc taaagaagct       300
taccctgact ctaagtactg tgagagacat atgcatagag caagaaccg ttcttcctca        360 agaaagcctc ctcctactca attcactcca aatctctttc tcgactcttc ttccagaaga       420
agaagaagtg gatacatgga tgatttcttc tccatagaac cttccgggtc aatcaaaagc       480
tgctctggct cagcaatgga agataatgat gatggctcat gtagaggcat caacaacgag       540
gagaagcagc cggatcgaca ttgcttcatc cttggtactg acttgaggac acgtgagagg       600
ccattgatgt tagaggagaa gctgaaacaa agagatcatg ataatgaaga gagcaagga        660 agcaagaggt tttataggtt tcttgatgaa tggccttctt                             700
```

<210> SEQ ID NO 43
<211> LENGTH: 1098
<212> TYPE: DNA
<213> ORGANISM: Arabidopsis thaliana

<400> SEQUENCE: 43

```
atggactttc tcaaagtttc agacaagaca acaattccat atagaagtga ttctttgttt        60
agtttgaatc agcaacaata caaagagtct tcttttggat tcagagacat ggagattcat       120
ccgcatccta ctccatatgc aggaaatgga cttttgggtt gttattacta ttacccttc        180 acaaacgcac aattgaagga gcttgagaga caagcaatga tctacaagta catgatcgca       240
tctattcctg ttcctttcga tctacttgtt tcttcaccat cctctgcctc tccttgtaac       300
aataaaaaca tcgccggaga tttagagccg ggaagatgcc ggagaacaga cggaaagaaa       360
tggagatgcg cgaaagaagt cgtctctaat cacaaatact gtgagaaaca cttacacaga       420
ggtcgtcctc gttcaagaaa gcatgtggaa cctccttatt ctcgccctaa caacaatggt       480
ggttctgtga aaaacagaga tctcaaaaag cttcctcaaa agttatctag tagttccatc       540
aaagacaaaa cacttgagcc aatggaggtt tcatcatcaa tctcaaacta tagagactcc       600
agaggaagtg agaaatttac tgtattggca acaacagagc aagagaacaa gtatctgaat       660
ttcatagatg tatggtccga tggagtaaga tcatctgaaa aacagagtac aacttcaaca       720
cctgtttctt cttccaatgg caatctctct ctttactcgc ttgatctctc aatgggagga       780
aacaacttaa tgggccaaga cgaaatgggc ctgatacaaa tgggcttagg tgtaatcggg       840
tcgggtagta aggatcatca cgggtatggt ccttatggtg tgacttcttc actagaggag       900
atgtcaagct ggcttgctcc gatgtctacc acacctggtg gaccattagc ggagatactg       960
aggccgagta cgaatttggc gatctctggt gatatcgaat cgtatagctt gatggagact      1020
cccactccaa gctcgtcccc gtctagagtg atgaagaaga tgactagttc agtgtccgac      1080
gaaagcagcc aggtttag                                                   1098
```

<210> SEQ ID NO 44
<211> LENGTH: 1482
<212> TYPE: DNA
<213> ORGANISM: Arabidopsis thaliana

<400> SEQUENCE: 44

```
atgaggatgc ttcttgggat tccttacgta gacaagtcgg ttcttttccaa ctctgttctt        60 gagagaggca agcaggataa aagcaaacta ttgttagtcg acaaatgcca ttatgagctt       120
gatgttgaag aacgcaagga agattttgtt ggtgggtttg gatttggtgt tgtagaaaat       180
tcgcataaag acgttatggt gctacctcat catcactatt atccatcata ttcatcacct       240
tcctcttctt ctttgtgtta ctgttctgct ggtgttagcg atcccatgtt ctctgtttct       300
agcaatcagg cttacacttc ttctcacagt ggtatgttca cacccgccgg ttctggttct       360
gctgctgtga ctgtagcaga tccttttttc tccttgagct cttcagggga aatgagaaga       420
agtatgaacg aagatgctgg tgcagctttc agcgaagctc aatggcatga gcttgagagg       480
cagaggaata tatacaagta catgatggct tctgttcctg ttcctccaga gcttctcaca       540 cccttttccca agaaccacca atcaaacact aacccggatg tggatacata taggagtgga       600
atgtttagta tttatgctga ttacaagaat ctgccgttgt ctatgtggat gacagtaact       660
gtggcagtgg cgacaggagg ctcattgcag ctggggattg cttcaagcgc aagcaataac       720
acggctgatc tggagccatg gaggtgcaag agaacagatg gaagaaatg gaggtgctct        780 agaaacgtga ttcctgatca gaaatactgt gagagacaca cacacaagag ccgtcctcgt       840
tcaagaaagc atgtggaatc atctcaccaa tcatctcacc acaatgacat tcgtacggct       900
aagaatgata ctagccagct tgtgagaact tatcctcagt tttacggaca acctataagc       960
cagatccctg tgctttctac tcttccgtct gcctcctctc catatgatca ccacagagga      1020
ctgaggtggt ttacgaaaga agatgatgcc attggaacct aaacccggga gactcaagaa      1080
gctgtccagc tgaaagttgg atcaagcaga gagctcaaac ggggattcga ttatgatctg      1140
aatttcaggc agaaagagcc aatagtagac cagagctttg gagcattgca gggtctatta      1200
agtctaaacc agacaccaca acataaccaa gaaacaacga gtttgttgt agaaggaaag       1260 caagatgaag cgatgggaag ctctctgaca ctctcaatgg ctggaggagg catggaggaa      1320
acagagggaa caaaccagca tcagtgggtt agccatgaag gtccatcatg gctctattca      1380
acaacaccag gtggaccatt ggctgaagca ctgtgtctcg gtgtctccaa caacccaagt      1440
tctagtacta ctactagtag ctgcagcaga agctcaagct aa                          1482

<210> SEQ ID NO 45
<211> LENGTH: 1290
<212> TYPE: DNA
<213> ORGANISM: Arabidopsis thaliana

<400> SEQUENCE: 45
atgcagagcc taaaatgga gcaggaggag gttgaggagg agaggatgag gaataagtgg         60
ccgtggatga aggcggcgca gttaatgag tttcggatgc aagctttggt gtatagatac        120
atagaggctg gtctccgtgt gcctcatcat ctcgtggtgc ctatttggaa cagtcttgct       180
ctctcttctt cctccaatta caactatcac tcttcttctc tgttgagtaa caagggagta      240
acccatatcg acacgttgga aactgaacca actaggtgca ggagaacaga tgggaagaaa       300
tggcgctgta gcaacacggt ccttctattc gagaagtact gtgaacggca catgcataga       360
ggtcgtaaac gttcaagaaa gcttgtggaa tcttcttctg aggttgcttc atcatcaacc       420
aaatacgaca acacttatgg tttggatagg tataacgaga gtcagagtca tcttcatggg       480
acaatctcgg gttctagtaa tgcgcaggta gttaccattg cttcactgcc tagtgccaga       540
tcctgtgaaa atgtcattcg tccgtctttta gtgatctctg aattcacaaa caaaagtgtg       600
agtcacggca gaaagaacat ggagatgagt tatgatgact ttattaatga aaaagaggcg       660
```

```
agtatgtgtg ttggagttgt tcctcttcaa ggtgatgaga gcaaaccttc ggttcaaaag      720
ttcttccctg aggtatctga taaatgctta gaagctgcaa aattctcaag caacaggaag      780
aatgatataa ttgcaagaag cagagaatgg aagaatatga atgttaatgg tggtttgttt     840
catggtatcc acttttctcc agacactgtt cttcaagaac gtggttgttt tcgtttacaa     900
ggagttgaaa cagacaatga accaggaagg tgccgaagaa cagatgggaa gaagtggaga     960
tgcagcaaag atgttttgtc tggtcagaag tactgcgata agcacatgca tagaggtatg    1020
aagaagaagc atccagttga tactactaac tcacatgaga atgccgggtt tagcccgtta    1080
accgtggaaa cagctgttag atcggttgtg ccttgcaaag atggagatga ccagaagcat    1140
tctgtttcag tcatgggaat tacactgccc cgagtttctg atgagaagag cactagcagt    1200
tgcagtaccg acactaccat tactgacaca gctttaaggg gtgaagacga cgatgaggag    1260
tacttgtctt tgttttcacc aggtgtttag                                      1290

<210> SEQ ID NO 46
<211> LENGTH: 530
<212> TYPE: PRT
<213> ORGANISM: Arabidopsis thaliana

<400> SEQUENCE: 46

Met Asp Leu Gly Val Arg Val Ser Gly His Glu Thr Val Ser Ser Pro
1               5                   10                  15

Gly Gln Thr Glu Leu Gly Ser Gly Phe Ser Asn Lys Gln Glu Arg Ser
            20                  25                  30

Gly Phe Asp Gly Glu Asp Cys Trp Arg Ser Ser Lys Leu Ser Arg Thr
        35                  40                  45

Ser Thr Asp Gly Phe Ser Ser Pro Ala Ser Ala Lys Thr Leu Ser
    50                  55                  60

Phe His Gln Gly Ile Pro Leu Leu Arg Ser Thr Thr Ile Asn Asp Pro
65                  70                  75                  80

Arg Lys Gly Gln Glu His Met Leu Ser Phe Ser Ser Ala Ser Gly Lys
                85                  90                  95

Ser Asp Val Ser Pro Tyr Leu Gln Tyr Cys Arg Asn Ser Gly Tyr Gly
            100                 105                 110

Leu Gly Gly Met Met Asn Thr Ser Asn Met His Gly Asn Leu Leu Thr
        115                 120                 125

Gly Val Lys Gly Pro Phe Ser Leu Thr Gln Trp Ala Glu Leu Glu Gln
130                 135                 140

Gln Ala Leu Ile Tyr Lys Tyr Ile Thr Ala Asn Val Pro Val Pro Ser
145                 150                 155                 160

Ser Leu Leu Leu Ser Leu Lys Lys Ser Phe Phe Pro Tyr Gly Ser Leu
                165                 170                 175

Pro Pro Asn Ser Phe Gly Trp Gly Ser Phe His Leu Gly Phe Ser Gly
            180                 185                 190

Gly Asn Met Asp Pro Glu Pro Gly Arg Cys Arg Arg Thr Asp Gly Lys
        195                 200                 205

Lys Trp Arg Cys Ser Arg Asp Ala Val Pro Asp Gln Lys Tyr Cys Glu
    210                 215                 220

Arg His Ile Asn Arg Gly Arg His Arg Ser Arg Lys Pro Val Glu Gly
225                 230                 235                 240

Gln Asn Gly His Asn Thr Asn Ala Ala Ala Ala Ser Ala Ala
                245                 250                 255
```

```
Ala Ser Thr Ala Ala Val Ser Lys Ala Ala Ala Gly Thr Ser Ala
            260                 265                 270

Val Ala Met Arg Gly Ser Asp Asn Asn Asn Ser Leu Ala Ala Val
        275                 280                 285

Gly Thr Gln His His Thr Asn Asn Gln Ser Thr Asp Ser Leu Ala Asn
    290                 295                 300

Arg Val Gln Asn Ser Arg Gly Ala Ser Val Phe Pro Ala Thr Met Asn
305                 310                 315                 320

Leu Gln Ser Lys Glu Thr His Pro Lys Gln Ser Asn Asn Pro Phe Glu
                325                 330                 335

Phe Gly Leu Ile Ser Ser Asp Ser Leu Leu Asn Pro Ser His Lys Gln
            340                 345                 350

Ala Ser Tyr Ala Thr Ser Ser Lys Gly Phe Gly Ser Tyr Leu Asp Phe
        355                 360                 365

Gly Asn Gln Ala Lys His Ala Gly Asn His Asn Asn Val Asp Ser Trp
    370                 375                 380

Pro Glu Glu Leu Lys Ser Asp Trp Thr Gln Leu Ser Met Ser Ile Pro
385                 390                 395                 400

Met Ala Pro Ser Ser Pro Val Gln Asp Lys Leu Ala Leu Ser Pro Leu
                405                 410                 415

Arg Leu Ser Arg Glu Phe Asp Pro Ala Ile His Met Gly Leu Gly Val
            420                 425                 430

Asn Thr Glu Phe Leu Asp Pro Gly Lys Lys Thr Asn Asn Trp Ile Pro
        435                 440                 445

Ile Ser Trp Gly Asn Asn Asn Ser Met Gly Gly Pro Leu Gly Glu Val
    450                 455                 460

Leu Asn Ser Thr Thr Asn Ser Pro Lys Phe Gly Ser Ser Pro Thr Gly
465                 470                 475                 480

Val Leu Gln Lys Ser Thr Phe Gly Ser Leu Ser Asn Ser Ser Ser Ala
                485                 490                 495

Ser Ser Thr Ile Ile Gly Asp Asn Asn Asn Lys Asn Gly Asp Gly Lys
            500                 505                 510

Asp Pro Leu Gly Pro Thr Thr Leu Met Asn Thr Ser Ala Thr Ala Pro
        515                 520                 525

Ser Leu
    530

<210> SEQ ID NO 47
<211> LENGTH: 535
<212> TYPE: PRT
<213> ORGANISM: Arabidopsis thaliana

<400> SEQUENCE: 47

Met Asp Ile Gly Val His Val Leu Gly Ser Val Thr Ser Asn Glu Asn
1               5                   10                  15

Glu Ser Leu Gly Leu Lys Glu Leu Ile Gly Thr Lys Gln Asp Arg Ser
            20                  25                  30

Gly Phe Ile Gly Glu Asp Cys Leu Gln Arg Ser Leu Lys Leu Ala Arg
        35                  40                  45

Thr Thr Thr Arg Ala Glu Glu Glu Asn Leu Ser Ser Ser Val Ala
    50                  55                  60

Ala Ala Tyr Cys Lys Thr Met Ser Phe His Gln Gly Ile Pro Leu Met
65                  70                  75                  80

Arg Ser Ala Ser Pro Leu Ser Ser Asp Ser Arg Arg Gln Glu Gln Met
                85                  90                  95
```

Leu Ser Phe Ser Asp Lys Pro Asp Ala Leu Asp Phe Ser Lys Tyr Val
            100                 105                 110

Gly Leu Asp Asn Ser Ser Asn Asn Lys Asn Ser Leu Ser Pro Phe Leu
            115                 120                 125

His Gln Ile Pro Pro Pro Ser Tyr Phe Arg Ser Gly Gly Tyr Gly
            130                 135                 140

Ser Gly Gly Met Met Met Asn Met Ser Met Gln Gly Asn Phe Thr Gly
145                 150                 155                 160

Val Lys Gly Pro Phe Thr Leu Thr Gln Trp Ala Glu Leu Glu Gln Gln
                    165                 170                 175

Ala Leu Ile Tyr Lys Tyr Ile Thr Ala Asn Val Pro Val Pro Ser Ser
            180                 185                 190

Leu Leu Ile Ser Ile Lys Lys Ser Phe Tyr Pro Tyr Gly Ser Leu Pro
            195                 200                 205

Pro Ser Ser Phe Gly Trp Gly Thr Phe His Leu Gly Phe Ala Gly Gly
            210                 215                 220

Asn Met Asp Pro Glu Pro Gly Arg Cys Arg Arg Thr Asp Gly Lys Lys
225                 230                 235                 240

Trp Arg Cys Ser Arg Asp Ala Val Pro Asp Gln Lys Tyr Cys Glu Arg
                    245                 250                 255

His Ile Asn Arg Gly Arg His Arg Ser Arg Lys Pro Val Glu Val Gln
            260                 265                 270

Ser Gly Gln Asn Gln Thr Ala Ala Ala Ser Lys Ala Val Thr Thr
            275                 280                 285

Pro Gln Gln Pro Val Val Ala Gly Asn Thr Asn Arg Ser Asn Ala Arg
            290                 295                 300

Ala Ser Ser Asn Arg Ser Leu Ala Ile Gly Ser Gln Tyr Ile Asn Pro
305                 310                 315                 320

Ser Thr Glu Ser Leu Pro Asn Asn Arg Gly Val Ser Ile Tyr Pro Ser
                    325                 330                 335

Thr Val Asn Leu Gln Pro Lys Glu Ser Pro Val Ile His Gln Lys His
            340                 345                 350

Arg Asn Asn Asn Pro Phe Glu Phe Gly His Ile Ser Ser Asp Ser
            355                 360                 365

Leu Leu Asn Pro Asn Thr Ala Lys Thr Tyr Gly Ser Ser Phe Leu Asp
            370                 375                 380

Phe Ser Asn Gln Glu Lys His Ser Gly Asn His Asn His Asn Ser
385                 390                 395                 400

Trp Pro Glu Glu Leu Thr Ser Asp Trp Thr Gln Leu Ser Met Ser Ile
                    405                 410                 415

Pro Ile Ala Ser Ser Ser Pro Ser Ser Thr His Asn Asn Asn Asn Ala
            420                 425                 430

Gln Glu Lys Thr Thr Leu Ser Pro Leu Arg Leu Ser Arg Glu Leu Asp
            435                 440                 445

Leu Ser Ile Gln Thr Asp Glu Thr Thr Ile Glu Pro Thr Val Lys Lys
            450                 455                 460

Val Asn Thr Trp Ile Pro Ile Ser Trp Gly Asn Ser Leu Gly Gly Pro
465                 470                 475                 480

Leu Gly Glu Val Leu Asn Ser Thr Thr Asn Ser Pro Thr Phe Gly Ser
                    485                 490                 495

Ser Pro Thr Gly Val Leu Gln Lys Ser Thr Phe Cys Ser Leu Ser Asn
            500                 505                 510

Asn Ser Ser Val Ser Ser Pro Ile Ala Glu Asn Asn Arg His Asn Gly
            515                 520                 525

Asp Tyr Phe His Tyr Thr Thr
        530                 535

<210> SEQ ID NO 48
<211> LENGTH: 397
<212> TYPE: PRT
<213> ORGANISM: Arabidopsis thaliana

<400> SEQUENCE: 48

Met Met Ser Leu Ser Gly Ser Ser Gly Arg Thr Ile Gly Arg Pro Pro
1               5                   10                  15

Phe Thr Pro Thr Gln Trp Glu Glu Leu Glu His Gln Ala Leu Ile Tyr
            20                  25                  30

Lys Tyr Met Val Ser Gly Val Pro Val Pro Pro Glu Leu Ile Phe Ser
        35                  40                  45

Ile Arg Arg Ser Leu Asp Thr Ser Leu Val Ser Arg Leu Leu Pro His
    50                  55                  60

Gln Ser Leu Gly Trp Gly Cys Tyr Gln Met Gly Phe Gly Arg Lys Pro
65                  70                  75                  80

Asp Pro Glu Pro Gly Arg Cys Arg Arg Thr Asp Gly Lys Lys Trp Arg
                85                  90                  95

Cys Ser Arg Glu Ala Tyr Pro Asp Ser Lys Tyr Cys Glu Lys His Met
            100                 105                 110

His Arg Gly Arg Asn Arg Ala Arg Lys Ser Leu Asp Gln Asn Gln Thr
        115                 120                 125

Thr Thr Thr Pro Leu Thr Ser Pro Ser Leu Ser Phe Thr Asn Asn Asn
130                 135                 140

Asn Pro Ser Pro Thr Leu Ser Ser Ser Ser Ser Asn Ser Ser Ser Ser
145                 150                 155                 160

Thr Thr Tyr Ser Ala Ser Ser Ser Met Asp Ala Tyr Ser Asn Ser
                165                 170                 175

Asn Arg Phe Gly Leu Gly Gly Ser Ser Ser Asn Thr Arg Gly Tyr Phe
            180                 185                 190

Asn Ser His Ser Leu Asp Tyr Pro Tyr Pro Ser Thr Ser Pro Lys Gln
        195                 200                 205

Gln Gln Gln Thr Leu His His Ala Ser Ala Leu Ser Leu His Gln Asn
    210                 215                 220

Thr Asn Ser Thr Ser Gln Phe Asn Val Leu Ala Ser Ala Thr Asp His
225                 230                 235                 240

Lys Asp Phe Arg Tyr Phe Gln Gly Ile Gly Glu Arg Val Gly Gly Val
                245                 250                 255

Gly Glu Arg Thr Phe Phe Pro Glu Ala Ser Arg Ser Phe Gln Asp Ser
            260                 265                 270

Pro Tyr His His His Gln Gln Pro Leu Ala Thr Val Met Asn Asp Pro
        275                 280                 285

Tyr His His Cys Ser Thr Asp His Asn Lys Ile Asp His His Thr
    290                 295                 300

Tyr Ser Ser Ser Ser Ser Gln His Leu His Asp His Asp His
305                 310                 315                 320

Arg Gln Gln Gln Cys Phe Val Leu Gly Ala Asp Met Phe Asn Lys Pro
                325                 330                 335

Thr Arg Ser Val Leu Ala Asn Ser Ser Arg Gln Asp Gln Asn Gln Glu
            340                 345                 350

```
Glu Asp Glu Lys Asp Ser Ser Glu Ser Ser Lys Lys Ser Leu His His
            355                 360                 365

Phe Phe Gly Glu Asp Trp Ala Gln Asn Lys Asn Ser Ser Asp Ser Trp
370                 375                 380

Leu Asp Leu Ser Ser His Ser Arg Leu Asp Thr Gly Ser
385                 390                 395

<210> SEQ ID NO 49
<211> LENGTH: 244
<212> TYPE: PRT
<213> ORGANISM: Arabidopsis thaliana

<400> SEQUENCE: 49

Met Ala Thr Arg Ile Pro Phe Thr Glu Ser Gln Trp Glu Glu Leu Glu
1               5                   10                  15

Asn Gln Ala Leu Val Phe Lys Tyr Leu Ala Ala Asn Met Pro Val Pro
            20                  25                  30

Pro His Leu Leu Phe Leu Ile Lys Arg Pro Phe Leu Phe Ser Ser Ser
        35                  40                  45

Ser Ser Ser Ser Ser Ser Ser Phe Phe Ser Pro Thr Leu Ser Pro
50                  55                  60

His Phe Gly Trp Asn Val Tyr Glu Met Gly Met Gly Arg Lys Ile Asp
65                  70                  75                  80

Ala Glu Pro Gly Arg Cys Arg Arg Thr Asp Gly Lys Lys Trp Arg Cys
                85                  90                  95

Ser Lys Glu Ala Tyr Pro Asp Ser Lys Tyr Cys Glu Arg His Met His
            100                 105                 110

Arg Gly Lys Asn Arg Ser Ser Arg Lys Pro Pro Thr Gln Phe
            115                 120                 125

Thr Pro Asn Leu Phe Leu Asp Ser Ser Arg Arg Arg Ser Gly
        130                 135                 140

Tyr Met Asp Asp Phe Phe Ser Ile Glu Pro Ser Gly Ser Ile Lys Ser
145                 150                 155                 160

Cys Ser Gly Ser Ala Met Glu Asp Asn Asp Gly Ser Cys Arg Gly
                165                 170                 175

Ile Asn Asn Glu Glu Lys Gln Pro Asp Arg His Cys Phe Ile Leu Gly
            180                 185                 190

Thr Asp Leu Arg Thr Arg Glu Arg Pro Leu Met Leu Glu Glu Lys Leu
        195                 200                 205

Lys Gln Arg Asp His Asp Asn Glu Glu Glu Gly Ser Lys Arg Phe
    210                 215                 220

Tyr Arg Phe Leu Asp Glu Trp Pro Ser Ser Lys Ser Ser Val Ser Thr
225                 230                 235                 240

Ser Leu Phe Ile

<210> SEQ ID NO 50
<211> LENGTH: 365
<212> TYPE: PRT
<213> ORGANISM: Arabidopsis thaliana

<400> SEQUENCE: 50

Met Asp Phe Leu Lys Val Ser Asp Lys Thr Thr Ile Pro Tyr Arg Ser
1               5                   10                  15

Asp Ser Leu Phe Ser Leu Asn Gln Gln Gln Tyr Lys Glu Ser Ser Phe
            20                  25                  30
```

Gly Phe Arg Asp Met Glu Ile His Pro His Pro Thr Pro Tyr Ala Gly
            35                  40                  45

Asn Gly Leu Leu Gly Cys Tyr Tyr Tyr Pro Phe Thr Asn Ala Gln
 50                  55                  60

Leu Lys Glu Leu Glu Arg Gln Ala Met Ile Tyr Lys Tyr Met Ile Ala
65                  70                  75                  80

Ser Ile Pro Val Pro Phe Asp Leu Leu Val Ser Ser Pro Ser Ser Ala
                85                  90                  95

Ser Pro Cys Asn Asn Lys Asn Ile Ala Gly Asp Leu Glu Pro Gly Arg
                100                 105                 110

Cys Arg Arg Thr Asp Gly Lys Lys Trp Arg Cys Ala Lys Glu Val Val
            115                 120                 125

Ser Asn His Lys Tyr Cys Glu Lys His Leu His Arg Gly Arg Pro Arg
    130                 135                 140

Ser Arg Lys His Val Glu Pro Pro Tyr Ser Arg Pro Asn Asn Asn Gly
145                 150                 155                 160

Gly Ser Val Lys Asn Arg Asp Leu Lys Lys Leu Pro Gln Lys Leu Ser
                165                 170                 175

Ser Ser Ser Ile Lys Asp Lys Thr Leu Glu Pro Met Glu Val Ser Ser
                180                 185                 190

Ser Ile Ser Asn Tyr Arg Asp Ser Arg Gly Ser Glu Lys Phe Thr Val
            195                 200                 205

Leu Ala Thr Thr Glu Gln Glu Asn Lys Tyr Leu Asn Phe Ile Asp Val
    210                 215                 220

Trp Ser Asp Gly Val Arg Ser Ser Glu Lys Gln Ser Thr Thr Ser Thr
225                 230                 235                 240

Pro Val Ser Ser Asn Gly Asn Leu Ser Leu Tyr Ser Leu Asp Leu
                245                 250                 255

Ser Met Gly Gly Asn Asn Leu Met Gly Gln Asp Glu Met Gly Leu Ile
                260                 265                 270

Gln Met Gly Leu Gly Val Ile Gly Ser Gly Ser Glu Asp His His Gly
            275                 280                 285

Tyr Gly Pro Tyr Gly Val Thr Ser Ser Leu Glu Glu Met Ser Ser Trp
    290                 295                 300

Leu Ala Pro Met Ser Thr Thr Pro Gly Gly Pro Leu Ala Glu Ile Leu
305                 310                 315                 320

Arg Pro Ser Thr Asn Leu Ala Ile Ser Gly Asp Ile Glu Ser Tyr Ser
                325                 330                 335

Leu Met Glu Thr Pro Thr Pro Ser Ser Ser Pro Ser Arg Val Met Lys
                340                 345                 350

Lys Met Thr Ser Ser Val Ser Asp Glu Ser Ser Gln Val
            355                 360                 365

<210> SEQ ID NO 51
<211> LENGTH: 493
<212> TYPE: PRT
<213> ORGANISM: Arabidopsis thaliana

<400> SEQUENCE: 51

Met Arg Met Leu Leu Gly Ile Pro Tyr Val Asp Lys Ser Val Leu Ser
1               5                   10                  15

Asn Ser Val Leu Glu Arg Gly Lys Gln Asp Lys Ser Lys Leu Leu Leu
                20                  25                  30

Val Asp Lys Cys His Tyr Glu Leu Asp Val Glu Glu Arg Lys Glu Asp
            35                  40                  45

-continued

Phe Val Gly Gly Phe Gly Phe Val Val Glu Asn Ser His Lys Asp
    50              55                  60

Val Met Val Leu Pro His His Tyr Tyr Pro Ser Tyr Ser Ser Pro
65              70              75              80

Ser Ser Ser Ser Leu Cys Tyr Cys Ser Ala Gly Val Ser Asp Pro Met
            85              90              95

Phe Ser Val Ser Ser Asn Gln Ala Tyr Thr Ser Ser His Ser Gly Met
            100             105             110

Phe Thr Pro Ala Gly Ser Gly Ser Ala Ala Val Thr Val Ala Asp Pro
            115             120             125

Phe Phe Ser Leu Ser Ser Ser Gly Glu Met Arg Arg Ser Met Asn Glu
130             135                     140

Asp Ala Gly Ala Ala Phe Ser Glu Ala Gln Trp His Glu Leu Glu Arg
145                 150             155                     160

Gln Arg Asn Ile Tyr Lys Tyr Met Met Ala Ser Val Pro Val Pro Pro
                165             170             175

Glu Leu Leu Thr Pro Phe Pro Lys Asn His Gln Ser Asn Thr Asn Pro
            180             185             190

Asp Val Asp Thr Tyr Arg Ser Gly Met Phe Ser Ile Tyr Ala Asp Tyr
            195             200             205

Lys Asn Leu Pro Leu Ser Met Trp Met Thr Val Thr Val Ala Val Ala
210                 215             220

Thr Gly Gly Ser Leu Gln Leu Gly Ile Ala Ser Ser Ala Ser Asn Asn
225             230             235             240

Thr Ala Asp Leu Glu Pro Trp Arg Cys Lys Arg Thr Asp Gly Lys Lys
            245             250             255

Trp Arg Cys Ser Arg Asn Val Ile Pro Asp Gln Lys Tyr Cys Glu Arg
                260             265             270

His Thr His Lys Ser Arg Pro Arg Ser Arg Lys His Val Glu Ser Ser
            275             280             285

His Gln Ser Ser His His Asn Asp Ile Arg Thr Ala Lys Asn Asp Thr
    290             295             300

Ser Gln Leu Val Arg Thr Tyr Pro Gln Phe Tyr Gly Gln Pro Ile Ser
305             310             315             320

Gln Ile Pro Val Leu Ser Thr Leu Pro Ser Ala Ser Ser Pro Tyr Asp
            325             330             335

His His Arg Gly Leu Arg Trp Phe Thr Lys Glu Asp Asp Ala Ile Gly
            340             345             350

Thr Leu Asn Pro Glu Thr Gln Glu Ala Val Gln Leu Lys Val Gly Ser
    355             360             365

Ser Arg Glu Leu Lys Arg Gly Phe Asp Tyr Asp Leu Asn Phe Arg Gln
    370             375             380

Lys Glu Pro Ile Val Asp Gln Ser Phe Gly Ala Leu Gln Gly Leu Leu
385             390             395             400

Ser Leu Asn Gln Thr Pro Gln His Asn Gln Glu Thr Arg Gln Phe Val
            405             410             415

Val Glu Gly Lys Gln Asp Glu Ala Met Gly Ser Ser Leu Thr Leu Ser
            420             425             430

Met Ala Gly Gly Gly Met Glu Glu Thr Glu Gly Thr Asn Gln His Gln
            435             440             445

Trp Val Ser His Glu Gly Pro Ser Trp Leu Tyr Ser Thr Thr Pro Gly
    450             455             460

Gly Pro Leu Ala Glu Ala Leu Cys Leu Gly Val Ser Asn Asn Pro Ser
465                 470                 475                 480

Ser Ser Thr Thr Thr Ser Ser Cys Ser Arg Ser Ser Ser
                485                 490

<210> SEQ ID NO 52
<211> LENGTH: 429
<212> TYPE: PRT
<213> ORGANISM: Arabidopsis thaliana

<400> SEQUENCE: 52

Met Gln Ser Pro Lys Met Glu Gln Glu Val Glu Glu Arg Met
1               5                   10                  15

Arg Asn Lys Trp Pro Trp Met Lys Ala Ala Gln Leu Met Glu Phe Arg
                20                  25                  30

Met Gln Ala Leu Val Tyr Arg Tyr Ile Glu Ala Gly Leu Arg Val Pro
            35                  40                  45

His His Leu Val Val Pro Ile Trp Asn Ser Leu Ala Leu Ser Ser Ser
        50                  55                  60

Ser Asn Tyr Asn Tyr His Ser Ser Leu Leu Ser Asn Lys Gly Val
65                  70                  75                  80

Thr His Ile Asp Thr Leu Glu Thr Glu Pro Thr Arg Cys Arg Arg Thr
                85                  90                  95

Asp Gly Lys Lys Trp Arg Cys Ser Asn Thr Val Leu Leu Phe Glu Lys
            100                 105                 110

Tyr Cys Glu Arg His Met His Arg Gly Arg Lys Arg Ser Arg Lys Leu
        115                 120                 125

Val Glu Ser Ser Ser Glu Val Ala Ser Ser Ser Thr Lys Tyr Asp Asn
130                 135                 140

Thr Tyr Gly Leu Asp Arg Tyr Asn Glu Ser Gln Ser His Leu His Gly
145                 150                 155                 160

Thr Ile Ser Gly Ser Ser Asn Ala Gln Val Val Thr Ile Ala Ser Leu
                165                 170                 175

Pro Ser Ala Arg Ser Cys Glu Asn Val Ile Arg Pro Ser Leu Val Ile
            180                 185                 190

Ser Glu Phe Thr Asn Lys Ser Val Ser His Gly Arg Lys Asn Met Glu
        195                 200                 205

Met Ser Tyr Asp Asp Phe Ile Asn Glu Lys Ala Ser Met Cys Val
210                 215                 220

Gly Val Val Pro Leu Gln Gly Asp Glu Ser Lys Pro Ser Val Gln Lys
225                 230                 235                 240

Phe Phe Pro Glu Val Ser Asp Lys Cys Leu Glu Ala Ala Lys Phe Ser
                245                 250                 255

Ser Asn Arg Lys Asn Asp Ile Ile Ala Arg Ser Arg Glu Trp Lys Asn
            260                 265                 270

Met Asn Val Asn Gly Leu Phe His Gly Ile His Phe Ser Pro Asp
        275                 280                 285

Thr Val Leu Gln Glu Arg Gly Cys Phe Arg Leu Gln Gly Val Glu Thr
290                 295                 300

Asp Asn Glu Pro Gly Arg Cys Arg Arg Thr Asp Gly Lys Lys Trp Arg
305                 310                 315                 320

Cys Ser Lys Asp Val Leu Ser Gly Gln Lys Tyr Cys Asp Lys His Met
                325                 330                 335

His Arg Gly Met Lys Lys Lys His Pro Val Asp Thr Thr Asn Ser His
            340                 345                 350

```
Glu Asn Ala Gly Phe Ser Pro Leu Thr Val Glu Thr Ala Arg Ser
        355                 360                 365

Val Val Pro Cys Lys Asp Gly Asp Gln Lys His Ser Val Ser Val
370                 375                 380

Met Gly Ile Thr Leu Pro Arg Val Ser Asp Lys Ser Thr Ser Ser
385                 390                 395                 400

Cys Ser Thr Asp Thr Thr Ile Thr Asp Thr Ala Leu Arg Gly Glu Asp
            405                 410                 415

Asp Asp Glu Glu Tyr Leu Ser Leu Phe Ser Pro Gly Val
            420                 425
```

<210> SEQ ID NO 53
<211> LENGTH: 1047
<212> TYPE: DNA
<213> ORGANISM: Oryza sativa

<400> SEQUENCE: 53

| | | | | | |
|---|---|---|---|---|---|
| atgctgagct | cgtcgccctc | ggcggcggcg | ccggggatag | agggtacca | gccgcagcgc | 60 |
| ggggcggcgg | tcttcacggc | ggcgcagtgg | gcggagctgg | agcagcaggc | gctcatttac | 120 |
| aagtacctcg | tcgccggtgt | ccccgtcccg | ggcgatctcc | tcctcccaat | ccgccccac | 180 |
| tcctccgccg | ccgccaccta | ctccttcgcc | aaccccgccg | ccgcgcccct | ctaccaccac | 240 |
| caccaccacc | cctctctgag | ctattatgcc | tactatggca | agaagcttga | ccctgagccg | 300 |
| tggcgttgcc | gccgcaccga | cggcaagaag | tggcggtgct | ccaaggaggc | gcacccgac | 360 |
| tccaagtact | gcgagcgcca | catgcaccgt | ggccgcaacc | gttcaagaaa | gcctgtggaa | 420 |
| tccaagaccg | ctgcccctgc | gccccagtcg | cagccccagc | tgtccaatgt | cacgaccgcg | 480 |
| actcacgaca | ccgatgcgcc | tctcccgtca | ctcactgtgg | gtgctaaaac | ccacggtctg | 540 |
| tcccttggtg | gtgctggctc | gtcgcagttc | catgtcgacg | caccatcgta | cggcagcaag | 600 |
| tactctcttg | gagctaaagc | tgatgtgggt | gaactgagct | tcttctcagg | agcatcagga | 660 |
| aacaccaggg | gcttcaccat | tgattctcca | acagatagct | catggcattc | actgccttcc | 720 |
| agtgtaccc | cataccgat | gtcaaagcca | agggactctg | gcctcctacc | aggtgcctac | 780 |
| tcctactccc | accttgaacc | ttcacaggaa | cttggccagg | tcaccatcgc | ctcgctgtcc | 840 |
| caagagcagg | agcgccgctc | ttttggtggt | ggagcgggg | ggatgctagg | aaatgtgaag | 900 |
| cacgagaacc | agccgctgag | gcctttcttc | gatgagtggc | ctgggaggcg | agactcgtgg | 960 |
| tcggagatgg | atgaggagag | gtccaaccag | acctccttct | cgacaacccca | gctctcgatc | 1020 |
| tccatcccga | tgcccagatg | tgattga | | | | 1047 |

<210> SEQ ID NO 54
<211> LENGTH: 1371
<212> TYPE: DNA
<213> ORGANISM: Oryza sativa

<400> SEQUENCE: 54

| | | | | | |
|---|---|---|---|---|---|
| atgcaggtg | caatggccag | ggtgaggggt | cccttcacgc | cgtctcagtg | gatcgagctg | 60 |
| gagcaccagg | cgctgatata | caagtacttg | gctgcgaata | gccctgtacc | acacagcctc | 120 |
| ctcatcccca | tcaggaggag | cctcacatcg | ccctactcac | ctgcctactt | tggctcaagc | 180 |
| acattgggat | ggggatcttt | ccagctgggc | tactccggca | gcgcggatcc | ggagcccggc | 240 |
| cggtgccgcc | ggacgacgg | caagaaatgg | cggtgctcga | gggatgcggt | cgccgaccag | 300 |
| aagtactgtg | agcgacacat | gaaccgggga | cgccaccgtt | caagaaagca | tgtggaaggc | 360 |

-continued

```
cagcctggcc atgccgcgaa agcgatgccc gcggcggtgg cagcagccgc tgcctctgct    420
acccagccta gtgctccggc cgcccacagt ggcggagctg ttgctggcct cgctatcaac    480
catcagcacc agcaaatgaa gaactacgct gccaacactg ccaatccttg ctctctgcaa    540
tatagcaggg atctggcaaa caagcataat gagagtgaac aagtgcaaga ctcagacagt    600
ctctcgatgc tgacttccat tagcacgaga aatacgggca gcctgtttcc gttctcaaaa    660
caacataatc cttttgaagt gtccaactca aggccagatt ttggcctagt atcacctgat    720
tcactgatga gttctcctca tagctccttg gagaacgtca atttgctcac ttcgcagagt    780
ctgaatgaac aacagagttc agtttccctt caacactttg tggactggcc aaggacacct    840
gcacaaggag ctctcgcatg gcctgatgct gaagacatgc aagctcagag aagccagctc    900
tcaatatctg ctccaatggc gtcttctgac ctgtcatcag cctcaacatc tcccatccat    960
gagaagctga tgttgtcacc acttaaactg agccgtgaat atagtcctat tggtctcggt   1020
tttgcagcaa atagagatga ggttaaccag ggagaagcaa actggatgcc tatgttccgt   1080
gattctttga tgggcggacc attgggagag gttttaacca agaataacaa catggaagca   1140
aggaattgcc tatcggagtc tctgaatctt ttaaatgatg gctgggattc aagctcaggg   1200
tttgattcat ccccagttgg tgttctgcag aagaccacct ttggatcagt atccagtagc   1260
accggaagca gtcctagact ggagaatcat agtgtttatg atggcaacag taacctgcgg   1320
gatgatctcg gttcagttgt tgtaaatcat ccgagcatcc gcctggtgtg a            1371
```

<210> SEQ ID NO 55
<211> LENGTH: 1236
<212> TYPE: DNA
<213> ORGANISM: Oryza sativa

<400> SEQUENCE: 55

```
atggcaatgg cgacccctac gaccaacggc agcttccttc ttggatcagg gttggattgt     60
ggaagctcag atgtggcaag aatgcagggg gttttagcaa gggttagggg gccattcaca    120
ccaacacaat ggatggagct ggagcaccag gctctgatct acaagcacat tgtggcgaat    180
gcgccggtac cggccggctt gctcctcccc atcaggagaa gcctccatcc accagtgttc    240
ccacacttct cctctggtgg cattcttggc tccagctcct tgggatgggg gtcatttcag    300
ctgggctatt ctgggagtgc tgactccgag cccgggagat gccgtcgaac cgatggcaag    360
aaatggcggt gctcgagaga cgcagttgtc gaccaaaagt actgcgagcg gcacataaac    420
cggggtcgcc accgttcaag aaagcatgtg gaaggccaat ctagccatgc cgcaaaagca    480
acggttcccg ccatagcaca accacccatt ggtgcatcta atggcaaatt gtcaggcagc    540
catggtgtgt caaatgagct cacgaaaacc ttggctacta acaggatgat gttggataaa    600
gcaaatctta ttgaacgctc ccaggactac actaatcagc aacacaacat cctacagaac    660
aacacaaaag gtgataattg gtctgaagag atgtcctcac aagcagacta tgcagtaatc    720
cctgctggct ctctcatgaa cacaccgcaa tcggcgaatt taaatccaat tccccagcaa    780
caacgctgta agcagtcact ctttggcaaa gggatacagc atgatgacat tcagctgtcg    840
atatccattc ccgtggataa ctccgactta cccactaact acaacaaggc tcaaatggac    900
catgtagtag gcggttcatc gaatggcgga aacaacacgc gagcaagttg gataccgggc    960
tcctgggaag cgtccatagg tggacctctg ggtgagttct tcaccaacac cagcagcgca   1020
tcagacgaca aaggcaaaag ccgccacccg ccatctttga acctcttagc tgatggacat   1080
```

| | |
|---|---|
| actacaagtc cacagctgca atcgcccacc ggagtcctgc agatgactag cttcagttca | 1140 |
| gtgcccagca gcactgttag tagtcctgca ggcagcctct gcaatggctt gctcacttca | 1200 |
| ggcctggtga atgcccagac tgtccaaaca ctgtga | 1236 |

<210> SEQ ID NO 56
<211> LENGTH: 1230
<212> TYPE: DNA
<213> ORGANISM: Oryza sativa

<400> SEQUENCE: 56

| | |
|---|---|
| atgctgagct cttgtggtgg ccatggccat ggaaatccaa gaagcttgca agaagaacac | 60 |
| catggcagat gtggtgagca gcaaggtgga ggaggaggag gagggcaaga gcaagagcaa | 120 |
| gatgggttct tggtgagaga ggcaagggca tccccaccat ctccatcttc ttcatcattt | 180 |
| cttggatcca caagctcttc ttgttctgga ggaggaggag gagggcagat gttgagcttc | 240 |
| tcctccccca atggaacagc agggttgggc ttgagctcag gaggaagcat gcaggggtc | 300 |
| ttggcaaggg tcagggggcc gttcacccca acacagtgga tggagctgga gcaccaggca | 360 |
| ctgatctaca agcacattgc tgcaaatgtt tctgtccctt ccagcttgct cctccccatc | 420 |
| aggagaagcc tccatccatg gggatgggga tcattccctc ctggctgtgc tgatgtagaa | 480 |
| cccagaagat gccgccgcac agacggcaag aagtggcggt gctccagaga tgctgttggg | 540 |
| gatcagaagt attgtgagcg acacataaac cgtggtcgcc atcgttcaag aaagcatgtg | 600 |
| gaaggccgaa aggcgacact caccattgca gaaccatcca cggttattgc tgctggtgta | 660 |
| tcatctcgcg gccacactgt ggctcggcag aagcaggtga aggctcagc tgctactgtc | 720 |
| tctgatcctt tctcgagaca atccaacagg aaatttctgg agaaacagaa cgttgtcgac | 780 |
| caattgtctc ccatggattc atttgatttc tcatccacac aatcttctcc aaactatgac | 840 |
| aatgtagcat tgtcaccact gaagttgcac catgatcatg atgaatctta catcgggcat | 900 |
| ggagcaggca gttcatcaga aaaggcagt atgatgtacg aaagtcggtt aacagtctct | 960 |
| aaggaaacac ttgatgatgg acctttaggt gaagttttca aagaaagaa ttgccaatca | 1020 |
| gcttctacag aaatcttaac tgaaaaatgg actgagaacc ccaacttaca ttgcccatct | 1080 |
| ggaatcctac aaatggctac taagttcaat tcaatttcca gcggcaacac agtaaatagt | 1140 |
| ggtggcaccg cagtggagaa tcttatcact gataatggat atcttactgc aagaatgatg | 1200 |
| aatcctcata ttgtcccaac acttctctaa | 1230 |

<210> SEQ ID NO 57
<211> LENGTH: 1281
<212> TYPE: DNA
<213> ORGANISM: Oryza sativa

<400> SEQUENCE: 57

| | |
|---|---|
| atgtttgctg acttctctgc tgctgccatg gagcttggag aggtgttggg cttgcaagga | 60 |
| ctcacagtgc catccaccaa ggagggtgat ctgagcctca tcaagagagc tgctgctggt | 120 |
| agcttcaccc aggctgctgc tgcatcatac ccttcccct tcttgatga acagaagatg | 180 |
| ctcagattcg ccaaggctgc tcacacattg ccatcaggtt tggattttgg gagggaaaat | 240 |
| gagcagaggt tcttgttgtc taggaccaag aggcctttca ctccctcaca gtggatggag | 300 |
| ctggagcacc aggctctcat ttacaagtat ctcaatgcaa aggcccctat accttccagc | 360 |
| ctgctcattt caatcagcaa aagcttcaga tcatcagcta acagaatgag ctggaggcct | 420 |
| ctctatcaag gcttcccaaa tgcagactct gacccagaac ctggaagatg ccgtcgaaca | 480 |

```
gatggcaaga aatggcggtg ttcaaaggag gccatggccg accacaagta ttgtgagagg    540
cacatcaaca gaaaccgcca ccgttcaaga aagcctgtgg aaaaccaaag tagaaagact    600
gtgaaagaga caccgtgtgc tggctcattg ccatcttctg tcgggcaggg cagcttcaag    660
aaggcaaaag ttaatgaaat gaagccacgc agtatcagct attggacaga tagttttgaac   720 aggacaatgg cgaacaaaga gaaaggaaac aaagctgctg aagaaaacaa tggcccactg    780
ctaaatttaa cgaatcaaca gccaacattg tccctgttct ctcagttgaa gcaacagaac    840
aaaccggaga agttcaatac agcaggagac agtgaatcga tttcttcaaa taccatgttg    900
aagccttggg agagcagcaa ccagcagaac aacaaaagca ttcctttcac caagatgcat    960
gatcgtggat gccttcagtc agtccttcag aatttcagct tgcctaagga cgagaaaatg   1020
gagtttcaga aaagcaaaga ttccaatgtc atgacagttc catcaacttt ctattcctcg   1080
ccagaggacc cacgcgtcag ctgccatgca cctaatatgg cacaaatgca agaggatagc   1140
atctcaagtt cttgggagat gcctcaaggt ggacctctag gtgagatctt gacaaactcc   1200
aaaaatcctg acgattcaat catgaaacca gaagcaaggc catatggttg gttactgaac   1260
ctcgaggatc atgcaatgtg a                                             1281

<210> SEQ ID NO 58
<211> LENGTH: 636
<212> TYPE: DNA
<213> ORGANISM: Oryza sativa

<400> SEQUENCE: 58
atggatgagg agaaggaagc cgactcgccg cagccaccgt ccaagctgcc tcgcctctcc     60
ggcgctgacc cgaatgccgg agtggtgacc atggcagcac cccgccgcc ggtgggtctt    120 gggctggggc ttggactcgg cggcgacagc cgcggcgagc gtgacgtgga agcgtcggcg    180
gcggcggcgc acaaggcgac ggcgctgacg ttcatgcagc agcaggagct ggagcaccag    240
gtgctcatct accgctactt cgccgcgggc gcgcccgtgc cggtgcacct cgtgctcccc    300
atctggaaga gcgtcgcgtc ctcctccttc ggcccgcacc gcttcccttc cctggcagtg    360
atggggttgg ggaacctgtg cttcgactac cggagcagca tggagccgga cccagggcgg    420
tgcaggcgca cggacggcaa gaagtggcgg tgctcgcgcg acgtggtgcc ggggcacaag    480
tactgcgagc ggcacgtcca ccgcggacgc ggccgttcaa gaaagcctgt ggaagcctcc    540
gcggccgcca ccccggcgaa caacggcggc ggcggtggca tcgtcttctc ccccaccagc    600
gtcctcctcg cccacggcac cgcgcgcgcc acctga                             636

<210> SEQ ID NO 59
<211> LENGTH: 810
<212> TYPE: DNA
<213> ORGANISM: Oryza sativa

<400> SEQUENCE: 59
atggcggcgg aggggaggc caagaaggac agcgccagca accctcccgg gggaggaggc      60
ggcggaggtg gagggaggga ggaggaggat agcagcctgg ctgtcgggga ggcggcggtc    120
ggggtgggcg aggctggtgg aggaggagga ggagggagaa aggcggatcg agaggaggag    180
gaggggaagg aggatgtgga ggagggcggc gtgtgtaagg atctggtgct cgtcgaggac    240
gccgtccccg tcgaggatcc ggaggaagcc gcagcaactg cagcacttca ggaagaaatg    300
aaagcgctcg ttgaatccgt cccagttggt gctggggcgg cattcaccgc gatgcaacta    360
```

-continued

| | |
|---|---|
| caggagcttg agcagcaatc tcgtgtctac cagtatatgg ctgcccgtgt gcctgtgcct | 420 |
| actcatctcg tcttcccaat atggaagagt gttactggtg catcttctga aggcgcccag | 480 |
| aagtacccga cattgatggg gttggcaaca ctctgcttgg actttggaaa gaacccagaa | 540 |
| ccagaacctg ggaggtgccg gcgaactgat ggaaagaagt ggcggtgctg agaaatgca | 600 |
| attgcaaatg agaaatattg cgaacgccat atgcaccgtg gccgcaagcg tcctgtacag | 660 |
| cttgttgtcg aggatgacga gcctgattct acctcagggt cgaaaccagc atctggcaag | 720 |
| gccaccgaag gtggcaagaa gactgatgac aagagctcaa gtagcaagaa gcttgcagtg | 780 |
| gcagcaccag ctgctgtgga gtctacatga | 810 |

<210> SEQ ID NO 60
<211> LENGTH: 711
<212> TYPE: DNA
<213> ORGANISM: Oryza sativa

<400> SEQUENCE: 60

| | |
|---|---|
| atgttggccg agggaaggca agtctacttg ccgccgccgc cgccgtccaa gcttcctcgt | 60 |
| ctctccggca ccgatccaac cgacggcgtg gtgacgatgg cagcgccgtc gccgctggtt | 120 |
| cttgggctgg gtctcggtct gggcggcagc ggcagcgaca gcagtgggag cgacgcggaa | 180 |
| gcgtctgcgg ccaccgtgcg ggaggcgcgg ccgccgtcgg cgctgacgtt catgcagcgg | 240 |
| caggagctgg agcagcaggt gctcatctac cgctacttcg ccgccggcgc gcctgtgccg | 300 |
| gttcacctcg tgctgcccat atggaagagc atcgccgccg cctcctcgtt cggcccgcaa | 360 |
| agctttccct ccctgacggg cctggggagc ctgtgcttcg actacaggag cagcatggag | 420 |
| ccggagccgg ggcggtgccg gcgcacggac ggcaagaagt ggcggtgctc gcgcgacgtg | 480 |
| gtgccggggc acaagtattg cgagcggcac gtccaccgtg gccgcggccg ttcaagaaag | 540 |
| cctatggaag cctctgcagc agtcgctccc acatatctcc cggtccggcc ggcactccac | 600 |
| accgtcgcca ccctcgccac cagcgcgcca tcgctgtcgc acctcggttt ctcctccgcc | 660 |
| agcaaagtgc tcctcgccca ccaccaccac ggcaccacgc gcgctacttg a | 711 |

<210> SEQ ID NO 61
<211> LENGTH: 356
<212> TYPE: PRT
<213> ORGANISM: Oryza sativa

<400> SEQUENCE: 61

Met Leu Ser Ser Pro Ser Ala Ala Ala Pro Gly Ile Gly Gly Tyr
1               5                   10                  15

Gln Pro Gln Arg Gly Ala Ala Val Phe Thr Ala Ala Gln Trp Ala Glu
                20                  25                  30

Leu Glu Gln Gln Ala Leu Ile Tyr Lys Tyr Leu Val Ala Gly Val Pro
            35                  40                  45

Val Pro Gly Asp Leu Leu Pro Ile Arg Pro His Ser Ser Ala Ala
        50                  55                  60

Ala Thr Tyr Ser Phe Ala Asn Pro Ala Ala Pro Phe Tyr His His
65                  70                  75                  80

His His His Pro Ser Leu Ser Tyr Tyr Ala Tyr Gly Lys Lys Leu
                85                  90                  95

Asp Pro Glu Pro Trp Arg Cys Arg Arg Thr Asp Gly Lys Lys Trp Arg
            100                 105                 110

Cys Ser Lys Glu Ala His Pro Asp Ser Lys Tyr Cys Glu Arg His Met
        115                 120                 125

```
His Arg Gly Arg Asn Arg Ser Arg Lys Pro Val Glu Ser Lys Thr Ala
            130                 135                 140

Ala Pro Ala Pro Gln Ser Gln Pro Gln Leu Ser Asn Val Thr Thr Ala
145                 150                 155                 160

Thr His Asp Thr Asp Ala Pro Leu Pro Ser Leu Thr Val Gly Ala Lys
                165                 170                 175

Thr His Gly Leu Ser Leu Gly Ala Gly Ser Ser Gln Phe His Val
            180                 185                 190

Asp Ala Pro Ser Tyr Gly Ser Lys Tyr Ser Leu Gly Ala Lys Ala Asp
                195                 200                 205

Val Gly Glu Leu Ser Phe Phe Ser Gly Ala Ser Gly Asn Thr Arg Gly
            210                 215                 220

Phe Thr Ile Asp Ser Pro Thr Asp Ser Ser Trp His Ser Leu Pro Ser
225                 230                 235                 240

Ser Val Pro Pro Tyr Pro Met Ser Lys Pro Arg Asp Ser Gly Leu Leu
                245                 250                 255

Pro Gly Ala Tyr Ser Tyr Ser His Leu Glu Pro Ser Gln Glu Leu Gly
            260                 265                 270

Gln Val Thr Ile Ala Ser Leu Ser Gln Glu Gln Glu Arg Arg Ser Phe
            275                 280                 285

Gly Gly Gly Ala Gly Gly Met Leu Gly Asn Val Lys His Glu Asn Gln
            290                 295                 300

Pro Leu Arg Pro Phe Phe Asp Glu Trp Pro Gly Arg Arg Asp Ser Trp
305                 310                 315                 320

Ser Glu Met Asp Glu Glu Arg Ser Asn Gln Thr Ser Phe Ser Thr Thr
                325                 330                 335

Gln Leu Ser Ile Ser Ile Pro Met Pro Arg Cys Gly Ser Pro Ile Gly
            340                 345                 350

Pro Arg Leu Pro
            355

<210> SEQ ID NO 62
<211> LENGTH: 456
<212> TYPE: PRT
<213> ORGANISM: Oryza sativa

<400> SEQUENCE: 62

Met Gln Gly Ala Met Ala Arg Val Arg Gly Pro Phe Thr Pro Ser Gln
1               5                   10                  15

Trp Ile Glu Leu Glu His Gln Ala Leu Ile Tyr Lys Tyr Leu Ala Ala
            20                  25                  30

Asn Ser Pro Val Pro His Ser Leu Leu Ile Pro Ile Arg Arg Ser Leu
        35                  40                  45

Thr Ser Pro Tyr Ser Pro Ala Tyr Phe Gly Ser Ser Thr Leu Gly Trp
    50                  55                  60

Gly Ser Phe Gln Leu Gly Tyr Ser Gly Ser Ala Asp Pro Glu Pro Gly
65              70                  75                  80

Arg Cys Arg Arg Thr Asp Gly Lys Lys Trp Arg Cys Ser Arg Asp Ala
                85                  90                  95

Val Ala Asp Gln Lys Tyr Cys Glu Arg His Met Asn Arg Gly Arg His
                100                 105                 110

Arg Ser Arg Lys His Val Glu Gly Gln Pro Gly His Ala Ala Lys Ala
            115                 120                 125

Met Pro Ala Ala Val Ala Ala Ala Ala Ser Ala Thr Gln Pro Ser
```

```
                130                 135                 140
Ala Pro Ala Ala His Ser Gly Gly Ala Val Ala Gly Leu Ala Ile Asn
145                 150                 155                 160

His Gln His Gln Gln Met Lys Asn Tyr Ala Ala Asn Thr Ala Asn Pro
                165                 170                 175

Cys Ser Leu Gln Tyr Ser Arg Asp Leu Ala Asn Lys His Asn Glu Ser
                180                 185                 190

Glu Gln Val Gln Asp Ser Asp Ser Leu Ser Met Leu Thr Ser Ile Ser
                195                 200                 205

Thr Arg Asn Thr Gly Ser Leu Phe Pro Phe Ser Lys Gln His Asn Pro
210                 215                 220

Phe Glu Val Ser Asn Ser Arg Pro Asp Phe Gly Leu Val Ser Pro Asp
225                 230                 235                 240

Ser Leu Met Ser Ser Pro His Ser Ser Leu Glu Asn Val Asn Leu Leu
                245                 250                 255

Thr Ser Gln Ser Leu Asn Glu Gln Gln Ser Ser Val Ser Leu Gln His
                260                 265                 270

Phe Val Asp Trp Pro Arg Thr Pro Ala Gln Gly Ala Leu Ala Trp Pro
                275                 280                 285

Asp Ala Glu Asp Met Gln Ala Gln Arg Ser Gln Leu Ser Ile Ser Ala
                290                 295                 300

Pro Met Ala Ser Ser Asp Leu Ser Ser Ala Ser Thr Ser Pro Ile His
305                 310                 315                 320

Glu Lys Leu Met Leu Ser Pro Leu Lys Leu Ser Arg Glu Tyr Ser Pro
                325                 330                 335

Ile Gly Leu Gly Phe Ala Ala Asn Arg Asp Glu Val Asn Gln Gly Glu
                340                 345                 350

Ala Asn Trp Met Pro Met Phe Arg Asp Ser Leu Met Gly Gly Pro Leu
                355                 360                 365

Gly Glu Val Leu Thr Lys Asn Asn Asn Met Glu Ala Arg Asn Cys Leu
                370                 375                 380

Ser Glu Ser Leu Asn Leu Leu Asn Asp Gly Trp Asp Ser Ser Ser Gly
385                 390                 395                 400

Phe Asp Ser Ser Pro Val Gly Val Leu Gln Lys Thr Thr Phe Gly Ser
                405                 410                 415

Val Ser Ser Thr Gly Ser Ser Pro Arg Leu Glu Asn His Ser Val
                420                 425                 430

Tyr Asp Gly Asn Ser Asn Leu Arg Asp Asp Leu Gly Ser Val Val Val
                435                 440                 445

Asn His Pro Ser Ile Arg Leu Val
450                 455

<210> SEQ ID NO 63
<211> LENGTH: 411
<212> TYPE: PRT
<213> ORGANISM: Oryza sativa

<400> SEQUENCE: 63

Met Ala Met Ala Thr Pro Thr Thr Asn Gly Ser Phe Leu Leu Gly Ser
1               5                   10                  15

Gly Leu Asp Cys Gly Ser Ser Asp Val Ala Arg Met Gln Gly Val Leu
                20                  25                  30

Ala Arg Val Arg Gly Pro Phe Thr Pro Thr Gln Trp Met Glu Leu Glu
                35                  40                  45
```

His Gln Ala Leu Ile Tyr Lys His Ile Val Ala Asn Ala Pro Val Pro
    50                  55                  60

Ala Gly Leu Leu Leu Pro Ile Arg Arg Ser Leu His Pro Pro Val Phe
65                  70                  75                  80

Pro His Phe Ser Ser Gly Gly Ile Leu Gly Ser Ser Ser Leu Gly Trp
                85                  90                  95

Gly Ser Phe Gln Leu Gly Tyr Ser Gly Ser Ala Asp Ser Glu Pro Gly
            100                 105                 110

Arg Cys Arg Arg Thr Asp Gly Lys Lys Trp Arg Cys Ser Arg Asp Ala
        115                 120                 125

Val Val Asp Gln Lys Tyr Cys Glu Arg His Ile Asn Arg Gly Arg His
130                 135                 140

Arg Ser Arg Lys His Val Glu Gly Gln Ser Ser His Ala Ala Lys Ala
145                 150                 155                 160

Thr Val Pro Ala Ile Ala Gln Pro Pro Ile Gly Ala Ser Asn Gly Lys
                165                 170                 175

Leu Ser Gly Ser His Gly Val Ser Asn Glu Leu Thr Lys Thr Leu Ala
            180                 185                 190

Thr Asn Arg Met Met Leu Asp Lys Ala Asn Leu Ile Glu Arg Ser Gln
        195                 200                 205

Asp Tyr Thr Asn Gln Gln His Asn Ile Leu Gln Asn Asn Thr Lys Gly
    210                 215                 220

Asp Asn Trp Ser Glu Glu Met Ser Ser Gln Ala Asp Tyr Ala Val Ile
225                 230                 235                 240

Pro Ala Gly Ser Leu Met Asn Thr Pro Gln Ser Ala Asn Leu Asn Pro
                245                 250                 255

Ile Pro Gln Gln Gln Arg Cys Lys Gln Ser Leu Phe Gly Lys Gly Ile
            260                 265                 270

Gln His Asp Asp Ile Gln Leu Ser Ile Ser Ile Pro Val Asp Asn Ser
        275                 280                 285

Asp Leu Pro Thr Asn Tyr Asn Lys Ala Gln Met Asp His Val Val Gly
    290                 295                 300

Gly Ser Ser Asn Gly Gly Asn Asn Thr Arg Ala Ser Trp Ile Pro Gly
305                 310                 315                 320

Ser Trp Glu Ala Ser Ile Gly Gly Pro Leu Gly Glu Phe Phe Thr Asn
                325                 330                 335

Thr Ser Ser Ala Ser Asp Asp Lys Gly Lys Ser Arg His Pro Pro Ser
            340                 345                 350

Leu Asn Leu Leu Ala Asp Gly His Thr Thr Ser Pro Gln Leu Gln Ser
        355                 360                 365

Pro Thr Gly Val Leu Gln Met Thr Ser Phe Ser Ser Val Pro Ser Ser
    370                 375                 380

Thr Val Ser Ser Pro Ala Gly Ser Leu Cys Asn Gly Leu Leu Thr Ser
385                 390                 395                 400

Gly Leu Val Asn Ala Gln Thr Val Gln Thr Leu
                405                 410

<210> SEQ ID NO 64
<211> LENGTH: 409
<212> TYPE: PRT
<213> ORGANISM: Oryza sativa

<400> SEQUENCE: 64

Met Leu Ser Ser Cys Gly Gly His Gly His Gly Asn Pro Arg Ser Leu
1               5                   10                  15

Gln Glu Glu His His Gly Arg Cys Gly Glu Gln Gln Gly Gly Gly
                20                  25                  30

Gly Gly Gly Gln Glu Gln Gln Asp Gly Phe Leu Val Arg Glu Ala
            35                  40                  45

Arg Ala Ser Pro Pro Ser Pro Ser Ser Ser Phe Leu Gly Ser Thr
 50                  55                  60

Ser Ser Ser Cys Ser Gly Gly Gly Gly Gln Met Leu Ser Phe
 65              70                  75                  80

Ser Ser Pro Asn Gly Thr Ala Gly Leu Gly Leu Ser Ser Gly Ser
                 85                  90                  95

Met Gln Gly Val Leu Ala Arg Val Arg Gly Pro Phe Thr Pro Thr Gln
             100                 105                 110

Trp Met Glu Leu Glu His Gln Ala Leu Ile Tyr Lys His Ile Ala Ala
             115                 120                 125

Asn Val Ser Val Pro Ser Ser Leu Leu Leu Pro Ile Arg Arg Ser Leu
 130                 135                 140

His Pro Trp Gly Trp Gly Ser Phe Pro Pro Gly Cys Ala Asp Val Glu
145                 150                 155                 160

Pro Arg Arg Cys Arg Arg Thr Asp Gly Lys Lys Trp Arg Cys Ser Arg
                 165                 170                 175

Asp Ala Val Gly Asp Gln Lys Tyr Cys Glu Arg His Ile Asn Arg Gly
             180                 185                 190

Arg His Arg Ser Arg Lys His Val Glu Gly Arg Lys Ala Thr Leu Thr
             195                 200                 205

Ile Ala Glu Pro Ser Thr Val Ile Ala Ala Gly Val Ser Ser Arg Gly
 210                 215                 220

His Thr Val Ala Arg Gln Lys Gln Val Lys Gly Ser Ala Ala Thr Val
225                 230                 235                 240

Ser Asp Pro Phe Ser Arg Gln Ser Asn Arg Lys Phe Leu Glu Lys Gln
                 245                 250                 255

Asn Val Val Asp Gln Leu Ser Pro Met Asp Ser Phe Asp Phe Ser Ser
             260                 265                 270

Thr Gln Ser Ser Pro Asn Tyr Asp Asn Val Ala Leu Ser Pro Leu Lys
             275                 280                 285

Leu His His Asp His Asp Glu Ser Tyr Ile Gly His Gly Ala Gly Ser
 290                 295                 300

Ser Ser Glu Lys Gly Ser Met Met Tyr Glu Ser Arg Leu Thr Val Ser
305                 310                 315                 320

Lys Glu Thr Leu Asp Asp Gly Pro Leu Gly Glu Val Phe Lys Arg Lys
                 325                 330                 335

Asn Cys Gln Ser Ala Ser Thr Glu Ile Leu Thr Glu Lys Trp Thr Glu
             340                 345                 350

Asn Pro Asn Leu His Cys Pro Ser Gly Ile Leu Gln Met Ala Thr Lys
             355                 360                 365

Phe Asn Ser Ile Ser Ser Gly Asn Thr Val Asn Ser Gly Gly Thr Ala
 370                 375                 380

Val Glu Asn Leu Ile Thr Asp Asn Gly Tyr Leu Thr Ala Arg Met Met
385                 390                 395                 400

Asn Pro His Ile Val Pro Thr Leu Leu
                 405

<210> SEQ ID NO 65
<211> LENGTH: 426

<212> TYPE: PRT
<213> ORGANISM: Oryza sativa

<400> SEQUENCE: 65

```
Met Phe Ala Asp Phe Ser Ala Ala Met Glu Leu Gly Glu Val Leu
1               5                   10                  15

Gly Leu Gln Gly Leu Thr Val Pro Ser Thr Lys Glu Gly Asp Leu Ser
                20                  25                  30

Leu Ile Lys Arg Ala Ala Gly Ser Phe Thr Gln Ala Ala Ala Ala
            35                  40                  45

Ser Tyr Pro Ser Pro Phe Leu Asp Glu Gln Lys Met Leu Arg Phe Ala
        50                  55                  60

Lys Ala Ala His Thr Leu Pro Ser Gly Leu Asp Phe Gly Arg Glu Asn
65                  70                  75                  80

Glu Gln Arg Phe Leu Leu Ser Arg Thr Lys Arg Pro Phe Thr Pro Ser
                85                  90                  95

Gln Trp Met Glu Leu Glu His Gln Ala Leu Ile Tyr Lys Tyr Leu Asn
            100                 105                 110

Ala Lys Ala Pro Ile Pro Ser Ser Leu Leu Ile Ser Ile Ser Lys Ser
        115                 120                 125

Phe Arg Ser Ser Ala Asn Arg Met Ser Trp Arg Pro Leu Tyr Gln Gly
    130                 135                 140

Phe Pro Asn Ala Asp Ser Asp Pro Glu Pro Gly Arg Cys Arg Arg Thr
145                 150                 155                 160

Asp Gly Lys Lys Trp Arg Cys Ser Lys Glu Ala Met Ala Asp His Lys
                165                 170                 175

Tyr Cys Glu Arg His Ile Asn Arg Asn Arg His Arg Ser Arg Lys Pro
            180                 185                 190

Val Glu Asn Gln Ser Arg Lys Thr Val Lys Glu Thr Pro Cys Ala Gly
        195                 200                 205

Ser Leu Pro Ser Ser Val Gly Gln Gly Ser Phe Lys Lys Ala Lys Val
    210                 215                 220

Asn Glu Met Lys Pro Arg Ser Ile Ser Tyr Trp Thr Asp Ser Leu Asn
225                 230                 235                 240

Arg Thr Met Ala Asn Lys Glu Lys Gly Asn Lys Ala Ala Glu Glu Asn
                245                 250                 255

Asn Gly Pro Leu Leu Asn Leu Thr Asn Gln Gln Pro Thr Leu Ser Leu
            260                 265                 270

Phe Ser Gln Leu Lys Gln Gln Asn Lys Pro Glu Lys Phe Asn Thr Ala
        275                 280                 285

Gly Asp Ser Glu Ser Ile Ser Ser Asn Thr Met Leu Lys Pro Trp Glu
    290                 295                 300

Ser Ser Asn Gln Gln Asn Asn Lys Ser Ile Pro Phe Thr Lys Met His
305                 310                 315                 320

Asp Arg Gly Cys Leu Gln Ser Val Leu Gln Asn Phe Ser Leu Pro Lys
                325                 330                 335

Asp Glu Lys Met Glu Phe Gln Lys Ser Lys Asp Ser Asn Val Met Thr
            340                 345                 350

Val Pro Ser Thr Phe Tyr Ser Ser Pro Glu Asp Pro Arg Val Ser Cys
        355                 360                 365

His Ala Pro Asn Met Ala Gln Met Gln Glu Asp Ser Ile Ser Ser Ser
    370                 375                 380

Trp Glu Met Pro Gln Gly Gly Pro Leu Gly Ile Leu Thr Asn Ser
385                 390                 395                 400
```

```
Lys Asn Pro Asp Asp Ser Ile Met Lys Pro Glu Ala Arg Pro Tyr Gly
            405                 410                 415

Trp Leu Leu Asn Leu Glu Asp His Ala Met
            420                 425

<210> SEQ ID NO 66
<211> LENGTH: 211
<212> TYPE: PRT
<213> ORGANISM: Oryza sativa

<400> SEQUENCE: 66

Met Asp Glu Glu Lys Glu Ala Asp Ser Pro Gln Pro Pro Ser Lys Leu
1               5                   10                  15

Pro Arg Leu Ser Gly Ala Asp Pro Asn Ala Gly Val Val Thr Met Ala
            20                  25                  30

Ala Pro Pro Pro Val Gly Leu Gly Leu Gly Leu Gly Leu Gly Gly
        35                  40                  45

Asp Ser Arg Gly Glu Arg Asp Val Glu Ala Ser Ala Ala Ala His
    50                  55                  60

Lys Ala Thr Ala Leu Thr Phe Met Gln Gln Gln Glu Leu Glu His Gln
65                  70                  75                  80

Val Leu Ile Tyr Arg Tyr Phe Ala Ala Gly Ala Pro Val Pro Val His
                85                  90                  95

Leu Val Leu Pro Ile Trp Lys Ser Val Ala Ser Ser Phe Gly Pro
            100                 105                 110

His Arg Phe Pro Ser Leu Ala Val Met Gly Leu Gly Asn Leu Cys Phe
        115                 120                 125

Asp Tyr Arg Ser Ser Met Glu Pro Asp Pro Gly Arg Cys Arg Arg Thr
    130                 135                 140

Asp Gly Lys Lys Trp Arg Cys Ser Arg Asp Val Val Pro Gly His Lys
145                 150                 155                 160

Tyr Cys Glu Arg His Val His Arg Gly Arg Gly Arg Ser Arg Lys Pro
                165                 170                 175

Val Glu Ala Ser Ala Ala Ala Thr Pro Ala Asn Asn Gly Gly Gly Gly
            180                 185                 190

Gly Ile Val Phe Ser Pro Thr Ser Val Leu Leu Ala His Gly Thr Ala
        195                 200                 205

Arg Ala Thr
    210

<210> SEQ ID NO 67
<211> LENGTH: 269
<212> TYPE: PRT
<213> ORGANISM: Oryza sativa

<400> SEQUENCE: 67

Met Ala Ala Glu Gly Glu Ala Lys Lys Asp Ser Ala Ser Asn Pro Pro
1               5                   10                  15

Gly Gly Gly Gly Gly Gly Gly Gly Glu Glu Glu Glu Asp Ser Ser
            20                  25                  30

Leu Ala Val Gly Glu Ala Ala Val Gly Val Gly Glu Ala Gly Gly
        35                  40                  45

Gly Gly Gly Gly Glu Lys Ala Asp Arg Glu Glu Glu Gly Lys Glu
    50                  55                  60

Asp Val Glu Glu Gly Gly Val Cys Lys Asp Leu Val Leu Val Glu Asp
65                  70                  75                  80
```

-continued

Ala Val Pro Val Glu Asp Pro Glu Ala Ala Thr Ala Ala Leu
             85                  90                  95

Gln Glu Glu Met Lys Ala Leu Val Glu Ser Val Pro Val Gly Ala Gly
            100                 105                 110

Ala Ala Phe Thr Ala Met Gln Leu Gln Glu Leu Glu Gln Gln Ser Arg
        115                 120                 125

Val Tyr Gln Tyr Met Ala Ala Arg Val Pro Val Pro Thr His Leu Val
    130                 135                 140

Phe Pro Ile Trp Lys Ser Val Thr Gly Ala Ser Ser Glu Gly Ala Gln
145                 150                 155                 160

Lys Tyr Pro Thr Leu Met Gly Leu Ala Thr Leu Cys Leu Asp Phe Gly
                165                 170                 175

Lys Asn Pro Glu Pro Glu Pro Gly Arg Cys Arg Arg Thr Asp Gly Lys
            180                 185                 190

Lys Trp Arg Cys Trp Arg Asn Ala Ile Ala Asn Glu Lys Tyr Cys Glu
        195                 200                 205

Arg His Met His Arg Gly Arg Lys Arg Pro Val Gln Leu Val Val Glu
    210                 215                 220

Asp Asp Glu Pro Asp Ser Thr Ser Gly Ser Lys Pro Ala Ser Gly Lys
225                 230                 235                 240

Ala Thr Glu Gly Gly Lys Lys Thr Asp Asp Lys Ser Ser Ser Ser Lys
                245                 250                 255

Lys Leu Ala Val Ala Ala Pro Ala Ala Val Glu Ser Thr
            260                 265

<210> SEQ ID NO 68
<211> LENGTH: 236
<212> TYPE: PRT
<213> ORGANISM: Oryza sativa

<400> SEQUENCE: 68

Met Leu Ala Glu Gly Arg Gln Val Tyr Leu Pro Pro Pro Pro Pro Ser
1               5                   10                  15

Lys Leu Pro Arg Leu Ser Gly Thr Asp Pro Thr Asp Gly Val Val Thr
            20                  25                  30

Met Ala Ala Pro Ser Pro Leu Val Leu Gly Leu Gly Leu Gly Leu Gly
        35                  40                  45

Gly Ser Gly Ser Asp Ser Ser Gly Ser Asp Ala Glu Ala Ser Ala Ala
    50                  55                  60

Thr Val Arg Glu Ala Arg Pro Pro Ser Ala Leu Thr Phe Met Gln Arg
65                  70                  75                  80

Gln Glu Leu Glu Gln Gln Val Leu Ile Tyr Arg Tyr Phe Ala Ala Gly
                85                  90                  95

Ala Pro Val Pro Val His Leu Val Leu Pro Ile Trp Lys Ser Ile Ala
            100                 105                 110

Ala Ala Ser Ser Phe Gly Pro Gln Ser Phe Pro Ser Leu Thr Gly Leu
        115                 120                 125

Gly Ser Leu Cys Phe Asp Tyr Arg Ser Ser Met Glu Pro Glu Pro Gly
    130                 135                 140

Arg Cys Arg Arg Thr Asp Gly Lys Lys Trp Arg Cys Ser Arg Asp Val
145                 150                 155                 160

Val Pro Gly His Lys Tyr Cys Glu Arg His Val His Arg Gly Arg Gly
                165                 170                 175

Arg Ser Arg Lys Pro Met Glu Ala Ser Ala Ala Val Ala Pro Thr Tyr

```
              180                 185                 190
Leu Pro Val Arg Pro Ala Leu His Thr Val Ala Thr Leu Ala Thr Ser
            195                 200                 205

Ala Pro Ser Leu Ser His Leu Gly Phe Ser Ser Ala Ser Lys Val Leu
        210                 215                 220

Leu Ala His Thr Thr Thr Gly Thr Thr Arg Ala Thr
225                 230                 235
```

<210> SEQ ID NO 69
<211> LENGTH: 1506
<212> TYPE: DNA
<213> ORGANISM: Zea mays

<400> SEQUENCE: 69

| | | | | | |
|---|---|---|---|---|---|
| ccatctggcc | atctcccctt | ccctgctcc | cccgaagcag | caagccagcc | tgcccacccg | 60 |
| cagccatcac | ctccgccgct | ctccaccatg | aatcccatcc | accagcacga | catcgtaccc | 120 |
| aatccttcgt | gactgttgcc | tccgcgcatc | tccgggagca | atggaaggag | gccgagatgt | 180 |
| gttcttaggt | gcggcggcaa | gggcgccgcc | gccgccgccg | tcttgcccgt | tcacggatc | 240 |
| cgctaccgcc | acccgctccg | gtggagcgca | gatgctcagc | ttctcctcca | atggcgtagc | 300 |
| agggttgggt | ctgtgctcag | gtgccagcaa | gatgcagggt | gtgttgtcga | gggtgaggag | 360 |
| gcccttcact | ccgacgcagt | ggatggagct | ggagcaccag | gccctgatct | acaagcactt | 420 |
| cgctgtgaat | gcccctgtgc | cgtccagctt | gctcctccct | atcaaaagaa | gcctcaatcc | 480 |
| atggagcagc | cttggctcca | gctcattggg | atgggcacca | tttcgttccg | gctctgctga | 540 |
| tgcagaacca | ggaagatgcc | gccgcacaga | tggcaagaag | tggcggtgct | ctagagatgc | 600 |
| tgtcggggac | caaaaatact | gtgagcgata | cataaaacgt | ggttgccacc | gttcaagaaa | 660 |
| gcatgtggaa | ggccgaaagg | caacaccgac | cactgcagat | ccaaccatgg | ctgtttctgg | 720 |
| tggttcattg | ttgcacagcc | atgctgttgc | ttggcagcag | cagggcaaaa | gctcagctgc | 780 |
| taatgtgact | gatccattct | cactagggtc | caacaggaat | ttgctggata | agcagaatct | 840 |
| aggtgaccag | ttctctgtat | ccacttccat | ggactccttt | gacttctcat | catcacattc | 900 |
| ttccccaaac | caagccaaag | ttgcattttc | accggtggcc | atgcagcacg | aacatgatca | 960 |
| gctgtatctt | gtgcatggag | ccggcagctc | agcagaaaac | gttaacaagt | ctcaggatgg | 1020 |
| tcagctgcta | gtctcgaggg | aaacaattga | cgacggacct | ctgggcgagg | tgttcaaggg | 1080 |
| caagagttgc | cagtcagcat | ccgcagacat | cttaactgac | cattggactt | cgactcgtga | 1140 |
| cttgcgtcct | ccaaccggag | tcctacaaat | gtctagcagc | aacacagtgc | cagcagagaa | 1200 |
| tcacacgagt | aacagtagct | atctcatggc | gaggatggcg | aattctcaga | ccgtcccaac | 1260 |
| actccactga | gtgttcatca | ggctggtctt | tgttgggacc | acaaaataac | tgaagccatg | 1320 |
| ttgatgtcct | gagtttgctg | atacagtgat | actaggtttt | cagtcgagtc | ttgtaactcc | 1380 |
| tgttttagag | ttgttatatg | ttcacgtcat | gttgcctttc | attttcggtt | tcattcgat | 1440 |
| gggtgtacta | ataatttctt | tccttcttac | ctgtgaagga | tttgagttcc | aatctgagac | 1500 |
| gtgggt | | | | | | 1506 |

<210> SEQ ID NO 70
<211> LENGTH: 1028
<212> TYPE: DNA
<213> ORGANISM: Zea mays

<400> SEQUENCE: 70

| | |
|---|---|
| tcccttcacc gctgcctcga cccgcgccga aagatacctt tcccccccctt cctctcgcgc | 60 |
| cgccgttttg gtgcgaccat ggcggcgag ggggaggcca agaacccgtc cggcggtggc | 120 |
| gaaggggta accccagca ccagcaggca gtgcaggctg cgccggcgga gccgccaatg | 180 |
| gcacagggg aagcggtgca ggaggctgga gcgcaggcga cgggacaaga gccgaggg | 240 |
| gagaaggcga atcgagatgg ggagggaagc gcggggaga aggacgacgg cgcgtgcaga | 300 |
| gatctggttc tggttgagga tccggaggtg ctcgccgtcg aggacccgga ggaagctgca | 360 |
| gcaaccgcag cactccagga agaaatgaaa gcgctcgtgg catccgtccc tgacggtgct | 420 |
| ggggcagcat tcacagccat gcagcttcag gagctagagc agcagtcccg ggtttatcag | 480 |
| tacatggctg cccgagtacc tgtgcctact cacctcgtct tccccgtatg gaagagtgta | 540 |
| accggtgcat cctctgaagg cgcccagaag taccctactt tgttgggctt agcaacactc | 600 |
| tgcttggact tcgggaagaa ccctgaacca gaaccaggga ggtgccggcg aacggatggc | 660 |
| aaaaaatggc gatgttggag aaacactatt ccaaacgaga agtactgcga acgccgcatg | 720 |
| catcgcggtc gcaagcgtcc tgtacaggtc gtcgaggaag ccgagcctga ctctgcttca | 780 |
| ggctcaaaat ctgctcccgg caaggccacc gaaggcgcca agaaggttgg cgacaagagc | 840 |
| ccaggtagca agaagcttgc cgtggcggcg gcagctgcag ctgctgcgca gtctacgtaa | 900 |
| ttgatgcagc attttagtag tcgcaggaag agcatggcgg cgctggcaac tagcgccttc | 960 |
| ttttcattgc atgtgatctt tagctataac ctcatttagc acactcccag tggtgtccgt | 1020 |
| gggaggag | 1028 |

<210> SEQ ID NO 71
<211> LENGTH: 1516
<212> TYPE: DNA
<213> ORGANISM: Zea mays

<400> SEQUENCE: 71

| | |
|---|---|
| ttcggcacga cccaacaatg cacaccaaca tccactccct cgtcaggctc ctctccccca | 60 |
| aatgagcgct gagttctgcg ctgctgcggg tgtcgtggcc atggagctcg ggtcggaga | 120 |
| tgcgctgggg ctgcagcaag gcatcgcaat caccgcgcca tcgcccaggg acagcgacct | 180 |
| gggtcttctc aagcgagcag gcctcaccca ggctgcggct gctgcccct accctcccc | 240 |
| cttccttgac ggggagaaga tgctcaggtt ctccaaggcg gctcacacat cgcactcagg | 300 |
| cttggatttt ggaggcccag gtgagcaggc tttcctgctg tccaggacca agatgccatt | 360 |
| tactccctcg cagtggatgg agctggggca ccaggctctg atatacaagt acctcaatgc | 420 |
| aaaggcccc ataccttcca gcctgctcat ttcaatcagc aagagcttca gatcatccaa | 480 |
| tagagtgagc tggaggcctc tgtatcaagg ctacacaaat gcagactctg acccagaacc | 540 |
| tgggagatgc cgacgaacgg atggaaagaa gtggcggtgc tccaaggaag caatggctga | 600 |
| tcacaagtac tgtgagcggc acatcaacag aaaccgtcac cgttcaagaa agcctgtgga | 660 |
| aaatcaacct aagaagacca ccaaggaggt gcctgctgct gctggctcat taccatgtgc | 720 |
| tgggccacaa ggtagcttga agaaggcaaa agttaatgac tccaagccag gcactgtcag | 780 |
| ctattgggca gatagtttaa acaggacaat gttgagcaga gagaaagcaa acaaaccgac | 840 |
| ggaagatagc tctttgctgc ttacttctac gaacagccaa cccacctggt ccctgctctc | 900 |
| tcagctgaag cagcaaaaca aaccagataa gttaggcccc acactggaaa atgagtcaaa | 960 |
| cccagacaca atattgaaag cctggggtgg caaccagcct agccacaaga gcatttcctc | 1020 |
| tacagagcgc catgatgctg aatcccctcca atcagtcctt caaaatctca gcctagccca | 1080 |

```
gaatgagaag atggagtcag aaaaggacaa atattctgat tccgtgctag tttcgtcgac    1140
tttctattct gcaggcggtc caagagctac ctgccttaca cctaacatga cacaggtgaa    1200
gcaggattgc atatcaagct cttgggagat gcctcaaggt ggacctctag gcgaaatctt    1260
aacgaactcc aagaatagca aggacttaag caagtgcaaa ccaaggtcat atggttggtt    1320
gttgaatctt gaccatgcac catgattcct caatccatga agagcttgac atagatgtcc    1380
catcatgtag gcaaacaatg gtcagaaaaa ggttatgacc acattgcttg ccccatgcat    1440
gcttgctatc tacatttgta tttctgttgc gtagcattta gctagttgaa ttatcagttc    1500
ttctggatac ggctgt                                                   1516

<210> SEQ ID NO 72
<211> LENGTH: 945
<212> TYPE: DNA
<213> ORGANISM: Zea mays

<400> SEQUENCE: 72
agagcgccgt atcacctgtc tctccgtcca ccgccgtctc gatccgcgcc aaagatacct     60
ttcccccacc ccttcctcgc gccgccgttt ggtgcgacca tgacggcgga ggggaggcc     120 aagaacccgt cggccggtgg cggaggggat aaccccagc accagcaggc tgcgccggcg    180
ccggcgccgg cacaggggga agtggcgcag gaggctgcag tgcaggggac gggacaagag    240
caggagcggg acaaggcgga tcgagaggtg cagggcggcg cggggagaa ggacgacggc    300 gcgtgcagag atctggtcct ggtcgaggat ccggaggtcc tcgccgtcga ggatccggag    360
gaagctgcag caaccgcagc actccaggaa gaaatgaaag cgcttgtggc atcgatccct    420
gatggtgctg gagcagcatt cacagccatg cagcttcagg agctagagca gcagtcccgg    480
gtgtaccagt acatggctgc ccgagtacct gtgcctactc acctcgtctt cccggtatgg    540
aagagtgtga ccggtgcatc ctctgaaggc gcccagaagt accctacttt gatgggctta    600
gcaacgctct gcttggactt tgggaagaac ccggaaccag aaccagggag gtgtcggcga    660
acagatggta agaaatggcg atgttggaga aacactatcc caaacgagaa atactgcgaa    720
cgtcacatgc atcgtggccg caagcgtcct gtacaggttt tcctggagga cgacgagccc    780
gattctgctt cagggtcaaa acccgccgct cctggcaagg ctaccgaagg tgccaagaag    840
gccgatgaca gagcccaag cagcaagaag cttgcagtgg cagcgcctgc cgctgtgcag    900
tctacatagt caattgcagc tttagtagcc cgcagaaaga gcata                    945

<210> SEQ ID NO 73
<211> LENGTH: 1099
<212> TYPE: DNA
<213> ORGANISM: Zea mays

<400> SEQUENCE: 73
cgcatccgtt ctctatcgaa agggaggagg aggagcgcgc gggagtgggc tgggggccca     60
ccgatgctga gctcggcgtc ctcggccggg gcggccatgg ggatgggcgg cgggtaccaa    120
caccagccgc tgccactgcc gcagcgcggg gcggcggccg cggtcttcac cgccgcgcag    180
tgggcggagc tggagcagca ggcgctcatc tacaagtacc tcatggccgg cgtccccgtc    240
ccgcccgatc tcctccgccc cgccccccac gccgccgcct tctccttcgc cagccccgcc    300
gcgtcgccct tctaccatca ccaccaccac caccgtccc tgagttacta cgcctactac    360
gggaagaagc tggacccgga gccgtggcgg tgccgccgca ccgacggcaa gaagtggcgg    420
```

```
tgctccaagg aggcgcaccc cgactccaag tactgcgagc gccacatgca ccgtggccgc    480
aaccgttcaa gaaagcctgt ggaatccaag accgcctcct cgccgcccca gctgtccacc    540
gtcgtcacca ccaccaccac ccgggaggcc gccgccgcga cgcccctcga gtccctcgcg    600
ggggcggggg gtaaggctca cggcctgtcc ctcggcggcg gggctggctc gtcgcacctc    660
agcgtcgacg cttcgaacac tcactttcgc tatggcagca agtaccctct ggagctaaa    720 tccgatgctg gcgagctgag cttcttctca ggagcaccag gaactccag ggcttcacc     780 attgattctc cagcagataa ctcttggcac tccctgccat ccaacgtgcc cccgtttaca   840
ctgtccaagg gcagagattc tggcctcctg cctggagcgc caccagtcgt cgttcagcag    900
cagcggggcc ggcgctggtg ggttgctggg gagcgtgaag caggagaacc agccgctgag    960
gcccttcttc gacgagtggc ctgggacgcg ggactcgtgg tcggagatgg acgacgcgag   1020
gtccagtagg acctccttct cgacgaccca gctctccatc tccattccga tgcccagatg   1080
tgattgagaa cgaagctcg                                                1099

<210> SEQ ID NO 74
<211> LENGTH: 1328
<212> TYPE: DNA
<213> ORGANISM: Zea mays

<400> SEQUENCE: 74
cctcccgtca gcctcttctt ctcccccctga tgagcgctga gttctgtgct gccgccgctg   60
gtgctgtggc catggagctc ggagtcgggg atgtgatggg gctgcagcaa ggcatcgccg    120
ccgccaccgg gccatcgtcc ggagacagcg acctgggtct tctcaagcga gcaggcctcg    180
cccaggcagc cacctcctac ccctcccctt cctcgaccca acagaagatg ctcaggttct    240
ccaaggcggc ggcggctcac acgtcgccct caggcctaga tttcggagga ggcccaagcg    300
agcaggcttt cctgctgtcc aggaccaagc ggccgttcac ccgtcgcag tggatggagc     360 tggagcacca ggctctcata tacaagtatc tcaatgccaa ggcccccata ccttccagcc    420
tgctcgtttc catcagcaag agcttcaggt catccaacag agtgagctgg aggcctcttt   480
accaaggcta cgcaaacgca gactccgacc cagaacctgg gaggtgccgg cggacagacg    540
gaaagaagtg gcggtgctct aaggaggcga tgcctgatca caagtactgc gagcgccaca    600
tcaataggaa ccgccaccgt tcaagaaagc ctgtggaaaa ccaacctaga aagaccagca    660
aggaggtgcc taccgctgct gctggctcgt tgccgtgtgc cgggccacaa ggtagcttga    720
agaaggcaaa agttaatgac tccaagccag gcactggcag ctattggaca gatagcttaa    780
acaggacaat gctgagcagg gagaaggcaa acaaaccgac ggaagacgag tctttgctgc    840
ttagttctac gaagaacagc cagcccacct tgtccctgct cactcaactg aagcagcaga    900
acaaaccaga taagttaggt cccacaccgg aaaatgagcc gaactcggac acaatgttga    960
aagcctgggg tggcagccac cacaagaaca tttcctccac acagcgccat gacgctgaat    1020
ccctccaatc agtcctccaa aattcagcc tagcccagaa tgacaggttg gagtcagaaa     1080
agaacagata ttctgattcc gtgctagtct catcggcttt ctattctgca gacggtccac   1140
aaactacctg ccttacacct aacatgacac aagtgcagca ggactgcata tcaagctcct    1200
gggagatgcc tcaaggtgga cctctaggcg agatcttaac gaactccaag attagtgagg    1260
actcaagcaa gtgtggatct aggtcatatg gttggctatt gaatcttgac catgcaccat    1320
gattcctc                                                            1328
```

```
<210> SEQ ID NO 75
<211> LENGTH: 369
<212> TYPE: PRT
<213> ORGANISM: Zea mays

<400> SEQUENCE: 75
```

| | | | | | | | | | | | | | | |
|---|---|---|---|---|---|---|---|---|---|---|---|---|---|---|
| Met | Glu | Gly | Gly | Arg | Asp | Val | Phe | Leu | Gly | Ala | Ala | Arg | Ala | Pro |
| 1 | | | | 5 | | | | | 10 | | | | | 15 |
| Pro | Pro | Pro | Pro | Ser | Cys | Pro | Phe | His | Gly | Ser | Ala | Thr | Ala | Thr | Arg |
| | | | 20 | | | | | 25 | | | | | 30 | | |
| Ser | Gly | Gly | Ala | Gln | Met | Leu | Ser | Phe | Ser | Ser | Asn | Gly | Val | Ala | Gly |
| | | 35 | | | | | 40 | | | | | 45 | | | |
| Leu | Gly | Leu | Cys | Ser | Gly | Ala | Ser | Lys | Met | Gln | Gly | Val | Leu | Ser | Arg |
| | 50 | | | | | 55 | | | | | 60 | | | | |
| Val | Arg | Arg | Pro | Phe | Thr | Pro | Thr | Gln | Trp | Met | Glu | Leu | Glu | His | Gln |
| 65 | | | | | 70 | | | | | 75 | | | | | 80 |
| Ala | Leu | Ile | Tyr | Lys | His | Phe | Ala | Val | Asn | Ala | Pro | Val | Pro | Ser | Ser |
| | | | | 85 | | | | | 90 | | | | | 95 | |
| Leu | Leu | Leu | Pro | Ile | Lys | Arg | Ser | Leu | Asn | Pro | Trp | Ser | Ser | Leu | Gly |
| | | | 100 | | | | | 105 | | | | | 110 | | |
| Ser | Ser | Ser | Leu | Gly | Trp | Ala | Pro | Phe | Arg | Ser | Gly | Ser | Ala | Asp | Ala |
| | | | 115 | | | | | 120 | | | | | 125 | | |
| Glu | Pro | Gly | Arg | Cys | Arg | Arg | Thr | Asp | Gly | Lys | Lys | Trp | Arg | Cys | Ser |
| 130 | | | | | 135 | | | | | 140 | | | | | |
| Arg | Asp | Ala | Val | Gly | Asp | Gln | Lys | Tyr | Cys | Glu | Arg | Tyr | Ile | Lys | Arg |
| 145 | | | | 150 | | | | | 155 | | | | | 160 | |
| Gly | Cys | His | Arg | Ser | Arg | Lys | His | Val | Glu | Gly | Arg | Lys | Ala | Thr | Pro |
| | | | | 165 | | | | | 170 | | | | | 175 | |
| Thr | Thr | Ala | Asp | Pro | Thr | Met | Ala | Val | Ser | Gly | Gly | Ser | Leu | Leu | His |
| | | | 180 | | | | | 185 | | | | | 190 | | |
| Ser | His | Ala | Val | Ala | Trp | Gln | Gln | Gln | Gly | Lys | Ser | Ser | Ala | Ala | Asn |
| | | 195 | | | | | 200 | | | | | 205 | | | |
| Val | Thr | Asp | Pro | Phe | Ser | Leu | Gly | Ser | Asn | Arg | Asn | Leu | Leu | Asp | Lys |
| | 210 | | | | | 215 | | | | | 220 | | | | |
| Gln | Asn | Leu | Gly | Asp | Gln | Phe | Ser | Val | Ser | Thr | Ser | Met | Asp | Ser | Phe |
| 225 | | | | | 230 | | | | | 235 | | | | | 240 |
| Asp | Phe | Ser | Ser | Ser | His | Ser | Ser | Pro | Asn | Gln | Ala | Lys | Val | Ala | Phe |
| | | | | 245 | | | | | 250 | | | | | 255 | |
| Ser | Pro | Val | Ala | Met | Gln | His | Glu | His | Asp | Gln | Leu | Tyr | Leu | Val | His |
| | | | 260 | | | | | 265 | | | | | 270 | | |
| Gly | Ala | Gly | Ser | Ser | Ala | Glu | Asn | Val | Asn | Lys | Ser | Gln | Asp | Gly | Gln |
| | | 275 | | | | | 280 | | | | | 285 | | | |
| Leu | Leu | Val | Ser | Arg | Glu | Thr | Ile | Asp | Asp | Gly | Pro | Leu | Gly | Glu | Val |
| | 290 | | | | | 295 | | | | | 300 | | | | |
| Phe | Lys | Gly | Lys | Ser | Cys | Gln | Ser | Ala | Ser | Ala | Asp | Ile | Leu | Thr | Asp |
| 305 | | | | | 310 | | | | | 315 | | | | | 320 |
| His | Trp | Thr | Ser | Thr | Arg | Asp | Leu | Arg | Pro | Pro | Thr | Gly | Val | Leu | Gln |
| | | | | 325 | | | | | 330 | | | | | 335 | |
| Met | Ser | Ser | Ser | Asn | Thr | Val | Pro | Ala | Glu | Asn | His | Thr | Ser | Asn | Ser |
| | | | 340 | | | | | 345 | | | | | 350 | | |
| Ser | Tyr | Leu | Met | Ala | Arg | Met | Ala | Asn | Ser | Gln | Thr | Val | Pro | Thr | Leu |
| | | | | 355 | | | | | 360 | | | | | 365 | |
| His | | | | | | | | | | | | | | | |

-continued

```
<210> SEQ ID NO 76
<211> LENGTH: 273
<212> TYPE: PRT
<213> ORGANISM: Zea mays

<400> SEQUENCE: 76

Met Ala Ala Glu Gly Glu Ala Lys Asn Pro Ser Gly Gly Glu Gly
1               5                   10                  15

Gly Asn Pro Gln His Gln Gln Ala Val Gln Ala Ala Pro Ala Glu Pro
            20                  25                  30

Pro Met Ala Gln Gly Glu Ala Val Gln Glu Ala Gly Ala Gln Ala Thr
        35                  40                  45

Gly Gln Glu Pro Glu Gly Glu Lys Ala Asn Arg Asp Gly Glu Gly Ser
    50                  55                  60

Ala Gly Glu Lys Asp Asp Gly Ala Cys Arg Asp Leu Val Leu Val Glu
65                  70                  75                  80

Asp Pro Glu Val Leu Ala Val Glu Asp Pro Glu Glu Ala Ala Ala Thr
                85                  90                  95

Ala Ala Leu Gln Glu Glu Met Lys Ala Leu Val Ala Ser Val Pro Asp
            100                 105                 110

Gly Ala Gly Ala Ala Phe Thr Ala Met Gln Leu Gln Glu Leu Glu Gln
        115                 120                 125

Gln Ser Arg Val Tyr Gln Tyr Met Ala Ala Arg Val Pro Val Pro Thr
    130                 135                 140

His Leu Val Phe Pro Val Trp Lys Ser Val Thr Gly Ala Ser Ser Glu
145                 150                 155                 160

Gly Ala Gln Lys Tyr Pro Thr Leu Leu Gly Leu Ala Thr Leu Cys Leu
                165                 170                 175

Asp Phe Gly Lys Asn Pro Glu Pro Glu Pro Gly Arg Cys Arg Arg Thr
            180                 185                 190

Asp Gly Lys Lys Trp Arg Cys Trp Arg Asn Thr Ile Pro Asn Glu Lys
        195                 200                 205

Tyr Cys Glu Arg Arg Met His Arg Gly Arg Lys Arg Pro Val Gln Val
    210                 215                 220

Val Glu Glu Ala Glu Pro Asp Ser Ala Ser Gly Ser Lys Ser Ala Pro
225                 230                 235                 240

Gly Lys Ala Thr Glu Gly Ala Lys Lys Val Gly Asp Lys Ser Pro Gly
                245                 250                 255

Ser Lys Lys Leu Ala Val Ala Ala Ala Ala Ala Ala Gln Ser
            260                 265                 270

Thr

<210> SEQ ID NO 77
<211> LENGTH: 427
<212> TYPE: PRT
<213> ORGANISM: Zea mays

<400> SEQUENCE: 77

Met Ser Ala Glu Phe Cys Ala Ala Ala Gly Val Val Ala Met Glu Leu
1               5                   10                  15

Gly Val Gly Asp Ala Leu Gly Leu Gln Gln Gly Ile Ala Ile Thr Ala
            20                  25                  30

Pro Ser Pro Arg Asp Ser Asp Leu Gly Leu Leu Lys Arg Ala Gly Leu
        35                  40                  45

Thr Gln Ala Ala Ala Ala Ala Pro Tyr Pro Ser Pro Phe Leu Asp Gly
    50                  55                  60
```

```
Glu Lys Met Leu Arg Phe Ser Lys Ala Ala His Thr Ser His Ser Gly
 65                  70                  75                  80

Leu Asp Phe Gly Gly Pro Gly Glu Gln Ala Phe Leu Leu Ser Arg Thr
                 85                  90                  95

Lys Met Pro Phe Thr Pro Ser Gln Trp Met Glu Leu Gly His Gln Ala
            100                 105                 110

Leu Ile Tyr Lys Tyr Leu Asn Ala Lys Ala Pro Ile Pro Ser Ser Leu
            115                 120                 125

Leu Ile Ser Ile Ser Lys Ser Phe Arg Ser Ser Asn Arg Val Ser Trp
130                 135                 140

Arg Pro Leu Tyr Gln Gly Tyr Thr Asn Ala Asp Ser Asp Pro Glu Pro
145                 150                 155                 160

Gly Arg Cys Arg Arg Thr Asp Gly Lys Lys Trp Arg Cys Ser Lys Glu
                165                 170                 175

Ala Met Ala Asp His Lys Tyr Cys Glu Arg His Ile Asn Arg Asn Arg
            180                 185                 190

His Arg Ser Arg Lys Pro Val Glu Asn Gln Pro Lys Lys Thr Thr Lys
            195                 200                 205

Glu Val Pro Ala Ala Gly Ser Leu Pro Cys Ala Gly Pro Gln Gly
210                 215                 220

Ser Leu Lys Lys Ala Lys Val Asn Asp Ser Lys Pro Gly Thr Val Ser
225                 230                 235                 240

Tyr Trp Ala Asp Ser Leu Asn Arg Thr Met Leu Ser Arg Glu Lys Ala
                245                 250                 255

Asn Lys Pro Thr Glu Asp Ser Ser Leu Leu Thr Ser Thr Asn Ser
            260                 265                 270

Gln Pro Thr Trp Ser Leu Leu Ser Gln Leu Lys Gln Gln Asn Lys Pro
            275                 280                 285

Asp Lys Leu Gly Pro Thr Leu Glu Asn Glu Ser Asn Pro Asp Thr Ile
290                 295                 300

Leu Lys Ala Trp Gly Gly Asn Gln Pro Ser His Lys Ser Ile Ser Ser
305                 310                 315                 320

Thr Glu Arg His Asp Ala Glu Ser Leu Gln Ser Val Leu Gln Asn Leu
                325                 330                 335

Ser Leu Ala Gln Asn Glu Lys Met Glu Ser Glu Lys Asp Lys Tyr Ser
            340                 345                 350

Asp Ser Val Leu Val Ser Ser Thr Phe Tyr Ser Ala Gly Gly Pro Arg
            355                 360                 365

Ala Thr Cys Leu Thr Pro Asn Met Thr Gln Val Lys Gln Asp Cys Ile
            370                 375                 380

Ser Ser Ser Trp Glu Met Pro Gln Gly Gly Pro Leu Gly Glu Ile Leu
385                 390                 395                 400

Thr Asn Ser Lys Asn Ser Lys Asp Leu Ser Lys Cys Lys Pro Arg Ser
                405                 410                 415

Tyr Gly Trp Leu Leu Asn Leu Asp His Ala Pro
            420                 425

<210> SEQ ID NO 78
<211> LENGTH: 269
<212> TYPE: PRT
<213> ORGANISM: Zea mays

<400> SEQUENCE: 78

Met Thr Ala Glu Gly Glu Ala Lys Asn Pro Ser Ala Gly Gly Gly Gly
```

```
1               5                   10                  15
Asp Asn Pro Gln His Gln Gln Ala Ala Pro Ala Pro Ala Gln
                20                  25                  30
Gly Glu Val Ala Gln Glu Ala Val Gln Gly Thr Gly Gln Glu Gln
                35                  40                  45
Glu Arg Asp Lys Ala Asp Arg Glu Val Gln Gly Gly Ala Gly Glu Lys
            50                  55                  60
Asp Asp Gly Ala Cys Arg Asp Leu Val Leu Val Glu Asp Pro Glu Val
65                  70                  75                  80
Leu Ala Val Glu Asp Pro Glu Glu Ala Ala Thr Ala Ala Leu Gln
                    85                  90                  95
Glu Glu Met Lys Ala Leu Val Ala Ser Ile Pro Asp Gly Ala Gly Ala
                100                 105                 110
Ala Phe Thr Ala Met Gln Leu Gln Glu Leu Glu Gln Gln Ser Arg Val
                115                 120                 125
Tyr Gln Tyr Met Ala Ala Arg Val Pro Val Pro Thr His Leu Val Phe
            130                 135                 140
Pro Val Trp Lys Ser Val Thr Gly Ala Ser Ser Glu Gly Ala Gln Lys
145                 150                 155                 160
Tyr Pro Thr Leu Met Gly Leu Ala Thr Leu Cys Leu Asp Phe Gly Lys
                    165                 170                 175
Asn Pro Glu Pro Glu Pro Gly Arg Cys Arg Arg Thr Asp Gly Lys Lys
                180                 185                 190
Trp Arg Cys Arg Asn Thr Ile Pro Asn Glu Lys Tyr Cys Glu Arg
                195                 200                 205
His Met His Arg Gly Arg Lys Arg Pro Val Gln Val Phe Leu Glu Asp
                210                 215                 220
Asp Glu Pro Asp Ser Ala Ser Gly Ser Lys Pro Ala Pro Gly Lys
225                 230                 235                 240
Ala Thr Glu Gly Ala Lys Lys Ala Asp Asp Lys Ser Pro Ser Ser Lys
                    245                 250                 255
Lys Leu Ala Val Ala Ala Pro Ala Ala Val Gln Ser Thr
                260                 265

<210> SEQ ID NO 79
<211> LENGTH: 321
<212> TYPE: PRT
<213> ORGANISM: Zea mays

<400> SEQUENCE: 79

Met Leu Ser Ser Ala Ser Ser Ala Gly Ala Ala Met Gly Met Gly Gly
1               5                   10                  15
Gly Tyr Gln His Gln Pro Leu Pro Leu Pro Gln Arg Gly Ala Ala
                20                  25                  30
Ala Val Phe Thr Ala Ala Gln Trp Ala Glu Leu Glu Gln Gln Ala Leu
                35                  40                  45
Ile Tyr Lys Tyr Leu Met Ala Gly Val Pro Val Pro Pro Asp Leu Leu
            50                  55                  60
Arg Pro Ala Pro His Ala Ala Phe Ser Phe Ala Ser Pro Ala Ala
65                  70                  75                  80
Ser Pro Phe Tyr His His His His His Pro Ser Leu Ser Tyr Tyr
                    85                  90                  95
Ala Tyr Tyr Gly Lys Lys Leu Asp Pro Glu Pro Trp Arg Cys Arg Arg
                100                 105                 110
```

```
Thr Asp Gly Lys Lys Trp Arg Cys Ser Lys Glu Ala His Pro Asp Ser
            115                 120                 125

Lys Tyr Cys Glu Arg His Met His Arg Gly Arg Asn Arg Ser Arg Lys
130                 135                 140

Pro Val Glu Ser Lys Thr Ala Ser Ser Pro Gln Leu Ser Thr Val
145                 150                 155                 160

Val Thr Thr Thr Thr Thr Arg Glu Ala Ala Ala Thr Pro Leu Glu
                165                 170                 175

Ser Leu Ala Gly Ala Gly Gly Lys Ala His Gly Leu Ser Leu Gly Gly
            180                 185                 190

Gly Ala Gly Ser Ser His Leu Ser Val Asp Ala Ser Asn Thr His Phe
        195                 200                 205

Arg Tyr Gly Ser Lys Tyr Pro Leu Gly Ala Lys Ser Asp Ala Gly Glu
    210                 215                 220

Leu Ser Phe Phe Ser Gly Ala Pro Gly Asn Ser Arg Gly Phe Thr Ile
225                 230                 235                 240

Asp Ser Pro Ala Asp Asn Ser Trp His Ser Leu Pro Ser Asn Val Pro
                245                 250                 255

Pro Phe Thr Leu Ser Lys Gly Arg Asp Ser Gly Leu Leu Pro Gly Ala
            260                 265                 270

Pro Pro Val Val Val Gln Gln Arg Gly Arg Arg Trp Trp Val Ala
        275                 280                 285

Gly Glu Arg Glu Ala Gly Glu Pro Ala Ala Glu Ala Leu Leu Arg Arg
    290                 295                 300

Val Ala Trp Asp Ala Gly Leu Val Val Gly Asp Gly Arg Arg Glu Val
305                 310                 315                 320

Gln

<210> SEQ ID NO 80
<211> LENGTH: 430
<212> TYPE: PRT
<213> ORGANISM: Zea mays

<400> SEQUENCE: 80

Met Ser Ala Glu Phe Cys Ala Ala Ala Gly Ala Val Ala Met Glu
1               5                   10                  15

Leu Gly Val Gly Asp Val Met Gly Leu Gln Gln Gly Ile Ala Ala Ala
            20                  25                  30

Thr Gly Pro Ser Ser Gly Asp Ser Asp Leu Gly Leu Leu Lys Arg Ala
        35                  40                  45

Gly Leu Ala Gln Ala Ala Thr Ser Tyr Pro Ser Pro Phe Leu Asp Gln
    50                  55                  60

Gln Lys Met Leu Arg Phe Ser Lys Ala Ala Ala His Thr Ser Pro
65                  70                  75                  80

Ser Gly Leu Asp Phe Gly Gly Pro Ser Glu Gln Ala Phe Leu Leu
            85                  90                  95

Ser Arg Thr Lys Arg Pro Phe Thr Pro Ser Gln Trp Met Glu Leu Glu
        100                 105                 110

His Gln Ala Leu Ile Tyr Lys Tyr Leu Asn Ala Lys Ala Pro Ile Pro
    115                 120                 125

Ser Ser Leu Leu Val Ser Ile Ser Lys Ser Phe Arg Ser Ser Asn Arg
130                 135                 140

Val Ser Trp Arg Pro Leu Tyr Gln Gly Tyr Ala Asn Ala Asp Ser Asp
145                 150                 155                 160
```

-continued

```
Pro Glu Pro Gly Arg Cys Arg Arg Thr Asp Gly Lys Lys Trp Arg Cys
            165                 170                 175
Ser Lys Glu Ala Met Pro Asp His Lys Tyr Cys Glu Arg His Ile Asn
        180                 185                 190
Arg Asn Arg His Arg Ser Arg Lys Pro Val Glu Asn Gln Pro Arg Lys
            195                 200                 205
Thr Ser Lys Glu Val Pro Thr Ala Ala Ala Gly Ser Leu Pro Cys Ala
        210                 215                 220
Gly Pro Gln Gly Ser Leu Lys Lys Ala Lys Val Asn Asp Ser Lys Pro
225                 230                 235                 240
Gly Thr Gly Ser Tyr Trp Thr Asp Ser Leu Asn Arg Thr Met Leu Ser
            245                 250                 255
Arg Glu Lys Ala Asn Lys Pro Thr Glu Asp Glu Ser Leu Leu Leu Ser
        260                 265                 270
Ser Thr Lys Asn Ser Gln Pro Thr Leu Ser Leu Leu Thr Gln Leu Lys
    275                 280                 285
Gln Gln Asn Lys Pro Asp Lys Leu Gly Pro Thr Pro Glu Asn Glu Pro
290                 295                 300
Asn Ser Asp Thr Met Leu Lys Ala Trp Gly Gly Ser His His Lys Asn
305             310                 315                 320
Ile Ser Ser Thr Gln Arg His Asp Ala Glu Ser Leu Gln Ser Val Leu
            325                 330                 335
Gln Asn Phe Ser Leu Ala Gln Asn Asp Arg Leu Glu Ser Glu Lys Asn
        340                 345                 350
Arg Tyr Ser Asp Ser Val Leu Val Ser Ser Ala Phe Tyr Ser Ala Asp
    355                 360                 365
Gly Pro Gln Thr Thr Cys Leu Thr Pro Asn Met Thr Gln Val Gln Gln
370                 375                 380
Asp Cys Ile Ser Ser Ser Trp Glu Met Pro Gln Gly Gly Pro Leu Gly
385                 390                 395                 400
Glu Ile Leu Thr Asn Ser Lys Ile Ser Glu Asp Ser Ser Lys Cys Gly
            405                 410                 415
Ser Arg Ser Tyr Gly Trp Leu Leu Asn Leu Asp His Ala Pro
        420                 425                 430
```

<210> SEQ ID NO 81
<211> LENGTH: 1197
<212> TYPE: DNA
<213> ORGANISM: Artificial Sequence
<220> FEATURE:
<223> OTHER INFORMATION: Arabidopsis GRF3 with a mutated miR396-target
      site (At-rGRF3)

<400> SEQUENCE: 81

```
atggatttgc aactgaaaca atggagaagc cagcagcagc aacaacatca gacagagtca      60
gaagaacaac cttctgcagc taagatacca aaacatgtct ttgaccagat tcattctcac     120
actgcaactt ctactgctct tcctctcttt accctgagc ctacttcttc taaactctcc     180
tctttgtctc ctgattcttc ctccaggttc cccaagatgg ggagcttctt tagctgggca     240
cagtggcaag aacttgaact acaagctctg atctacaggt acatgttggc tggtgctgct     300
gttcctcagg agctcctttt accaatcaag aaaagccttc tccatctatc tccttcctac     360
tttcttcacc atcctcttca acacctacct cattaccaac ctgcttggta tttgggaagg     420
gcagcgatgg atcctgagcc aggcagatgc aggagaacgg atggtaagaa gtggagatgt     480
tcaagagacg tcttcgctgg ccacaagtat tgcgagcgcc acatgcaccg tggccgcaac     540
```

```
cgttctagaa aaccagtaga gactccaacc accgtcaatg caactgccac gtccatggct    600
tcatcagtag cagccgcagc caccactaca acagcaacaa caacatctac gtttgctttt    660
ggtggtggtg gtggtagtga ggaagtggtt ggtcaaggag gatcttttct cttctctggc    720
tcttctaact cttcatctga acttctccac cttagtcaaa gttgttcgga gatgaagcaa    780
gaaagcaaca acatgaacaa caagaggcca tacgagtccc acatcggatt cagtaacaac    840
agatcagatg gaggacacat cctgaggccc ttctttgacg attggcctcg ttcttcgctc    900
caagaagctg acaatagttc aagccccatg agctcagcca cttgtctctc catctccatg    960
cccgggaact cttcctcaga cgtctctctg aagctgtcca caggcaacga gagggagcc    1020 cggagcaaca acaatgggag agatcagcaa acatgagct ggtggagcgg tggaggttcc    1080
aaccaccatc atcacaacat gggcggacca ttggccgaag ccctgagatc ttcttcctca    1140
tcttccccaa ccagtgttct ccatcagctt ggtgtctcga cacaagcctt tcattga     1197
```

<210> SEQ ID NO 82
<211> LENGTH: 1092
<212> TYPE: DNA
<213> ORGANISM: Artificial Sequence
<220> FEATURE:
<223> OTHER INFORMATION: Glycine max GRF with a mutated miR396-target
      site (Gm-rGRF)

<400> SEQUENCE: 82

```
atggacttcc atctgaagca atggagaaac cagcacgagt cagaggaaca acattctaca     60
aagatgccaa aacttctccc tgaatcccat caacaacaac agccatcagc ctctgcactc    120
cctttgtttg tacctgaacc caacagcagc aaagtcagca ccctattatt tcccaggatg    180
gggagctact tcagcttgtc tcagtggcag gagcttgagt tgcaggcttt gatattcagg    240
tacatgttgg ctggtgctgc tgttcctcct gaactccttc aaccaatcaa gaaaagcctt    300
cttcattctc cacactatta cctccatcac cctctccaac attaccaacc ttctgcttgg    360
tattggggta gaggagcgat ggatccggag ccagggcggt gccggagaac cgacggcaag    420
aagtggcgct gttcgaggga cgtggtggct gggcaaaagt actgtgagcg ccacatgcac    480
cgtggaagaa accgttctag aaaaccagta gagctaccca caccaactag tgctattaac    540
aattgtggtg taactggagt tggatcccta ggaccaggtg cttcatcatc ttccatttgt    600
tcaccaccct tagcttctgc ttcattcaaa tctccttttg atcttcatct tgatgaacgt    660
tcctctggga ccaagaatga agacgaagat catgtgggtg gggatggcag atcaggtgga    720
ggtggtggcc atatgctgag gcatttcttc gatgattggc cacgatcact ccaagactct    780
gacaacgttg aaaacaatgc tgctgctggc cgtagcctct ctatttcaat gcccggtgct    840
tcctcggatg tgtcattgaa attgtccacg ggctatggag aggactcggg cccaggaaat    900
gagaatgtaa gcctcgagcc agagcagctg cagttgaatt gggccggagg atgggcctcg    960
tctaatcaag tggcttcgat gggaggtcca cttgctgagg cactcagatc atctacttca    1020
acctcatctc ccactagtgt tttgcatcgt cacttgcctc gtggatctga gaccagcttt    1080
attagcacct ga                                                        1092
```

<210> SEQ ID NO 83
<211> LENGTH: 1269
<212> TYPE: DNA
<213> ORGANISM: Artificial Sequence
<220> FEATURE:
<223> OTHER INFORMATION: Oryza sativa GRF4 with a mutated miR396-target site (Os-rGRF4.1)

<400> SEQUENCE: 83

```
atgcctccct gtctccggcg gtggccgacc accgctcgtc cccggcagcc gcgaccgcct     60
ccctcctccc cttctgccgc tccaccccgc tctccgcgta agcaacgcga acccgcggct    120
acaacccatt ttcttggctc cagtggtgca tgtgacaaca cggtgagacg ttgtgtgtgg    180
gtgggtgggt gcaggggcgg tggtggcgtc gcgatggggg aggacgcgcc gatgaccgcg    240
aggtggccgc cggcggcggc ggcgaggctg ccgccgttca ccgcggcgca gtacgaggag    300
ctggagcagc aggcgctcat atacaagtac ctggtggcag gcgtgcccgt cccgccggat    360
ctcgtgctcc ccatccgccg cggactcgac tccctcgccg cccgcttcta caaccatccc    420
gcccttggat atggtccgta cttcggcaag aagctggacc agagccaggc gcggtgccgg    480
cgtacggacg gcaagaaatg cggtgctcg aaggaggccg cgccggattc caagtactgc    540
gagcgccaca tgcaccgcgg ccgcaaccgt tctagaaaac cagtagagac gcagctggtc    600
gcccagtccc aaccgcctc atctgttgtc ggttctgcgg cggcgcccct tgctgctgcc    660
tccaatggca gcagcttcca aaaccactct ctttaccctg ctattgccgg cagcaatggc    720
ggggcgggg gaggaacat gcccagctca tttggctcgg cgttgggttc tcagctgcac    780
atggataatg ctgcccctta tgcagctgtt ggtggtggaa caggcaaaga tctcaggtat    840
actgcttatg gcaaagatc tttggcggat gagcagagtc aactcattac tgaagctatc    900
aacacatcta ttgaaaatcc atggcggctg ctgccatctc agaactcgcc atttccctt    960
tcaagctatt ctcagctggg ggcactaagt gaccttggtc agaacacccc cagctcactt   1020
tcaaaggttc agaggcagcc actttcgttc tttgggaacg actatgcggc tgtcgattct   1080
gtgaagcaag agaaccagac gctgcgtccc ttctttgatg agtggccaaa gggaagggat   1140
tcatggtcag acctcgctga tgagaatgct aatctttcgt cattctcagg cacccaactg   1200
tcgatctcca taccaatggc atcctctgac ttctcggcgg ccagttctcg atcaactaat   1260
ggtgactga                                                            1269
```

<210> SEQ ID NO 84
<211> LENGTH: 11332
<212> TYPE: DNA
<213> ORGANISM: Artificial Sequence
<220> FEATURE:
<223> OTHER INFORMATION: JD16 vector sequence

<400> SEQUENCE: 84

```
ttgatcccga ggggaaccct gtggttggca tgcacataca aatggacgaa cggataaacc     60
ttttcacgcc cttttaaata tccgttattc aataaacgc tcttttctct taggtttacc    120
cgccaatata tcctgtcaaa cactgatagt ttaaactgaa ggcgggaaac gacaatctga    180
tccaagctca agctgctcta gccaatacgc aaaccgcctc tccccgcgcg ttggccgatt    240
cattaatgca gctggcacga caggtttccc gactggaaag cgggcagtga gcgcaacgca    300
attaatgtga gttagctcac tcattaggca ccccaggctt tacactttat gcttccggct    360
cgtatgttgt gtggaattgt gagcggataa caatttcaca caggaaacag ctatgaccat    420
gattacgaat tcggtcccca gattagcctt ttcaatttca gaaagaatgc taacccacag    480
atggttagag aggcttacgc agcaggtctc atcaagacga tctacccgag caataatctc    540
caggaaatca aataccttcc caagaaggtt aaagatgcag tcaaaagatt caggactaac    600
tgcatcaaga acacagagaa agatatattt ctcaagatca gaagtactat tccagtatgg    660
```

```
acgattcaag gcttgcttca caaaccaagg caagtaatag agattggagt ctctaaaaag      720
gtagttccca ctgaatcaaa ggccatggag tcaaagattc aaatagagga cctaacagaa      780
ctcgccgtaa agactggcga acagttcata cagagtctct tacgactcaa tgacaagaag      840
aaaatcttcg tcaacatggt ggagcacgac acacttgtct actccaaaaa tatcaaagat      900
acagtctcag aagaccaaag gcaattgag acttttcaac aaagggtaat atccggaaac       960
ctcctcggat tccattgccc agctatctgt cactttattg tgaagatagt ggaaaaggaa     1020
ggtggctcct acaaatgcca tcattgcgat aaaggaaagg ccatcgttga agatgcctct     1080
gccgacagtg gtcccaaaga tggaccccca cccacgagga gcatcgtgga aaaagaagac     1140
gttccaacca cgtcttcaaa gcaagtggat tgatgtgata tctccactga cgtaagggat     1200
gacgcacaat cccactatcc ttcgcaagac ccttcctcta tataaggaag ttcatttcat     1260
ttggagagaa cacgggggac gagctcggta cccggggatc ccccggacca tgcaacagca     1320
cctgatgcag atgcagccca tgatggctgg ttactacccc agcaatgtta cctctgatca     1380
tatccaacag tacttggacg aaaacaaatc gttgattctg aagattgttg agtctcaaaa     1440
ctctggaaaa cttagcgaat gcgccgagaa tcaagcaagg cttcaacgca acctaatgta     1500
cctagctgca atagcagatt ctcagcctca gccaccaagt gtgcatagcc agtatggatc     1560
tgctggtggt gggatgattc agggagaagg agggtcacac tatttgcagc agcaacaagc     1620
gactcaacag caacagatga ctcagcagtc tctaatggcg gctcgatctt caatgttgta     1680
tgctcagcaa cagcagcagc agcagcctta cgcgacgctt cagcatcagc aattgcacca     1740
tagccagctt ggaatgagct cgagcagcgg aggaggagga agcagtggtc tccatatcct     1800
tcagggagag gctggtgggt ttcatgattt tggccgtggg aagccggaaa tgggaagtgg     1860
tggtggcggt gaaggcagag gaggaagttc aggggatggt ggagaaaccc tttacttgaa     1920
atcatcagat gatgggaatt gaaaggtcga ctacccatac gacgttccag actacgcttc     1980
tttgggtggt tctagcccaa gctcagagct ccaccgcggt ggcggccgca tcttttaccc     2040
atacgatgtt cctgactatg cgggctatcc ctatgacgtc ccggactatg caggatgact     2100
cgacctgcag agctttcgtt cgtatcatcg gtttcgacaa cgttcgtcaa gttcaatgca     2160
tcagtttcat tgcgcacaca ccagaatcct actgagttcg agtattatgg cattgggaaa     2220 catgttttc ttgtaccatt tgttgtgctt gtaatttact gtgtttttta ttcggttttc      2280
gctatcgaac tgtgaaatgg aaatggatgg agaagagtta atgaatgata tggtccttt      2340 gttcattctc aaattaatat tatttgtttt ttctcttatt tgttgtgtgt tgaatttgaa     2400
aatataagag atatgcaaac attttgtttt gagtaaaaat gtgtcaaatc gtggcctcta     2460
atgaccgaag ttaatatgag gagtaaaaca cttgtagttg taccattatg cttattcact     2520
aggcaacaaa tatattttca gacctagaaa agctgcaaat gttactgaat acaagtatgt     2580
cctcttgtgt tttagacatt tatgaacttt cctttatgta attttccaga atccttgtca     2640
gattctaatc attgctttat aattatagtt atactcatgg atttgtagtt gagtatgaaa     2700 atattttta atgcatttta tgacttgcca attgattgac aacatgcatc aatcgaagct     2760
tgcatgcctg caggtcctgc tgagcctcga catgttgtcg caaaattcgc cctggacccg     2820
cccaacgatt tgtcgtcact gtcaaggttt gacctgcact tcatttgggg cccacataca     2880
ccaaaaaaat gctgcataat tctcggggca gcaagtcggt tacccggccg ccgtgctgga     2940 ccggggttgaa tggtgcccgt aactttcggt agagcggacg gccaatactc aacttcaagg    3000
```

```
aatctcaccc atgcgcgccg gcggggaacc ggagttccct tcagtgaacg ttattagttc    3060
gccgctcggt gtgtcgtaga tactagcccc tggggccttt tgaaatttga ataagattta    3120
tgtaatcagt cttttaggtt tgaccggttc tgccgctttt tttaaaattg gatttgtaat    3180
aataaaacgc aattgtttgt tattgtggcg ctctatcata gatgtcgcta taaacctatt    3240
cagcacaata tattgttttc attttaatat tgtacatata agtagtaggg tacaatcagt    3300
aaattgaacg gagaatatta ttcataaaaa tacgatagta acgggtgata tattcattag    3360
aatgaaccga aaccggcggt aaggatctga gctacacatg ctcaggtttt ttacaacgtg    3420
cacaacagaa ttgaaagcaa atatcatgcg atcataggcg tctcgcatat ctcattaaag    3480
caggactcta ggatcgatcc cccgggtcat cacatctcgg tgacgggcag gaccggacgg    3540
ggcggtaccg gcaggctgaa gtccagctgc cagaaaccca cgtcatgcca gttcccgtgc    3600
ttgaagccgg ccgcccgcag catgccgcgg ggggcatatc cgagcgcctc gtgcatgcgc    3660
acgctcgggt cgttgggcag cccgatgaca gcgaccacgc tcttgaagcc ctgtgcctcc    3720
agggacttca gcaggtgggt gtagagcgtg gagcccagtc ccgtccgctg gtggcggggg    3780
gagacgtaca cggttgactc ggccgtccag tcgtaggcgt tgcgtgcctt ccaggggccc    3840
gcgtaggcga tgccggcgac ctcgccgtcc acctcggcga cgagccaggg atagcgctcc    3900
cgcagacgga cgaggtcgtc cgtccactcc tgcggttcct gcggctcggt acggaagttg    3960
accgtgcttg tctcgatgta gtggttgacg atggtgcaga ccgccggcat gtccgcctcg    4020
gtggcacggc ggatgtcggc cgggcgtcgt tctgggctca tggtaattgt aaatagtaat    4080
tgtaatgttg ttgttgtttg ttgttgttgg taattgttgt aaaaatagag ctcttatact    4140
cgaggaattc gctagagtcg atttggtgta tcgagattgg ttatgaaatt cagatgctag    4200
tgtaatgtat tggtaatttg ggaagatata ataggaagca aggctattta tccatttctg    4260
aaaaggcgaa atggcgtcac cgcgagcgtc acgcgcattc cgttcttgct gtaaagcgtt    4320
gtttggtaca cttttgacta gcgaggcttg gcgtgtcagc gtatctattc aaaagtcgtt    4380
aatggctgcg gatcaagaaa aagttggaat agaaacagaa tacccgcgaa attcaggccc    4440
ggttgccatg tcctacacgc cgaaataaac gaccaaatta gtagaaaaat aaaaactgac    4500
tcggatactt acgtcacgtc ttgcgcactg atttgaaaaa tctcaatata aacaaagacg    4560
gccacaagaa aaaaccaaaa caccgatatt cattaatctt atctagtttc tcaaaaaaat    4620
tcatatcttc cacacgtgaa aatgccaatt tctcagacct acctcggctc tgcgaaggcc    4680
cccgctggta tcaaaagttt ttatttcatc cgacatggcg cgaccgacct caacgagaag    4740
gaaattgtcg tgaacggtga aagctctggg ggcgtgcaag gttccggaac gaacatcggt    4800
ctcaatgcaa aaggggaacg ccaggctctg ttggcccctc gaaattcggc gttaattcag    4860
tacattaaaa acgtccgcaa tgtgttatta agttgtctaa gcgtcaattt gtttacacca    4920
caatatatcc tgccaccagc cagccaacag ctccccgacc ggcagctcgg cacaaaatca    4980
ccactcgata caggcagccc atcagtccgg gacggcgtca gcgggagagc cgttgtaagg    5040
cggcagactt tgctcatgtt accgatgcta ttcggaagaa cggcaactaa gctgccgggt    5100
ttgaaacacg gatgatctcg cggagggtag catgttgatt gtaacgatga cagagcgttg    5160
ctgcctgtga tcaattcggg cacgaaccca gtggacataa gcctcgttcg gttcgtaagc    5220
tgtaatgcaa gtagcgtaac tgccgtcacg caactggtcc agaaccttga ccgaacgcag    5280
cggtggtaac ggcgcagtgg cggttttcat ggcttcttgt tatgacatgt ttttttgggg    5340
tacagtctat gcctcgggca tccaagcagc aagcgcgtta cgccgtgggt cgatgtttga    5400
```

-continued

```
tgttatggag cagcaacgat gttacgcagc agggcagtcg ccctaaaaca aagttaaaca   5460
tcatggggga agcggtgatc gccgaagtat cgactcaact atcagaggta gttggcgtca   5520
tcgagcgcca tctcgaaccg acgttgctgg ccgtacattt gtacggctcc gcagtggatg   5580
gcggcctgaa gccacacagt gatattgatt tgctggttac ggtgaccgta aggcttgatg   5640
aaacaacgcg gcgagctttg atcaacgacc ttttggaaac ttcggcttcc cctggagaga   5700
gcgagattct ccgcgctgta gaagtcacca ttgttgtgca cgacgacatc attccgtggc   5760
gttatccagc taagcgcgaa ctgcaatttg agaatggca gcgcaatgac attcttgcag   5820
gtatcttcga gccagccacg atcgacattg atctggctat cttgctgaca aaagcaagag   5880
aacatagcgt tgccttggta ggtccagcgg cggaggaact ctttgatccg gttcctgaac   5940
aggatctatt tgaggcgcta aatgaaacct aacgctatg gaactcgccg cccgactggg   6000
ctggcgatga gcgaaatgta gtgcttacgt tgtcccgcat ttggtacagc gcagtaaccg   6060
gcaaaatcgc gccgaaggat gtcgctgccg actgggcaat ggagcgcctg ccggcccagt   6120
atcagcccgt catacttgaa gctagacagg cttatcttgg acaagaagaa gatcgcttgg   6180
cctcgcgcgc agatcagttg gaagaatttg tccactacgt gaaaggcgag atcaccaagg   6240
tagtcggcaa ataatgtcta gctagaaatt cgttcaagcc gacgccgctt cgccggcgtt   6300
aactcaagcg attagatgca ctaagcacat aattgctcac agccaaacta tcaggtcaag   6360 tctgcttta ttatttttaa gcgtgcataa taagccctac acaaattggg agatatatca   6420
tgcatgacca aaatccctta acgtgagttt tcgttccact gagcgtcaga ccccgtagaa   6480
aagatcaaag gatcttcttg agatcctttt tttctgcgcg taatctgctg cttgcaaaca   6540
aaaaaaccac cgctaccagc ggtggtttgt ttgccggatc aagagctacc aactcttttt   6600
ccgaaggtaa ctggcttcag cagagcgcag ataccaaata ctgtccttct agtgtagccg   6660
tagttaggcc accacttcaa gaactctgta gcaccgccta catacctcgc tctgctaatc   6720
ctgttaccag tggctgctgc cagtggcgat aagtcgtgtc ttaccgggtt ggactcaaga   6780
cgatagttac cggataaggc gcagcggtcg ggctgaacgg ggggttcgtg cacacagccc   6840
agcttggagc gaacgaccta caccgaactg agatacctac agcgtgagct atgagaaagc   6900
gccacgcttc ccgaagggag aaaggcggac aggtatccgg taagcggcag gtcggaaca   6960 ggagagcgca cgagggagct tccaggggga aacgcctggt atctttatag tcctgtcggg   7020
tttcgccacc tctgacttga gcgtcgattt ttgtgatgct cgtcaggggg cggagccta   7080 tggaaaaacg ccagcaacgc ggcctttta cggttcctgg cctttgctg gcctttgct   7140 cacatgttct ttcctgcgtt atccctgat tctgtggata accgtattac cgcctttgag   7200
tgagctgata ccgctcgccg cagccgaacg accgagcgca gcgagtcagt gagcgaggaa   7260
gcggaagagc gcctgatgcg gtatttctc cttacgcatc tgtgcggtat ttcacaccgc   7320
atatggtgca ctctcagtac aatctgctct gatgccgcat agttaagcca gtatacactc   7380
cgctatcgct acgtgactgg gtcatggctg cgccccgaca cccgccaaca cccgctgacg   7440
cgccctgacg ggcttgtctg ctcccggcat ccgcttacag acaagctgtg accgtctccg   7500
ggagctgcat gtgtcagagg ttttcaccgt catcaccgaa acgcgcgagg cagggtgcct   7560
tgatgtgggc gccggcggtc gagtggcgac ggcgcggctt gtccgcgccc tggtagattg   7620 cctgccgta ggccagccat ttttgagcgg ccagcgccg cgataggccg acgcgaagcg   7680
gcggggcgta gggagcgcag cgaccgaagg gtaggcgctt tttgcagctc ttcggctgtg   7740
```

```
cgctggccag acagttatgc acaggccagg cgggttttaa gagttttaat aagttttaaa    7800
gagttttagg cggaaaaatc gccttttttc tcttttatat cagtcactta catgtgtgac    7860
cggttcccaa tgtacggctt tgggttccca atgtacgggt tccggttccc aatgtacggc    7920
tttgggttcc caatgtacgt gctatccaca ggaaagagac cttttcgacc tttttcccct    7980
gctagggcaa tttgccctag catctgctcc gtacattagg aaccggcgga tgcttcgccc    8040
tcgatcaggt tgcggtagcg catgactagg atcgggccag cctgccccgc ctcctccttc    8100
aaatcgtact ccggcaggtc atttgacccg atcagcttgc gcacggtgaa acagaacttc    8160
ttgaactctc cggcgctgcc actgcgttcg tagatcgtct tgaacaacca tctggcttct    8220
gccttgcctg cggcgcggcg tgccaggcgg tagagaaaac ggccgatgcc gggatcgatc    8280
aaaaagtaat cggggtgaac cgtcagcacg tccgggttct tgccttctgt gatctcgcgg    8340
tacatccaat cagctagctc gatctcgatg tactccggcc gcccggtttc gctctttacg    8400
atcttgtagc ggctaatcaa ggcttcaccc tcggataccg tcaccaggcg gccgttcttg    8460
gccttcttcg tacgctgcat ggcaacgtgc gtggtgttta accgaatgca ggtttctacc    8520
aggtcgtctt tctgctttcc gccatcggct cgccggcaga acttgagtac gtccgcaacg    8580
tgtggacgga acacgcggcc gggcttgtct cccttccctt cccggtatcg gttcatggat    8640
tcggttagat gggaaaccgc catcagtacc aggtcgtaat cccacacact ggccatgccg    8700
gccggccctg cggaaacctc tacgtgcccg tctggaagct cgtagcggat cacctcgcca    8760
gctcgtcggt cacgcttcga cagacggaaa acggccacgt ccatgatgct gcgactatcg    8820
cgggtgccca cgtcatagag catcggaacg aaaaaatctg gttgctcgtc gcccttgggc    8880
ggcttcctaa tcgacggcgc accggctgcc ggcggttgcc gggattcttt gcggattcga    8940
tcagcggccg cttgccacga ttcaccgggg cgtgcttctg cctcgatgcg ttgccgctgg    9000
gcggcctgcg cggccttcaa cttctccacc aggtcatcac ccagcgccgc gccgatttgt    9060
accgggccgg atggtttgcg accgtcacgc cgattcctcg ggcttgggggg ttccagtgcc    9120
attgcagggc cggcagacaa cccagccgct tacgcctggc caaccgcccg ttcctccaca    9180
catggggcat tccacggcgt cggtgcctgg ttgttcttga ttttccatgc cgcctccttt    9240
agccgctaaa attcatctac tcatttattc atttgctcat ttactctggt agctgcgcga    9300
tgtattcaga tagcagctcg gtaatggtct tgccttggcg taccgcgtac atcttcagct    9360
tggtgtgatc ctccgccggc aactgaaagt tgacccgctt catggctggc gtgtctgcca    9420
ggctggccaa cgttgcagcc ttgctgctgc gtgcgctcgg acggccggca cttagcgtgt    9480
ttgtgctttt gctcattttc tctttacctc attaactcaa atgagttttg atttaatttc    9540
agcggccagc gcctggacct cgcgggcagc gtcgccctcg ggttctgatt caagaacggt    9600
tgtgccggcg gcggcagtgc ctgggtagct cacgcgctgc gtgatacggg actcaagaat    9660
gggcagctcg tacccggcca gcgcctcggc aacctcaccg ccgatgcgcg tgcctttgat    9720
cgcccgcgac acgacaaagg ccgcttgtag ccttccatcc gtgacctcaa tgcgctgctt    9780
aaccagctcc accaggtcgg cggtggccca tatgtcgtaa gggcttggct gcaccggaat    9840
cagcacgaag tcgctgcctg tgatcgcgga cacagccaag tccgccgcct ggggcgctcc    9900
gtcgatcact acgaagtcgc gccggccgat ggccttcacg tcgcggtcaa tcgtcgggcg    9960
gtcgatgccg acaacggtta gcggttgatc ttcccgcacg ccgcccaat cgcgggcact    10020
gccctgggga tcggaatcga ctaacagaac atcggcccg gcgagttgca gggcgcggc    10080
tagatgggtt gcgatggtcg tcttgcctga cccgcctttc tggttaagta cagcgataac    10140
```

```
cttcatgcgt tccccttgcg tatttgttta tttactcatc gcatcatata cgcagcgacc    10200
gcatgacgca agctgtttta ctcaaataca catcaccttt ttagacggcg gcgctcggtt    10260
tcttcagcgg ccaagctggc cggccaggcc gccagcttgg catcagacaa accggccagg    10320
atttcatgca gccgcacggt tgagacgtgc gcgggcggct cgaacacgta cccggccgcg    10380
atcatctccg cctcgatctc ttcggtaatg aaaaacggtt cgtcctggcc gtcctggtgc    10440
ggtttcatgc ttgttcctct tggcgttcat tctcggcggc cgccagggcg tcggcctcgg    10500
tcaatgcgtc ctcacggaag gcaccgcgcc gcctggcctc ggtgggcgtc acttcctcgc    10560
tgcgctcaag tgcgcggtac agggtcgagc gatgcacgcc aagcagtgca gccgcctctt    10620
tcacggtgcg gccttcctgg tcgatcagct cgcgggcgtg cgcgatctgt gccggggtga    10680
gggtagggcg ggggccaaac ttcacgcctc gggccttggc ggcctcgcgc ccgctccggg    10740
tgcggtcgat gattagggaa cgctcgaact cggcaatgcc ggcgaacacg gtcaacacca    10800
tgcggccggc cggcgtggtg gtgtcggccc acggctctgc caggctacgc aggcccgcgc    10860
cggcctcctg gatgcgctcg gcaatgtcca gtaggtcgcg ggtgctgcgg gccaggcggt    10920
ctagcctggt cactgtcaca acgtcgccag ggcgtaggtg gtcaagcatc ctggccagct    10980
ccgggcggtc gcgcctggtg ccggtgatct tctcggaaaa cagcttggtg cagccggccg    11040
cgtgcagttc ggcccgttgg ttggtcaagt cctggtcgtc ggtgctgacg cgggcatagc    11100
ccagcaggcc agcggcggcg ctcttgttca tggcgtaatg tctccggttc tagtcgcaag    11160
tattctactt tatgcgacta aaacacgcga caagaaaacg ccaggaaaag ggcagggcgg    11220
cagcctgtcg cgtaacttag gacttgtgcg acatgtcgtt ttcagaagac ggctgcactg    11280
aacgtcagaa gccgactgca ctatagcagc ggaggggttg gatcaaagta ct           11332
```

<210> SEQ ID NO 85
<211> LENGTH: 13627
<212> TYPE: DNA
<213> ORGANISM: Artificial Sequence
<220> FEATURE:
<223> OTHER INFORMATION: RER32 vector sequence

<400> SEQUENCE: 85

```
ttgatcccga ggggaaccct gtggttggca tgcacataca aatggacgaa cggataaacc      60
ttttcacgcc cttttaaata tccgttattc taataaacgc tcttttctct taggtttacc     120
cgccaatata tcctgtcaaa cactgatagt ttaaactgaa ggcgggaaac gacaatctga     180
tccaagctca agctgctcta gccaatacgc aaaccgcctc tccccgcgcg ttggccgatt     240
cattaatgca gctggcacga caggtttccc gactggaaag cgggcagtga gcgcaacgca     300
attaatgtga gttagctcac tcattaggca ccccaggctt tacactttat gcttccggct     360
cgtatgttgt gtggaattgt gagcggataa caatttcaca caggaaacag ctatgaccat     420
gattacgaat tgaaacgca ggcccattta catcctccaa aacaaagaa gcaatagaat      480 ccggaactga attaaaaaca tacaaaccaa gaggtaaaga aaacgcatag ttagctaacc     540
cgtccgcaag acgattgacc tcctatacac cgtgagaaat acggactaac cagtcccttg     600
atatgaagcc ataacacaaa cgtagtagga aagatagagg atgagaatcc ggtatccctg     660
tctgtaaaaa cccaaccacg atcttcgaat ccacttccag ctcaaggcgt gttattcctt     720
gctcccagac tatgtgtaac ccatagtaga gtccccacaa ctctgctagt ggcgctgaac     780
agatttcgat attcaaagca aaacccccaa cccagttctc gttcccatca cgcaccgcac     840
```

```
ctcccgctgc tgctaacccg ggattctctc tcgaggctcc atccatgttc aactagcctg    900
atgaatttat taaactcatg tttccatttt ttttcccacc agttatgtta gtttgattaa    960
tttttcagtc aattttggca taacgcttta aaataattat atcaaaataa tattttcagt   1020
ttttctgcaa cagattcatt ccaccaagaa ttcagccgat tctacccgaa ttaatattac   1080
cattttcgga ctagatctat gaacgaaggt acaaaattaa tcagttaaaa agaaaatag    1140
agtggcaagt actacatcta gtgccgtatg atatgataat ataggaacct aaacgaattt   1200
tatactaatt caaatttaaa agtagttagg tttgtcacaa atgcaaatta caaattatat   1260
cgacgtaacg cttactcatt aaataatcta aattacttgg ttaaaagact aattaaaatat   1320
tcttaacaag taggcttttg ttttcattat aaaacaaatt aaaaagctat actaatataa   1380
aaatggagat tggtatttcc aaagcagcaa agacagaaaa actgcaggtt attatctctc   1440
catcttcatc ttgcagagtg gttctttctg ggttttctga cttgcttttc atttttttat   1500
tgatacaaat gttaaaccaa ttattttaaa tagtctttga gattaatgaa gagagatttg   1560
tgaacacaat taataaagag ttatactata gtagtagtct tttttactgt atagtatttt   1620
ctccccgcat ctgtcttgtc tcactgtctt tttctcgcaa gtctctctat taaaaacctc   1680
tttccctcta ctctgtcctt tctctctctg cagaagaagc tcagatacag aaactgacta   1740
ccaagaacaa agcttttttcc ttcgagcaaa gaaagttctt ttttcttttc ttttgctctt   1800
cgtaacccaa ccaacaagac tttcataagc tattaaatca gaaccctgga agacaaaaaa   1860
ggggaaaaac cattatcctt aaagtaacca acacttctct ctctctttct tcaatggatt   1920
tgcaactgaa acaatggaga agccagcagc agcaacaaca tcagacagag tcagaagaac   1980
aaccttctgc agctaagata ccaaaacatg tctttgacca gattcattct cacactgcaa   2040
cttctactgc tcttcctctc tttacccctg agcctacttc ttctaaactc tcctctttgt   2100
ctcctgattc ttcctccagg ttccccagtg agtcttttct tcctcttatc ttatctttct   2160
tgataaagaa ttagactttt cattcatata gtttgtgttt aattgatttt gattcctttt   2220
tgtagagatg gggagcttct ttagctgggc acagtggcaa gaacttgaac tacaagctct   2280
gatctacagg tacatgttgg ctggtgctgc tgttcctcag gagctccttt taccaatcaa   2340
gaaaagcctt ctccatctat ctccttccta ctttcttcac catcctcttc aacacctacc   2400
tcattaccaa cctgcttgtg agtctcgaga acagtcttca tctatctatt ttttaaaatat   2460
aaatgggttt tgtgctactg gtgttggagt tgtgttccca agatccagac tttcaatatt   2520
agtatattat ctcgttttgc caatcttgaa gatctaaaca tgtgtgaatg ggattaagta   2580
ggattagaat cttgttattg atctgatatg tgatatgaat gttgaaaaca gggtatttgg   2640
gaagggcagc gatggatcct gagccaggca gatgcaggag aacggatggt aagaagtgga   2700
gatgttcaag agacgtcttc gctggccaca agtattgcga gcgccacatg caccgtggcc   2760
gcaaccgttc tagaaaacca gtagagactc caaccaccgt caatgcaact gccacgtcca   2820
tggcttcatc agtagcagcc gcagccacca ctacaacagc aacaacaaca tctacgtttg   2880
cttttggtgg tggtggtggt agtgaggaag tggttggtca aggaggatct tcttcttct   2940
ctggctcttc taactcttca tctgaacttc tccaccttag tcaaggtaa taaaagaaa    3000
ctgtttttt ttctcttagg tctgtctgtt ttagctgttg aactttatgg tcaaaacatt   3060
aaacttaaac acattgactt ttttatttct ttagtgttga gccaataaga ttcatggttg   3120
agattttaga caattgtttt gaataataat gaaatcgatt taaagcaata ctgattcttg   3180
atttattagt atgaagtatg aactaatgat atacacaact tggtttgtat gttcatagcg   3240
```

```
atgttgtgaa gagagggta atgttggaaa ttgagagaca catccttatc attttagggt    3300
tggttggttt gtttgtttgt tgaattatga gtttgatttc attgtgaaaa tatctttctt    3360
tcttttttct tattgtgttg agagataatg ataacattgg atttgataga atctataatt    3420
tgaagctagg tgtgagactt ttcaaacaga gaaatagaa agagagagaa atggtaggac    3480
cttagtgaaa gctgacccat atatgtctca tatcttgcag aaaagttaaa gcttttagat    3540
tcttctgcac ccacctcccc tatccacaca caacacatga tatacaaaac actcacttta    3600
taattctatt tctatttact gcttaatcaa ttcttataaa acccacatta aaaggtactt    3660
ttaaagccta taaactaata taaaggctac tactgtctgc aactttgttg ttgaagccta    3720
aatgtggttt ctcttttgac aaattattgc ttttgtgctt tgttttcacc aatgagatgt    3780
ggattctgtt aacagttgtt cggagatgaa gcaagaaagc aacaacatga caacaagag    3840
gccatacgag tcccacatcg gattcagtaa caacagatca gatggaggac acatcctgag    3900
gcccttcttt gacgattggc ctcgttcttc gctccaagaa gctgacaata gttcaagccc    3960
catgagctca gccacttgtc tctccatctc catgcccggg aactcttcct cagacgtctc    4020
tctgaagctg tccacaggca acgaagaggg agcccggagc aacaacaatg ggagagatca    4080
gcaaaacatg agctggtgga gcggtggagg ttccaaccac catcatcaca acatgggcgg    4140
accattggcc gaagccctga gatcttcttc ctcatcttcc ccaaccagtg ttctccatca    4200
gcttggtgtc tcgacacaag ccttttcattg accagtgtaa aaccaacaca caatgcggt    4260
ttttactgtg ttttttggttt ttatccaaat ttcctgtata aagaggggag cttttgttg    4320
tcctcttccc tttttctttt aagatttccc ttgtatctgt agcctttctc tgcagatttt    4380
atatcctcaa agatttgttt ttggaaattc atgtctaaat aggatctacg atgaagctta    4440
ggcaaaatgt cgacctgcag agctttcgtt cgtatcatcg gtttcgacaa cgttcgtcaa    4500
gttcaatgca tcagtttcat tgcgcacaca ccagaatcct actgagttcg agtattatgg    4560
cattgggaaa catgttttc ttgtaccatt tgttgtgctt gtaatttact gtgttttta    4620
ttcggttttc gctatcgaac tgtgaaatgg aaatggatgg agaagagtta atgaatgata    4680
tggtcctttt gttcattctc aaattaatat tatttgtttt ttctcttatt tgttgtgtgt    4740
tgaatttgaa aatataagag atatgcaaac attttgtttt gagtaaaaat gtgtcaaatc    4800
gtggcctcta atgaccgaag ttaatatgag gagtaaaaca cttgtagttg taccattatg    4860
cttattcact aggcaacaaa tatattttca gacctagaaa agctgcaaat gttactgaat    4920
acaagtatgt cctcttgtgt tttagacatt tatgaacttt cctttatgta attttccaga    4980
atccttgtca gattctaatc attgctttat aattatagtt atactcatgg atttgtagtt    5040
gagtatgaaa atattttta atgcatttta tgacttgcca attgattgac aacatgcatc    5100
aatcgaagct tggcactggc cgtcgtttta caacgtcgtg actgggaaaa ccctggcgtt    5160
acccaactta atcgccttgc agcacatccc ccttcgccca gctggcgtaa tagcgaagag    5220
gcccgcaccg atcgcccttc ccaacagttg cgcagcctga atggcgaatg ctagagcagc    5280
ttgccaacat ggtggagcac gacactctcg tctactccaa gaatatcaaa gatacagtct    5340
cagaagacca aagggctatt gagacttttc aacaaagggt aatatcggga aacctcctcg    5400
gattccattg cccagctatc tgtcacttca tcaaaaggac agtagaaaag gaaggtggca    5460
cctacaaatg ccatcattgc gataaaggaa aggctatcgt tcaagatgcc tctgccgaca    5520
gtggtcccaa agatggaccc ccacccacga ggagcatcgt ggaaaaagaa gacgttccaa    5580
```

```
ccacgtcttc aaagcaagtg gattgatgtg ataacatggt ggagcacgac actctcgtct    5640
actccaagaa tatcaaagat acagtctcag aagaccaaag ggctattgag acttttcaac    5700
aaagggtaat atcgggaaac ctcctcggat tccattgccc agctatctgt cacttcatca    5760
aaaggacagt agaaaggaa ggtggcacct acaaatgcca tcattgcgat aaaggaaagg     5820
ctatcgttca agatgcctct gccgacagtg gtcccaaaga tggacccca cccacgagga     5880 gcatcgtgga aaaagaagac gttccaacca cgtcttcaaa gcaagtggat tgatgtgata    5940
tctccactga cgtaagggat gacgcacaat cccactatcc ttcgcaagac ccttcctcta    6000
tataaggaag ttcatttcat ttggagagga cacgctgaaa tcaccagtct ctctctacaa    6060
atctatctct ctcgattcgc agatctgtcg atcgaccatg gggattgaac aagatggatt    6120
gcacgcaggt tctccggccg cttgggtgga gaggctattc ggctatgact gggcacaaca    6180
gacaatcggc tgctctgatg ccgccgtgtt ccggctgtca gcgcagggc gcccggttct     6240 ttttgtcaag accgacctgt ccggtgccct gaatgaactc caggacgagg cagcgcggct    6300
atcgtggctg gccacgacgg gcgttccttg cgcagctgtg ctcgacgttg tcactgaagc    6360
gggaagggac tggctgctat tgggcgaagt gccggggcag gatctcctgt catctcacct    6420
tgctcctgcc gagaaagtat ccatcatggc tgatgcaatg cggcggctgc atacgcttga    6480
tccggctacc tgcccattcg accaccaagc gaaacatcgc atcgagcgag cacgtactcg    6540 gatgaagcc ggtcttgtcg atcaggatga tctggacgaa gagcatcagg ggctcgcgcc     6600
agccgaactg ttcgccaggc tcaaggcgcg catgcccgac ggcgaggatc tcgtcgtgac    6660
acatggcgat gcctgcttgc cgaatatcat ggtggaaaat ggccgctttt ctggattcat    6720
cgactgtggc cggctgggtg tggcggaccg ctatcaggac atagcgttgg ctacccgtga    6780
tattgctgaa gagcttggcg gcgaatgggc tgaccgcttc ctcgtgcttt acggtatcgc    6840
cgctcccgat tcgcagcgca tcgccttcta tcgccttctt gacgagttct tctgagcggg    6900
actctggggt tcgatcgat cctctagcta gagtcgatcg acatcgagtt tctccataat     6960
aatgtgtgag tagttcccag ataagggaat tagggttctt atagggtttc gctcacgtgt    7020
tgagcatata agaaaccctt agtatgtatt tgtatttgta aaatacttct atcaataaaa    7080
tttctaattc ctaaaaccaa atccagtac taaaatccag atcacctaaa gtccctatag      7140
atcccccgaa ttaattcggc gttaattcag tacattaaaa acgtccgcaa tgtgttatta    7200
agttgtctaa gcgtcaattt gtttacacca caatatatcc tgccaccagc cagccaacag    7260
ctccccgacc ggcagctcgg cacaaaatca ccactcgata caggcagccc atcagtccgg    7320
gacggcgtca gcgggagagc cgttgtaagg cggcagactt tgctcatgtt accgatgcta    7380
ttcggaagaa cggcaactaa gctgccgggt ttgaaacacg gatgatctcg cggagggtag    7440
catgttgatt gtaacgatga cagagcgttg ctgcctgtga tcaattcggg cacgaaccca    7500
gtggacataa gcctcgttcg gttcgtaagc tgtaatgcaa gtagcgtaac tgccgtcacg    7560
caactggtcc agaaccttga ccgaacgcag cggtggtaac ggcgcagtgg cggttttcat    7620
ggcttcttgt tatgacatgt ttttttgggg tacagtctat gcctcgggca tccaagcagc    7680
aagcgcgtta cgccgtgggt cgatgtttga tgttatggag cagcaacgat gttacgcagc    7740
agggcagtcg ccctaaaaca aagttaaaca tcatggggga agcggtgatc gccgaagtat    7800
cgactcaact atcagaggta gttggcgtca tcgagcgcca tctcgaaccg acgttgctgg    7860
ccgtacattt gtacggctcc gcagtggatg gcggcctgaa gccacacagt gatattgatt    7920
tgctggttac ggtgaccgta aggcttgatg aaacaacgcg gcgagctttg atcaacgacc    7980
```

```
ttttggaaac ttcggcttcc cctggagaga gcgagattct ccgcgctgta gaagtcacca   8040
ttgttgtgca cgacgacatc attccgtggc gttatccagc taagcgcgaa ctgcaatttg   8100
gagaatggca gcgcaatgac attcttgcag gtatcttcga gccagccacg atcgacattg   8160
atctggctat cttgctgaca aaagcaagag aacatagcgt tgccttggta ggtccagcgg   8220
cggaggaact ctttgatccg gttcctgaac aggatctatt tgaggcgcta atgaaacct    8280 taacgctatg gaactcgccg cccgactggg ctggcgatga gcgaaatgta gtgcttacgt   8340
tgtcccgcat ttggtacagc gcagtaaccg gcaaaatcgc gccgaaggat gtcgctgccg   8400
actgggcaat ggagcgcctg ccggcccagt atcagcccgt catacttgaa gctagacagg   8460
cttatcttgg acaagaagaa gatcgcttgg cctcgcgcgc agatcagttg gaagaatttg   8520
tccactacgt gaaaggcgag atcaccaagg tagtcggcaa ataatgtcta gctagaaatt   8580
cgttcaagcc gacgccgctt cgccggcgtt aactcaagcg attagatgca ctaagcacat   8640
aattgctcac agccaaacta tcaggtcaag tctgctttta ttatttttaa gcgtgcataa   8700
taagccctac acaaattggg agatatatca tgcatgacca aaatcccttta cgtgagttt   8760 tcgttccact gagcgtcaga ccccgtagaa aagatcaaag gatcttcttg agatcctttt   8820
tttctgcgcg taatctgctg cttgcaaaca aaaaaaccac cgctaccagc ggtggtttgt   8880
ttgccggatc aagagctacc aactctttt ccgaaggtaa ctggcttcag cagagcgcag   8940
ataccaaata ctgtccttct agtgtagccg tagttaggcc accacttcaa gaactctgta   9000
gcaccgccta catacctcgc tctgctaatc ctgttaccag tggctgctgc cagtggcgat   9060
aagtcgtgtc ttaccgggtt ggactcaaga cgatagttac cggataaggc gcagcggtcg   9120
ggctgaacgg ggggttcgtg cacacagccc agcttggagc gaacgaccta caccgaactg   9180
agatacctac agcgtgagct atgagaaagc gccacgcttc ccgaagggag aaaggcggac   9240
aggtatccgg taagcggcag ggtcggaaca ggagagcgca cgagggagct tccaggggga   9300
aacgcctggt atctttatag tcctgtcggg tttcgccacc tctgacttga gcgtcgattt   9360
ttgtgatgct cgtcaggggg gcggagccta tggaaaaacg ccagcaacgc ggccttttta   9420
cggttcctgg ccttttgctg gccttttgct cacatgttct ttcctgcgtt atcccctgat   9480
tctgtggata accgtattac cgcctttgag tgagctgata ccgctcgccg cagccgaacg   9540
accgagcgca gcgagtcagt gagcgaggaa gcggaagagc gcctgatgcg gtattttctc   9600
cttacgcatc tgtgcggtat ttcacaccgc atatggtgca ctctcagtac aatctgctct   9660
gatgccgcat agttaagcca gtatacactc cgctatcgct acgtgactgg gtcatggctg   9720
cgccccgaca cccgccaaca cccgctgacg cgccctgacg ggcttgtctg ctcccggcat   9780
ccgcttacag acaagctgtg accgtctccg ggagctgcat gtgtcagagg ttttcaccgt   9840
catcaccgaa acgcgcgagg cagggtgcct tgatgtgggc gccggcggtc gagtggcgac   9900
ggcgcggctt gtccgcgccc tggtagattg cctggccgta ggcagccat ttttgagcgg    9960 ccagcggccg cgataggccg acgcgaagcg gcgggcgta gggagcgcag cgaccgaagg   10020
gtaggcgctt tttgcagctc ttcggctgtg cgctggccag acagttatgc acaggccagg  10080
cgggttttaa gagttttaat aagttttaaa gagtttagg cggaaaaatc gcctttttc    10140 tcttttatat cagtcactta catgtgtgac cggttcccaa tgtacggctt tgggttccca  10200
atgtacgggt tccggttccc aatgtacggc tttgggttcc caatgtacgt gctatccaca  10260
ggaaagagac cttttcgacc ttttccccct gctagggcaa tttgccctag catctgctcc  10320
```

```
gtacattagg aaccggcgga tgcttcgccc tcgatcaggt tgcggtagcg catgactagg   10380
atcgggccag cctgccccgc ctcctccttc aaatcgtact ccggcaggtc atttgacccg   10440
atcagcttgc gcacggtgaa acagaacttc ttgaactctc cggcgctgcc actgcgttcg   10500
tagatcgtct tgaacaacca tctggcttct gccttgcctg cggcgcggcg tgccaggcgg   10560
tagagaaaac ggccgatgcc gggatcgatc aaaaagtaat cggggtgaac cgtcagcacg   10620
tccgggttct tgccttctgt gatctcgcgg tacatccaat cagctagctc gatctcgatg   10680
tactccggcc gcccggtttc gctctttacg atcttgtagc ggctaatcaa ggcttcaccc   10740
tcggataccg tcaccaggcg gccgttcttg gccttcttcg tacgctgcat ggcaacgtgc   10800
gtggtgttta accgaatgca ggtttctacc aggtcgtctt tctgctttcc gccatcggct   10860
cgccggcaga acttgagtac gtccgcaacg tgtggacgga acacgcggcc gggcttgtct   10920
cccttcccty cccggtatcg gttcatggat tcggttagat gggaaaccgc catcagtacc   10980
aggtcgtaat cccacacact ggccatgccg gccggccctg cggaaacctc tacgtgcccg   11040
tctggaagct cgtagcggat cacctcgcca gctcgtcggt cacgcttcga cagacggaaa   11100
acggccacgt ccatgatgct gcgactatcg cgggtgccca cgtcatagag catcggaacg   11160
aaaaaatctg gttgctcgtc gcccttgggc ggcttcctaa tcgacggcgc accggctgcc   11220
ggcggttgcc gggattcttt gcggattcga tcagcggccg cttgccacga ttcaccgggg   11280
cgtgcttctg cctcgatgcg ttgccgctgg gcggcctgcg cggccttcaa cttctccacc   11340
aggtcatcac ccagcgccgc ccgatttgt accgggccgg atggtttgcg accgtcacgc   11400
cgattcctcg ggcttggggg ttccagtgcc attgcagggc cggcagacaa cccagccgct   11460
tacgcctggc caaccgcccg ttcctccaca catgggcat tccacggcgt cggtgcctgg   11520
ttgttcttga ttttccatgc cgcctccttt agccgctaaa attcatctac tcatttattc   11580
atttgctcat ttactctggt agctgcgcga tgtattcaga tagcagctcg gtaatggtct   11640
tgccttggcg taccgcgtac atcttcagct tggtgtgatc ctccgccggc aactgaaagt   11700
tgacccgctt catggctggc gtgtctgcca ggctggccaa cgttgcagcc ttgctgctgc   11760
gtgcgctcga acggccggca cttagcgtgt ttgtgctttt gctcattttc tctttacctc   11820
attaactcaa atgagttttg atttaatttc agcggccagc gcctggacct cgcgggcagc   11880
gtcgccctcg ggttctgatt caagaacggt tgtgccggcg gcggcagtgc ctgggtagct   11940
cacgcgctgc gtgatacggg actcaagaat gggcagctcg tacccggcca gcgcctcggc   12000
aacctcaccg ccgatgcgcg tgcctttgat cgcccgcgac acgacaaagg ccgcttgtag   12060
ccttccatcc gtgacctcaa tgcgctgctt aaccagctcc accaggtcgg cggtggccca   12120
tatgtcgtaa gggcttggct gcaccggaat cagcacgaag tcggctgcct tgatcgcgga   12180
cacagccaag tccgccgcct ggggcgctcc gtcgatcact acgaagtcgc gccggccgat   12240
ggccttcacg tcgcggtcaa tcgtcggcg gtcgatgccg acaacggtta gcggttgatc   12300
ttcccgcacg gccgcccaat cgcgggcact gccctgggga tcggaatcga ctaacagaac   12360
atcggccccg gcgagttgca gggcgcgggc tagatgggtt gcgatggtcg tcttgcctga   12420
cccgcctttc tggttaagta cagcgataac cttcatgcgt tccccttgcg tatttgttta   12480
tttactcatc gcatcatata cgcagcgacc gcatgacgca agctgtttta ctcaaataca   12540
catcaccttt ttagacggcg gcgctcggtt tcttcagcgg ccaagctggc cggccaggcc   12600
gccagcttgg catcagacaa accggccagg atttcatgca gccgcacggt tgagacgtgc   12660
gcgggcggct cgaacacgta cccggccgcg atcatctccg cctcgatctc ttcggtaatg   12720
```

-continued

```
aaaaacggtt cgtcctggcc gtcctggtgc ggtttcatgc ttgttcctct tggcgttcat    12780
tctcggcggc cgccagggcg tcggcctcgg tcaatgcgtc ctcacggaag gcaccgcgcc    12840
gcctggcctc ggtgggcgtc acttcctcgc tgcgctcaag tgcgcggtac agggtcgagc    12900
gatgcacgcc aagcagtgca gccgcctctt tcacggtgcg gccttcctgg tcgatcagct    12960
cgcgggcgtg cgcgatctgt gccggggtga gggtagggcg ggggccaaac ttcacgcctc    13020
gggccttggc ggcctcgcgc cgctccgggt gcggtcgat gattagggaa cgctcgaact    13080
cggcaatgcc ggcgaacacg gtcaacacca tgcggccggc cggcgtggtg gtgtcggccc    13140
acggctctgc caggctacgc aggcccgcgc cggcctcctg gatgcgctcg gcaatgtcca    13200
gtaggtcgcg ggtgctgcgg gccaggcggt ctagcctggt cactgtcaca acgtcgccag    13260
ggcgtaggtg gtcaagcatc ctggccagct ccgggcggtc gcgcctggtg ccggtgatct    13320
tctcggaaaa cagcttggtg cagccggccg cgtgcagttc ggcccgttgg ttggtcaagt    13380
cctggtcgtc ggtgctgacg cgggcatagc ccagcaggcc agcggcggcg ctcttgttca    13440
tggcgtaatg tctccggttc tagtcgcaag tattctactt tatgcgacta aaacacgcga    13500
caagaaaacg ccaggaaaag ggcagggcgg cagcctgtcg cgtaacttag gacttgtgcg    13560
acatgtcgtt ttcagaagac ggctgcactg aacgtcagaa gccgactgca ctatagcagc    13620
ggagggg                                                              13627
```

<210> SEQ ID NO 86
<211> LENGTH: 21
<212> TYPE: DNA
<213> ORGANISM: Artificial Sequence
<220> FEATURE:
<223> OTHER INFORMATION: Modified miR396 target site sequence
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 86

```
cgttcnagaa anccngtnga n                                              21
```

<210> SEQ ID NO 87
<211> LENGTH: 1608
<212> TYPE: DNA
<213> ORGANISM: Arabidopsis thaliana

<400> SEQUENCE: 87

```
atggatattg tgttcatgt tcttgggtcg gttactagta atgaaaatga gtcacttggt      60
ctaaaagagc ttataggaac taaacaagat agatccggat tcatcggtga ggattgcttg    120
caacgaagct tgaagctagc aagaacgaca actagagcgg aagaagaaga aaacttgtct    180
```

```
tcttctgttg cagctgctta ttgcaaaacg atgtcgtttc accaaggcat tcctctcatg    240
agatctgctt ctcctctttc ctctgattct cgccgtcaag aacaaatgct tagcttctca    300
gataaaccag acgctcttga tttcagtaaa tatgtcggtt tggataatag cagtaataac    360
aagaactctc tctcgccgtt tcttcaccag attcctccac cttcttactt tagaagctca    420
ggaggatatg gttctggtgg aatgatgatg aacatgagca tgcaagggaa cttcacaggt    480
gttaaaggac cttttacatt gactcaatgg gctgagttag agcaacaggc gttgatctat    540
aagtacatca cagccaatgt ccctgttcct tctagtttgc tcatctctat caagaagtct    600
tttatccctt acggatcttt gcctcctagt tccttcggat ggggaacttt ccatctcggt    660
ttcgcaggcg gtaacatgga ccctgagcca gggagatgcc gcagaacaga tgggaagaaa    720
tggcggtgct caagagacgc cgttcctgat cagaaatact gtgaaagaca tcaacaga     780 ggccgtcatc gttcaagaaa gcctgtggaa gtccaatctg gccaaaacca aaccgccgct    840
gctgcatcca aagcggttac tacaccacaa cagcctgttg tcgctggtaa tactaacaga    900
agcaatgccc gtgcatcaag caaccgcagc ctcgccattg gaagtcaata tatcaatcct    960
tctacagaat cttttaccta acacagagga gtttcgatat atccttccac cgtcaactta   1020
caacccaagg aatctccggt tattcatcag aaacacagaa acaacaacaa ccctttttgag   1080 tttggacaca tatcctctga ttcgttactc aacccgaata ccgcaaagac ctatggatca   1140
tcgttcttgg atttcagcag caaccaagag aagcattcag ggaatcacaa tcacaattct   1200
tggcctgaag agctgacatc agattggaca cagctctcaa tgtcaattcc aatagcatca   1260
tcatcccctt cctccacaca caacaacaac aatgctcaag aaaaaacaac actctcgcct   1320
ctcaggctat cccgcgagct tgacctatcg atccaaaccg atgaaacaac aatcgagcct   1380
actgtgaaaa aggtgaatac ttggatacca atctcatggg gaaactcctt aggaggtcct   1440
ctaggtgaag tactaaacag tacaacgaat agtccaacat ttggatcttc tcctacaggg   1500
gttttgcaaa agtccacatt tgttcactc tctaacaaca gctccgtgag cagccccatt   1560
gcagagaaca acagacacaa tggcgattac tttcattaca caacctga                1608
```

<210> SEQ ID NO 88
<211> LENGTH: 1191
<212> TYPE: DNA
<213> ORGANISM: Carica papaya

<400> SEQUENCE: 88

```
atggacttgc atctgaaaca atggaggaac cagcatgagt cagagcaaca accttctgcg     60
aagataccaa aacttctcct tgatccacat caacaaaacc catctgcctc agcttctgct    120
tctcttgcac tcccttttgtt tgtacctgaa cagccctcta ccaaactcac caacctgtca    180
gcgttgccag attcatcctc tagatttccc aagatgggaa gctactttag tttggctcag    240
tggcaggagc tggagttgca ggctttgatc tacagataca tgttagctgg tgctgccgtt    300
cctcccgagc tcctccagcc aatcaagaaa agtctccttc actcttctcc atatttcctc    360
catcatcctc ttcaacatta cgctcattat cagcctgctt ggtattggag cagagctgcc    420
ctggatccgg agccgggtcg gtgccggaga acagatggaa agaaatggag gtgctcaaga    480
gatgtggtgg ctggccagaa atattgcgag cgccacatgc accgtggccg caaccgttca    540
agaaagcctg tggaaatccc cacgccgaac accaccgccg ccgtcactcc actctccgta    600
gccgcctcaa cggtttcttc tctgggtgct ggtggtggtg gtctcggtgg cagcgacact    660
ttcaaatcca ccggtccaat ctccatgaca ttgccggcaa tggtggctaa tgggccgagc    720
```

-continued

```
ttcggcctcg ccggaccggc tagctccgct gatctcctgc acctgaatca tagttcctca    780
gagttcagga ttgagaacaa gggcctcttt gaagcccaaa acgaagttga caacagacct    840
gacggccaca ttctaaggca ttttttttgat gattggcccc gatcacttca agaacctgat    900
aatgctggga ggaatgctag ccctatgagc tcctccacct gtctcacaat tcatcctcc     960 gatgtgtcgt tgaaactgtc aactggtaat gcagatgaac tcaccaccag ggacggcgaa   1020
agggatcaac tgcagttgaa ttgggctgcc ggatgggcga caaaccaaat gggaggacct   1080
ctagctgagg cattgcgttc ctccacttca aattcttcac ccaccagtgt cttacatcag   1140
ttgccgcgga actctgccac agaatctagt tacgttagca cctgtgttta g            1191
```

<210> SEQ ID NO 89
<211> LENGTH: 396
<212> TYPE: PRT
<213> ORGANISM: Carica papaya

<400> SEQUENCE: 89

```
Met Asp Leu His Leu Lys Gln Trp Arg Asn Gln His Glu Ser Glu Gln
1               5                   10                  15

Gln Pro Ser Ala Lys Ile Pro Lys Leu Leu Asp Pro His Gln Gln
            20                  25                  30

Asn Pro Ser Ala Ser Ala Ser Leu Ala Leu Pro Leu Phe Val
        35                  40                  45

Pro Glu Gln Pro Ser Thr Lys Leu Thr Asn Leu Ser Ala Leu Pro Asp
    50                  55                  60

Ser Ser Ser Arg Phe Pro Lys Met Gly Ser Tyr Phe Ser Leu Ala Gln
65                  70                  75                  80

Trp Gln Glu Leu Glu Leu Gln Ala Leu Ile Tyr Arg Tyr Met Leu Ala
                85                  90                  95

Gly Ala Ala Val Pro Pro Glu Leu Leu Gln Pro Ile Lys Lys Ser Leu
            100                 105                 110

Leu His Ser Ser Pro Tyr Phe Leu His His Pro Leu Gln His Tyr Ala
        115                 120                 125

His Tyr Gln Pro Ala Trp Tyr Trp Ser Arg Ala Ala Leu Asp Pro Glu
    130                 135                 140

Pro Gly Arg Cys Arg Arg Thr Asp Gly Lys Lys Trp Arg Cys Ser Arg
145                 150                 155                 160

Asp Val Val Ala Gly Gln Lys Tyr Cys Glu Arg His Met His Arg Gly
                165                 170                 175

Arg Asn Arg Ser Arg Lys Pro Val Glu Ile Pro Thr Pro Asn Thr Thr
            180                 185                 190

Ala Ala Val Thr Pro Leu Ser Val Ala Ala Ser Thr Val Ser Ser Leu
        195                 200                 205

Gly Ala Gly Gly Gly Leu Gly Gly Ser Asp Thr Phe Lys Ser Thr
    210                 215                 220

Gly Pro Ile Ser Met Thr Leu Pro Ala Met Val Ala Asn Gly Pro Ser
225                 230                 235                 240

Phe Gly Leu Ala Gly Pro Ala Ser Ser Ala Asp Leu Leu His Leu Asn
                245                 250                 255

His Ser Ser Ser Glu Phe Arg Ile Glu Asn Lys Gly Leu Phe Glu Ala
            260                 265                 270

Gln Asn Glu Val Asp Asn Arg Pro Asp Gly His Ile Leu Arg His Phe
        275                 280                 285
```

```
Phe Asp Asp Trp Pro Arg Ser Leu Gln Glu Pro Asp Asn Ala Gly Arg
290                 295                 300

Asn Ala Ser Pro Met Ser Ser Thr Cys Leu Thr Ile Ser Ser Ser
305                 310                 315                 320

Asp Val Ser Leu Lys Leu Ser Thr Gly Asn Ala Asp Glu Leu Thr Thr
                325                 330                 335

Arg Asp Gly Glu Arg Asp Gln Leu Gln Leu Asn Trp Ala Ala Gly Trp
                340                 345                 350

Ala Thr Asn Gln Met Gly Gly Pro Leu Ala Glu Ala Leu Arg Ser Ser
            355                 360                 365

Thr Ser Asn Ser Ser Pro Thr Ser Val Leu His Gln Leu Pro Arg Asn
370                 375                 380

Ser Ala Thr Glu Ser Ser Tyr Val Ser Thr Cys Val
385                 390                 395

<210> SEQ ID NO 90
<211> LENGTH: 588
<212> TYPE: DNA
<213> ORGANISM: Arabidopsis thaliana

<400> SEQUENCE: 90
```

| | | | | | |
|---|---|---|---|---|---|
| atgcagcagc | agcagtctcc | gcaaatgttt | ccgatggttc | cgtcgattcc | ccctgctaac | 60 |
| aacatcacta | ccgaacagat | ccaaaagtac | cttgatgaga | caagaagct | gattatggcc | 120 |
| atcatggaaa | accagaatct | cggtaaactt | gctgagtgcg | cccagtacca | agctcttctc | 180 |
| cagaagaact | tgatgtatct | tgctgcaatt | gctgatgctc | aaccccacc | acctacgcca | 240 |
| ggaccttcac | catctacagc | tgtcgctgcc | cagatggcaa | caccgcattc | tgggatgcaa | 300 |
| ccacctagct | acttcatgca | acacccacaa | gcatccctg | cagggatttt | cgctccaagg | 360 |
| ggtcctttac | agtttggtag | cccactccag | tttcaggatc | cgcaacagca | gcagcagata | 420 |
| catcagcaag | ctatgcaagg | acacatgggg | attagaccaa | tgggtatgac | caacaacggg | 480 |
| atgcagcatg | cgatgcaaca | accagaaacc | ggtcttggag | gaaacgtggg | gcttagagga | 540 |
| ggaaagcaag | atggagcaga | tggacaagga | aaagatgatg | gcaagtga | | 588 |

```
<210> SEQ ID NO 91
<211> LENGTH: 672
<212> TYPE: DNA
<213> ORGANISM: Arabidopsis thaliana

<400> SEQUENCE: 91
```

| | | | | | |
|---|---|---|---|---|---|
| atgcagcaat | ctccacagat | gattccgatg | gttcttcctt | catttccgcc | caccaataat | 60 |
| atcaccaccg | aacagatcca | aaagtatctt | gatgagaaca | gaagctgat | aatggcgatc | 120 |
| ttggaaaatc | agaacctcgg | taaacttgca | gaatgtgctc | agtatcaagc | tcttctccag | 180 |
| aagaatttga | tgtatctcgc | tgcaattgcg | gatgctcaac | ctcagccacc | agcagctaca | 240 |
| ctaacatcag | gagccatgac | tccccaagca | atggctccta | atccgtcatc | aatgcagcca | 300 |
| ccaccaagct | acttcatgca | gcaacatcaa | gctgtgggaa | tggctcaaca | aatacctcct | 360 |
| gggattttcc | ctcctagagg | tccattgcaa | tttggtagcc | cgcatcagtt | tctggatccg | 420 |
| cagcaacagt | tacatcaaca | agctatgcaa | gggcacatgg | ggattagacc | aatgggtttg | 480 |
| aataataaca | acggactgca | acatcaaatg | caccaccatg | aaactgctct | tgccgcaaac | 540 |
| aatgcgggtc | ctaacgatgc | tagtggagga | ggtaaaccgg | atgggaccaa | tatgagccag | 600 |
| agtggagctg | atgggcaagg | tggctcagcc | gctagacatg | gcggtggtga | tgcaaaaact | 660 |

-continued

| gaaggaaaat ga | 672 |

<210> SEQ ID NO 92
<211> LENGTH: 618
<212> TYPE: DNA
<213> ORGANISM: Oryza sativa

<400> SEQUENCE: 92

| atgcagcagc agatggccat gccggcgggg gccgccgccg ccgcggtgcc gccggcggcc | 60 |
| ggcatcacca ccgagcagat ccaaaagtat ttggatgaaa ataaacagct aattttggcc | 120 |
| atcctggaaa atcaaaacct agggaagttg gctgaatgtg ctcagtacca agctcagctt | 180 |
| caaaagaatc tcttgtatct ggctgccatt gcagatgccc aaccacctca gaatccagga | 240 |
| agtcgccctc agatgatgca gcctggtgct accccaggtg ctgggcatta catgtcccaa | 300 |
| gtaccgatgt tccctccaag aactccctta accccacaac agatgcaaga gcagcagcag | 360 |
| cagcaactcc agcaacagca agctcaggct ctagccttcc ccggccagat gctaatgaga | 420 |
| ccaggtactg tcaatggcat gcaatctatc ccagttgctg accctgctcg cgcagccgat | 480 |
| cttcagacgg cagcaccggg ctcggtagat ggccgaggaa acaagcagga tgcaacctcg | 540 |
| gagccttccg ggaccgagag ccacaagagt gcgggagcag ataacgacgc aggcggtgac | 600 |
| atagcggaga agtcctga | 618 |

<210> SEQ ID NO 93
<211> LENGTH: 558
<212> TYPE: DNA
<213> ORGANISM: Oryza sativa

<400> SEQUENCE: 93

| atgcagcagc agccgatgcc gatgcccgcg caggcgccgc cgacggccgg aatcaccacc | 60 |
| gagcagatcc aaaagtatct ggatgaaaac aagcagctta ttttggctat tttggaaaat | 120 |
| cagaatctgg gaaagttggc agaatgtgct cagtatcaag cgcagcttca gaagaatctc | 180 |
| ttgtacttgg ctgcaattgc tgatactcaa ccgcagacca ctataagccg tccccagatg | 240 |
| gtgccgcatg gtgcatcgcc ggggttaggg ggcaatacaa tgtcgcaggt gccaatgttc | 300 |
| ccccccagga cccctctaac gccccagcag atgcaggagc agcagctgca gcaacagcaa | 360 |
| gcccagctgc tctcgttcgg cggtcagatg gttatgaggc ctggcgttgt gaatggcatt | 420 |
| cctcagcttc tgcaaggcga aatgcaccgc ggagcagatc accagaacgc tggcggggcc | 480 |
| acctcggagc cttccgagag ccacaggagc accggcaccg aaaatgacgg tggaagcgac | 540 |
| ttcggcgatc aatcctaa | 558 |

<210> SEQ ID NO 94
<211> LENGTH: 684
<212> TYPE: DNA
<213> ORGANISM: Oryza sativa

<400> SEQUENCE: 94

| atgcagcagc aacacctgat gcagatgaac cagggcatga tgggggggata tgcttcccct | 60 |
| accaccgtca ccactgatct cattcagcag tatctggatg agaacaagca gctgatcctg | 120 |
| gccatccttg acaaccagaa caatgggaag gtggaagagt gcgctcggaa ccaagctaag | 180 |
| ctccagcaca atctcatgta cctcgccgcc atcgccgaca gccagccgcc gcagacggcc | 240 |
| gccatgtccc agtatccgtc gaacctgatg atgcagtccg ggcgaggta catgccgcag | 300 |
| cagtcggcgc agatgatggc gccgcagtcg ctgatggcgg cgaggtcttc gatgatgtac | 360 |

```
gcgcagccgg cgctgtcgcc gctccagcag cagcagcagc agcaggcggc ggcggcgcac    420
gggcagctgg gcatgggctc ggggggcacc accagcgggt tcagcatcct ccacggcgag    480
gccagcatgg gcggcggcgg cggcggcggt ggcgccggta acagcatgat gaacgccggc    540
gtgttctccg acttcggacg cggcggcggc ggcggcggca aggagggtgtc cacctcgctg    600 tccgtcgacg tccggggcgc caactccggc gcccagagcg gcgacgggga gtacctcaag    660
ggcaccgagg aggaaggcag ctag                                           684
```

<210> SEQ ID NO 95
<211> LENGTH: 210
<212> TYPE: PRT
<213> ORGANISM: Arabidopsis thaliana
<400> SEQUENCE: 95

```
Met Gln Gln His Leu Met Gln Met Gln Pro Met Met Ala Gly Tyr Tyr
1               5                   10                  15

Pro Ser Asn Val Thr Ser Asp His Ile Gln Gln Tyr Leu Asp Glu Asn
                20                  25                  30

Lys Ser Leu Ile Leu Lys Ile Val Glu Ser Gln Asn Ser Gly Lys Leu
            35                  40                  45

Ser Glu Cys Ala Glu Asn Gln Ala Arg Leu Gln Arg Asn Leu Met Tyr
        50                  55                  60

Leu Ala Ala Ile Ala Asp Ser Gln Pro Gln Pro Ser Val His Ser
65                  70                  75                  80

Gln Tyr Gly Ser Ala Gly Gly Gly Met Ile Gln Gly Glu Gly Ser
                85                  90                  95

His Tyr Leu Gln Gln Gln Gln Ala Thr Gln Gln Gln Met Thr Gln
                100                 105                 110

Gln Ser Leu Met Ala Ala Arg Ser Ser Met Leu Tyr Ala Gln Gln Gln
            115                 120                 125

Gln Gln Gln Gln Pro Tyr Ala Thr Leu Gln His Gln Leu His His
        130                 135                 140

Ser Gln Leu Gly Met Ser Ser Ser Ser Gly Gly Gly Ser Ser Gly
145                 150                 155                 160

Leu His Ile Leu Gln Gly Glu Ala Gly Gly Phe His Asp Phe Gly Arg
                165                 170                 175

Gly Lys Pro Glu Met Gly Ser Gly Gly Gly Glu Gly Arg Gly Gly
            180                 185                 190

Ser Ser Gly Asp Gly Gly Glu Thr Leu Tyr Leu Lys Ser Ser Asp Asp
        195                 200                 205

Gly Asn
    210
```

<210> SEQ ID NO 96
<211> LENGTH: 195
<212> TYPE: PRT
<213> ORGANISM: Arabidopsis thaliana
<400> SEQUENCE: 96

```
Met Gln Gln Gln Gln Ser Pro Gln Met Phe Pro Met Val Pro Ser Ile
1               5                   10                  15

Pro Pro Ala Asn Asn Ile Thr Thr Glu Gln Ile Gln Lys Tyr Leu Asp
                20                  25                  30

Glu Asn Lys Lys Leu Ile Met Ala Ile Met Glu Asn Gln Asn Leu Gly
            35                  40                  45
```

Lys Leu Ala Glu Cys Ala Gln Tyr Gln Ala Leu Leu Gln Lys Asn Leu
            50                  55                  60

Met Tyr Leu Ala Ala Ile Ala Asp Ala Gln Pro Pro Pro Thr Pro
 65                  70                  75                  80

Gly Pro Ser Pro Ser Thr Ala Val Ala Ala Gln Met Ala Thr Pro His
                     85                  90                  95

Ser Gly Met Gln Pro Pro Ser Tyr Phe Met Gln His Pro Gln Ala Ser
                    100                 105                 110

Pro Ala Gly Ile Phe Ala Pro Arg Gly Pro Leu Gln Phe Gly Ser Pro
                115                 120                 125

Leu Gln Phe Gln Asp Pro Gln Gln Gln Gln Ile His Gln Gln Ala
            130                 135                 140

Met Gln Gly His Met Gly Ile Arg Pro Met Gly Met Thr Asn Asn Gly
145                 150                 155                 160

Met Gln His Ala Met Gln Gln Pro Glu Thr Gly Leu Gly Gly Asn Val
                165                 170                 175

Gly Leu Arg Gly Gly Lys Gln Asp Gly Ala Asp Gly Gln Gly Lys Asp
                180                 185                 190

Asp Gly Lys
        195

<210> SEQ ID NO 97
<211> LENGTH: 223
<212> TYPE: PRT
<213> ORGANISM: Arabidopsis thaliana

<400> SEQUENCE: 97

Met Gln Gln Ser Pro Gln Met Ile Pro Met Val Leu Pro Ser Phe Pro
  1               5                  10                  15

Pro Thr Asn Asn Ile Thr Thr Glu Gln Ile Gln Lys Tyr Leu Asp Glu
                 20                  25                  30

Asn Lys Lys Leu Ile Met Ala Ile Leu Glu Asn Gln Asn Leu Gly Lys
             35                  40                  45

Leu Ala Glu Cys Ala Gln Tyr Gln Ala Leu Leu Gln Lys Asn Leu Met
         50                  55                  60

Tyr Leu Ala Ala Ile Ala Asp Ala Gln Pro Gln Pro Pro Ala Ala Thr
 65                  70                  75                  80

Leu Thr Ser Gly Ala Met Thr Pro Gln Ala Met Ala Pro Asn Pro Ser
                 85                  90                  95

Ser Met Gln Pro Pro Ser Tyr Phe Met Gln His Gln Ala Val
                100                 105                 110

Gly Met Ala Gln Gln Ile Pro Pro Gly Ile Phe Pro Pro Arg Gly Pro
                115                 120                 125

Leu Gln Phe Gly Ser Pro His Gln Phe Leu Asp Pro Gln Gln Gln Leu
            130                 135                 140

His Gln Gln Ala Met Gln Gly His Met Gly Ile Arg Pro Met Gly Leu
145                 150                 155                 160

Asn Asn Asn Asn Gly Leu Gln His Gln Met His His His Glu Thr Ala
                165                 170                 175

Leu Ala Ala Asn Asn Ala Gly Pro Asn Asp Ala Ser Gly Gly Gly Lys
                180                 185                 190

Pro Asp Gly Thr Asn Met Ser Gln Ser Gly Ala Asp Gly Gln Gly Gly
            195                 200                 205

Ser Ala Ala Arg His Gly Gly Gly Asp Ala Lys Thr Glu Gly Lys

<210> SEQ ID NO 98
<211> LENGTH: 205
<212> TYPE: PRT
<213> ORGANISM: Oryza sativa

<400> SEQUENCE: 98

Met Gln Gln Gln Met Ala Met Pro Ala Gly Ala Ala Ala Ala Val
1               5                   10                  15

Pro Pro Ala Ala Gly Ile Thr Thr Glu Gln Ile Gln Lys Tyr Leu Asp
            20                  25                  30

Glu Asn Lys Gln Leu Ile Leu Ala Ile Leu Glu Asn Gln Asn Leu Gly
        35                  40                  45

Lys Leu Ala Glu Cys Ala Gln Tyr Gln Ala Gln Leu Gln Lys Asn Leu
    50                  55                  60

Leu Tyr Leu Ala Ala Ile Ala Asp Ala Gln Pro Pro Gln Asn Pro Gly
65                  70                  75                  80

Ser Arg Pro Gln Met Met Gln Pro Gly Ala Thr Pro Gly Ala Gly His
                85                  90                  95

Tyr Met Ser Gln Val Pro Met Phe Pro Pro Arg Thr Pro Leu Thr Pro
            100                 105                 110

Gln Gln Met Gln Glu Gln Gln Gln Gln Leu Gln Gln Gln Gln Ala
        115                 120                 125

Gln Ala Leu Ala Phe Pro Gly Gln Met Leu Met Arg Pro Gly Thr Val
    130                 135                 140

Asn Gly Met Gln Ser Ile Pro Val Ala Asp Pro Ala Arg Ala Ala Asp
145                 150                 155                 160

Leu Gln Thr Ala Ala Pro Gly Ser Val Asp Gly Arg Gly Asn Lys Gln
                165                 170                 175

Asp Ala Thr Ser Glu Pro Ser Gly Thr Glu Ser His Lys Ser Ala Gly
            180                 185                 190

Ala Asp Asn Asp Ala Gly Gly Asp Ile Ala Glu Lys Ser
        195                 200                 205

<210> SEQ ID NO 99
<211> LENGTH: 185
<212> TYPE: PRT
<213> ORGANISM: Oryza sativa

<400> SEQUENCE: 99

Met Gln Gln Gln Pro Met Pro Met Pro Ala Gln Ala Pro Pro Thr Ala
1               5                   10                  15

Gly Ile Thr Thr Glu Gln Ile Gln Lys Tyr Leu Asp Glu Asn Lys Gln
            20                  25                  30

Leu Ile Leu Ala Ile Leu Glu Asn Gln Asn Leu Gly Lys Leu Ala Glu
        35                  40                  45

Cys Ala Gln Tyr Gln Ala Gln Leu Gln Lys Asn Leu Leu Tyr Leu Ala
    50                  55                  60

Ala Ile Ala Asp Thr Gln Pro Gln Thr Thr Ile Ser Arg Pro Gln Met
65                  70                  75                  80

Val Pro His Gly Ala Ser Pro Gly Leu Gly Gln Tyr Met Ser Gln
                85                  90                  95

Val Pro Met Phe Pro Pro Arg Thr Pro Leu Thr Pro Gln Gln Met Gln
            100                 105                 110

Glu Gln Gln Leu Gln Gln Gln Gln Ala Gln Leu Leu Ser Phe Gly Gly

```
                115                 120                 125
Gln Met Val Met Arg Gly Val Val Asn Gly Ile Pro Gln Leu Leu
    130                 135                 140

Gln Gly Glu Met His Arg Gly Ala Asp His Gln Asn Ala Gly Gly Ala
145                 150                 155                 160

Thr Ser Glu Pro Ser Glu Ser His Arg Ser Thr Gly Thr Glu Asn Asp
                165                 170                 175

Gly Gly Ser Asp Phe Gly Asp Gln Ser
            180                 185

<210> SEQ ID NO 100
<211> LENGTH: 227
<212> TYPE: PRT
<213> ORGANISM: Oryza sativa

<400> SEQUENCE: 100

Met Gln Gln Gln His Leu Met Gln Met Asn Gln Gly Met Met Gly Gly
1               5                   10                  15

Tyr Ala Ser Pro Thr Thr Val Thr Thr Asp Leu Ile Gln Gln Tyr Leu
                20                  25                  30

Asp Glu Asn Lys Gln Leu Ile Leu Ala Ile Leu Asp Asn Gln Asn Asn
            35                  40                  45

Gly Lys Val Glu Glu Cys Ala Arg Asn Gln Ala Lys Leu Gln His Asn
50                  55                  60

Leu Met Tyr Leu Ala Ala Ile Ala Asp Ser Gln Pro Pro Gln Thr Ala
65                  70                  75                  80

Ala Met Ser Gln Tyr Pro Ser Asn Leu Met Met Gln Ser Gly Ala Arg
                85                  90                  95

Tyr Met Pro Gln Gln Ser Ala Gln Met Met Ala Pro Gln Ser Leu Met
                100                 105                 110

Ala Ala Arg Ser Ser Met Met Tyr Ala Gln Pro Ala Leu Ser Pro Leu
            115                 120                 125

Gln Gln Gln Gln Gln Gln Ala Ala Ala His Gly Gln Leu Gly
130                 135                 140

Met Gly Ser Gly Gly Thr Thr Ser Gly Phe Ser Ile Leu His Gly Glu
145                 150                 155                 160

Ala Ser Met Gly Gly Gly Gly Gly Gly Gly Ala Gly Asn Ser Met
                165                 170                 175

Met Asn Ala Gly Val Phe Ser Asp Phe Gly Arg Gly Gly Gly Gly Gly
            180                 185                 190

Gly Lys Glu Gly Ser Thr Ser Leu Ser Val Asp Val Arg Gly Ala Asn
            195                 200                 205

Ser Gly Ala Gln Ser Gly Asp Gly Glu Tyr Leu Lys Gly Thr Glu Glu
        210                 215                 220

Glu Gly Ser
225

<210> SEQ ID NO 101
<211> LENGTH: 33
<212> TYPE: DNA
<213> ORGANISM: Artificial Sequence
<220> FEATURE:
<223> OTHER INFORMATION: Arabidopsis chromosome: start-end sequence in
      binary plasmid

<400> SEQUENCE: 101
cgcaaccgtt caagaaagcc tgtggaaact cca                              33
```

```
<210> SEQ ID NO 102
<211> LENGTH: 33
<212> TYPE: DNA
<213> ORGANISM: Artificial Sequence
<220> FEATURE:
<223> OTHER INFORMATION: Arabidopsis chromosome: start-end sequence in
      binary plasmid

<400> SEQUENCE: 102
cgcaaccgtt ctagaaaacc agtagagact cca                                33

<210> SEQ ID NO 103
<211> LENGTH: 33
<212> TYPE: DNA
<213> ORGANISM: Artificial Sequence
<220> FEATURE:
<223> OTHER INFORMATION: Arabidopsis chromosome: start-end sequence in
      binary plasmid

<400> SEQUENCE: 103
cgtcatcgtt ctagaaaacc ggtcgaagtc caa                                33

<210> SEQ ID NO 104
<211> LENGTH: 22
<212> TYPE: DNA
<213> ORGANISM: Artificial Sequence
<220> FEATURE:
<223> OTHER INFORMATION: Forward primer for AtGRF3 gene

<400> SEQUENCE: 104
gtcttcgctg gccacaagta tt                                            22

<210> SEQ ID NO 105
<211> LENGTH: 22
<212> TYPE: DNA
<213> ORGANISM: Artificial Sequence
<220> FEATURE:
<223> OTHER INFORMATION: Reverse primer for AtGRF3 gene

<400> SEQUENCE: 105
tgttgctgtt gtagtggtgg ct                                            22

<210> SEQ ID NO 106
<211> LENGTH: 23
<212> TYPE: DNA
<213> ORGANISM: Artificial Sequence
<220> FEATURE:
<223> OTHER INFORMATION: Forward primer for AtGRF2 gene

<400> SEQUENCE: 106
cacatcaaca gaggccgtca tcg                                           23

<210> SEQ ID NO 107
<211> LENGTH: 25
<212> TYPE: DNA
<213> ORGANISM: Artificial Sequence
<220> FEATURE:
<223> OTHER INFORMATION: Reverse primer for AtGRF2 gene

<400> SEQUENCE: 107
aaccggagat tccttgggtt gtaag                                         25

<210> SEQ ID NO 108
<211> LENGTH: 22
<212> TYPE: DNA
```

```
<213> ORGANISM: Artificial Sequence
<220> FEATURE:
<223> OTHER INFORMATION: Forward primer for AtGIF1 gene

<400> SEQUENCE: 108
ttggacgaaa acaaatcgtt ga                                              22

<210> SEQ ID NO 109
<211> LENGTH: 22
<212> TYPE: DNA
<213> ORGANISM: Artificial Sequence
<220> FEATURE:
<223> OTHER INFORMATION: Reverse primer for AtGIF1 gene

<400> SEQUENCE: 109
ctgttgctgt tgagtcgctt gt                                              22

<210> SEQ ID NO 110
<211> LENGTH: 50
<212> TYPE: DNA
<213> ORGANISM: Artificial Sequence
<220> FEATURE:
<223> OTHER INFORMATION: Retrotransposon stem-loop oligonucleotide

<400> SEQUENCE: 110
gtctcctctg gtgcagggtc cgaggtattc gcaccagagg agacmagttc                50

<210> SEQ ID NO 111
<211> LENGTH: 20
<212> TYPE: DNA
<213> ORGANISM: Artificial Sequence
<220> FEATURE:
<223> OTHER INFORMATION: Forward primer for stem-loop RT-qPCR

<400> SEQUENCE: 111
ggcggttcca cagcttttctt                                                20

<210> SEQ ID NO 112
<211> LENGTH: 21
<212> TYPE: DNA
<213> ORGANISM: Artificial Sequence
<220> FEATURE:
<223> OTHER INFORMATION: Reverse primer for stem-loop RT-qPCR

<400> SEQUENCE: 112
tggtgcaggg tccgaggtat t                                               21

<210> SEQ ID NO 113
<211> LENGTH: 15
<212> TYPE: DNA
<213> ORGANISM: Arabidopsis thaliana

<400> SEQUENCE: 113
ttctttgacg attgg                                                      15

<210> SEQ ID NO 114
<211> LENGTH: 5
<212> TYPE: PRT
<213> ORGANISM: Arabidopsis thaliana

<400> SEQUENCE: 114

Phe Phe Asp Asp Trp
1               5

<210> SEQ ID NO 115
```

<210> SEQ ID NO 115
<211> LENGTH: 15
<212> TYPE: DNA
<213> ORGANISM: Artificial Sequence
<220> FEATURE:
<223> OTHER INFORMATION: Mutagenized rGRF3 cDNA sequence

<400> SEQUENCE: 115
gctgctgacg atgct                                                    15

<210> SEQ ID NO 116
<211> LENGTH: 5
<212> TYPE: PRT
<213> ORGANISM: Artificial Sequence
<220> FEATURE:
<223> OTHER INFORMATION: Mutagenized rGRF3 encoded sequence

<400> SEQUENCE: 116

Ala Ala Asp Asp Ala
1               5

<210> SEQ ID NO 117
<211> LENGTH: 6
<212> TYPE: PRT
<213> ORGANISM: Artificial Sequence
<220> FEATURE:
<223> OTHER INFORMATION: Sequence motif
<220> FEATURE:
<221> NAME/KEY: MISC_FEATURE
<222> LOCATION: (4)..(4)
<223> OTHER INFORMATION: Xaa may be Asp or Glu

<400> SEQUENCE: 117

Phe Phe Asp Xaa Trp Pro
1               5

<210> SEQ ID NO 118
<211> LENGTH: 22
<212> TYPE: DNA
<213> ORGANISM: Arabidopsis thaliana

<400> SEQUENCE: 118
ccguucaaga aagccugugg aa                                            22

<210> SEQ ID NO 119
<211> LENGTH: 21
<212> TYPE: DNA
<213> ORGANISM: Arabidopsis thaliana

<400> SEQUENCE: 119
uuccacagcu uucuugaacu u                                             21

<210> SEQ ID NO 120
<211> LENGTH: 8
<212> TYPE: PRT
<213> ORGANISM: Arabidopsis thaliana

<400> SEQUENCE: 120

His Arg Ser Arg Lys Pro Val Glu
1               5

<210> SEQ ID NO 121
<211> LENGTH: 22
<212> TYPE: DNA
<213> ORGANISM: Artificial Sequence
<220> FEATURE:
<223> OTHER INFORMATION: Modified GRF3 sequence (rGRF3)

```
<400> SEQUENCE: 121
ccguucuaga aaaccaguag ag                                                22

<210> SEQ ID NO 122
<211> LENGTH: 30
<212> TYPE: DNA
<213> ORGANISM: Arabidopsis thaliana

<400> SEQUENCE: 122
gcgaaccgtt caagaaagcc tgtggaaagt                                        30

<210> SEQ ID NO 123
<211> LENGTH: 30
<212> TYPE: DNA
<213> ORGANISM: Artificial Sequence
<220> FEATURE:
<223> OTHER INFORMATION: Arabidopsis thaliana GRF3 mutant

<400> SEQUENCE: 123
cgcaaccgtt ctagaaaacc agtagagact                                        30

<210> SEQ ID NO 124
<211> LENGTH: 30
<212> TYPE: DNA
<213> ORGANISM: Artificial Sequence
<220> FEATURE:
<223> OTHER INFORMATION: Arabidopsis thaliana GRF3 mutant

<400> SEQUENCE: 124
cgtcatcgtt ctagaaaacc ggtcgaactc                                        30

<210> SEQ ID NO 125
<211> LENGTH: 21
<212> TYPE: DNA
<213> ORGANISM: artificial sequence
<220> FEATURE:
<223> OTHER INFORMATION: miR396b

<400> SEQUENCE: 125
uucaaguucu uucgacaccu u                                                 21

<210> SEQ ID NO 126
<211> LENGTH: 21
<212> TYPE: DNA
<213> ORGANISM: artificial sequence
<220> FEATURE:
<223> OTHER INFORMATION: rGRF3  miR396b

<400> SEQUENCE: 126
uucaaguucu uucgacaccu u                                                 21

<210> SEQ ID NO 127
<211> LENGTH: 6
<212> TYPE: PRT
<213> ORGANISM: artificial sequence
<220> FEATURE:
<223> OTHER INFORMATION: mutated miR396 target site

<400> SEQUENCE: 127

Phe Phe Asp Asp Trp Pro
1               5

<210> SEQ ID NO 128
<211> LENGTH: 6
<212> TYPE: PRT
```

```
<213> ORGANISM: artificial sequence
<220> FEATURE:
<223> OTHER INFORMATION: modified miR396 target site

<400> SEQUENCE: 128

Phe Phe Asp Glu Trp Pro
1               5
```